(12) United States Patent
Lawrence et al.

(10) Patent No.: US 9,878,999 B2
(45) Date of Patent: Jan. 30, 2018

(54) PROTEASOME CHYMOTRYPSIN-LIKE INHIBITION USING PI-1833 ANALOGS

(71) Applicant: H. Lee Moffitt Cancer Center and Research Institute, Inc., Tampa, FL (US)

(72) Inventors: Harshani R. Lawrence, Tampa, FL (US); Said M. Sebti, Tampa, FL (US); Sevil Ozcan, Lutz, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 188 days.

(21) Appl. No.: 14/035,453

(22) Filed: Sep. 24, 2013

(65) Prior Publication Data

US 2014/0073650 A1    Mar. 13, 2014

Related U.S. Application Data

(63) Continuation of application No. PCT/US2012/030574, filed on Mar. 26, 2012.

(60) Provisional application No. 61/467,051, filed on Mar. 24, 2011, provisional application No. 61/471,472, filed on Apr. 4, 2011.

(51) Int. Cl.
*A61K 31/497*     (2006.01)
*C07D 413/04*     (2006.01)
*C07D 271/04*     (2006.01)
*C07D 271/06*     (2006.01)

(52) U.S. Cl.
CPC ......... *C07D 413/04* (2013.01); *C07D 271/04* (2013.01); *C07D 271/06* (2013.01)

(58) Field of Classification Search
None
See application file for complete search history.

(56) References Cited

U.S. PATENT DOCUMENTS

| | | | |
|---|---|---|---|
| 4,753,674 | A | 6/1988 | Takematsu et al. |
| 2005/0176710 | A1 | 8/2005 | Schwink et al. |
| 2011/0257176 | A1 | 10/2011 | Villoutreix et al. |
| 2014/0073650 | A1 | 3/2014 | Lawrence et al. |

FOREIGN PATENT DOCUMENTS

| | | | | |
|---|---|---|---|---|
| WO | WO2008023248 | A3 | 2/2008 | |
| WO | WO2010001365 | * | 1/2010 | ......... A61K 31/4196 |
| WO | WO2010001365 | A1 | 1/2010 | |
| WO | WO2010118046 | A1 | 10/2010 | |
| WO | WO2010138600 | A3 | 12/2010 | |

OTHER PUBLICATIONS

Li et al., Encyclopedia of Chemical Processing "Chiral Drug Separation" p. 449-458, c/o. 2006.*
M. Kawai et al. / Bioorg. Med. Chem. Lett. 17 (2007) 5537-5542.*
Thornber, Chem. Soc. Rev. 1979, 8, pp. 563-580.*
https://en.wikipedia.org/wiki/Benzyl_group, last accessed Sep. 21, 2016.
Hulteen & Martin, Introducing chemical transport selectivity into gold nanotube membranes. J Am Chem Soc. Jul. 1998; 120(26):6603-6604.
Handbook of Food Products Manufacturing. Hui, Ed. (John Wiley & Sons, Inc., 2007).
Dougherty, Cation—π interactions in chemistry and biology: a new view of benzene, Phe, Tyr, and Trp. Science. Jan. 12, 1996; 171(5246):163-8.
Ozcan, et al., Oxadiazole-isopropylamides as Potent and Noncovalent Proteasome Inhibitors. J Med Chem. May 23, 2013; 56(10):3783-805.
http://www.chemvista.org/hyperconjugation.html, last accessed Oct. 5, 2016.
https://www2.chemistry.msu.edu/faculty/reusch/virtbdjml/heterocy.htm, last accessed Oct. 5, 2016.
Kazi, et al., Discovery of PI-1840, a novel noncovalent and rapidly reversible proteasome inhibitor with anti-tumor activity. J Bio Chem. Apr. 25, 2014;289(17)11906-15.
http://www.mhhe.com/physsci/chemistry/carey/student/olc/graphics/carey04oc/ref/ch12substituenteffects.html, last accessed Aug. 6, 2015.
Aitken, et al., Science of synthesis: Houben-Weyl methods of molecular transformations. (Georg Thieme Verlag 2004, Stuttgart, Germany).
Dewick, Essentials of organic chemistry: for students of pharmacy, medicinal chemistry and biological chemistry. (John Wiley & Sons, Inc. 2006; Hoboken, NJ).
Adams J. Preclinical and clinical evaluation of proteasome inhibitor PS-341 for the treatment of cancer. Curr Opin Chem Biol 2002;6:493-500.
Adams J. Potential for proteasome inhibition in the treatment of cancer. Drug Discov Today 2003;8:307-15.

(Continued)

*Primary Examiner* — Sreeni Padmanabhan
*Assistant Examiner* — Jeanmarie Calvillo
(74) *Attorney, Agent, or Firm* — Michele L. Lawson; Robert J. Varkonyi; Smith & Hopen, P.A.

(57) ABSTRACT

Focused library synthesis and medicinal chemistry on an oxadiazole-isopropylamide core proteasome inhibitor provided the lead compound that strongly inhibits CT-L activity. Structure activity relationship studies indicate the amide moiety and two phenyl rings are sensitive toward synthetic modifications. Only para-substitution in the A-ring was important to maintain potent CT-L inhibitory activity. Hydrophobic residues in the A-ring's para-position and meta-pyridyl group at the B-ring significantly improved inhibition. The meta-pyridyl moiety improved cell permeability. The length of the aliphatic chain at the para position of the A-ring is critical with propyl yielding the most potent inhibitor, whereas shorter (i.e. ethyl, methyl or hydrogen) or longer (i.e. butyl, propyl and hexyl) chains demonstrating progressively less potency. Introduction of a stereogenic center next to the ether moiety (i.e. substitution of one of the hydrogens by methyl) demonstrated chiral discrimination in proteasome CT-L activity inhibition (the S-enantiomer was 35-40 fold more potent than the R-enantiomer).

20 Claims, 20 Drawing Sheets

(56) References Cited

OTHER PUBLICATIONS

Adams, J., Proteasome Inhibition in Cancer: Development of PS-341, Semin. Oncol. 2001, 28, 613-619.
Allegretti, et al. 2-Arylpropionic CXC Chemokine Receptor 1 (CXCR1) Ligands as Novel Noncompetitive CXCL8 Inhibitors. J. Med. Chem. 2005, 48, 4312-4331.
Almond JB, Cohen GM. The proteasome: a novel target for cancer chemotherapy. Leukemia 2002;16:433-43.
Basse, et al. Development of lipopeptides for inhibiting 20S proteasomes. Bioorg. Med. Chem. Lett. 2006, 16, 3277-3281.
Borissenko and Grail, 20S Proteasome and Its Inhibitors: Crystallographic Knowledge for Drug Development. Chem. Rev. (Washington, DC, U. S.) 2007, 107, 687-717.
Lawrence R. Dick, et al., Building on Bortezomib: second-generation proteasome inhibitors as anti-cancer therapy, Drug Discovery Today, vol. 15, No. 5/6, Mar. 2010, pp. 243-249.
Dou Q., Li B. Proteasome inhibitors as potential novel anticancer agents. Drug Resist Update 1999;2:215-223.
Dou Q., Goldfarb R. Evaluation of the proteasome inhibitor MLN-341 (PS-341). IDrugs 2002;5:828-834.
Dou Q., et al. Interruption of tumor cell cycle progression through proteasome inhibition: implications for cancer therapy. Progress in Cell Cycle Research, vol. 5, 2003, pp. 441-446.
Formicola, et al. Novel fluorinated pseudopeptides as proteasome inhibitors. Bioorg. Med. Chem. Lett. 2009, 19, 83-86.
Fuchs, Proteasome inhibition as a therapeutic strategy in patients with multiple myeloma. Mult. Myeloma 2009, 101-125.
Furet, et al. Structure-Based optimization of 2-aminobenzylstatine derivatives: potent and selective inhibitors of the chymotrypsin-Like activity of the human 20S proteasome. Bioorg. Med. Chem. Lett. 2002, 12, 1331-1334.
Furet, et al. Entry into a New Class of Potent Proteasome Inhibitors Having High Antiproliferative Activity by Structure-Based Design. J. Med. Chem. 2004, 47, 4810-4813.
Ge, et al. Discovery and Synthesis of Hydronaphthoquinones as Novel Proteasome Inhibitors. J. Med. Chem., Mar. 8, 2012;55(5):1978-98. Epub Feb. 14, 2012.
Genin, et al. Proteasome inhibitors: recent advances and new perspectives in medicinal chemistry. Curr. Top. Med. Chem. (Sharjah, United Arab Emirates) 2010, 10, 232-256.
Gezginci, et al. Antimycobacterial Activity of Substituted Isosteres of Pyridine- and Pyrazinecarboxylic Acids. 2. J. Med. Chem. 2001, 44, 1560-1563.
Goldberg AL. Functions of the proteasome: the lysis at the end of the tunnel. Science 1995;268:522-3.
Groll, et al. Structure of 20S proteasome from yeast at 2.4 .ANG. resolution. Nature (London) 1997, 386, 463-471.
Groll and Huber, Inhibitors of the eukaryotic 20S proteasome core particle: a structural approach. Biochim. Biophys. Acta, Mol. Cell Res. 2004, 1695, 33-44.
Groll, et al. Snapshots of the Fluorosalinosporamide/20S Complex Offer Mechanistic Insights for Fine Tuning Proteasome Inhibition. J. Med. Chem. 2009, 52, 5420-5428.
Groll, et al. Crystal structure of epoxomicin:20S proteasome reveals a molecular basis for selectivity of a',b'-epoxyketone proteasome inhibitors. J. Am. Chem. Soc. 2000, 122, 1237-1238.
Groll, et al. Crystal Structure of the Boronic Acid-Based Proteasome Inhibitor Bortezomib in Complex with the Yeast 20S Proteasome. Structure (Cambridge, MA, U. S.) 2006, 14, 451-456.
Dorsey, et al. CEP-18770: Discovery of a Potent, Selective and Orally Active Proteasome Inhibitor for the Treatment of Cancer. Frontiers in CNS and Oncology Medicinal Chemistry, ACS-EFMC, Siena, Italy, Oct. 7-9, 2007, COMC-027.
Jung, L., et al., Discovery, Development, and Clinical Applications of Bortezomib, Oncology 2004, 18, 4-13.
Kohno, et al. Structures of TMC-95A-D: Novel proteasome inhibitors from Apiospora montagnei Sacc. TC 1093. J. Org. Chem. 2000, 65, 990-995.
Kupperman, et al. Evaluation of the proteasome inhibitor MLN9708 in preclinical models of human cancer. Cancer Res 2010, 70, 1970-80.
Kupperman, et al. Evaluation of the proteasome inhibitor MLN9708 in preclinical models of human cancer. [Erratum to document cited in CA152:517050]. Cancer Res. 2010, 70, 3853.
Lara, P. N., et al., Proteasome Inhibition with PS-341 (Bortezomib) in Lung Cancer Therapy, Semin. Oncol. 2004, 31, 40-46.
Lam, et al. From natural products to clinical trials: NPI-0052 (salinosporamide a), a marine actinomycete-derived anticancer agent. Nat. Prod. Chem. Drug Discovery 2010, 355-373.
Lawrence, et al. Synthesis and biological evaluation of naphthoquinone analogs as a novel class of proteasome inhibitors. Bioorg. Med. Chem. 2010, 18, 5576-5592.
Piva, et al. CEP-18770: a novel, orally active proteasome inhibitor with a tumor-selective pharmacologic profile competitive with bortezomib. Blood 2008, 111, 2765-2775.
Schmidtke, et al. How an inhibitor of the HIV-I protease modulates proteasome activity. J. Biol. Chem. 1999, 274, 35734-35740.
Sharma, P. C.; Yadav, S.; Pahwa, R.; Kaushik, D.; Jain, S. Synthesis and evaluation of novel prodrugs of naproxen. Med. Chem. Res. 2011, 20, 648-655.
Sterz, et al. The potential of proteasome inhibitors in cancer therapy. Expert Opin. Invest. Drugs 2008, 17, 879-895.
Sunwoo J., et al. Novel proteasome inhibitor PS-341 inhibits activation of nuclear factor-kappa B, cell survival, tumor growth, and angiogenesis in squamous cell carcinoma. Clin Cancer Res 2001;7:1419-28.
Vorhees, et al., The proteasome as a target for cancer therapy. Clin Can Res. Dec. 15, 2003; 9: 6316-6325.
Yang, Q.; Olmsted, C.; Borhan, B. Absolute Stereochemical Determination of Chiral Carboxylic Acids. Org. Lett. 2002, 4, 3423-3426.
Zhou, et al. Design and Synthesis of an Orally Bioavailable and Selective Peptide Epoxyketone Proteasome Inhibitor (PR-047). J. Med. Chem. 2009, 52, 3028-3038.
PubChem Compound. Online compound summary retrieved from the Internet: <URL: http://pubchem.ncbi.nih.gov/search.cgi>. Oct. 8, 2010.
International Search Report and Written Opinion issued by the International Searching Authority dated Oct. 23, 2012 for international patent application No. PCT/US2012/030574.
International Preliminary Report on Patentability issued by the International Bureau dated Oct. 3, 2013 for international patent application No. PCT/US2012/030574.

* cited by examiner

IC$_{50}$ = 0.554 ± 0.226 µM

PI-1833

PI-1833
IC$_{50}$ = 0.55 ± 0.22 µM (commercial sample)

11ad $IC_{50} = 32 \pm 0.35$ nM

PROTEASOME CHYMOTRYPSIN-LIKE INHIBITION USING PI-1833 ANALOGS

CROSS REFERENCE TO RELATED APPLICATION

This application is a continuation of prior filed International Application, Serial Number PCT/US2012/030574 filed on Mar. 26, 2012, which claims priority to U.S. Provisional Patent Application No. 61/467,051, entitled "Proteasome Chymotrypsin-Like Inhibition using PI-1833 Analogs", filed on Mar. 24, 2011, and U.S. Provisional Patent Application No. 61/471,472, entitled "Proteasome Chymotrypsin-Like Inhibition using PI-1833 Analogs", filed on Apr. 4, 2011, the contents of which are herein incorporated by reference.

GOVERNMENT SUPPORT STATEMENT

This invention was made with Government support under Grant No. CA118210 awarded by the National Institute of Health. The Government has certain rights in the invention.

FIELD OF INVENTION

This invention relates to cancer treatment. Specifically, the invention provides novel compounds for inhibiting the proteasome for inhibiting tumor growth.

BACKGROUND OF THE INVENTION

Current tumor treatments include radiotherapy, chemotherapy, surgical resection, hormone therapy, or a combination of these treatments. Precise control of protein turnover is essential to cellular survival. In eukaryotes, the majority of protein degradation occurs through the UPP, which consists of the ubiquitin-conjugating system and the proteasome (Yamasaki, L. and Pagano, M. *Curr. Opin. Cell Biol.* 2004, 16, 623-628. Ciechanover, A.; Orian, A.; Schwartz, A. L. *J Cell Biochem Suppl* 2000, 34, 40-51; Ciechanover, A. *Cell* 1994, 79, 13-21; Hochstrasser, M. *Curr. Opin. Cell Biol.* 1995, 7, 215-223; Coux, O.; Tanaka, K.; Goldberg, A. L. *Annu Rev Biochem* 1996, 65, 801-847; Baumeister, W., et al. *Cell* 1998, 92, 367-380; Murata, S., et al. *Nat. Rev. Mol.* 2009, 10, 104-115). The proteasome is a massive multicatalytic protease comprising a 20S multisubunit structure which is capped by the 19S regulatory complex at each end, forming the core of the 26S proteasome, the major extralysosomal mediator of protein degradation (Groll, M., et al. *Nature* (London) 1997, 386, 463-471; Adams, *J. Nat. Rev. Cancer* 2004, 4, 349-360). The three main catalytic activities of the proteasome; peptidylglutamyl peptide hydrolysing (PGPH), trypsin-like (T-L), and chymotrypsin-like (CT-L), are mediated by three distinct catalytic β-1, β-2, and β-5 subunits respectively (Groll, M.; Bekers, C. R.; Ploegh, H. L.; Ovaa, H. *Structure*, 2006, 14, 451-456). The proteasome is responsible for degrading a large number of cellular proteins (Lowe J., et al. Crystal structure of the 20S proteasome from the archaeon *T. acidophilum* at 3.4 Å resolution. *Science* 1995; 268:533-9). The eukaryotic proteasome possesses at least three distinct activities: chymotrypsin-like (cleavage after hydrophobic residues), trypsin-like (cleavage after basic residues), and caspase-like (cleavage after acidic residues). These target proteins are first tagged with ubiquitin in order to be degraded by the proteasome.

Ubiquitination is mediated by the sequential action of an E1 Ub-activating enzyme, an E2 Ub-conjugating enzyme, and an E3 Ub-ligase. Once Ub-tagged, proteins bind to subunits in the 19S regulatory cap of the proteasome, where they are deubiquitinated and unfolded in an energy dependent manner. These are then fed into the catalytic inner chamber of the 20S complex, which generates peptides of 3-22 amino acids in size (Vorhees, et al., The proteasome as a target for cancer therapy. Clin Can Res. 2003 Dec. 15; 9: 6316-6325).

The ATP-dependent ubiquitin-proteosome pathway is responsible for the controlled degradation of proteins in eukaryotic cells (Hochstrasser, Ubiquitin, proteasomes, and the regulation of intracellular protein degradation. *Curr. Opin. Cell Biol.* 1995, 7, 215-23; Yamasaki and Pagano, Cell cycle, proteolysis and cancer. *Curr. Opin. Cell Biol.* 2004, 16, 623-628; Coux, et al. Structure and functions of the 20S and 26S proteasomes. *Annu Rev Biochem* 1996, 65, 801-47; Ciechanover, et al. The ubiquitin-mediated proteolytic pathway: mode of action and clinical implications. *J. Cell. Biochem.* 2000, 40-51; Ciechanover, The ubiquitin-proteasome proteolytic pathway. *Cell* (Cambridge, Mass.) 1994, 79, 13-21; Baumeister, et al. The proteasome: paradigm of a self-compartmentalizing protease. *Cell* 1998, 92, 367-80). The 26S proteosome is a multifunctional complex, consisting of a 19S regulatory particle (RP) and a 20S core particle (CP) (Groll, et al. Structure of 20S proteasome from yeast at 2.4.ANG. resolution. *Nature* (London) 1997, 386, 463-471). The three main catalytic activities of the proteasome; peptidylglutamyl peptide hydrolysing (PGPH), trypsin-like (T-L), and chymotrypsin-like (CT-L), are mediated by three distinct catalytic β-1, β-2, and β-5 subunits respectively (Groll and Huber, Inhibitors of the eukaryotic 20S proteasome core particle: a structural approach. *Biochim. Biophys. Acta, Mol. Cell. Res.* 2004, 1695, 33-44).

In a broad range of cell culture models, proteasome inhibitors rapidly induce tumor cell apoptosis, selectively activating the cell death program in oncogene-transformed, but not normal or untransformed cells, and are able to trigger apoptotic death in human cancer cells that are resistant to various anticancer agents (Adams J. Preclinical and clinical evaluation of proteasome inhibitor PS-341 for the treatment of cancer. Curr Opin Chem Biol 2002; 6:493-500; Dou Q., Goldfarb R. Evaluation of the proteasome inhibitor MLN-341 (PS-341). IDrugs 2002; 5:828-834). Inhibition of the chymotrypsin-like, but not the trypsin-like, activity has been found to be associated with induction of tumor cell apoptosis.

Apoptosis is a highly conserved cellular suicide program in multicellular organisms from worms to humans. This cellular death program serves as a means to maintain multicellular organisms by discarding damaged and undesirable cells. Faulty execution of apoptosis, including either excessive cell death or insufficient cell death, is a factor in many disease states including AIDS and cancer (Jacobson M., et al. Programmed cell death in animal development. Cell 1997; 88:347-54; Song Z., Steller H. Death by design: mechanism and control of apoptosis. Trends Cell Biol 1999; 9:M49-52). Apoptosis features several distinct events and morphological changes, such as loss of the mitochondrial membrane potential, proteolytic dismantling of cellular components, DNA fragmentation, and cellular condensation into apoptotic bodies that are removed by phagocytes (Green D., Reed J. Mitochondria and apoptosis. Science 1998; 281:1309-12; Earnshaw W., et al. Mammalian caspases: structure, activation, substrates, and functions during apoptosis. Annu Rev Biochem 1999; 68:383-424; Bratton S., et al. Protein complexes activate distinct caspase cascades in death receptor and stress-induced apoptosis. Exp Cell Res 2000; 256:27-33; Wyllie A., et al. Cell death: the significance of apoptosis. Int Rev Cytol 1980; 68:251-306). As a distinct series of cellular pathways, apoptosis potentially offers unique targets for chemotherapeutic intervention. It has been suggested that cancer cells are more sensitive to several apoptosis-inducing stimuli than normal cells, including proteasome inhibitors and those affecting cellular division (Adams J. Potential for proteasome inhibition in the treatment of cancer. Drug Discov Today 2003; 8:307-15; Dou Q., Li B. Proteasome inhibitors as potential novel anticancer agents. Drug Resist Update 1999; 2:215-223; Almond J B, Cohen G M. The proteasome: a novel target for cancer chemotherapy. Leukemia 2002; 16:433-43; Goldberg A L. Functions of the proteasome: the lysis at the end of the tunnel. Science 1995; 268:522-3; Dou Q., et al. Interruption of tumor cell cycle progression through proteasome inhibition: implications for cancer therapy. In Progress in Cell Cycle Research. Meijer L, Jezequel A, Roberge M, (eds.) Life in Progress Editions, Roscoff, 2003; pp. 441-446). Several regulatory proteins involved in cell cycle and apoptosis processes, such as cyclins, bcl-2 family members, and p53, are degraded by the ubiquitin-proteasome pathway (An B., et al. Novel dipeptidyl proteasome inhibitors overcome Bcl-2 protective function and selectively accumulate the cyclin-dependent kinase inhibitor p27 and induce apoptosis in transformed, but not normal, human fibroblasts. Cell Death Differ 1998; 5:1062-75; Lopes U., et al. p53-dependent induction of apoptosis by proteasome inhibitors. J Biol Chem 1997; 272:12893-6).

Owing to the central role of proteosome in maintaining homeostasis and hence its key position in many cellular processes, the development of proteasome inhibitors for CT-L activity has been the subject of considerable interest in the treatment of cancer due to its critical role in the degradation of apoptotic and tumor suppressor proteins (Borissenko and Groll, 20S Proteasome and Its Inhibitors: Crystallographic Knowledge for Drug Development. Chem. Rev. (Washington, D.C., U.S.) 2007, 107, 687-717; Genin, et al. Proteasome inhibitors: recent advances and new perspectives in medicinal chemistry. Curr. Top. Med. Chem. (Sharjah, United Arab Emirates) 2010, 10, 232-256). The antitumor activity of proteasome inhibitors has been confirmed by the results of bortezomib, a potent and selective dipeptidyl boronic acid proteasome inhibitor (Sunwoo J., et al. Novel proteasome inhibitor PS-341 inhibits activation of nuclear factor-kappa B, cell survival, tumor growth, and angiogenesis in squamous cell carcinoma. Clin Cancer Res 2001; 7:1419-28) that selectively inhibits the CT-L activity of 20S proteasome (Jung, L., et al. Oncology 2004, 18, 4-13; Lara, P. N., et al. Semin. Oncol. 2004, 31, 40-46. Adams, J. Semin. Oncol. 2001, 28, 613-619).

The proteasome inhibitors currently in the clinic are derived from 3 structural classes, seen in FIG. 1: In the first class, Bortezomib, which is a dipeptide boronic acid, was the first clinically approved proteasome inhibitor (Groll, et al. Snapshots of the Fluorosalinosporamide/20S Complex Offer Mechanistic Insights for Fine Tuning Proteasome Inhibition. J. Med. Chem. 2009, 52, 5420-5428; Groll, et al. Crystal structure of epoxomicin:20S proteasome reveals a molecular basis for selectivity of a',b'-epoxyketone proteasome inhibitors. J. Am. Chem. Soc. 2000, 122, 1237-1238). Similar to Bortezomib, MLN9708 (Kupperman, et al. Evaluation of the proteasome inhibitor MLN9708 in preclinical models of human cancer. Cancer Res 2010, 70, 1970-80; Kupperman, et al. Evaluation of the proteasome inhibitor MLN9708 in preclinical models of human cancer. [Erratum to document cited in CA152:517050]. Cancer Res. 2010, 70, 3853; Lawrence, et al. Building on bortezomib: second-generation proteasome inhibitors as anti-cancer therapy. Drug Discov Today 2010, 15, 243-9) (a modified dipeptidyl boronic acid which hydrolyses immediately in plasma) and CEP-18770 (Dorsey, et al. CEP-18770: Discovery of a Potent, Selective and Orally Active Proteasome Inhibitor for the Treatment of Cancer. Frontiers in CNS and Oncology Medicinal Chemistry, ACS-EFMC, Siena, Italy, Oct. 7-9 2007, COMC-027; Piva, et al. CEP-18770: a novel, orally active proteasome inhibitor with a tumor-selective pharmacologic profile competitive with bortezomib. Blood 2008, 111, 2765-2775; Sterz, et al. The potential of proteasome inhibitors in cancer therapy. Expert Opin. Invest. Drugs 2008, 17, 879-895) are also boronic acid derivatives. The second class includes β-lactone salinosporamide A (Fuchs, Proteasome inhibition as a therapeutic strategy in patients with multiple myeloma. Mult. Myeloma 2009, 101-125; Lam, et al. From natural products to clinical trials: NPI-0052 (salinosporamide A), a marine actinomycete-derived anticancer agent. Nat. Prod. Chem. Drug Discovery 2010, 355-373) (represented by NPI-0052) is a marine microbial natural product. The third class includes tetrapeptide epoxyketone carfilzomib (Zhou, et al. Design and Synthesis of an Orally Bioavailable and Selective Peptide Epoxyketone Proteasome Inhibitor (PR-047). J. Med. Chem. 2009, 52, 3028-3038), which is related to the natural product epoxomicin. Each inhibitor class reacts with the proteasome N-terminal threonine active sites by a distinct mechanism. Peptide boronic acids (Bortezomib, MLN9708 and CEP-18770) form a slowly reversible tetrahedral adduct with the OH group of the catalytic Thr-1 (Groll, et al. Crystal Structure of the Boronic Acid-Based Proteasome Inhibitor Bortezomib in Complex with the Yeast 20S Proteasome. Structure (Cambridge, Mass., U.S.) 2006, 14, 451-456). For the β-lactone NPI-0052, attack of the lactone ring by catalytic Thr-1$^{23}$ forms an ester bond (that undergo intramolecular rearrangement) which makes this compound an irreversible inhibitor. The epoxyketone (Groll, et al. Crystal structure of epoxomicin:20S proteasome reveals a molecular basis for selectivity of a',b'-epoxyketone proteasome inhibitors. J. Am. Chem. Soc. 2000, 122, 1237-1238) moiety of Carfilzomib reacts with the OH and the α-amino group of Thr-1 to form 2 covalent bonds, making the inhibition also irreversible.

Proteasome inhibitors are classified as reversible or irreversible inhibitors according to their chemical structure and mechanism of inhibition. Irreversible/covalent and slow reversible inhibitors as described above possess a chemically reactive group that bind to proteasome covalently; whereas non-covalent and rapidly reversible inhibitors inhibit the proteasome through a network of interactions (hydrophobic, hydrogen bonds, electrostatic and/or van der Waals). Examples of reversible proteosome inhibitors include Ritonavir (Schmidtke, et al. How an inhibitor of the HIV-I protease modulates proteasome activity. J. Biol. Chem. 1999, 274, 35734-35740), several benzylstatine derivatives (Furet, et al. Structure-Based optimization of 2-aminobenzylstatine derivatives: potent and selective inhibitors of the chymotrypsin-Like activity of the human 20S proteasome. Bioorg. Med. Chem. Lett. 2002, 12, 1331-1334), 5-trimethoxy-L-phenylalanine derivatives (Furet, et al. Entry into a New Class of Potent Proteasome Inhibitors Having High Antiproliferative Activity by Structure-Based Design. J. Med. Chem. 2004, 47, 4810-4813), lipopeptides (Basse, et al. Development of lipopeptides for inhibiting 20S proteasomes. Bioorg. Med. Chem. Lett. 2006, 16, 3277-3281), TMC-95A derivatives (Kohno, et al. Structures of TMC-95A-D: Novel proteasome inhibitors from Apiospora montagnei Sacc. TC 1093. *J. Org. Chem.* 2000, 65, 990-995) and fluorinated pseudopeptides (Formicola, et al. Novel fluorinated pseudopeptides as proteasome inhibitors. *Bioorg. Med. Chem. Lett.* 2009, 19, 83-86). Since non-covalent inhibitors do not have a reactive moiety, which is often associated with metabolic instability, poor specificity, and excessive reactivity, they have the advantage of exerting fewer side effects over the covalent and irreversible ones. It has been shown that the proteasome activity recovers at the same rate with irreversible inhibitors as with covalent and slowly reversible inhibitors, presumably due de novo proteasome synthesis. The clinical advantages/benefits of non-covalent and reversible proteasome inhibitors in cancer treatment are not well understood. We have been actively engaged in the discovery of novel proteasome inhibitors (Lawrence, et al. Synthesis and biological evaluation of naphthoquinone analogs as a novel class of proteasome inhibitors. *Bioorg. Med. Chem.* 2010, 18, 5576-5592; Ge, et al. Discovery and Synthesis of Hydronaphthoquinones as Novel Proteasome Inhibitors. *J. Med. Chem.,* 2012 Mar. 8; 55(5):1978-98. Epub 2012 Feb. 14).

The potent proteasome inhibitors reported to date have been developed as aldehydes, boronates, vinylsulfones and expoxyketones and these compounds function through covalent modification of the N-terminal threonine residue of β-5 subunit. However, toxicity and tumor cell resistance against Bortezomib, as well as other proteasome inhibitors, demand the development of improved and selective proteasome inhibitors.

SUMMARY OF THE INVENTION

Small, drug-like synthetic proteasome inhibitors that are selective for cancer over normal cells are rare, but clearly would have a potential advantage over the existing inhibitors. PI-1833 and PI-1840 are small drug-like compounds that do not contain any reactive moieties. These compounds have use as an irreversible proteosome inhibitor. As such, a compound comprising the formula

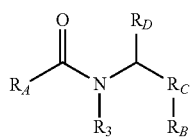

has been developed, which may be used in some embodiments as a proteasome inhibitor. The $R_A$ moiety is optionally

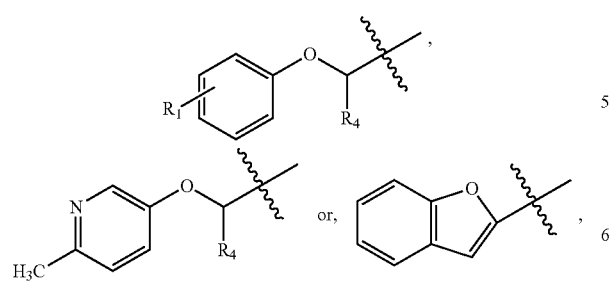

wherein $R_1$ can be H, ethyl, isopropyl, isobutyl, $CH_2CH_3$, Br, Ph, F, ortho-$CH_3$, meta-$CH_3$, para-$CH_3$, $CF_2H$, $CF_3$, F, Cl, Br, $NH_2$, CN, OX, OH, $C_6H_{10}$, $C_6H_{13}$, $C_5H_{11}$, $C_4H_9$, $C_3H_7$, or $NO_2$; and $R_4$ can be H, alkyl methyl, aryl methyl, OH, $OCH_3$, or $NH_2$. In particular, the $R_1$ moiety is optionally para-$CH_3$, $CF_3$, Cl, $C_3H_7$, $C_4H_9$, or isobutyl. Where the $R_1$ moiety is OX, X is an aryl or alkyl group.

The $R_B$ is optionally

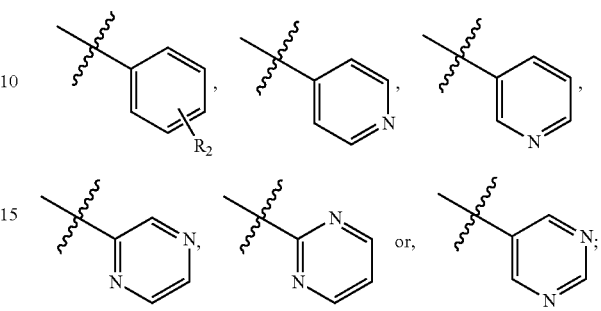

wherein $R_2$ is H, Cl, ortho-$CH_3$, meta-$CH_3$, para-$CH_3$, $CF_3$, F, or isopropyl. In specific embodiments, the $R_1$ and $R_2$ moieties are not the same group. $R_C$ is a heterocyclic aromatic five-member ring structure, wherein the heterocyclic aromatic five-member ring structure further comprises at least one heteroatom consisting of O, N, or S. In some embodiments, the heterocyclic aromatic five-member ring structure is

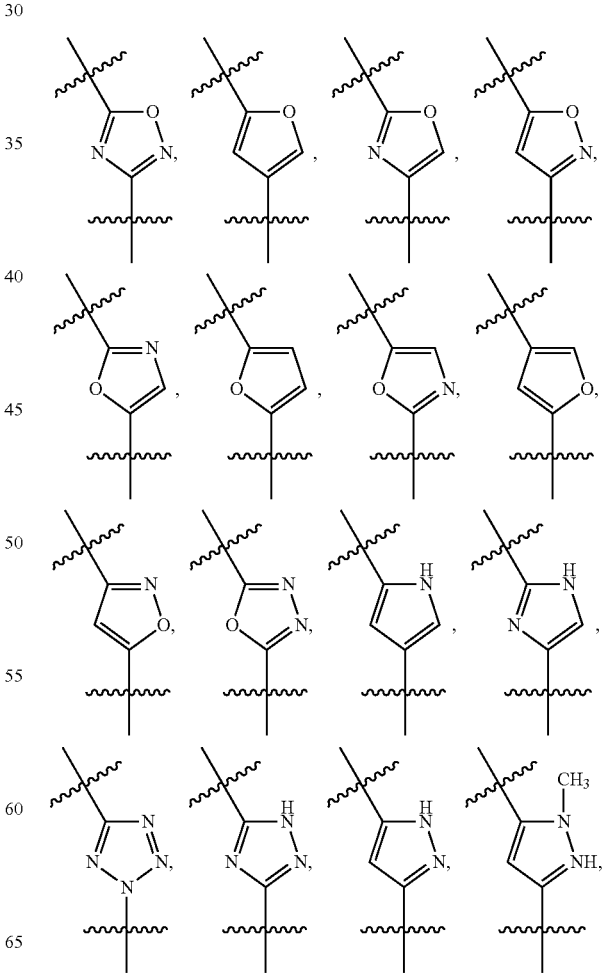

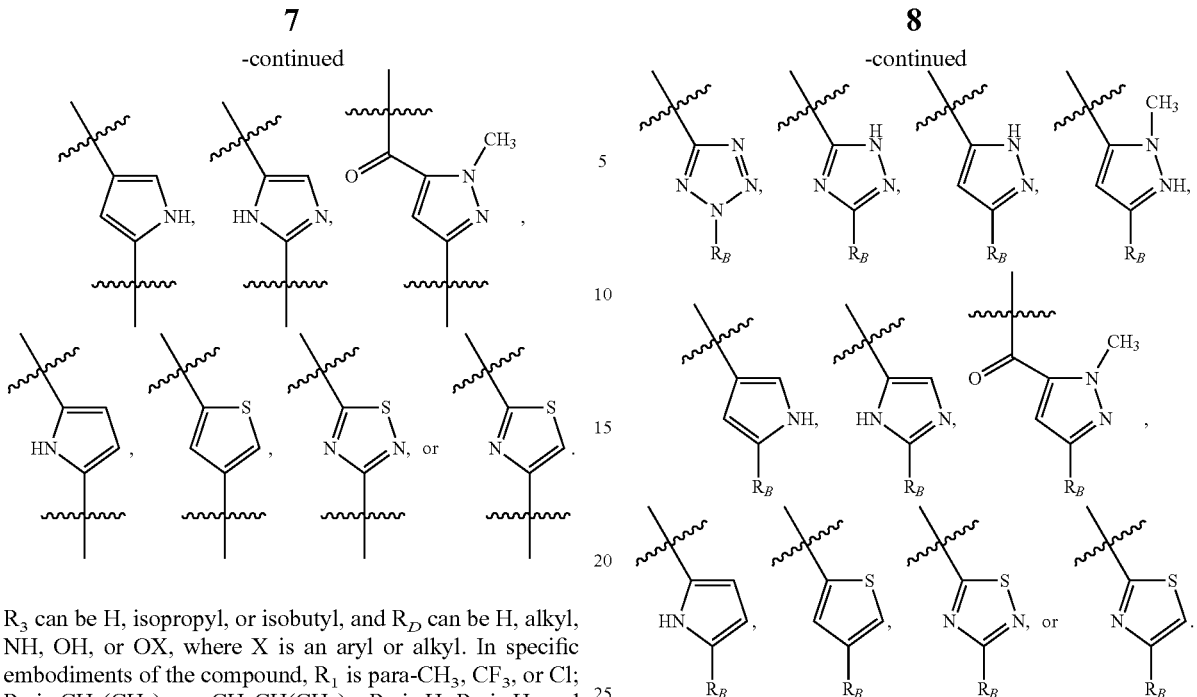

$R_3$ can be H, isopropyl, or isobutyl, and $R_D$ can be H, alkyl, NH, OH, or OX, where X is an aryl or alkyl. In specific embodiments of the compound, $R_1$ is para-$CH_3$, $CF_3$, or Cl; $R_3$ is $CH_2(CH_3)_2$, or $CH_2CH(CH_3)_2$; $R_4$ is H; $R_5$ is H; and $R_2$ is H, Cl, $CF_3$, or $CH_3$. The compound is optionally an S-enantiomer.

Compounds of formula II are also disclosed, as shown by

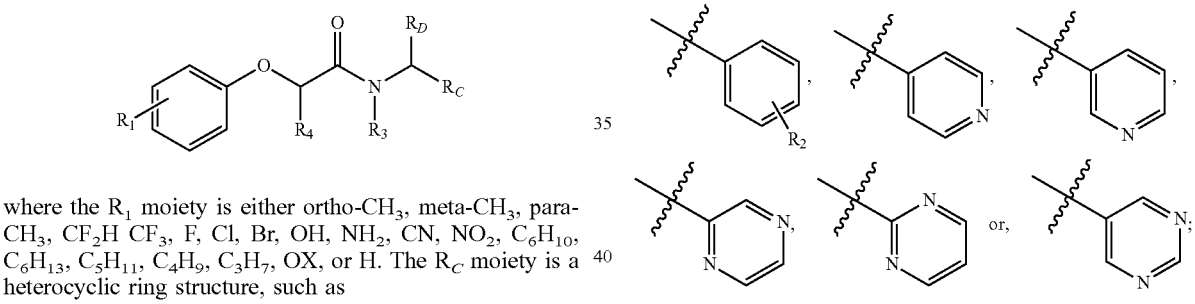

where the $R_1$ moiety is either ortho-$CH_3$, meta-$CH_3$, para-$CH_3$, $CF_2H$ $CF_3$, F, Cl, Br, OH, $NH_2$, CN, $NO_2$, $C_6H_{10}$, $C_6H_{13}$, $C_5H_{11}$, $C_4H_9$, $C_3H_7$, OX, or H. The $R_C$ moiety is a heterocyclic ring structure, such as

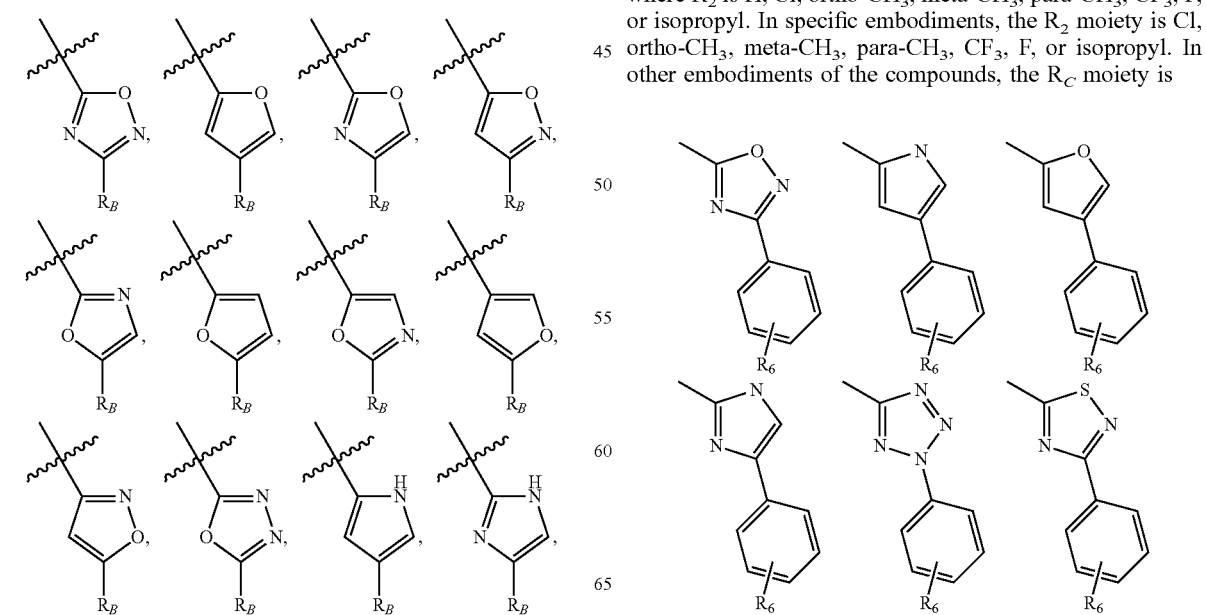

The $R_B$ attached to the heterocyclic ring structure is optionally where $R_2$ is H, Cl, ortho-$CH_3$, meta-$CH_3$, para-$CH_3$, $CF_3$, F, or isopropyl. In specific embodiments, the $R_2$ moiety is Cl, ortho-$CH_3$, meta-$CH_3$, para-$CH_3$, $CF_3$, F, or isopropyl. In other embodiments of the compounds, the $R_C$ moiety is where $R_6$ is ortho $CH_3$, meta $CH_3$, para $CH_3$, $CF_3$, OH, $NH_2$, CN, $NO_2$, OX, Cl, or H, and X is an alkyl or aryl. The $R_3$ moiety is optionally $CH(CH_3)_2$, cyclopropyl, $CH_2CH(CH_3)_2$, $CH_2CH_3$, OH, or H, the $R_4$ moiety alkyl methyl, aryl methyl, OH, OMe, or $NH_2$, and the $R_D$ moiety can be H, alkyl, NH, OH, OX, where X is an alkyl or aryl. The compound is optionally an S-enantiomer.

The compounds of the invention may be used to inhibit the chymotrypsin-like activity of proteasome, by administering at least one of the compounds disclosed above.

BRIEF DESCRIPTION OF THE DRAWINGS

For a fuller understanding of the invention, reference should be made to the following detailed description, taken in connection with the accompanying drawings, in which.

| Library 5 | |
|---|---|
| 5a | $R_1$ = para-$CH_3$—Ph |
| 5b | $R_1$ = para-$CF_3$—Ph |
| 5c | $R_1$ = Ph |
| 5d | $R_1$ = para-Cl—Ph |
| 5e | $R_1$ = para-phenyl-Ph |
| 5f | $R_1$ = para-F—Ph |
| 5g | $R_1$ = 6-bromonaphthalene |
| 5h | $R_1$ = meta-methyl-Ph |
| 5i | $R_1$ = ortho-methyl-Ph |
| 5j | $R_1$ = para-ethyl-Ph |
| 5k | $R_1$ = para-propyl-Ph |
| 5l | $R_1$ = para-butyl-Ph |
| 5m | $R_1$ = para-pentyl-Ph |
| 5n | $R_1$ = para-hexyl-Ph |
| 5o | $R_1$ = para-cyclohexyl-Ph |
| 5p | $R_1$ = para-isopropyl-Ph |
| 5q | $R_1$ = para-isobutyl-Ph |
| 5r | $R_1$ = para-$^t$butyl-Ph |
| 5s | $R_1$ = para-OH—Ph |
| 5t | $R_1$ = para-COOH—Ph |

| Library 10 | |
|---|---|
| 10a | $R_2$ = para-$CH_3$—Ph, $R_3$ = isopropyl |
| 10b | $R_2$ = para-$CF_3$—Ph, $R_3$ = isopropyl |
| 10c | $R_2$ = Ph, $R_3$ = isopropyl |
| 10d | $R_2$ = para-Cl—Ph, $R_3$ = isopropyl |
| 10e | $R_2$ = ortho-pyridyl, $R_3$ = isopropyl |
| 10f | $R_2$ = meta-pyridyl, $R_3$ = isopropyl |
| 10g | $R_2$ = para-pyridyl, $R_3$ = isopropyl |
| 10h | $R_2$ = 5-substituted pyrimidine, $R_3$ = isopropyl |
| 10i | $R_2$ = 2-substituted pyrimidine, $R_3$ = isopropyl |
| 10j | $R_2$ = para-pyridyl, $R_3$ = isopropyl |
| 10k | $R_2$ = para-$CH_3$—Ph, $R_3$ = methyl |
| 10l | $R_2$ = para-$CH_3$—Ph, $R_3$ = ethyl |
| 10m | $R_2$ = para-$CH_3$—Ph, $R_3$ = isobutyl |
| 10n | $R_2$ = para-$CH_3$—Ph, $R_3$ = H |
| 10o | $R_2$ = para-$CH_3$—Ph, $R_3$ = $^t$butyl |
| 10p | $R_2$ = para-$CH_3$—Ph, $R_3$ = cyclopropyl |
| 10q | $R_2$ = Ph, $R_3$ = cyclopropyl |

Figure 6:
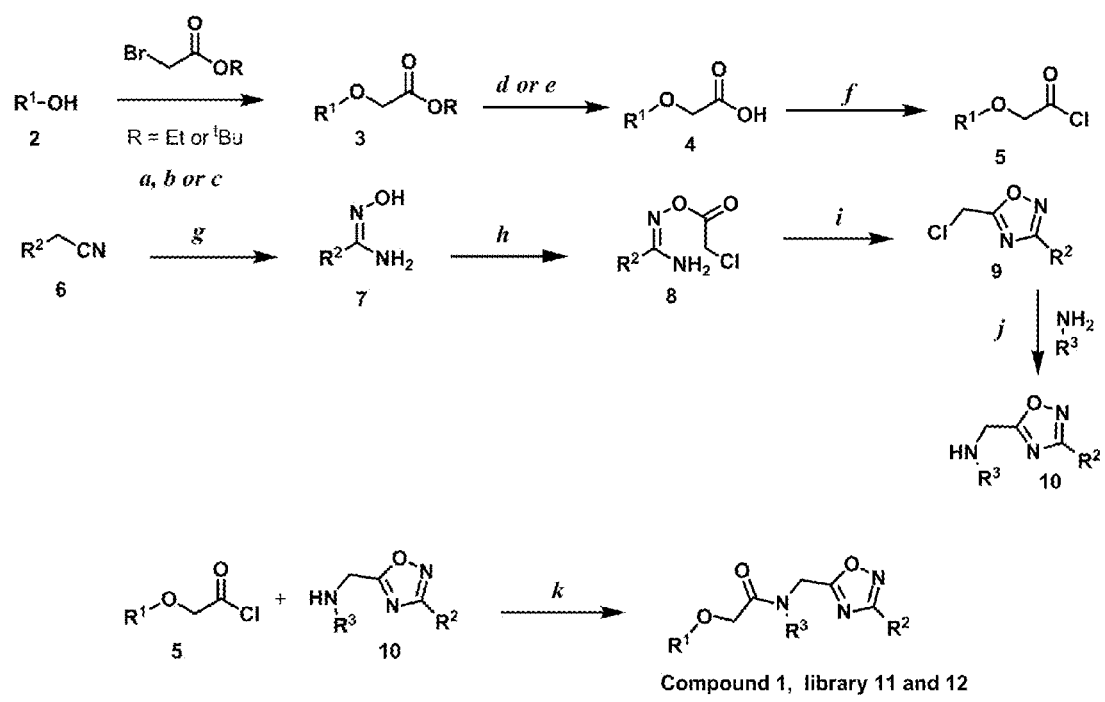
FIG. 6 is a synthetic route to compound 1, and libraries 11 and 12. Reagents and conditions: a Ethyl bromoacetate, $K_2CO_3$, $CH_3CN$, reflux, 12 h. b. tert-Butyl bromoacetate, DMF, 80° C., 14 h c. Ethyl bromoacetate, $K_2CO_3$, DMF, RT, 14 h. d. NaOH, THF, reflux, 30 min. e. $CF_3COOH$, DCM, r.t., 2 h (R=$^t$Bu). f. $SOCl_2$, benzene, reflux, 3 h. g. $NH_2OH \cdot HCl$, $Na_2CO_3$, Water, 70° C., 14 h. h. Chloroacetyl chloride, acetone, 30 min. i. toluene, reflux, 2 h. j. Isopropylamine, $K_2CO_3$, $CH_3CN$, reflux, 30 min. k. $Et_3N$, THF, 15 min. Library information is in Table 1 for library 11, Table 2 for library 12, or as follows.
Figure 7:
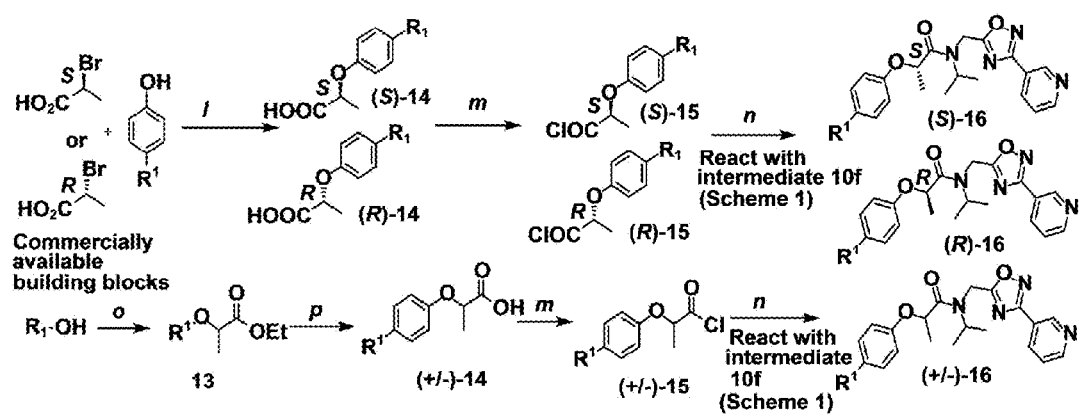

FIG. 7 is a synthetic route to library 16. Reagents and conditions: l. i NaH, THF, ii NaH, THF, iii NaOH, $H_2O$, iv HCl, $H_2O$. m. $SOCl_2$, benzene, reflux, 3 h. n. 10f, $Et_3N$, THF, 15 min. o. (±)-Ethyl 2-bromopropionate, $K_2CO_3$, $CH_3CN$, reflux, 12 h. p. NaOH, THF, reflux, 30 min. Scheme 1 references the reaction scheme shown in FIG. 6. Library information is in Table 3 for library 16 or as follows:

| Library 13 | |
|---|---|
| 13a | $R_1$ = methyl |
| 13b | $R_1$ = propyl |

| Library 14 | |
|---|---|
| 14a | $R_1$ = methyl, racemic mix |
| 14b | $R_1$ = methyl, S-isomer |
| 14c | $R_1$ = methyl, R-isomer |
| 14d | $R_1$ = propyl, racemic mix |
| 14e | $R_1$ = propyl, S-isomer |
| 14f | $R_1$ = propyl, R-isomer |

| Library 15 | |
|---|---|
| 15a | $R_1$ = methyl, racemic mix |
| 15b | $R_1$ = methyl, S-isomer |
| 15c | $R_1$ = methyl, R-isomer |
| 15d | $R_1$ = propyl, racemic mix |
| 15e | $R_1$ = propyl, S-isomer |
| 15f | $R_1$ = propyl, R-isomer |

| Library 16 | |
|---|---|
| 16a | $R_1$ = methyl, racemic mix |
| 16b | $R_1$ = methyl, S-isomer |
| 16c | $R_1$ = methyl, R-isomer |
| 16d | $R_1$ = propyl, racemic mix |
| 16e | $R_1$ = propyl, S-isomer |
| 16f | $R_1$ = propyl, R-isomer |

Figure 8:
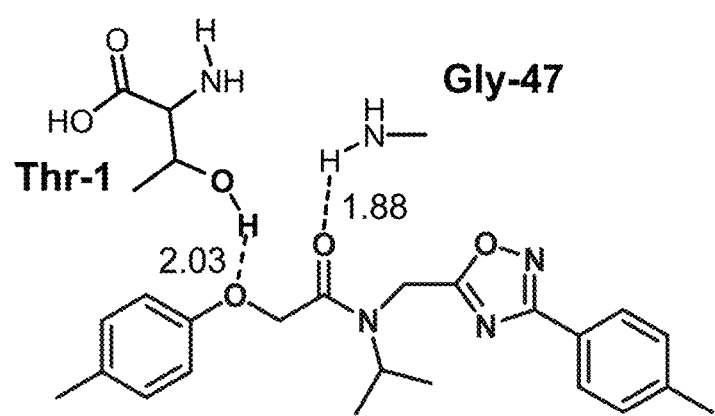

FIG. 8 is a diagrams showing the predicted binding interactions of PI-1833 in the b5 and b6 subunits of the 20S proteasome.

Figure 9:
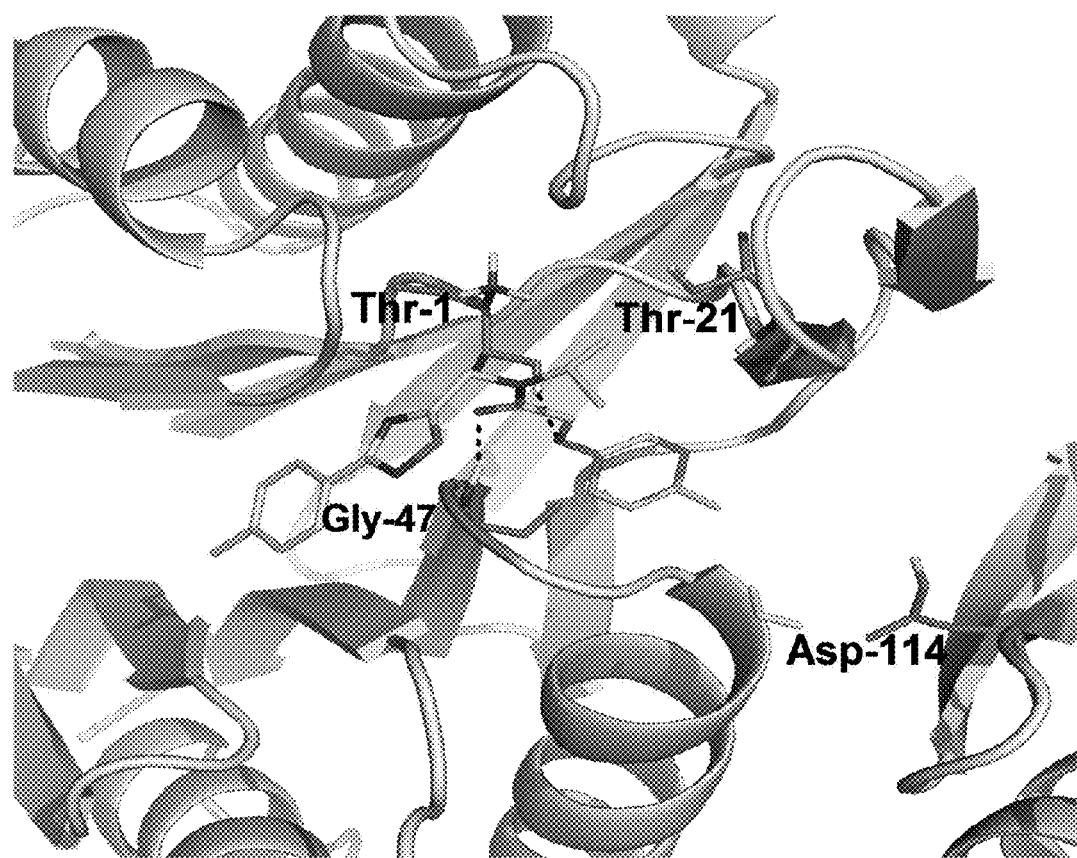

FIG. 9 is an illustration of the b5 and b6 subunits of the 20S proteasome and interaction with PI-1833.

Figure 10:
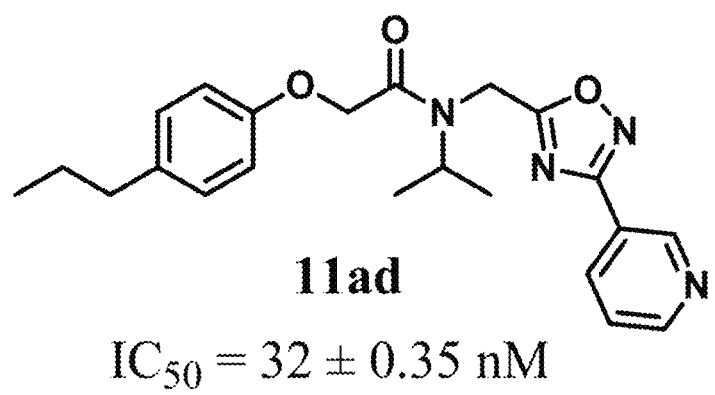

FIG. 10 is a diagram showing the lead compound PI-1840, entry 11ad, and its corresponding $IC_{50}$ value.

Figure 11:
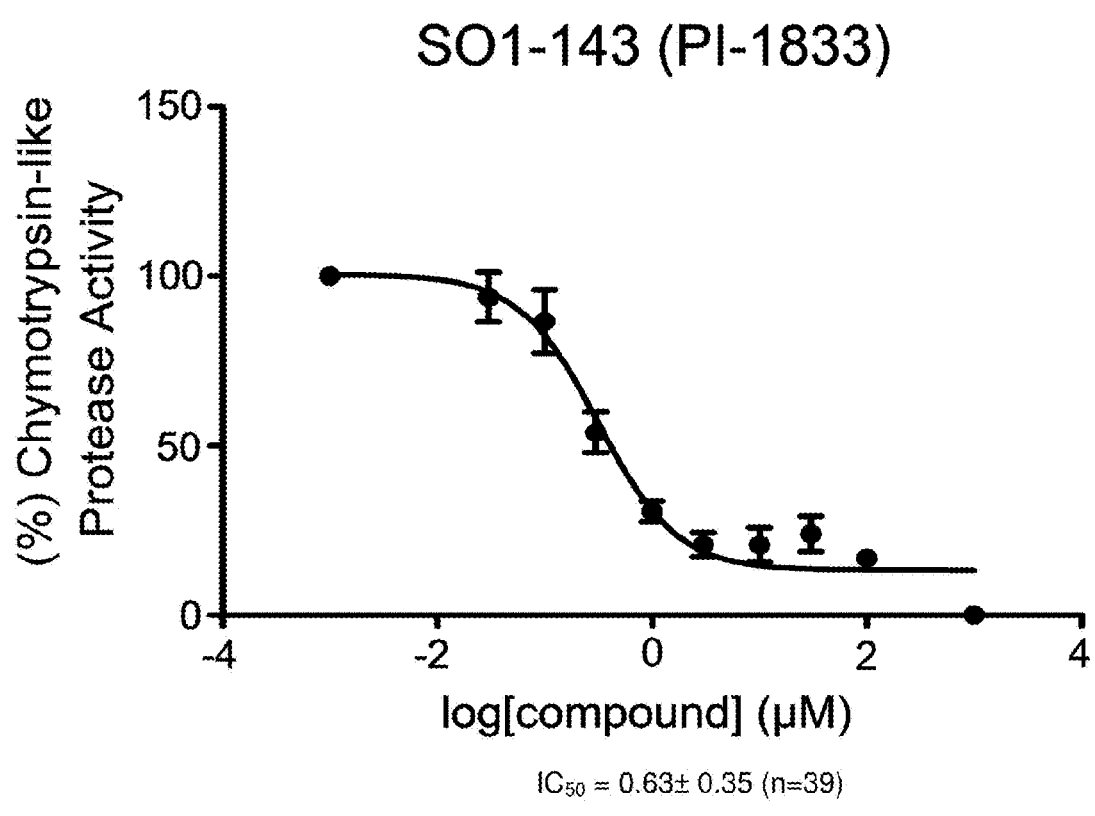

FIG. 11 is a graph showing the in vitro IC50 value for PI-1833 against the CT-L activity of purified 20S proteasome.

Figure 12:
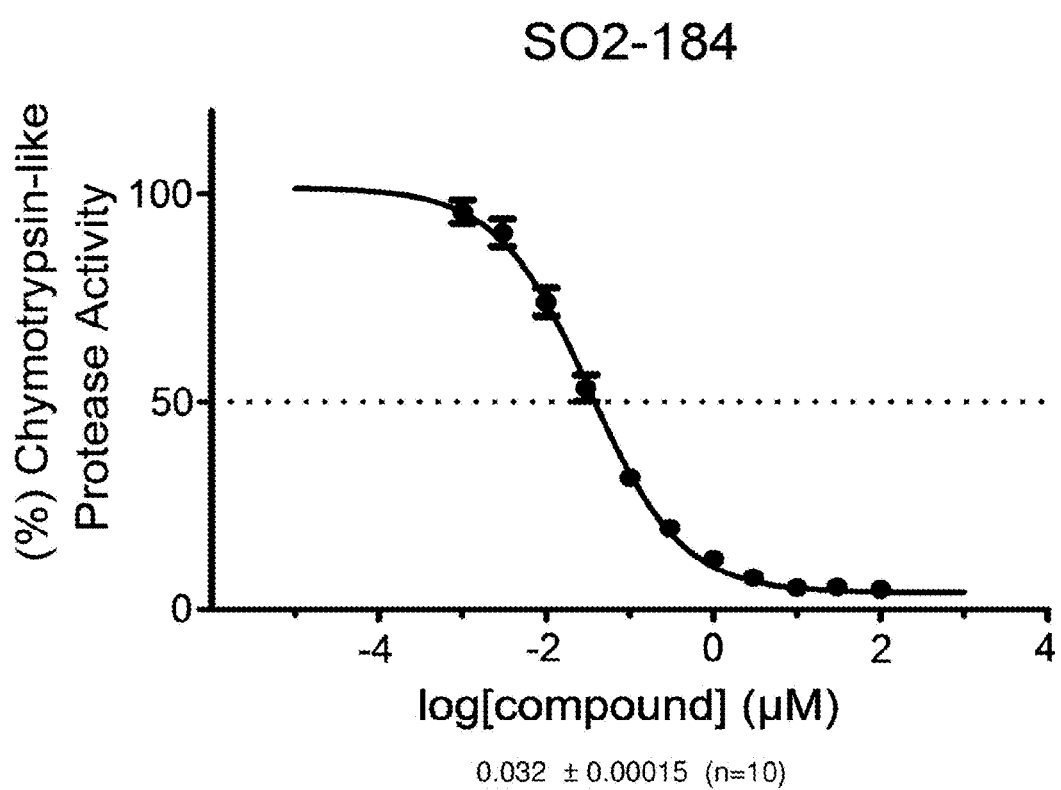

FIG. 12 is a graph showing the in vitro IC50 value for PI-1840 against the CT-L activity of purified 20S proteasome.

Figure 13:
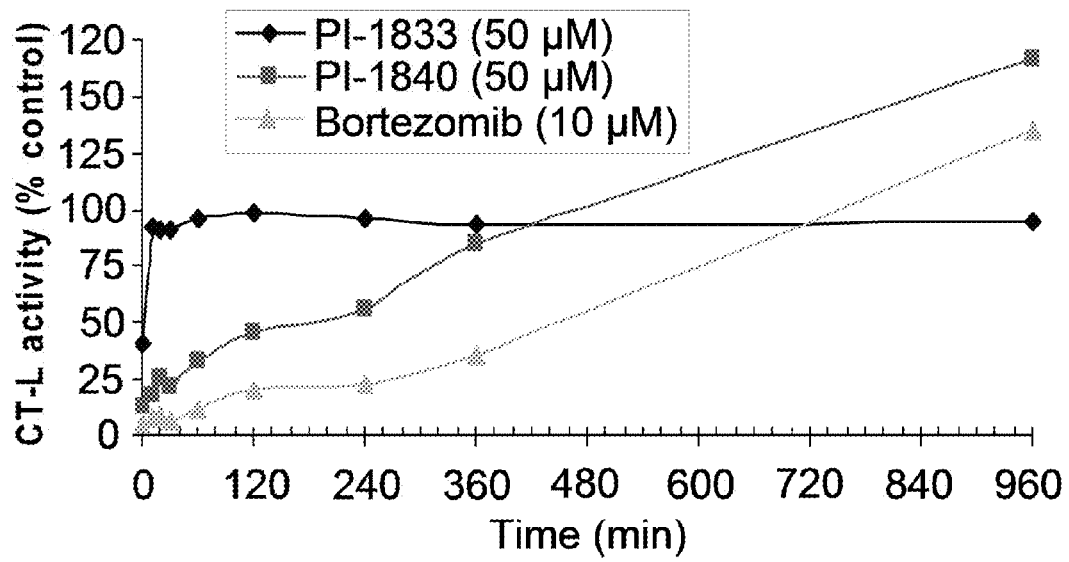

FIG. 13 is a graph showing the recovery of CT-L activity upon dialysis of the 20S proteasome-compound complexes after pre-incubation with PI-1833, PI-1840, and Bortezomib.

Figure 14:
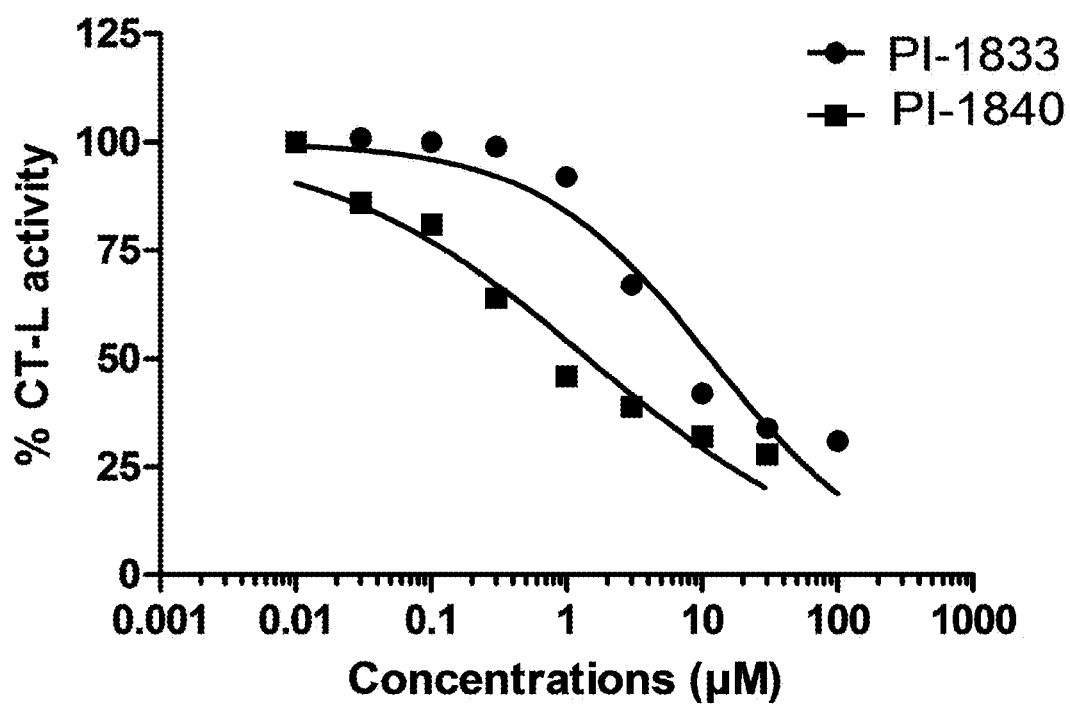

FIG. 14 is a graph showing PI-840 is more potent than PI-1833 at inhibiting CT-L activity in human breast cancer MDA-MB-468 cells.

Figure 15:
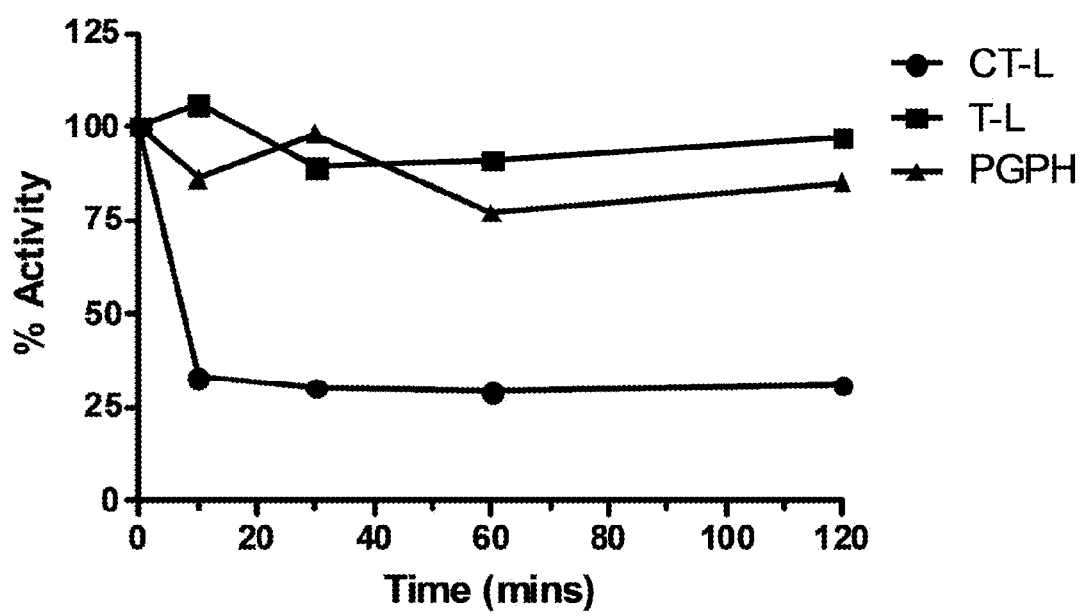

FIG. 15 is a graph showing PI-1840 inhibits CT-L but not T-L or PGPH activities within 10 min of MDA-MB-468 cells.

Figure 16:
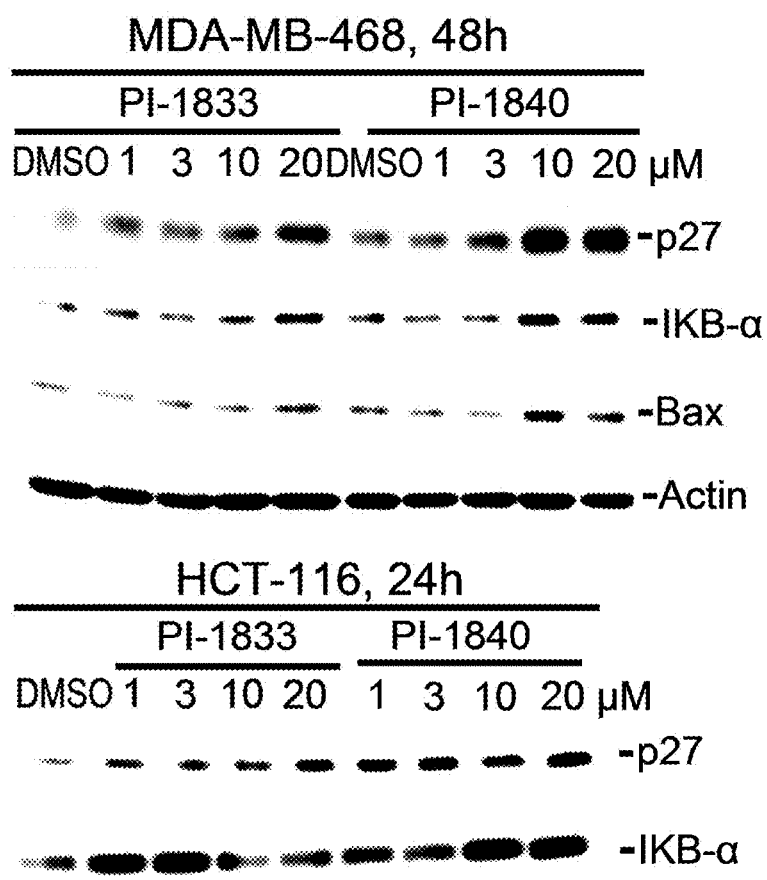

FIG. 16 is a blot showing PI-1840 is more potent than PI-1833 at accumulating the proteasome substrates p27, Bax and IKB.

Figure 17:
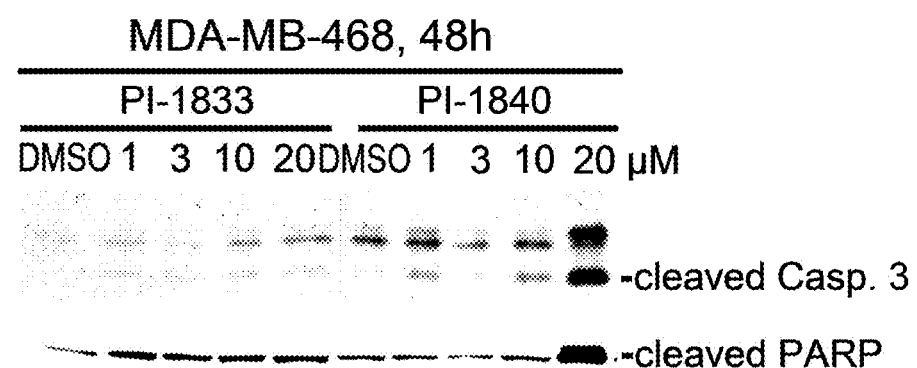

FIG. 17 is a blot showing the apoptotic potential of PI-1833 and PI-1840. Exponentially growing human breast cancer cells MDA-MB-468 and colon cancer cells HCT-116 were treated with different concentrations of PI-1833 or PI-1840 for 48 h or 24 h, followed by WB analysis for cleaved caspase-3 and cleaved PARP.

Figure 18:
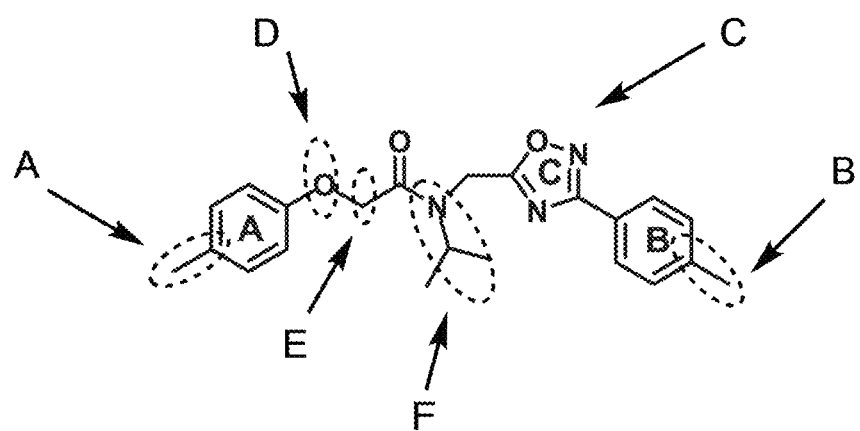

FIG. 18 is a diagram showing the modification sites around PI-1833 for the library synthesis.

Figure 19:
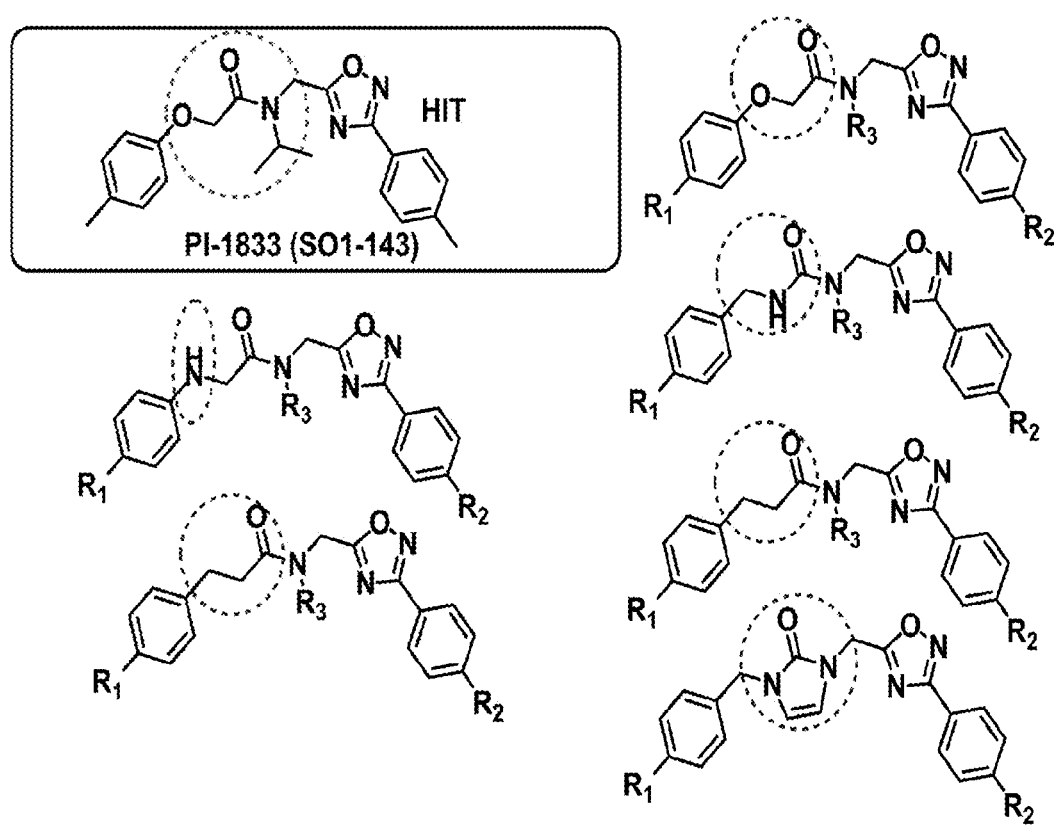

FIG. 19 is a diagram showing the on-going synthetic modifications to PI-1833.

Figure 20:
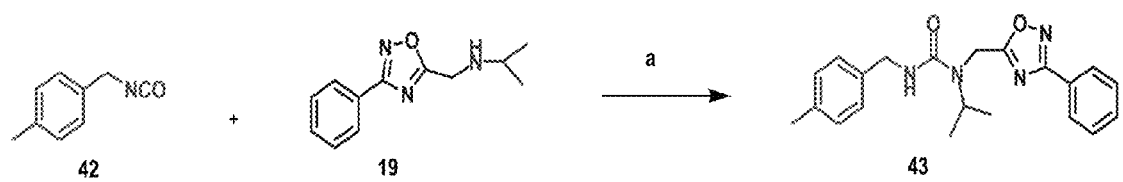

FIG. 20 is a diagram illustrating the synthesis of urea-modified PI-1833 analogs. Reagents and conditions: a $Et_3N$, benzene, reflux, 2 h, 78%.

Figure 21:
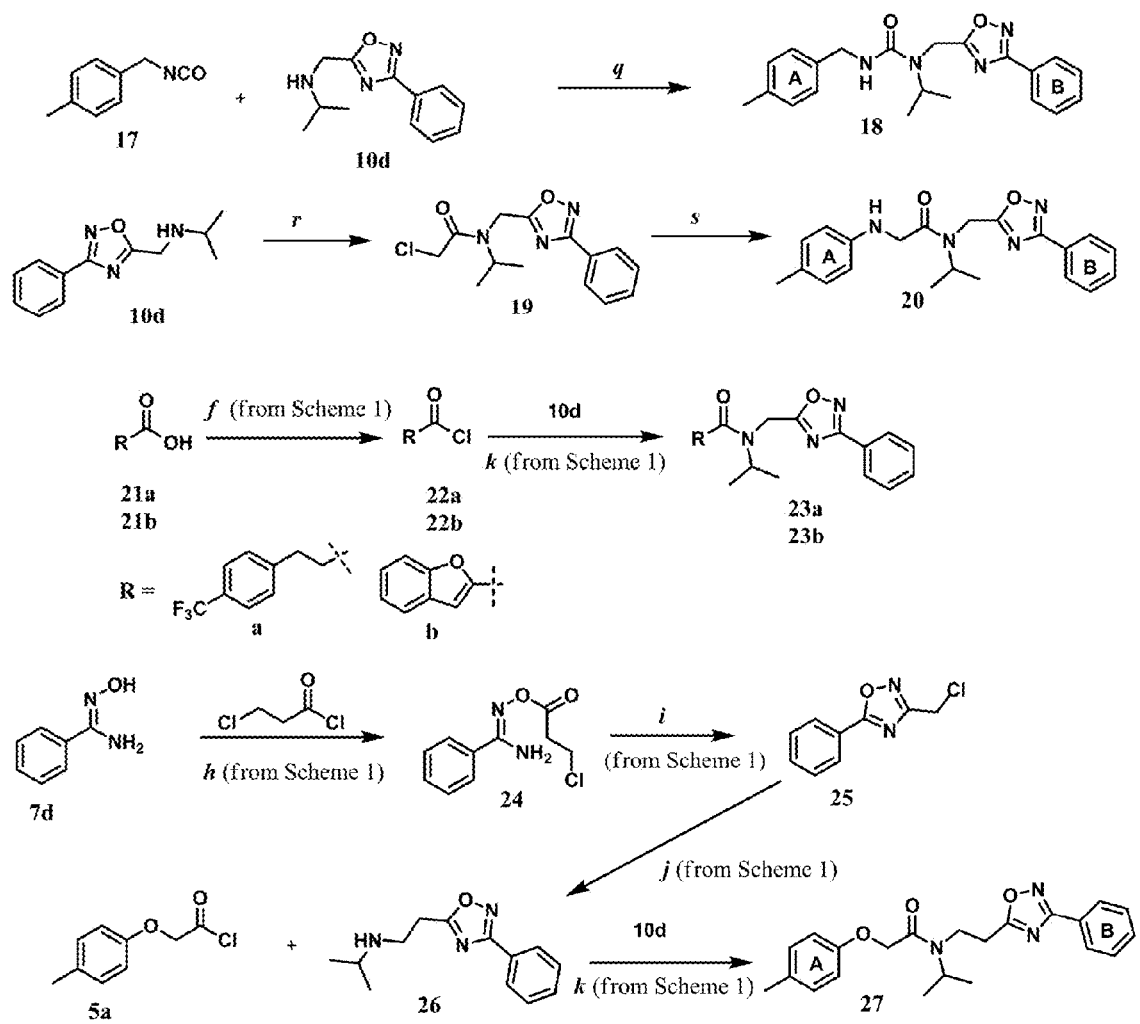

FIG. 21 is a synthetic route to for modifications to the backbone structure. Reagents and conditions i) q. $Et_3N$, benzene, reflux, 12 h, 78%, ii) r. Chloroacetyl chloride, $Et_3N$, THF, 15 min, 78%, s. para-Methylaniline, NaOAc, ethanol, reflux, 12 h, 73%, iii) f $SOCl_2$, benzene, reflux, 3 h, 95%, h. acetone, 30 min. i. toluene, reflux, 2 h. j. Isopropylamine, $K_2CO_3$, $CH_3CN$, reflux, 30 min. k. 10d, $Et_3N$, THF, 15 min, 78%. Scheme 1 references the reaction scheme shown in FIG. 6.

Figure 22:
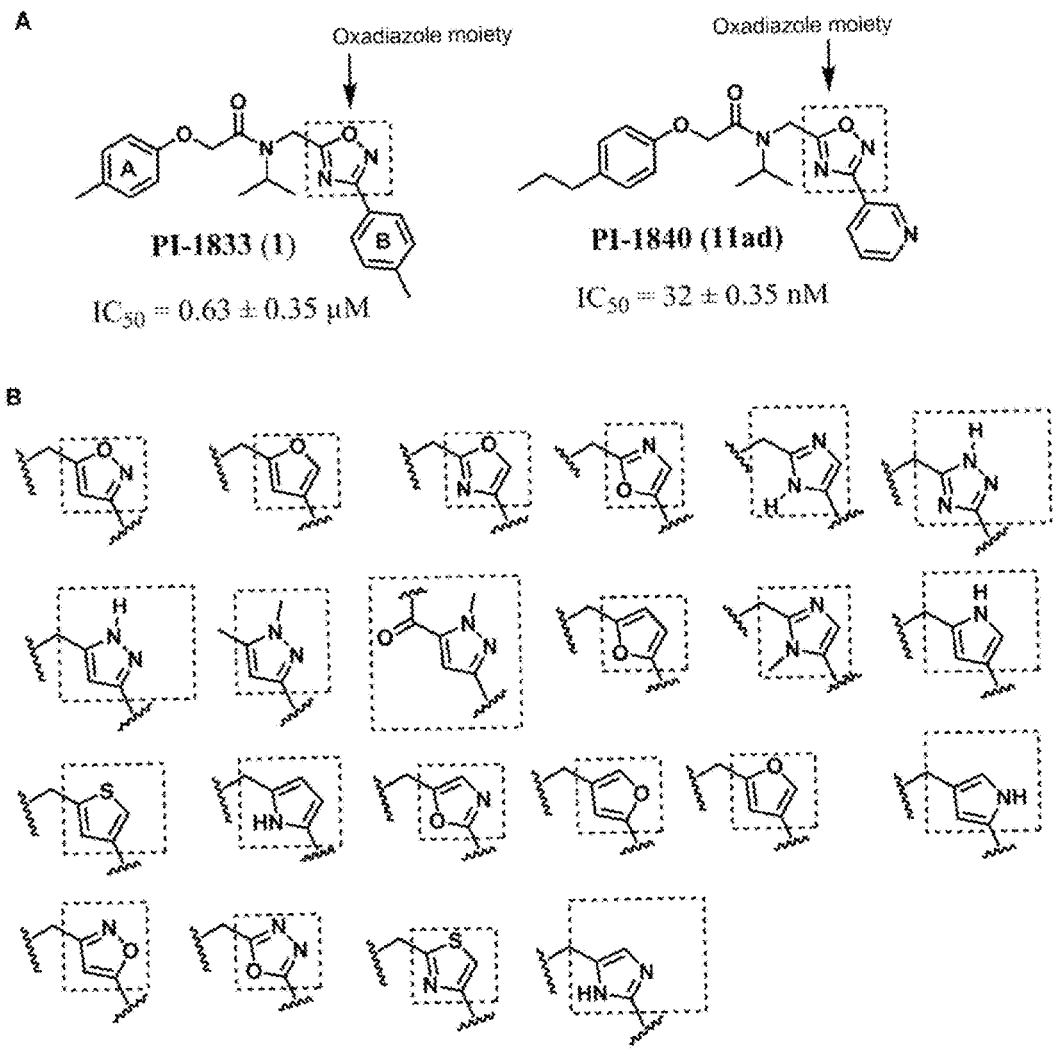

FIGS. 22(A) and (B) are diagrams showing (A) the structures of PI-1833 and PI-1840 identifying the heterocyclic oxadiazole moiety of the backbone structure and (B) different heterocyclic moieties that may replace the oxadiazole moiety in PI-1833/PI-1840 class of compounds.

DETAILED DESCRIPTION OF THE PREFERRED EMBODIMENT

The terms "about" and "approximately" mean means nearly and in the context of a numerical value or range set forth means±15% of the numerical The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., an antimalarial agent, etc.), "administration" and its variants are each understood to include concurrent and sequential introduction of the compound or prodrug thereof and other agents.

As used herein, the term "cancer" or "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

As used herein, "Ph" stands for phenyl.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to malaria, an effective amount comprises an amount sufficient to cause a reduction in the parasite load and/or to decrease the proliferation of the plasmodium or to prevent or delay other unwanted infection. In some embodiments, an effective amount is an amount sufficient to delay development. In some embodiments, an effective amount is an amount sufficient to prevent or delay occurrence and/or recurrence. An effective amount can be administered in one or more doses.

As used herein, "treatment" refers to obtaining beneficial or desired clinical results. Beneficial or desired clinical results include, but are not limited to, any one or more of: alleviation of one or more symptoms, diminishment of extent of the disease, stabilization (i.e., not worsening), preventing or delaying spread of the malaria, preventing or delaying occurrence or recurrence of malaria, delay or slowing of disease progression, amelioration of the malaria, and remission (whether partial or total). The methods of the invention contemplate any one or more of these aspects of treatment.

A therapeutically effective amount of the therapeutic compound or a pharmaceutically acceptable salt, hydrate, or solvate thereof refers to that amount being administered which will relieve, to some extent, one or more of the symptoms associated with the disorder being treated. In reference to the treatment of a proliferative cellular disorder, a therapeutically effective amount refers to the amount which: (1) reduces the size of a tumor, (2) inhibits (i.e. stopping or slowing to some extent) tumor metastasis, (3) inhibits (i.e. stopping or slowing to some extent) tumor growth, (4) inhibits (i.e. stopping or slowing to some extent) cellular proliferation, (5) inhibits (i.e. stopping or slowing to some extent) expression of any member of the E2F family and/or (6) inhibits (i.e. stopping or slowing to some extent) activity (e.g. DNA binding activity) of any member of the E2F family.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The therapeutic compound is administered and dosed in accordance with good medical practice, taking into account the clinical condition of the individual patient, the site and method of administration, scheduling of administration, patient age, sex, body weight, and other factors known to medical practitioners.

Example 1

Figure 1:
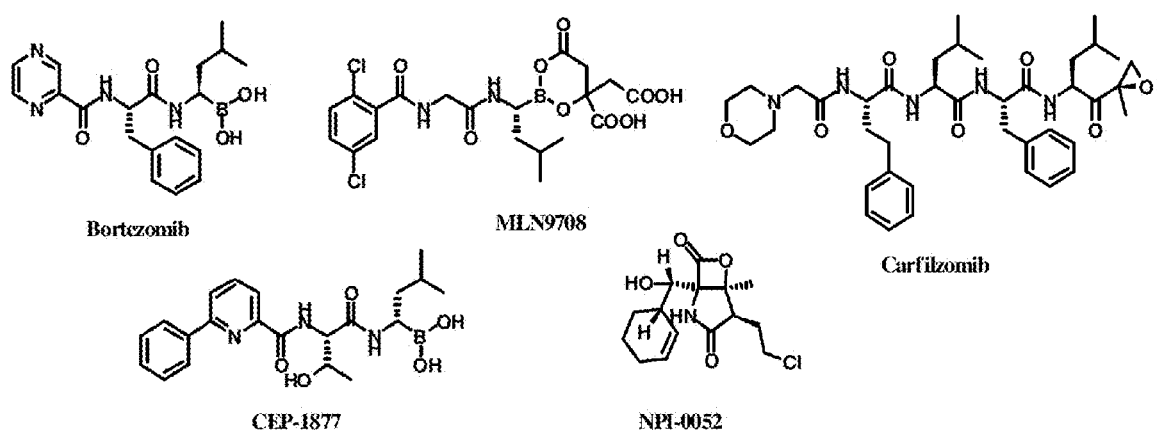
FIG. 1 is an illustration of the structures of clinically advanced proteasome inhibitors: Bortezomib (in clinic), MLN9708 (phase I), Carfilzomib (phase II), CEP-18770 (phase I) and NPI-0052 (phase I).
Figure 2:
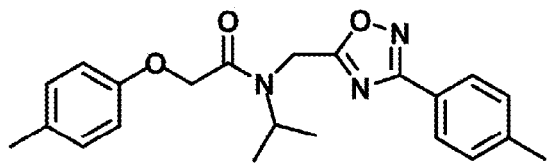
FIG. 2 is an illustration of an exemplary new compound, PI-1833, identified as a proteasome inhibitor.
Figure 3:
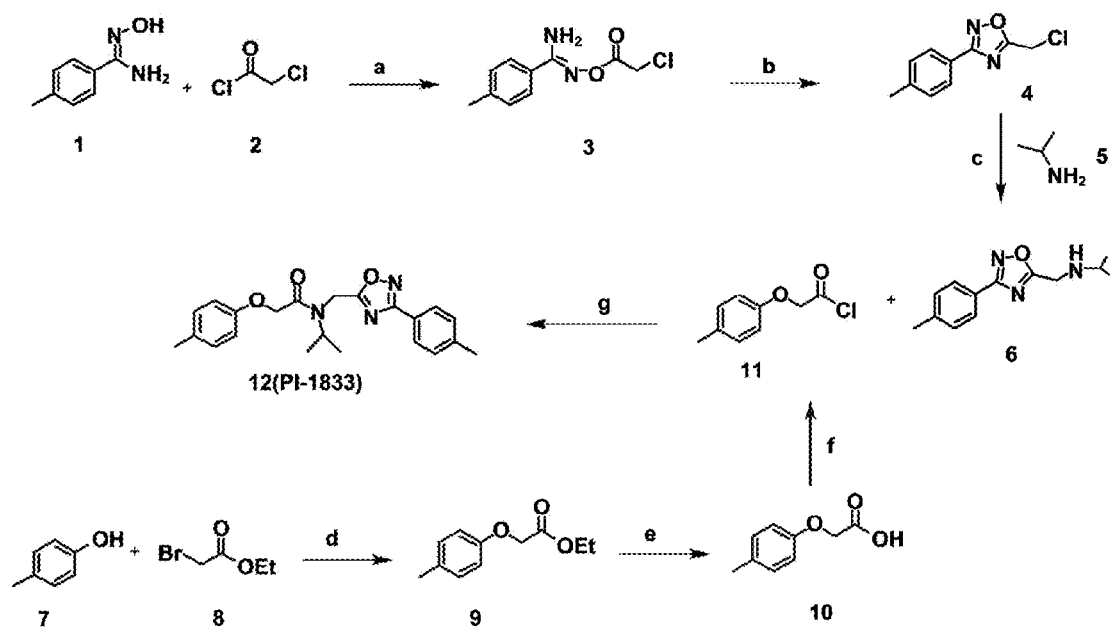
FIG. 3 is a diagram illustrating the synthesis of PI-1833. Reagents and conditions; a DIPEA, DCM, RT, 24 h, 81%, b toluene, reflux, 12 h, 100%, c $K_2CO_3$, $CH_3CN$, reflux, 30 min, 91%, d $K_2CO_3$, $CH_3CN$, reflux, 12 h, 90%; or $K_2CO_3$, acetone, reflux, 12 hr, 90%, e NaOH, THF, reflux, 30 min, 92%; or NaOH, ethanol, reflux, 30 min, 92%, f $SOCl_2$, benzene, reflux, 3 h, 94%, g $Et_3N$, THF, RT, 15 min, 88%.

High throughput screening of a 50,000 compound library against CT-L activity resulted in the discovery of PI-1833, a non-covalent and rapidly reversible proteasome inhibitor. Analysis of PI-1833, depicted in FIG. 2, exhibited an in-vitro $IC_{50}$ value of 0.65±0.39 μM. Testing in whole cell MDA-MB-468 (breast cancer cells) showed the $IC_{50}$ activity of PI-1833 was $IC_{50}$=1.1 μM. The compound 1 has not previously been reported as a proteasome inhibitor. PI-1833 was synthesized according to the protocols shown in, FIG. 3 to confirm both the structure and in-vitro chymotrypsin-like (CT-L) activity of the compound. Starting from N-Hydroxy-4-methyl-benzamidine 1, the right hand portion of the PI-1833 (compound 4) was synthesized, which was then reacted with isopropyl amine 5 to form the compound 6. The left hand portion of the molecule 11 was synthesized from p-cresol 7 and bromoethylacetae 8. In the last step, the two building blocks were combined to obtain the PI-1833 (compound 12), in good yield.

The in-house synthesized materials and commercial samples were rigorously analyzed using $^1$H NMR, $^{13}$C NMR, low resolution and formula guided mass spectrometry. The NMR of PI-1833 showed a mixture of rotamers about the amide bond (approximately 1:3 ratios). The in-house synthesized PI-1833 confirmed the CT-L inhibitory activity and the structure. The purity of the commercial and in-house synthesized compounds was also determined by HLPC (>95% HPLC purity, 30 min. methods) and LCMS. The whole cell activity (MBA-MD-468 breast cancer cell line was used) of PI-1833 was determined as 1 μM.

Example 2

The synthesis of the first generation analogs of PI-1833 were undertaken to understand the structural moieties important for activity and to evaluate SAR (structure activity relationship) data, which also confirms PI-1833 as an authentic proteasome inhibitor.

Figure 4:
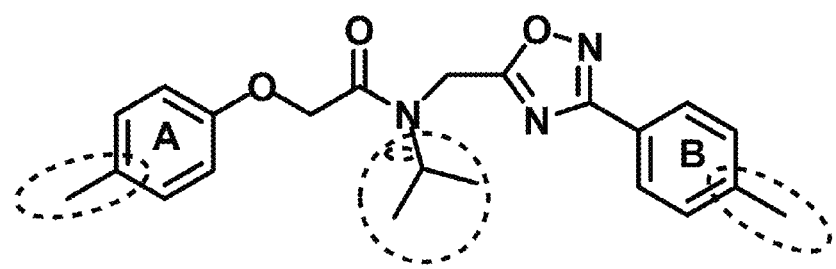
FIG. 4 is a diagram of PI-1833 structure modifications for first generation Analogs of PI-1833.

Initial synthetic modifications included substitution of the methyl groups on ring A and ring B with small hydrophobic groups such as Cl, $CF_3$, F, isopropyl and bi-phenyl groups, seen in FIG. 4. The isopropyl amide moiety was synthetically modified to isobutyl, methyl, ethyl and naked amide (isopropyl group substituted with H). The synthesis of these compounds is summarized in FIG. 5.

The acetyl chloride building block library 5, seen in FIG. 6, was synthesized from readily available phenol derivatives via the intermediates ester 3 and acid 4 using reported protocols. The oxadiazole portion of the compound 1 was synthesized from readily available nitrile building blocks 6. The nitrile building blocks were reacted with hydroxylamine hydrochloride and sodium carbonate at 70° C. in water to yield the hydroxyamidines 7 (Gezginci, et al. Antimycobacterial Activity of Substituted Isosteres of Pyridine- and Pyrazinecarboxylic Acids. 2. *J. Med. Chem.* 2001, 44, 1560-1563), as seen in FIG. 6, condition g. The 2-substituted pyrimidine oxime was synthesized from the corresponding ester (Ji, et al. Oxadiazole derivatives as nicotinic acetylcholine receptor subtype a4b2 positive allosteric modulators and their preparation, composition and use for the treatment of pain. 2010-US36213). The intermediate hydroxyamidine library 7 was reacted with chloroacetyl chloride (condition h) to provide the library 8 (Sindkhedkar, et al. Preparation of erythromycin macrolides and ketolides having antimicrobial activity. 2007-IB2405), which was cyclized in refluxing toluene to provide the oxadiazole portion of the pharmacophore 9. The library 9 was subsequently reacted with different alkyl amines (isopropyl-, isobutyl-, methyl-, ethyl-, cyclopropyl- and tert-butyl-amines) to obtain the amine-building block library 10, seen in FIG. 6, condition j. Library 10 was generated with a variety of substituted alkyl and hetero-alkyl $R^2$ moieties and library 5 with substituted/unsubstituted aromatic $R^1$ moieties. The two key building block libraries 10 and 5 were then reacted in the presence of triethylamine to provide the compound 1, library 11 and 12, seen in FIG. 6, and Tables 1 and 2, in good yields. The route described was efficient and convenient for rapid synthesis and optimization of substituted phenyl and the amide moieties. The final libraries were characterized using NMR, LC-MS, HRMS and the purity was >95% as determined by HPLC. The final compound library 11 and 12 showed 3:1 ratio of atropisomers (hindered rotation about the C—N bond) by $^1$H NMR spectroscopy.

TABLE 1

Compound 1, synthetic analogs of library 11 and SAR.

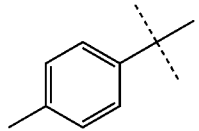

| Compound | Name | $R_1$ | $R_2$ | $IC_{50}$ (μM) Chymotrypsin-like activity |
|---|---|---|---|---|
| 1 | SO1-143 | 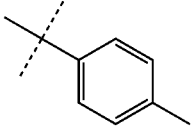 | | 0.63 ± 0.35 (n = 39) |

TABLE 1-continued

Compound 1, synthetic analogs of library 11 and SAR.

| Compound | Name | R₁ | R₂ | IC$_{50}$ (μM) Chymotrypsin-like activity |
|---|---|---|---|---|
| 11a | SO1-176 | 4-(F₃C)-C₆H₄- | 4-methylphenyl | 1.08 ± 0.33 (n = 4) |
| 11b | SO1-171 | 4-(F₃C)-C₆H₄- | phenyl | 0.43 ± 0.12 (n = 4) |
| 11c | SO1-170 | 4-(F₃C)-C₆H₄- | 4-(CF₃)-C₆H₄- | 2.53 ± 0.95 (n = 5) |
| 11d | SO1-169 | 4-(F₃C)-C₆H₄- | 4-Cl-C₆H₄- | 0.857 ± 0.35 (n = 9) |
| 11e | SO2-002 | 4-Cl-C₆H₄- | 4-methylphenyl | 1.12 ± 0.33 (n = 5) |
| 11f | SO1-180 | 4-Cl-C₆H₄- | 4-(CF₃)-C₆H₄- | 1.405 ± 0.185 (n = 2) |
| 11g | SO1-179 | 4-Cl-C₆H₄- | 4-Cl-C₆H₄- | 1.07 ± 0.05 (n = 4) |
| 11h | SO1-181 | 4-Cl-C₆H₄- | phenyl | 0.51 ± 0.16 (n = 6) |
| 11i | SO1-160 | 4-methylphenyl | 4-Cl-C₆H₄- | 0.45 ± 0.15 (n = 4) |

TABLE 1-continued

Compound 1, synthetic analogs of library 11 and SAR.

| Compound | Name | R₁ | R₂ | IC$_{50}$ (μM) Chymotrypsin-like activity |
|---|---|---|---|---|
| 11j | SO2-011 | phenyl | phenyl | 6.22 ± 1.11 (n = 2) |
| 11k | SO2-006 | phenyl | 4-methylphenyl | 8.47 ± 0.59 (n = 2) |
| 11l | SO2-010 | phenyl | 4-CF₃-phenyl | 15.11 ± 6.94 (n = 4) |
| 11m | SO1-172 | 4-methylphenyl | phenyl | 0.31 ± 0.08 (n = 4) |
| 11n | SO1-159 | 4-methylphenyl | 4-CF₃-phenyl | 0.97 ± 0.15 (n = 2) |
| 11o | SO2-058 | 3-methylphenyl | phenyl | >10 |
| 11p | SO2-073 | 2-methylphenyl | phenyl | >10 |
| 11q | SO2-045 | biphenyl | phenyl | >10 |

TABLE 1-continued
Compound 1, synthetic analogs of library 11 and SAR.
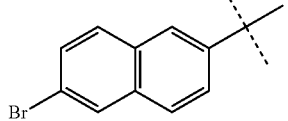
| Compound | Name | R₁ | R₂ | IC₅₀ (μM) Chymotrypsin-like activity |
|---|---|---|---|---|
| 11r | SO2-046 | 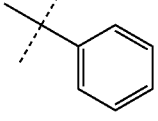 | 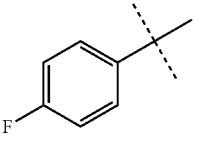 | >10 |
| 11s | SO2-030 | 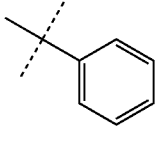 | 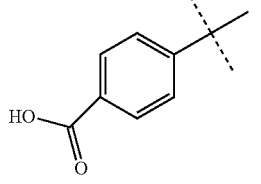 | 8.73 ± 3.05 (n = 4) |
| 11t | SO2-089 | 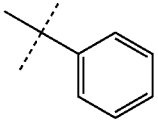 | 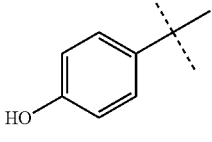 | 27.76 ± 20.83 (n = 5) |
| 11u | SO2-170 | 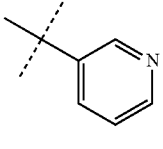 | 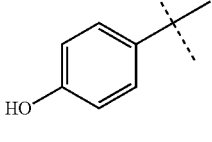 | 0.98 ± 0.50 (n = 3) |
| 11v | SO2-171 | 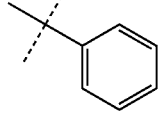 | 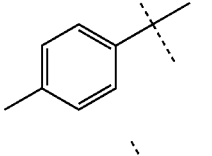 | 10.12 ± 4.52 (n = 3) |
| 11w | SO2-075 | 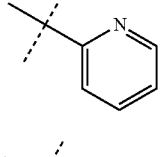 | 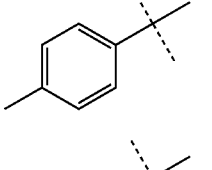 | 3.747 ± 1.47 (n = 6) |
| 11x | SO2-076 | 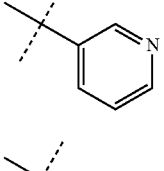 | 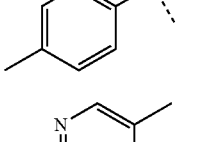 | 0.239 ± 0.097 (n = 6) |
| 11y | SO2-069 | 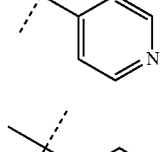 | 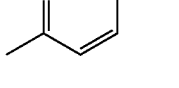 | 0.37 ± 0.046 (n = 4) |
| 11z | SO2-179 | 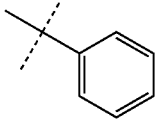 | | 4.00 ± 0.89 (n = 3) |

TABLE 1-continued

Compound 1, synthetic analogs of library 11 and SAR.

| Compound | Name | R₁ | R₂ | IC₅₀ (μM) Chymotrypsin-like activity |
|---|---|---|---|---|
| 11aa | SO2-050 | 4-ethylphenyl | phenyl | 0.267 ± 0.05 (n = 6) |
| 11ab | SO2-103 | 4-ethylphenyl | 3-pyridyl | 0.099 ± 0.032 (n = 14) |
| 11ac | SO3-030 | phenyl | 3-pyridyl | 3.12 ± 1.11 (n = 6) |
| 11ad | SO2-184 | 4-propylphenyl | 3-pyridyl | 0.032 ± 0.00015 (n = 10) |
| 11ae | SO3-026 | 4-butylphenyl | 3-pyridyl | 0.039 ± 0.011 (n = 7) |
| 11af | SO3-050 | 4-pentylphenyl | 3-pyridyl | 0.121 ± 0.040 (n = 3) |
| 11ag | SO3-051 | 4-hexylphenyl | 3-pyridyl | 0.428 ± 0.038 (n = 3) |
| 11ah | SO3-066 | 4-cyclohexylphenyl | 3-pyridyl | 1.356 ± 0.184 (n = 3) |
| 11ai | SO3-080 | 4-isopropylphenyl | 3-pyridyl | 0.436 ± 0.073 (n = 3) |

TABLE 1-continued
Compound 1, synthetic analogs of library 11 and SAR.
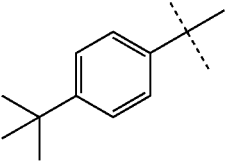
| Compound | Name | R₁ | R₂ | IC$_{50}$ (μM) Chymotrypsin-like activity |
|---|---|---|---|---|
| 11aj | SO3-079 | 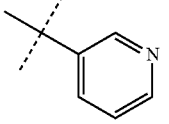 | 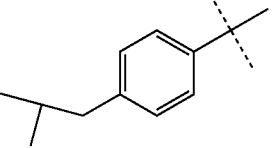 | 65.93 ± 33.68 (n = 3) |
| 11ak | SO3-089 | 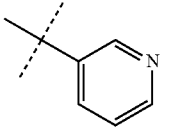 | 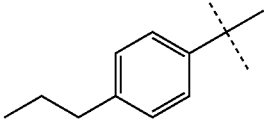 | 0.140 ± 0.052 (n = 3) |
| 11al | SO3-074 | 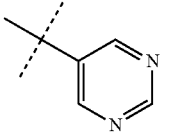 | 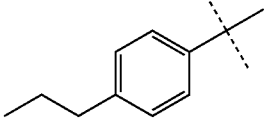 | 0.032 ± 0.003 (n = 3) |
| 11am | SO3-057 | 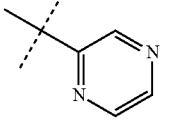 | 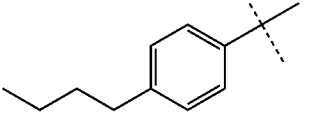 | 0.105 ± 0.031 (n = 3) |
| 11an | SO3-054 | 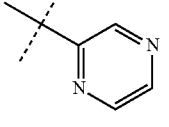 | 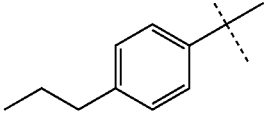 | 0.107 ± 0.013 (n = 3) |
| 11ao | SO3-096 | 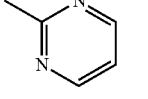 | 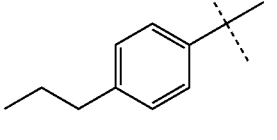 | 1.269 ± 0.226 (n = 3) |
| 11ap | SO3-126 | 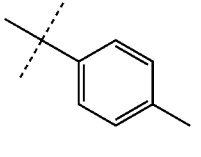 | 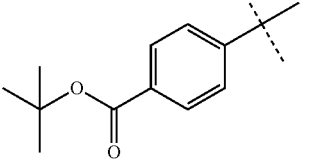 | NA |
| 11aq | SO2-068 | 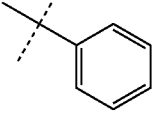 | | >10 μM |

TABLE 2

Synthetic analogs of Library 12 and SAR.

| Compound | Name | R₃ | IC$_{50}$ (μM) Chymotrypsin-like activity |
|---|---|---|---|
| 1 | SO1-143 | isopropyl | 0.63 ± 0.35 (n = 39) |
| 12a | SO1-157 | isobutyl | 2.37 ± 0.40 (n = 2) |
| 12b | SO2-012 | ethyl | 8.98 ± 5.21 (n = 4) |
| 12c | SO1-184 | methyl | 29.9 ± 3.9 (n = 2) |
| 12d | SO2-007 | H | −62% @10 μM. |
| 12e | SO2-070 | tert-butyl | −108.42 ± 118.76% (n = 5) @ 10 μM |
| 12f | SO3-084 | cyclopropyl | −8.36 ± 19.03% @ 10 μM |

Library 16 was analyzed for racemic, R and S enantiomers, seen in FIG. 7, by adding a methyl group adjacent to the phenoxy moiety in 1 to understand if this class of compounds shows chiral discrimination toward inhibition of the proteasome. A racemic mixture, and the R and S isomers (16a, 16b and 16c respectively, R$^1$=methyl, seen in Table 3, were synthesized from a moderately potent compound 11x, and as we developed detail SAR, the racemate and enantiomers (16c, 16d and 16e, R$^1$=propyl, Table 3) of the most potent compound 11ad were also synthesized to understand how the enantiomers influence the CT-L potency. Commercially available R and S 2-bromopropionic acid, FIG. 7, were reacted with para-methylphenol and para-propylphenol to obtain intermediate acid library 14 (Scheme 2). The acids 14 were converted to acid chlorides (harma, P. C.; Yadav, S.; Pahwa, R.; Kaushik, D.; Jain, S. Synthesis and evaluation of novel prodrugs of naproxen. *Med. Chem. Res.* 2011, 20, 648-655; Yang, Q.; Olmsted, C.; Borhan, B. Absolute Stereochemical Determination of Chiral Carboxylic Acids. *Org. Lett.* 2002, 4, 3423-3426; Allegretti, et al. 2-Arylpropionic CXC Chemokine Receptor 1 (CXCR1) Ligands as Novel Noncompetitive CXCL8 Inhibitors. *J. Med. Chem.* 2005, 48, 4312-4331) 15 that was subsequently reacted with building block 10f (R$^3$=isopropyl, R$^2$=meta-pyridyl, seen in FIG. 6, to obtain library 16. The synthetic route depicted in FIG. 7 provided final compounds 16 with overall retention of stereochemistry. The chiral purity of the library members of 16 was determined by chiral HPLC (see the details in supporting information). The chiral purity of the S-isomer (16b, R$^1$=Me) was found to be 92% and R-isomer (16c, R$^1$=Me) was 98%. Similarly 16e S-isomer (R$^1$=propyl) and 16f R-isomer (R$^1$=propyl) showed 91% and 98% chiral purity respectively. The racemic compounds 16a and 16d, shown in FIG. 7, were obtained first reacting para-methylphenol and para-propylphenol with ethyl 2-bromopropionate to give 13 which was hydrolyzed using NaOH in refluxing THF to provide the racemic intermediates 14. The intermediates 14 were converted to acid chlorides 15 and subsequently reacted with 10f to provide the required racemic compounds (±)-16a and (±)-16d. Racemic compounds were also used for chiral HPLC method development (i.e. separate enantiomers using a chiral column) and to assess the chiral purity of the individual R and S isomers.

TABLE 3

CT-L activities and SAR of the library 16.

| Compound | Name | R₁ | IC$_{50}$ (μM) CT-L |
|---|---|---|---|
| 16a racemic mixture | SO2-145 | (4-methylphenyl) | 0.38 ± 0.099 (n = 16) |

TABLE 3-continued

CT-L activities and SAR of the library 16.

| Compound | Name | R₁ | IC$_{50}$ (μM) CT-L |
|---|---|---|---|
| 16b S-isomer | SO3-019 | 4-methylphenyl | 0.214 ± 0.053 (n = 7) |
| 16c R-isomer | SO3-065 (R Isomer) | 4-methylphenyl | 7.52 ± 2.13 (n = 7) |
| 16d racemic mixture | SO3-106 | 4-propylphenyl | 0.289 0.056 |
| 16e S-isomer | SO3-110 | 4-propylphenyl | 0.075 0.029 |
| 16f R-isomer | SO3-109 | 4-propylphenyl | 2.18 ± 0.28 |

Modifications on the benzene rings with hydrophobic substituents retained the activity. The methyl or trifluoromethyl group on the ring A and hydrogen on the ring B improved the activity (from 700 nm to 300 nm). The SAR data are summarized in the Table 4.

TABLE 4

Summary of SAR of modifications around rings A and B.

| Compound | R₁ | R₂ | IC$_{50}$ (μM) Chymotrypsin-like activity |
|---|---|---|---|
| PI-1833 (23) | CH₃ | CH₃ | 0.716 ± 0.27 (n = 14) |
| 21 | CF₃ | CH₃ | 1.08 ± 0.33 (n = 4) |
| 22 | Cl | CH₃ | 1.04 ± 0.05 (n = 2) |
| 24 | H | CH₃ | 8.47 ± 0.59 (n = 2) |
| 27 | CH₃ | CF₃ | 0.97 ± 0.15 (n = 2) |
| 26 | Cl | CF₃ | 1.41 ± 0.19 (n = 2) |
| 25 | CF₃ | CF₃ | 2.05 ± 0.58 (n = 2) |
| 28 | H | CF₃ | 15.11 ± 6.94 (n = 4) |
| 35 | CH₃ | Cl | 0.45 ± 0.18 (n = 3) |
| 34 | CF₃ | Cl | 0.86 ± 0.35 (n = 9) |

TABLE 4-continued

Summary of SAR of modifications around rings A and B.

| | $R_1$ | $R_2$ | $IC_{50}$ (μM) Chymotrypsin-like activity |
|---|---|---|---|
| 33 | Cl | Cl | 1.07 ± 0.05 (n = 4) |
| 32 | H | H | 6.22 ± 1.11 (n = 2) |
| 31 | $CH_3$ | H | 0.32 ± 0.08 (n = 3) |
| 29 | $CF_3$ | H | 0.38 ± 0.09 (n = 3) |
| 30 | Cl | H | 0.51 ± 0.17 (n = 5) |

The structural components of PI-1833 suggest PI-1833 is a non covalent proteasome inhibitor. PI-1833 was docked to CT-L (β-5) subunit (Core B, Consortium for Functional Glycomics, La Jolla, Calif.) to identify and understand the medicinal chemistry of PI-1833 as a proteasome inhibitor. As seen in FIGS. 8 and 9, PI-1833 interacts with the proteasome at threonine 1 and 21, glycine 47 and aspartic acid 114. The generated analogs of PI-1833 show SAR results suggesting efficacious interaction with proteasomes. Further testing of the analoges show a series of potent (below 100 nM), non-covalent drug-like proteasome inhibitors were developed from this class of compounds, seen in Table 5.

TABLE 5

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | $IC_{50}$ (μM) Chymo-trypsin-like | Whole cell $IC_{50}$ (μM) Chymo-trypsin-like | Comments |
|---|---|---|---|---|
| SO1-143 (PI-1833)<br>M.W. = 379.45 | | 0.63 ± 0.35 (n = 39) | 1.1 (MDA-MB-468) | In house synthesized 7871833 HPLC > 99% |
| 7871833 (Chembridge)<br>M.W. = 379.45 | Primary 73%<br>$1^{st}$ cherry pick 74%<br>$2^{nd}$ cherry pick 67%<br>71% (n = 3) | 0.65 ± 0.38 (n = 4) | | HPLC > 99% |
| 7848496 (Chembridge) | | 4.12 ± 0.09 (n = 2) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | $IC_{50}$ (μM) Chymo-trypsin-like | Whole cell $IC_{50}$ (μM) Chymo-trypsin-like | Comments |
|---|---|---|---|---|
| 7869656 (Chembridge) | | 5.13 ± 0.09 (n = 2) | | |
| SO1-157<br>M.W. = 393.48 | | 2.37 ± 0.40 (n = 2) | | HPLC = 99.07% |
| SO1-159<br>M.W. = 433.42 | | 0.97 ± 0.15 (n = 2) | | HPLC = 99.32% |
| SO1-160<br>M.W. = 399.87 | | 0.45 ± 0.15 (n = 4) | | HPLC = 99.62% |
| SO1-169<br>M.W. = 453.84 | | 0.58 (FM) (Nov. 15, 2010) 0.857 ± 0.35 (n = 9) | | HPLC > 99% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 µM) Chymotrypsin-like | IC$_{50}$ (µM) Chymo-trypsin-like | Whole cell IC$_{50}$ (µM) Chymo-trypsin-like | Comments |
|---|---|---|---|---|
| SO1-170<br>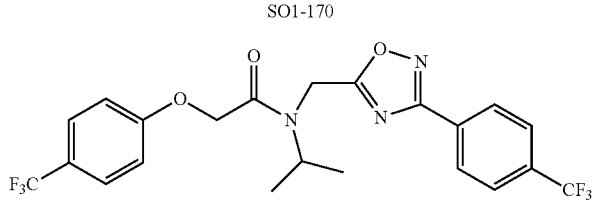<br>M.W. = 487.39 | | 2.53 ± 0.95 (n = 5) | | HPLC = 98.90% |
| SO1-171<br>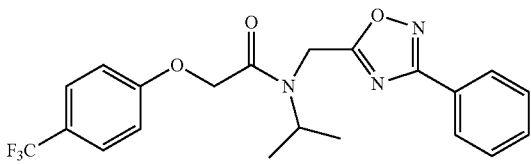<br>M.W. = 419.40 | | 0.43 ± 0.12 (n = 4) | | HPLC > 99% |
| SO1-172<br>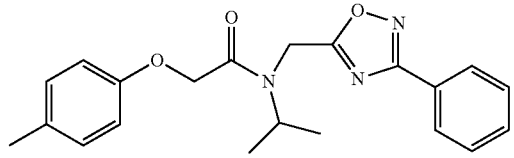<br>M.W. = 365.43 | 0 | 0.31 ± 0.08 (n = 4) | | HPLC = 96.29% |
| SO1-176<br>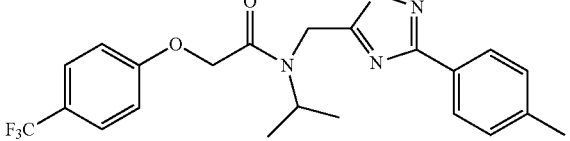<br>M.W. = 433.42 | | 1.08 ± 0.33 (n = 4) | | HPLC = 99.87% |
| SO1-179<br>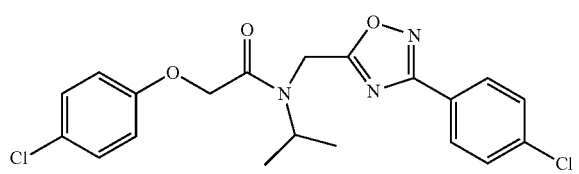<br>M.W. = 420.29 | | 1.07 ± 0.05 (n = 4) | | HPLC = 99.92% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | IC$_{50}$ (μM) Chymo-trypsin-like | Whole cell IC$_{50}$ (μM) Chymo-trypsin-like | Comments |
|---|---|---|---|---|
| SO1-180<br>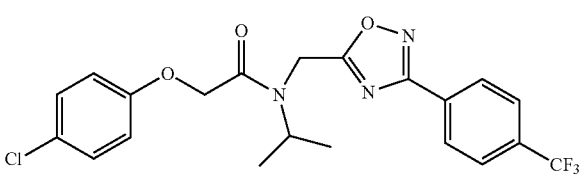<br>M.W. = 453.84 | | 1.405 ± 0.185 (n = 2) | | HPLC = 99.75% |
| SO1-181<br>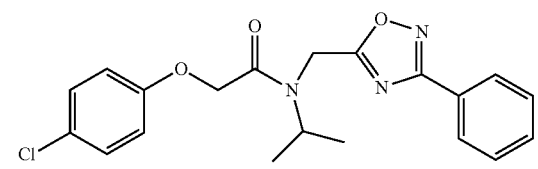<br>M.W. = 385.84 | | 0.51 ± 0.16 (n = 6) | | HPLC = 99.92% |
| SO1-184<br>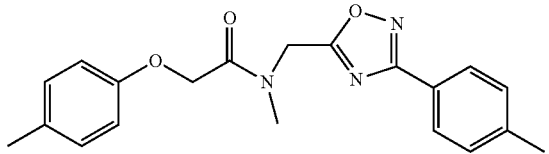<br>M.W. = 351.40 | | 29.9 ± 3.9 (n = 2) | | HPLC = 96.03% |
| SO2-002<br>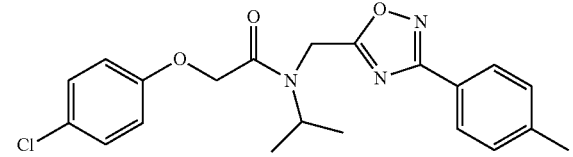<br>M.W. = 399.87 | | 1.12 ± 0.33 (n = 5) | | HPLC = 99.61% |
| SO2-006<br>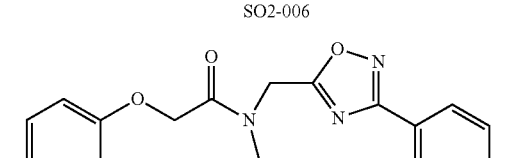<br>M.W. = 365.43 | | 8.47 ± 0.59 (n = 2) | | HPLC = 99.84% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | $IC_{50}$ (μM) Chymotrypsin-like | Whole cell $IC_{50}$ (μM) Chymotrypsin-like | Comments |
|---|---|---|---|---|
| SO2-007<br>M.W. = 337.37 | | −62.67% @ 10 μM Nov. 19, 2010 | | HPLC = 99.85% |
| SO2-010<br>M.W. = 419.40 | | 15.11 ± 6.94 (n = 4) | | HPLC > 99% |
| SO2-011<br>M.W. = 351.40 | | 6.22 ± 1.11 (n = 2) | | HPLC = 94.37% |
| SO2-012<br>M.W. = 365.43 | | 8.98 ± 5.21 (n = 4) | | HPLC = 99.62% |
| SO2-024<br>M.W. = 364.44 | −8.75 ± 17.37 | ND | | HPLC = 95.42% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening<br>Results<br>(%<br>Inhibition @<br>10 µM)<br>Chymotrypsin-<br>like | IC$_{50}$ (µM)<br>Chymo-<br>trypsin-<br>like | Whole cell<br>IC$_{50}$ (µM)<br>Chymo-<br>trypsin-<br>like | Comments |
|---|---|---|---|---|
| SO2-027<br>M.W. = 417.42 | | 44.03 ±<br>20.88<br>(n = 4) | | HPLC =<br>98.50% |
| SO2-030<br>M.W. = 369.39 | | 8.73 ±<br>3.05<br>(n = 4) | | HPLC ><br>99% |
| SO2-045<br>M.W. = 427.50 | <70% | ND | | HPLC =<br>99.6% |
| SO2-046<br>M.W. = 480.35 | <70% | ND | | HPLC =<br>99.25% |
| SO2-050<br>M.W. = 379.45 | | 0.267 ±<br>0.05<br>(n = 6) | | HPLC =<br>95.49% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening<br>Results<br>(%<br>Inhibition @<br>10 μM)<br>Chymotrypsin-<br>like | IC$_{50}$ (μM)<br>Chymo-<br>trypsin-<br>like | Whole cell<br>IC$_{50}$ (μM)<br>Chymo-<br>trypsin-<br>like | Comments |
|---|---|---|---|---|
| SO2-054<br>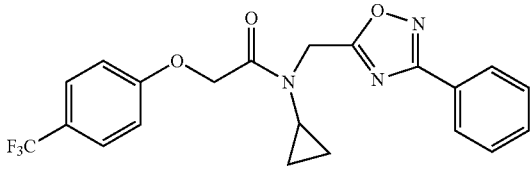<br>M.W. = 417.38 | 27.30<br>35.35<br>33.80 | 6.37 | | HPLC =<br>99.46% |
| SO2-058<br>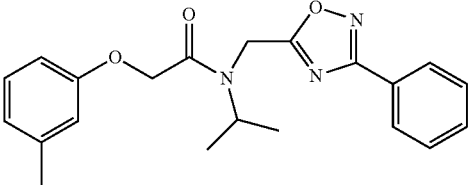<br>M.W. = 365.43 | <70% | ND | | HPLC =<br>94.51% |
| SO2-073<br>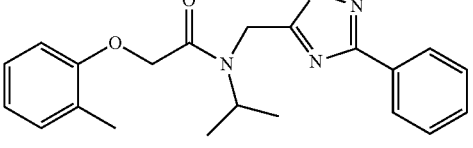<br>M.W. = 365.43 | | ND | | HPLC =<br>97.95% |
| SO2-075<br>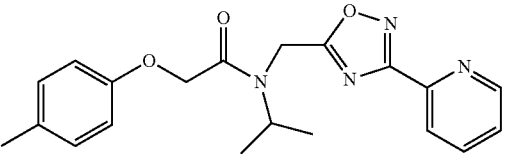<br>M.W. = 366.41 | | 3.747 ±<br>1.47<br>(n = 6) | | HPLC =<br>95.31% |
| SO2-076<br>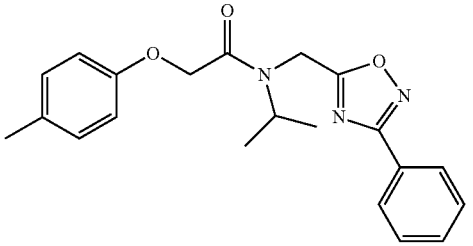<br>M.W. = 366.41 | | 0.22 ±<br>0.084<br>(n = 9) | | HPLC =<br>99.43% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results<br>(% Inhibition @ 10 μM) Chymotrypsin-like | IC$_{50}$ (μM) Chymo-trypsin-like | Whole cell IC$_{50}$ (μM) Chymo-trypsin-like | Comments |
|---|---|---|---|---|
| SO2-066<br>M.W. = 293.75 | −53.02 ± 23.42 (n = 4) | | | HPLC > 99% |
| SO2-068<br>M.W. = 451.51 | −62.02 ± 26.32 (n = 4) | | | HPLC = 99.81% |
| SO2-070<br>M.W. = 393.48 | −108.42 ± 118.76 (n = 5) | | | HPLC = 97.73% |
| SO2-089<br>M.W. = 395.41 | 27.76 ± 20.83 (n = 5) | | | HPLC > 99% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results<br>(% Inhibition @ 10 μM)<br>Chymotrypsin-like | $IC_{50}$ (μM)<br>Chymo-trypsin-like | Whole cell $IC_{50}$ (μM)<br>Chymo-trypsin-like | Comments |
|---|---|---|---|---|
| SO2-091<br>M.W. = 379.45 | 31.39 ± 11.20 (n = 4) | | | HPLC = 97.51% |
| SO2-103<br>M.W. = 380.44 | | 0.099 ± 0.032 (n = 14) | | HPLC = 94.88% |
| SO2-104<br>M.W. = 508.57 | −174.75 ± 134.18 (n = 5) | ND | | HPLC = 96.35% |
| SO2-069<br>M.W. = 366.41 | 95.72 ± 0.88 | 0.37 ± 0.046 (n = 4) | | HPLC = 97.29% |
| SO2-090<br>M.W. = 364.44 | 81.54 ± 2.77 | 5.67 ± 0.96 (n = 4) | | HPLC = 96.59% |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | IC$_{50}$ (μM) Chymotrypsin-like | Whole cell IC$_{50}$ (μM) Chymotrypsin-like | Comments |
|---|---|---|---|---|
| SO2-144<br>M.W. = 379.45 | 92.43 ± 0.82 | 0.92 ± 0.21 (n = 4) | | HPLC = 99.77% |
| SO2-145<br>M.W. = 380.44 | 92.93 ± 1.70 | 0.38 ± 0.099 (n = 16) | | |
| SO2-126<br>M.W. = 337.42 | 80.38 ± 3.04 | 12.52 ± 2.96 (n = 4) | | |
| SO2-089-meglumine salt<br>M.W. = 590.62 | −72.66 ± 44.80 (n = 6) | 9.54 ± 10.89 (n = 5) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | IC$_{50}$ (μM) Chymo-trypsin-like | Whole cell IC$_{50}$ (μM) Chymo-trypsin-like | Comments |
|---|---|---|---|---|
| SO2-104-meglumine salt<br>M.W. = 703.78 | −149.24 ± 157.49 (n = 5) | | | |
| SO2-179<br>M.W. = 366.41 | 70.56 ± 5.09 | 4.00 ± 0.89 | | |
| SO2-170<br>M.W. = 368.39 | 78.37 ± 6.33 | 0.98 ± 0.50 (n = 3) | | |
| SO2-171<br>M.W. = 367.40 | −5.85 ± 23.45 | 10.12 ± 4.52 (n = 3) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | IC$_{50}$ (μM) Chymo-trypsin-like | Whole cell IC$_{50}$ (μM) Chymo-trypsin-like | Comments |
|---|---|---|---|---|
| SO2-184 (PI-1840) 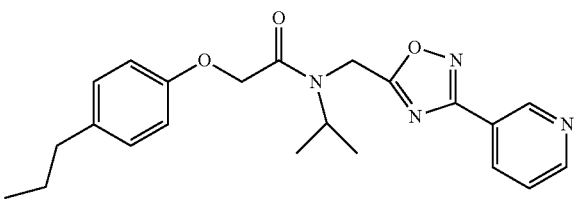 M.W. = 394.47 | 92.31 ± 2.19 | 0.032 ± 0.00015 (n = 10) | | HPLC = 96.36% |
| SO3-023 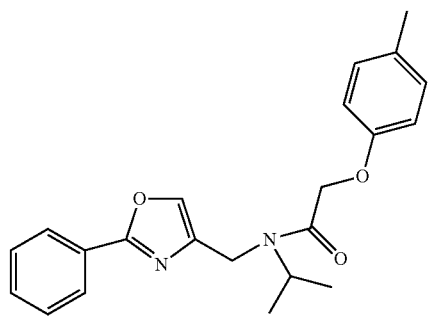 M.W. = 364.44 | | 0.14 ± 0.003 (n = 4) | | HPLC = 100% |
| SO3-026 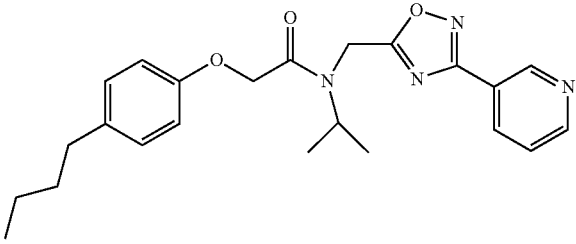 M.W. = 408.49 | | 0.039 ± 0.011 (n = 7) | | HPLC = 97.51% |
| SO3-029 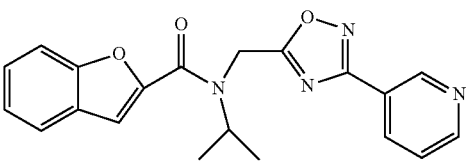 M.W. = 362.38 | | 0.379 ± 0.063 (n = 3) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | $IC_{50}$ (μM) Chymotrypsin-like | Whole cell $IC_{50}$ (μM) Chymotrypsin-like | Comments |
|---|---|---|---|---|
| SO3-030<br>M.W. = 352.39 | | 3.12 ± 1.11 (n = 6) | | HPLC = 97.50% |
| SO3-019<br>M.W. = 380.44 | | 0.214 ± 0.053 (n = 7) | | S isomer |
| SO3-065<br>M.W. = 380.44 | | 7.52 ± 2.13 (n = 7) | | R isomer |
| SO3-050<br>M.W. = 422.52 | | 0.121 ± 0.040 (n = 3) | | HPLC = 96.51% |
| SO3-051<br>M.W. = 436.55 | | 0.428 ± 0.038 (n = 3) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | IC$_{50}$ (μM) Chymo-trypsin-like | Whole cell IC$_{50}$ (μM) Chymo-trypsin-like | Comments |
|---|---|---|---|---|
| SO3-054<br>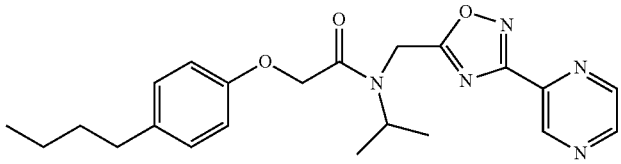<br>M.W. = 409.48 | | 0.107 ± 0.013 (n = 3) | | HPLC = 97.97% |
| SO3-057<br>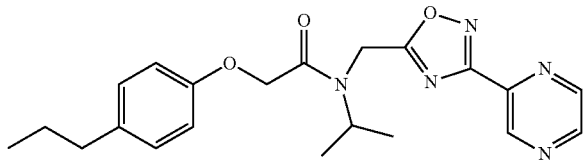<br>M.W. = 395.45 | | 0.105 ± 0.031 (n = 3) | | HPLC = 97.57% |
| SO3-074<br>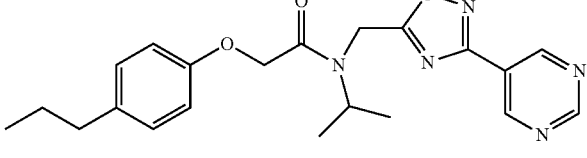<br>M.W. = 395.45 | | 0.032 ± 0.003 (n = 3) | | HPLC = 97.18% |
| SO3-066<br>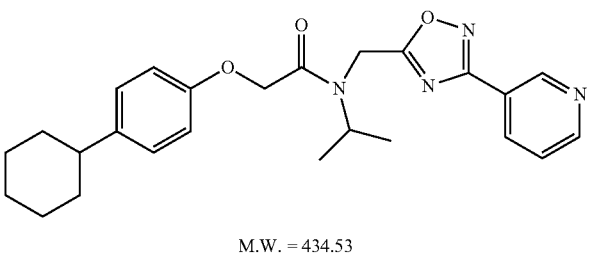<br>M.W. = 434.53 | | 1.356 ± 0.184 (n = 3) | | HPLC = 97.00% |
| SO3-079<br>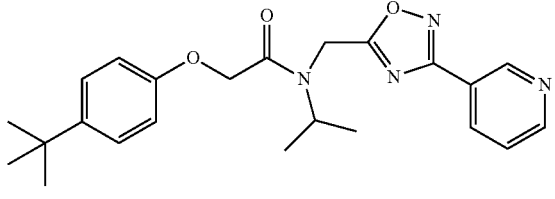<br>M.W. = 408.49 | | 65.93 ± 33.68 (n = 3) | | |

TABLE 5-continued

PI-1833 and aromatic-ring-substituted analogs synthesized to identify proteasome inhibitor compounds.

| Name<br>Molecular Wt<br>(Amt. Supplied mg)<br>Structure | Screening Results (% Inhibition @ 10 μM) Chymotrypsin-like | $IC_{50}$ (μM) Chymo-trypsin-like | Whole cell $IC_{50}$ (μM) Chymo-trypsin-like | Comments |
|---|---|---|---|---|
| SO3-080<br>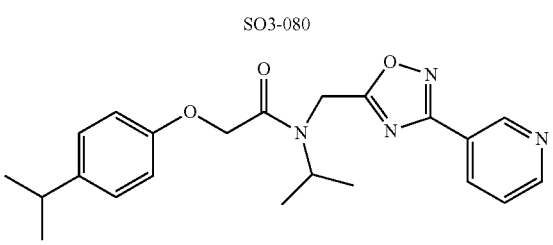<br>M.W. = 394.47 | | 0.436 ± 0.073 (n = 3) | | HPLC = 99.1% |
| SO3-084<br>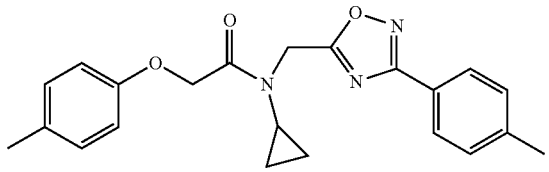<br>M.W. = 377.44 | −8.36 ± 19.03 | | | HPLC = 94.77% |
| SO3-089<br>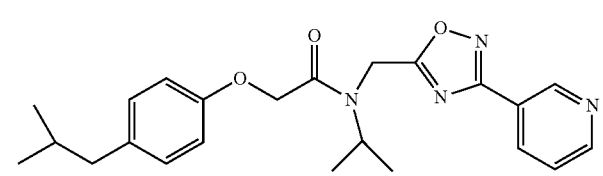<br>M.W. = 408.49 | | 0.140 ± 0.052 (n = 3) | | HPLC = 100% |
| SO3-096<br>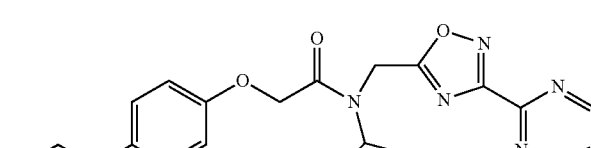<br>M.W. = 395.45 | | 1.269 ± 0.226 (n = 3) | | HPLC = 97.92% |
| SO3-109<br>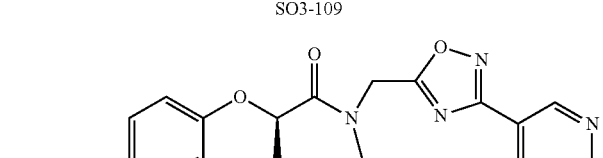<br>M.W. = 408.49 | | (2.389) (1.986) | | R isomer |

TABLE 5-continued

PI-1833 and aromatic-ring-substituted analogs synthesized to identify proteasome inhibitor compounds.

| Name Molecular Wt (Amt. Supplied mg) Structure | Screening Results (% Inhibition @ 10 µM) Chymotrypsin-like | $IC_{50}$ (µM) Chymo-trypsin-like | Whole cell $IC_{50}$ (µM) Chymo-trypsin-like | Comments |
|---|---|---|---|---|
| SO3-110 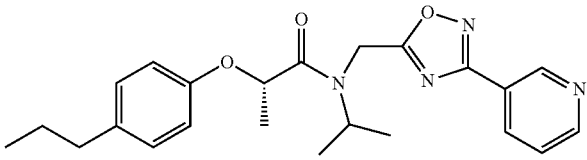 M.W. = 408.49 | | (0.0750) (0.02919) | | S isomer |
| SO3-106 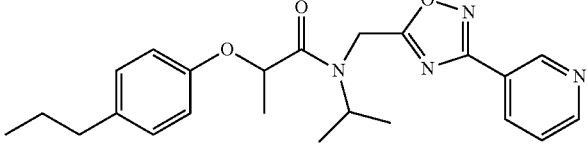 M.W. = 408.49 | | (0.2893) (0.0563) | | Racemic mixture |
| SO3-126 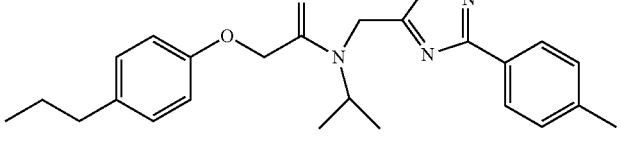 M.W. = 407.51 | | | | |

The phenyl rings in compound 1 were modified (i.e. library 11), as seen in FIG. 6 and Table 1. Changing the para-methyl in $R^1$ and $R^2$ to trifluoromethyl (11c), seen in Table 1, Entry 4, or chlorine (11g), seen in Table 1, Entry 8, showed inhibitory activities with $IC_{50}$ 2.53 and 1.07 µM respectively. Similarly, compounds 11a, 11d, 11e, 11f, 11i and 11n with small hydrophobic groups such as $CF_3$, methyl or Cl in the para-positions of $R^1$ and $R^2$ rings retained the in vitro CT-L inhibitory activities, seen in Table 1, Entries 2, 4-8, 10 and 15, possessed $IC_{50}$ values around 1 µM. Compounds 11b, 11h and 11m, seen in Table 1, Entries 3, 9 and 14, with an unsubstituted phenyl ring as $R^2$ showed slightly improved $IC_{50}$ values around 0.3 to 0.5 µM indicating para-substitution in the $R^2$ phenyl is not required for activity. However compound 11j with both unsubstituted phenyl rings resulted in 10 fold loss of CT-L activity, seen in Table 1, Entry 11, having an $IC_{50}$ value of 6.22 µM. Removal of the $R^1$ para-methyl group as in compounds 11k and 11l, seen in Table 1, Entries 12 and 13, also led to 13 and 25-fold loss of activity ($IC_{50}$ 8.4 and 15 µM respectively). The loss of in vitro potency of compounds 11j, 11k and 11l suggest that para-substitution in $R^1$ phenyl is important, and in some cases vital, to maintain CT-L proteasome activity. Changing the $R^1$ para-methyl to meta- or ortho-position as in compounds 11o and 11p, seen in Table 1, Entries 16 and 17, indicated loss of in vitro activity further suggesting that $R^1$ para-substitution is important for CT-L proteasome activity. Overall, the SAR indicated that the para-methyl group in $R^1$ together with the isopropyl amide in 1 were important to maintain the CT-L proteasome activity and loss of activity was consistently observed with unsubstituted $R^1$ aromatic rings.

Moieties at $R^1$ were then selected at the para-position (i.e. para substituted 6-bromonapthyl, biphenyl, OH, COOH, $CH_3$, ethyl, propyl, butyl) and unsubstituted aromatic $R^2$ rings (phenyl, pyridyl [ortho-meta- and para-], pyrimidine and pyrazine) for further synthetic modifications, as seen in Table 1, Library 11. The best in vitro CT-L inhibitory activity was demonstrated by compounds 11ad and 11ae, seen in Table 1, having $IC_{50}$ values of 32 and 39 nM respectively, that possessed a propyl or butyl group in the para-position of the $R^1$ phenyl ring and meta-pyridyl as $R^2$. The 20-fold improved activity of 11ad and 11ae demonstrated the key functional groups such as para-propyl or para-butyl, isopropylamide and the 3-pyridyl groups of the oxadiazole pharmacophore are important for CT-L proteasome inhibitory activity. The significantly improved in vitro potency of 11ad and 11ae were achieved by systematically changing the $R^1$ and $R^2$ moieties. Initially, compound 11x, seen in Table 1, Entry 25, was observed to have an $IC_{50}$ value of 0.239±0.09 µM with para-methylphenyl as $R^1$ and 3-pyridyl as $R^2$ that showed 2.5 fold improved CT-L activity compared to the hit 1. Similarly, 11aa, seen in Table 1, Entry 28, with an $IC_{50}$ value of 0.26±0.05 µM, with para-ethylphenyl as $R^1$ and unsubstituted phenyl group as $R^2$ showed 2 fold improved activity. The library member 11ab (combined features of 11x and 11aa) with para-ethylphenyl as $R^1$ and 3-pyridyl as $R^2$ showed 6-fold improved in vitro activity, as seen in Table 1, Entry 29, with an $IC_{50}$ value of 0.099±0.03 µM, and demonstrated the additive features of 11x and 11aa led to improvement in CT-L inhibitory activity. Interestingly, loss of CT-L activity observed with 11ac, Table 1, Entry 30, having an $IC_{50}$ value of 3.12±1.11 µM with an unsubstituted $R^1$ ring further highlighted the importance of para-substituted $R^1$ ring in 1 to maintain the CT-L activity. We found compound 11w, Table 1, Entry 24, $IC_{50}$=3.74±1.47 µM, with 2-pyridyl as $R^2$ was less active, while 11y, Table 1, Entry 26, with an $IC_{50}$ value of 0.37±0.04 µM with para-pyridyl moiety was more tolerated for CT-L activity. The compound 11z with a para-methyl substituted pyridyl as $R^1$ failed to retain the activity probably due to the H-bond acceptor (pyridyl) group.

With promising SAR data from the parent compound and aromatic substitutions, the compound 11ab was further modified to obtain the most potent analogs 11ad and 11ae. The hydrophobic ethyl group in 11ab was further extended to propyl (11ad), butyl (11ae), pentyl (11af), hexyl (11ag) and cyclohexyl (11ah) and as the length of the hydrophobic chain increased, the CT-L inhibitory activity was decreased, seen in Table 4, Entries 31-35, $IC_{50}$ changed from 32 nM to 1.3 µM. SAR studies on PI-1840 (compound 11ad), seen in FIG. 10, exhibited a 20-fold more potent analog, seen in FIGS. 11 and 12. Testing of compound PI-1840 and PI-1833 showed both compounds are non-covalent and rapidly reversible proteasome inhibitors, as seen in FIG. 13. In vitro testing of both PI-1833 and PI-1840 showed PI-1840 is more potent at inhibiting CT-L activity in human breast cancer, seen in FIG. 14, and acts through CT-L but not T-L or PGPH activities within 10 min of administration, seen in FIG. 15. Western blots were performed to analyze the cellular proteins to determine the pathway of action, and it was observed that PI-1840 is more potent at accumulating the proteasome substrates p27, Bax and IKB, seen in FIG. 16, and acts through efficiently inducing apoptosis, as seen in FIG. 17. The effects of PI-1840 are not restricted to breast cancer, as seen in Table 6.

TABLE 6

Exponentially growing different cancer cells with different genetic background or normal/immortalized breast cells treated with different concentrations of PI-1840 for 72 h or 96 h, followed by MTT assay to measure the tumor cell proliferation and viability.

| Cancer | Cell line(s) | Genetic background | 72 h | 96 h |
|---|---|---|---|---|
| Breast | MDA-MB-468 | WT K-Ras, mut p53 | 25.45 ± 5.83 | 11.6 |
|  | MDA-MB-231 | mut K-Ras | 132.63 ± 21.57 | 105.5 |
| Colon | HCT-116 | mut K-Ras, WT p53 | 40.93 ± 15.80 | 35.27 |
|  | HCT-116-p53$^{-/-}$ | mut K-Ras, p53$^{-/-}$ | 45.93 ± 19.90 | 31.06 |
|  | HCT-116-HKH2 | K-Ras$^{-/-}$, WT p53 | 43.02 ± 9.73 | 12.83 |
| Prostate | DU-145 | Bax$^{-/-}$ | 122.93 ± 25.19 | 158.7 |
|  | LNCaP | Bax$^{+/+}$ | 48.95 ± 6.81 | 17.25 |
|  | PC3 |  | 92.67 | 62.51 |
| Multiple myeloma | RPMI-8226 |  | 35.93 ± 11.15 | 34.74 |

TABLE 6-continued

Exponentially growing different cancer cells with different genetic background or normal/immortalized breast cells treated with different concentrations of PI-1840 for 72 h or 96 h, followed by MTT assay to measure the tumor cell proliferation and viability.

| Cancer | Cell line(s) | Genetic background | 72 h | 96 h |
|---|---|---|---|---|
| Pancreatic | Colo357 |  | N/A | 95.65 |
| Kidney | RX7-397 |  | N/A | 56.89 |
|  | MCF-10A | normal/immortalized | 63.07 ± 7.06 | N/A |

Compounds 11ad and 11ae displayed the best CT-L inhibitory activities with $IC_{50}$ values 32 nM and 39 nM respectively. These modifications were critical to understand the SAR around the $R^1$ binding region of the proteasome. Compounds 11af, 11ag and 11ah with para-pentyl, para-hexyl and para-cyclohexyl respectively showed 4-, 13- and 40-fold loss of CT-L activity, seen in Table 1, compared to 11ad or 11ae indicating longer chain hydrophobic substituents are less tolerated in the $R^1$ binding region of the CT-L domain. Compounds 11q and 11r that possessed large phenyl and Br-naphthyl as para-$R^1$ groups respectively, further indicated that large $R^1$ groups lead to poor CT-L inhibitory activity, Table 1, Entries 18, 19, <70% @ 10 µM. In contrast, replacement of methyl by small hydrophobic fluorine, Table 1, Entry 20, 11s, also led to poor CT-L inhibitory activity. The 20-fold loss of CT-L inhibitory activity of 11s with fluorine compared to 11b (Entry 3) is not surprising since fluorine is isosteric to hydrogen and as described previously we have already observed the detrimental effects of unsubstituted $R^1$ rings in compounds 11k, 11l and 11ac, seen in Table 1, toward the CT-L inhibitory activity. The hydrophilic COOH and OH groups in the para-position of the $R^1$ as in compounds 11t and 11v respectively also failed to maintain the CT-L inhibitory activity ($IC_{50}$=27 and 10 µM respectively) indicating H-bond acceptor/donor moieties are not desirable as $R^1$ substituents. However compound 11u with para-hydroxyphenyl as $R^1$ and meta-pyridyl as $R^2$ showed an $IC_{50}$ value around 1 µM (Entry 22) and comparison of in vitro CT-L inhibitory activities of 11u and 11v, Table 1, Entries 22 and 23, with para-hydroxyphenyl as $R^1$ highlight the importance of the para-pyridyl group for CT-L activity in this class of compounds.

Example 3

To further analyze Structure Activity Relationship (SAR) studies of PI-1833, synthetic modifications were carried out to the compound's backbone structure, as shown in the FIG. 18. To see the effect of isopropyl group on the CT-L activity, the isopropyl group was changed to methyl, ethyl, isobutyl and hydrogen by using the route depicted in FIG. 3.

The acetyl chloride building block library 5, seen in FIG. 6, was synthesized from readily available phenol derivatives via the intermediates ester 3 and acid 4 using reported protocols. The oxadiazole portion of the compound 1 was synthesized from readily available nitrile building blocks 6. The nitrile building blocks were reacted with hydroxylamine hydrochloride and sodium carbonate at 70° C. in water to yield the hydroxyamidines 7 (Gezginci, et al. Antimycobacterial Activity of Substituted Isosteres of Pyridine- and Pyrazinecarboxylic Acids. 2. *J. Med. Chem.* 2001, 44, 1560-1563), seen in FIG. 6, condition g. The 2-substituted pyrimidine oxime was synthesized from the corresponding ester (Ji, J.; Lee, C.-L.; Sippy, K. B.; Li, T.; Gopalakrishnan, M. Oxadiazole derivatives as nicotinic acetylcholine receptor subtype a4b2 positive allosteric modulators and their preparation, composition and use for the treatment of pain. 2010-US36213 2010138600, 20100526, 2010). The intermediate hydroxyamidine library 7 was reacted with chloroacetyl chloride (condition h) to provide the library 8 (Sindkhedkar, et al. Preparation of erythromycin macrolides and ketolides having antimicrobial activity. 2007-IB2405 2008023248, 20070822, 2008), which was cyclized in refluxing toluene to provide the oxadiazole portion of the pharmacophore 9. The library 9 was subsequently reacted with different alkyl amines (isopropyl-, isobutyl-, methyl-. ethyl-, cyclopropyl- and tert-butyl-amines) to obtain the amine-building block library 10 (condition j). For the synthesis of 10n ($R^3$=H), compound 9a ($R^2$=para-tolyl) was first reacted with phthalimide in the presence of potassium carbonate in refluxing acetonitrile, followed by reaction with hydrazine to obtain the compound 10n in high yield. Library 10 was generated with a variety of substituted alkyl and hetero-alkyl $R^2$ moieties and library 5 with substituted/unsubstituted aromatic $R^1$ moieties, seen in FIG. 6. Modifications to the two key building block libraries 10 and 5 were then reacted in the presence of triethylamine to provide the compound 1, library 11 and 12, seen in FIG. 6, and Tables 1 and 2, in good yields. The route described was efficient and convenient for rapid synthesis and optimization of substituted phenyl and the amide moieties. The final libraries 11, 12 and compound 1 were characterized using NMR, LC-MS, HRMS and the purity was >95% as determined by HPLC. The final compound library 11 and 12 (including compound 1) showed 3:1 ratio of atropisomers (hindered rotation about the C—N bond) by $^1$H NMR spectroscopy (see the experimental section).

When the isopropyl group in PI-1833 was changed to isobutyl (36), ethyl (37), methyl (38) or hydrogen (39), the loss of CT-L proteasome activity was observed. From these modifications, isopropyl group appears to play a key role on the CT-L proteasome activity. The results for these modifications are summarized in Table 7.

isopropyl group indicated approximately 3:1 ratio of atropisomers (isomers that exist due to the hindered rotation about the carbon-nitrogen bond). We observed similar ratio of atropisomers with 12b and 12c with ethyl (2:1), methyl (2:1) respectively. Compound 12d with unsubstituted amide, seen in Table 2. Entry 49, $R^3$=H, 12e with bulky tert-butyl group, Table 2, Entry 50, $R^3$=$^t$Bu, and 12f with cyclopropyl group (Entry 51, $R^3$=Cyclopropyl) did not show atropisomers by $^1$H NMR.

Figure 5:
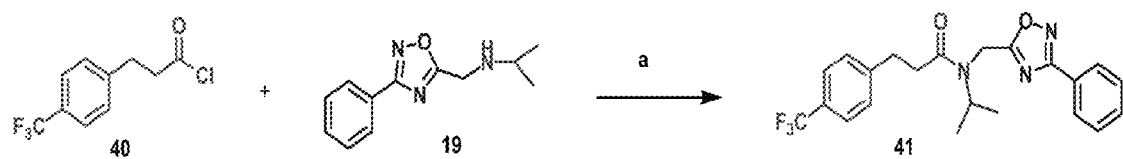
FIG. 5 is a diagram illustrating the synthesis of isopropyl-modified PI-1833 analogs. Reagents and conditions: a $Et_3N$, RT, 15 min., 88%.

Synthetic modifications performed on the backbone focused on an urea moiety or oxygen, as shown in FIG. 19, modified to determine the stringency of the backbone. Reacting the isocyante with the intermediate 19 provided the urea 43 as depicted in FIG. 20. Oxygen was changed to carbon to understand the interaction of the ether moiety in PI-1833 with Thr-1 as postulated by modeling, seen in FIGS. 8 and 9. The synthesis of the corresponding compound is shown in FIG. 5. When the ether moiety in PI-1833 was replaced with carbon (compound 41), CT-L the activity was diminished. This may be due to the loss of interactions between the oxygen and Thr-1 as predicted by modeling. Incorporation of a urea moiety in compound 43 also resulted in loss of CT-L activity. Results are summarized in Table 8.

The chemical space between the amide moiety and A and B rings of compound 1 were modified, as seen in FIG. 18. A urea moiety was introduced to assess the SAR. To install the urea moiety, intermediate 10d, seen in FIGS. 6 and 21, was reacted with commercially available isocyanate 17, and under these conditions urea 18 was obtained in good yield, seen in FIG. 21, condition q. The ether moiety (H-bond acceptor) in 1 was then replaced with NH(H-bond acceptor/donor) group. The amine 10d, seen in FIG. 6, was reacted with chloroacetyl chloride in the presence of triethylamine in THF at room temperature and then coupled with para-methylaniline using sodium acetate in refluxing ethanol to obtain 20, seen in FIG. 21, condition r and s, also in good yield. The ether oxygen moiety was also replaced by a methylene group using 3-(4-(trifluoromethyl)phenyl)propanoic acid (21a) as the starting compound. The phenylpropanoic acid 21a, seen in FIG. 21, was converted to the

TABLE 7

Inhibition against 20S CT-L proteasome activity.

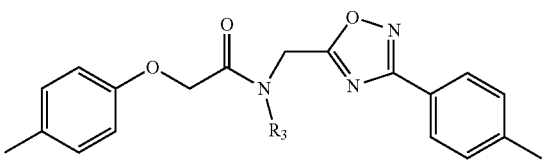

| | $R_3$ | $IC_{50}$ (µM) CT-L |
|---|---|---|
| 12 | isopropyl | 0.716 ± 0.27 (n = 14) |
| 36 | isobutyl | 2.37 ± 0.40 (n = 2) |
| 37 | $CH_2CH_3$ | 8.98 ± 5.21 (n = 4) |
| 38 | $CH_3$ | 29.9 ± 3.9 (n = 2) |
| 39 | H | ND |

Additional replacement of the isopropyl group with tert-butyl or cyclopropyl moieties also showed diminished CT-L activities of these compounds and confirmed the isopropyl group is best tolerated for inhibitory activity, as seen Table 2. The isobutyl amide 12a and ethyl amide 12b, seen in Table 2, Entries 46 and 47, showed 3- and 14-fold loss of activity ($IC_{50}$ 2.37 and 8.8 µM) respectively compared to 1, and methyl, H, cyclopropyl and tert-butyl as $R^3$ groups were detrimental for CT-L activity at 10 M (<70% inhibition @ 10 µM, 12c-12f). The $^1$H NMR of the compound 1 with corresponding acid chloride 22a and coupled with 10d to provide compound 23a, as seen in FIG. 21. The compound 23b with bulky sgroup was synthesized following the route in FIG. 21 from benzofuran-2-carboxylic acid (21b) via the acid chloride 22b and subsequent coupling with 10d. Analysis of $^1$H NMR spectroscopy of the compound 23b with bulky benzofuran moiety as expected prevented hindered rotation about the carbon-amide bond and generation of atropisomers. The intermediate 10d was chosen for synthesis of compounds 18, 20 23a and 23b since our early SAR indicated unsubstituted B ring retained in vitro CT-L potency together with para-$CH_3$ or para-$CF_3$ groups on the A ring.

The exciting findings related to compounds 11ad and 11ae prompted investigation of the SAR around para-propyl/butyl hydrophobic moieties and synthetic modifications around the spacer between the $R^1$ and the amide moiety. The para-position of the $R^1$ moiety was modified by synthesizing final compounds with branched hydrophobic moieties such as isopropyl, $^t$butyl and isobutyl as in 11ai, 11aj and 11ak respectively, seen in Table 1. All 3 compounds failed to improve the CT-L activity compared to 11ad or 11ae, and compound 11aj with para-tert-butyl group led to >35-fold loss of CT-L activity indicating branched hydrophobic groups are not tolerated in the $R^1$ binding region.

The para-propylphenyl or para-butylphenyl moieties were retained as $R^1$ and changed the meta-pyridyl ($R^2$ group) to pyrimidine, Table 1, 11al, 11ao, pyrazine (11am, 11an), and these changes did not lead to compounds with improved CT-L inhibitory activity. Interestingly, 11al with 5-pyrimidine (with both nitrogens in a meta-position) retained the in-vitro potency ($IC_{50}$=32 nM), whereas 2-pyrimidine 11ao (both nitrogens in an ortho-position) showed 40-fold loss of activity ($IC_{50}$=1.26 µM) indicating meta-nitrogen aromatic moiety is important for maintaining the in vitro potency in the binding region. In contrast compounds 11am and 11an with pyrazine (which possess one meta-positioned nitrogen) only showed a 3-fold loss of activity.

TABLE 8

Inhibition against 20S CT-L proteasome activity.

| Compound | $IC_{50}$ (µM) CT-L |
|---|---|
| 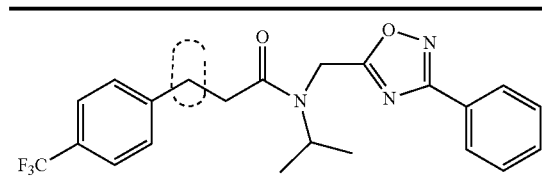 41 | 15.70 |
| 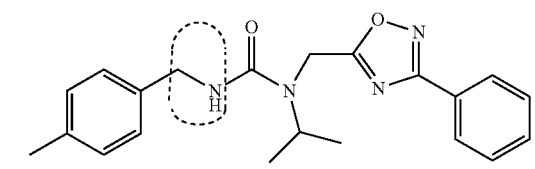 43 | ND |

Further testing of the analoges show a series of potent (below 100 nM), non-covalent drug-like proteasome inhibitors were developed from this class of compounds, seen in Table 9.

TABLE 9

Compound backbone-substituted analogs synthesized to identify proteasome inhibitor compounds.

| Name Molecular Wt (Amt. Supplied mg) Structure | Screening Results (% Inhibition @ 10 µM) Chymotrypsin-like | $IC_{50}$ (µM) Chymotrypsin-like | Whole cell $IC_{50}$ (µM) Chymotrypsin-like | Comments |
|---|---|---|---|---|
| SO2-024 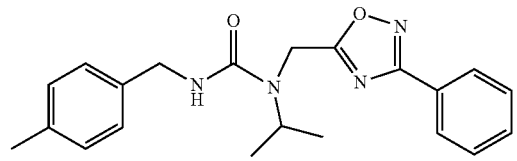 M.W. = 364.44 | | | | HPLC = 95.42% |

TABLE 9-continued

Compound backbone-substituted analogs synthesized to identify proteasome inhibitor compounds.

| Name Molecular Wt (Amt. Supplied mg) Structure | Screening Results (% Inhibition @ 10 μM) Chymotrypsin-like | IC$_{50}$ (μM) Chymotrypsin-like | Whole cell IC$_{50}$ (μM) Chymotrypsin-like | Comments |
|---|---|---|---|---|
| SO2-027<br>M.W. = 417.42 | | 15.70 | | HPLC = 98.50% |
| SO2-054<br>M.W. = 417.38 | | | | |
| SO2-007<br>M.W. = 337.37 | −62.67% @ 10 μM Nov. 19, 2010 | | | HPLC = 99.85% |
| SO1-184<br>M.W. = 351.40 | 9.97% @ 10 μM | 29.9 ± 3.9 (n = 2) | | HPLC = 96.03% |
| SO1-157<br>M.W. = 393.48 | | 2.37 ± 0.40 (n = 2) | | HPLC = 99.07% |

The synthetic modifications also provided compounds with a stereogenic center next to the ether moiety (by substituting one of the hydrogens with methyl) as described in the synthesis of library 16, seen in Table 3 and FIG. 8. We chose compound 11x, seen in Table 1, Entry 25, at an early stage of this study to derive chiral and racemic compounds. As we developed SAR, we introduced a stereogenic center to our most potent compound 11ad, seen in Table 1. Hence the respective chiral and racemic compounds, seen in Table 2, library 16, were derived from 11x and 11ad, the S and R enantiomers along with their racemic compounds were synthesized as described in FIG. 7, to investigate against the CT-L proteasome activity. The racemic 16a with para-methylphenyl as $R^1$ and 3-pyridyl as $R^2$, seen in Table 3, Entry 52, displayed an $IC_{50}$ value of 0.318 μM. While the S-enantiomer 16b was potent, seen in Table 3, Entry 53, with an $IC_{50}$ value of 0.214 μM, the R-enantiomer 16c showed 35-fold loss of activity. Similarly, S-enantiomer 16e was 40-fold more potent than the R-enantiomer 16f (with para-propylphenyl as $R^1$ and meta-pyridyl as $R^2$) and the racemic mixture 16d showed an $IC_{50}$ value of 0.289 μM. The marked differences in the $IC_{50}$ values of S- and R-isomers, seen in Table 3, Entries 16b vs 16C and 16e vs 16f, highlight that these compounds are chirally discriminated in inhibiting the 20S proteasome. This observation is critical for our on-going studies and identifying potent proteasome inhibitors, since less potent R-isomer can be used as a control for cell biology and animal studies.

The spacer groups in 1 were simultaneously modified using the synthetic routes in the FIG. 21. First, replacement of the ether-oxygen by methylene showed loss of CT-L activity, seen in Table 10, Entry 58, $IC_{50}$=15 μM. Furthermore, substituting the amide group by urea as in 18, seen in Table 10, Entry 59, $IC_{50}$=>10 μM, also led to loss of activity. Replacement of the ether (H-bond acceptor) with NH(H-bond donor/acceptor) also decreased the in vitro activity (Entry 60, 20, $IC_{50}$=5.67 μM). These synthetic modifications confirmed that the ether moiety as H-bond acceptor is critical for focused library synthesis and improving CT-L inhibitory activity. Extending the spacer between the amide and the oxadiazole by one carbon as shown in 24, seen in Table 10, Entry 61, 31% @ 10 μM, was detrimental for CT-L inhibitory activity, probably due to the increased flexibility of the structure.

TABLE 10

Modifications of the spacer between the amide $R^1$ phenyl and $R^2$ phenyl and CT-L activities.

| Entry # | Compound Structure and ID | Name | $IC_{50}$ (μM) CT-L |
|---|---|---|---|
| 58 | 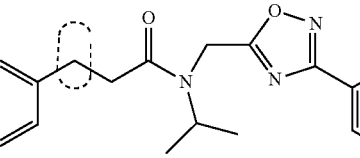 23a | SO2-027 | 15.70 |
| 59 | 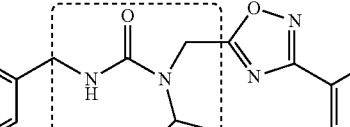 18 | SO2-024 | >10 |
| 60 | 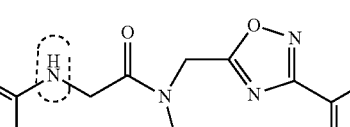 20 | SO2-090 | 5.67 ± 0.96 (n = 4) |
| 61 | 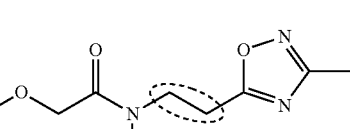 27 | SO2-091 | 31.39% ± 11.20 (n = 4) @ 10 μM |
| 62 | 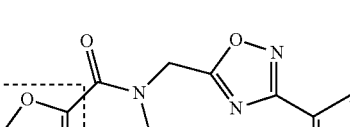 23b | SO3-029 | 0.379 ± 0.063 (n = 3) |

Example 4

Analysis of the Structure Activity Relationship (SAR) studies of PI-1833, PI-1840 and the remaining analogs against the proteasome showed synthetic modifications may be carried out on the oxadiazole moiety of the backbone. A listing of heterocyclic moieties to replace oxadiazole pharmacophore in PI-1833/PI-1840 class of compounds are seen in FIGS. 22(A) and (B).

Example 5

All reagents were purchased from commercial suppliers and used without further purification. Melting points were determined using a Barnstead international melting point apparatus and remain uncorrected. Proton NMR spectra were recorded on an Agilent-Varian Mercury 400 MHz spectrometer with CDCl$_3$ or DMSO-d$_6$ as the solvent. Carbon ($^{13}$C) NMR spectra are recorded at 100 MHz. All coupling constants are measured in Hertz (Hz) and the chemical shifts ($\delta_H$ and $\delta_C$) are quoted in parts per million (ppm) relative to TMS ($\delta$ 0), which was used as the internal standard. High resolution mass spectroscopy was carried out on an Agilent 6210 LC/MS (ESI-TOF). Low resolution mass spectroscopy (LRMS) was performed on an Agilent single quad G1956A (Chemistry Department, University of South Florida). Microwave reactions were performed in CEM 908005 model and Biotage initiator 8 machines. HPLC analysis was performed using a JASCO HPLC system equipped with a PU-2089 Plus quaternary gradient pump and a UV-2075 Plus UV-VIS detector, using an Alltech Kromasil C-18 column (150×4.6 mm, 5 μm) and Agilent Eclipse XDB-C18 (150×4.6 mm, 5 μm). Chiral HPLC analysis was performed using a JASCO HPLC system equipped with a PU-2089 Plus quaternary gradient pump and a UV-2075 Plus UV-VIS detector, using OD column 9cellulose tris (3,5-dimethylphenylcarbamate) coated on 10 μm silica gel. Melting points were recorded on an Optimelt automated melting point system (Stanford Research Systems). Thin layer chromatography was performed using silica gel 60 F254 plates (Fisher), with observation under UV when necessary. Anhydrous solvents (acetonitrile, dimethylformamide, ethanol, isopropanol, methanol and tetrahydrofuran) were used as purchased from Aldrich. Burdick and Jackson HPLC grade solvents (methanol, acetonitrile and water) were purchased from VWR for HPLC and high resolution mass analysis. HPLC grade TFA was purchased from Fisher.

SO1-133 (3a)

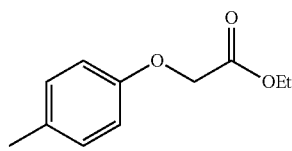

Chemical Formula: C$_{11}$H$_{14}$O$_3$
Exact Mass: 194.09
Molecular Weight: 194.23

Ethyl 2-(p-tolyloxy)acetate (SO1-133): (3a): To a solution of p-cresol (3.0 g, 28 mmol) in acetone (30 ml) was added potassium carbonate (11.6 g, 84 mmol) and ethyl bromoacetate (5.6 g, 33 mmol) and the mixture was refluxed overnight. Potassium carbonate was filtered and acetone was evaporated to give the pure compound as a white solid (4.2 g, 90%).

$^1$H NMR (400 MHz, CDCl$_3$) δ 7.08 (d, J=8.5 Hz, 2H), 6.81 (d, J=8.6 Hz, 2H), 4.59 (s, 2H), 4.26 (q, J=7.1 Hz, 2H), 2.28 (s, 3H), 1.29 (t, J=7.1 Hz, 3H).

SO1-148 (3b)

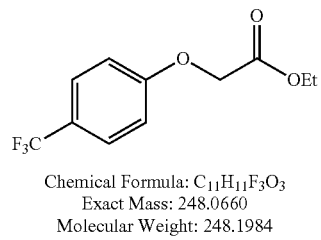 [SMILES: CCOC(=O)COc1ccc(C(F)(F)F)cc1]

Chemical Formula: C$_{11}$H$_{11}$F$_3$O$_3$
Exact Mass: 248.0660
Molecular Weight: 248.1984

Ethyl 2-(4-trifluoromethyl)phenoxy)acetate (SO1-148) (3b): This compound was synthesized using the same protocol for SO1-133 3a except using 4-(trifluoromethyl)phenol (2.43 g, 15.00 mmol), ethyl bromoacetate (3.01 g, 18.00 mmol) and potassium carbonate (10.35 g, 75.00 mmol). SO1-148 3b was isolated as a white solid. (3.61 g, 97%). $^1$H NMR (400 MHz, DMSO) δ 6.78 (d, J=8.4 Hz, 2H), 6.26 (d, J=8.5 Hz, 2H), 3.98 (d, J=1.2 Hz, 2H), 3.44 (q, J=7.1 Hz, 2H), 0.47 (q, J=7.1 Hz, 3H), SO1-173 (3d)

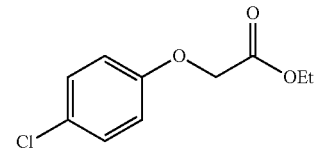

Chemical Formula: C$_{10}$H$_{11}$ClO$_3$
Exact Mass: 214.0397
Molecular Weight: 214.6455

Ethyl 2-(4-chloromethyl)phenoxy)acetate (SO1-173) (3d): This compound was synthesized using the same protocol for SO1-133 3a except using 4-(chloromethyl)phenol (2.70 g, 21.00 mmol), ethyl bromoacetate (4.21 g, 25.20 mmol) and potassium carbonate (14.49 g, 105.00 mmol). SO1-173 3d was isolated as a white solid. (4.18 g, 93%). $^1$H NMR (400 MHz, CDCl$_3$) δ 7.24 (d, J=8.5 Hz, 2H), 6.84 (dd, J=9.1, 0.5 Hz, 2H), 4.59 (s, 2H), 4.26 (q, J=7.2, 1H), 1.29 (t, J=7.2, 1H).

SO2-037 (3e)

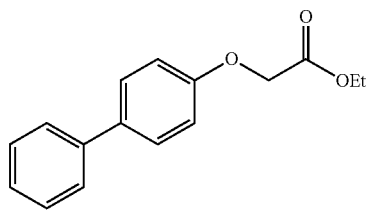

Chemical Formula: C$_{16}$H$_{16}$O$_3$
Exact Mass: 256.1099
Molecular Weight: 256.2964

Ethyl 2-(biphenyl-4-yloxy)acetate (SO2-037) (3e): To a solution of biphenyl-4-ol (2.00 g, 11.75 mmol), in DMF (20 ml) was added ethyl bromoacetate (2.35 g, 14.10 mmol) and potassium carbonate (8.11 g, 58.75 mmol) and stirred at rt overnight. The solution was diluted with DCM (20 ml) and washed with water (5×20 ml). Organic layer was dried and evaporated to provide SO2-037 3e as a white solid. (2.76 g, 90%). $^1$H NMR (400 MHz, CDCl$_3$) δ 7.58-7.47 (m, 4H), 7.41 (t, J=7.6 Hz, 2H), 7.31 (t, J=7.3 Hz, 1H), 6.99 (d, J=8.8 Hz, 2H), 4.65 (s, 2H), 4.28 (q, J=7.1 Hz, 2H), 1.31 (t, J=7.1 Hz, 3H).

SO2-039 (3g)

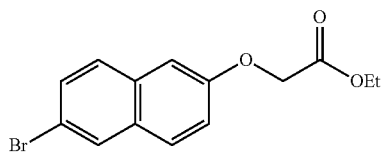

Chemical Formula: C$_{14}$H$_{13}$BrO$_3$
Exact Mass: 308.0048
Molecular Weight: 309.1552

Ethyl 2-(6-bromonapthalen-2-yloxy)acetate (SO2-039) (3g): This compound was synthesized using the same protocol for SO2-037 3e except using 6-bromonapthalen-2-ol (1.06 g, 4.75 mmol), ethyl bromoacetate (0.95 g, 5.70 mmol) and potassium carbonate (3.28 g, 23.75 mmol). SO2-039 was isolated as a white solid. (1.27 g, 82%). $^1$H NMR (400 MHz, CDCl$_3$) δ 7.92 (d, J=1.7 Hz, 1H), 7.67 (d, J=9.0 Hz, 1H), 7.58 (d, J=8.8 Hz, 1H), 7.50 (dd, J=8.7, 1.9 Hz, 1H), 7.34-7.14 (m, 1H), 7.03 (d, J=2.4 Hz, 1H), 4.29 (q, J=7.1 Hz, 2H), 1.30 (t, J=7.1 Hz, 3H).

SO2-049 (3h)

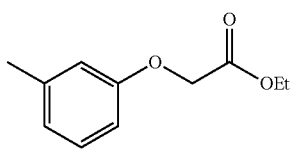

Chemical Formula: C$_{11}$H$_{14}$O$_3$
Exact Mass: 194.0943
Molecular Weight: 194.2271

Ethyl 2-(m-tolyloxy)acetate (SO2-049) (3h): This compound was synthesized using the same protocol for SO2-037 3e except using m-cresol (1.00 g, 9.25 mmol), in DMF (20 ml) was added ethyl bromoacetate (1.85 g, 11.10 mmol) and potassium carbonate (8.11 g, 46.25 mmol). SO2-049 3h was isolated as a yellow-brown solid. (1.67 g, 93%). $^1$H NMR (400 MHz, CDCl$_3$) δ 7.16 (t, J=7.9 Hz, 1H), 6.81 (dd, J=4.4, 3.7 Hz, 1H), 6.75-6.58 (m, 2H), 4.60 (s, 2H), 4.27 (q, J=7.1 Hz, 2H), 2.32 (s, 3H), 1.29 (t, J=7.1 Hz, 3H).

SO2-038 (3j)

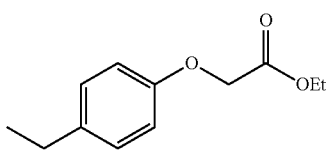

Chemical Formula: C$_{12}$H$_{16}$O$_3$
Exact Mass: 208.1099
Molecular Weight: 208.2536

Ethyl 2-(4-ethylphenoxy)acetate (SO2-038) (3j): This compound was synthesized using the same protocol for SO1-133 3a except using 4-ethylphenol (0.75 g, 6.14 mmol), ethyl bromoacetate (1.23 g, 7.37 mmol) and potassium carbonate (4.24 g, 30.70 mmol). SO2-038 3j was isolated as a viscous yellow liquid. (1.06 g, 85%).

$^1$H NMR (400 MHz, CDCl$_3$) δ 7.12 (dd, J=8.2, 0.6 Hz, 2H), 6.84 (d, J=8.7 Hz, 2H), 4.60 (s, 2H), 4.27 (q, J=7.1 Hz, 2H), 2.58 (t, J=7.6 Hz, 3H), 1.30 (t, J=7.1 Hz, 3H), 1.20 (t, J=7.6 Hz, 3H).

SO2-180 (3k)

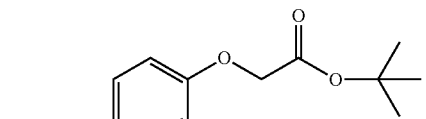

C$_{15}$H$_{22}$O$_3$
Exact Mass: 250.1569
Mol. Wt.: 250.3334 tert-Butyl 2-(4-propylphenoxy)acetate (SO2-180) (3k): A solution 4-propylphenol (500 mg, 3.67 mmol), tert-butyl 2-bromoacetate (716 mg, 3.67 mmol) and potassium carbonate (2.55 g, 18.5 mmol) in DMF (10 ml) were heated at 80° C. for 14 h. The solution was diluted with water (20 ml) and extracted with dichloromethane (2×20 ml). Organic phase was washed with water (5×20 ml), dried (MgSO$_4$) and evaporated. The residue was purified by column chromatography (EtOAc:hexane gradient elution) to obtain SO2-180 3k as a viscous liquid (753 mg, 82%).

$^1$H NMR (400 MHz, CDCl$_3$) δ 7.08 (d, J=8.7 Hz, 2H), 6.81 (d, J=8.7 Hz, 2H), 4.48 (s, 2H), 2.51 (t, J=7.4 Hz, 2H), 1.66-1.55 (m, 2H), 1.48 (s, 9H), 0.91 (t, J=7.3 Hz, 3H).

SO3-017 (3l)

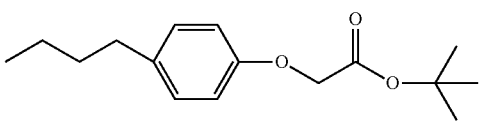

Chemical Formula: C$_{16}$H$_{24}$O$_3$
Exact Mass: 264.1725
Molecular Weight: 264.3600

Tert-butyl 2-(4-butylphenoxy)acetate (SO3-017) (3l): This compound was synthesized using the same protocol for SO2-180 3k except using 4-butylphenol (515 mg, 3.43 mmol), tert-butyl 2-bromoacetate (669 mg, 3.43 mmol) and potassium carbonate (2.37 g, 17.15 mmol) The compound SO3-017 3l was isolated as a yellow viscous liquid. (698 mg, 77%).

$^1$H NMR (400 MHz, CDCl$_3$) δ 7.08 (d, J=8.5 Hz, 2H), 6.80 (d, J=8.7 Hz, 2H), 4.48 (s, 2H), 2.54 (t, J=7.7 Hz, 2H), 1.61-1.48 (m, 2H), 1.38-1.25 (m, 2H), 0.91 (t, J=7.3 Hz, 3H).

SO3-043 (3m)

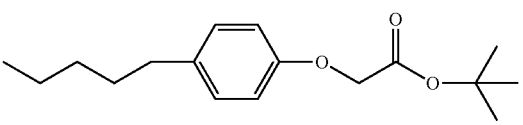

C$_{17}$H$_{26}$O$_3$
Exact Mass: 278.1882
Mol. Wt.: 278.3865

Tert-butyl 2-(4-pentylphenoxy)acetate (SO3-043) (3m): This compound was synthesized using the same protocol for SO2-180 3k except using 4-pentylphenol (500 mg, 3.04 mmol), tert-butyl 2-bromoacetate (593 mg, 3.04 mmol) and potassium carbonate (2.10 g, 15.2 mmol) The compound SO3-043 3m was isolated as a yellow viscous liquid. (584 mg, 69%). $^1$H NMR (400 MHz, cdcl$_3$) δ 7.08 (d, J=8.6 Hz, 2H), 6.81 (d, J=8.6 Hz, 2H), 4.48 (s, 2H), 2.56-2.50 (m, 2H), 1.62-1.50 (m, 2H), 1.48 (s, 9H), 1.35-1.26 (m, 4H), 0.88 (t, J=6.9 Hz, 3H).

SO3-042 (3n)

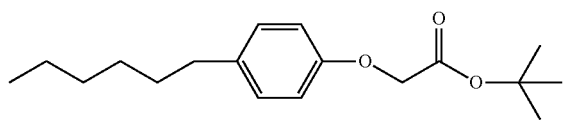

$C_{18}H_{28}O_3$
Exact Mass: 292.2038
Mol. Wt.: 292.4131

Tert-butyl 2-(4-pentylphenoxy)acetate (SO3-042) (3n): This compound was synthesized using the same protocol for SO2-180 3k except using 4-hexylphenol (500 mg, 2.81 mmol), tert-butyl 2-bromoacetate (548 mg, 2.81 mmol) and potassium carbonate (1.94 g, 14.10 mmol) The compound SO3-042 3n was isolated as a colorless viscous liquid. (608 mg, 74%). $^1$H NMR (400 MHz, CDCl$_3$) δ 7.08 (d, J=8.6 Hz, 2H), 6.80 (d, J=8.7 Hz, 2H), 4.48 (s, 2H), 2.57-2.47 (m, 2H), 1.62-1.52 (m, 2H), 1.48 (s, 9H), 1.28-1.17 (m, 6H), 0.87 (m, 3H).

SO3-058 (3o)

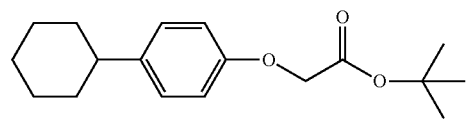

$C_{18}H_{26}O_3$
Exact Mass: 290.1882
Mol. Wt.: 290.3972

Tert-butyl 2-(4-cyclohexylphenoxy)acetate (SO3-058) (3o): This compound was synthesized using the same protocol for SO2-180 3k except using 4-cyclohexylphenol (1.67 g, 9.47 mmol), tert-butyl 2-bromoacetate (1.85 g, 9.47 mmol) and potassium carbonate (6.53 g, 47.4 mmol) The compound SO3-042 3o was isolated as a colorless viscous liquid. (1.95 g, 71%). $^1$H NMR (400 MHz, CDCl$_3$) δ 7.10 (d, J=8.6 Hz, 2H), 6.80 (d, J=8.7 Hz, 2H), 4.47 (s, 2H), 2.48-2.37 (m, 1H), 1.86-1.76 (m, 6H), 1.41-1.29 (m, 4H).

SO3-072 (3p)

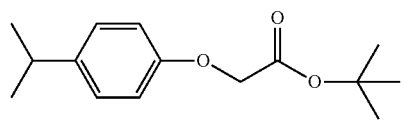

$C_{15}H_{22}O_3$
Exact Mass: 250.1569
Mol. Wt.: 250.3334

Tert-butyl 2-(4-isopropylphenoxy)acetate (SO3-072) (3p): This compound was synthesized using the same protocol for SO2-180 3k except using 4-cyclohexylphenol (2.40 g, 17.62 mmol), tert-butyl 2-bromoacetate (3.44 g, 17.62 mmol) and potassium carbonate (12.16 g, 88.10 mmol) The compound SO3-072 3o was isolated as a colorless viscous liquid. (3.00 g, 68%). $^1$H NMR (400 MHz, CDCl$_3$) δ 7.13 (d, J=8.8 Hz, 2H), 6.82 (d, J=8.8 Hz, 2H), 4.48 (s, 2H), 2.94-2.80 (m, 1H), 1.49 (s, 9H), 1.22 (d, J=6.9 Hz, 6H).

SO3-086 (3q)

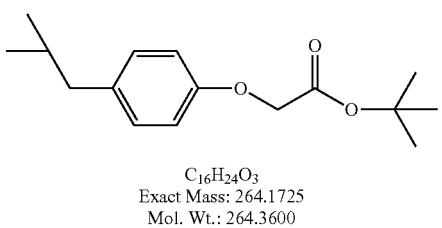 [SMILES: CC(C)Cc1ccc(OCC(=O)OC(C)(C)C)cc1]

$C_{16}H_{24}O_3$
Exact Mass: 264.1725
Mol. Wt.: 264.3600

Tert-butyl 2-(4-isobutylphenoxy)acetate (SO3-086) (3q): This compound was synthesized using the same protocol for SO2-180 3k except using 4-isobutylphenol (660 mg, 4.39 mmol), tert-butyl 2-bromoacetate (857 mg, 4.39 mmol) and potassium carbonate (3.03 g, 21.95 mmol) The compound SO3-086 3q was isolated as a colorless viscous liquid. (836 mg, 72%). $^1$H NMR (400 MHz, CDCl$_3$) δ 7.04 (d, J=8.6 Hz, 2H), 6.81 (d, J=8.7 Hz, 2H), 4.49 (s, 2H), 2.40 (d, J=7.2 Hz, 2H), 1.89-1.74 (m, 1H), 1.48 (s, 9H), 0.88 (d, J=6.6 Hz, 6H).

SO3-075 (3r)

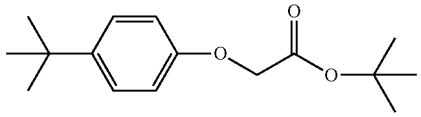

$C_{16}H_{24}O_3$
Exact Mass: 264.1725
Mol. Wt.: 264.3600

Tert-butyl 2-(4-tert-butylphenoxy)acetate (SO3-072) (3r): This compound was synthesized using the same protocol for SO2-180 3k except using 4-tert-butylphenol (1.63 g, 10.85 mmol), tert-butyl 2-bromoacetate (2.12 g, 10.85 mmol) and potassium carbonate (7.49 g, 54.25 mmol) The compound SO3-075 3r was isolated as a colorless viscous liquid. (2.07 g, 72%).

$^1$H NMR (400 MHz, CDCl$_3$) δ 7.30 (d, J=8.9 Hz, 2H), 6.84 (d, J=8.9 Hz, 2H), 4.50 (s, 2H), 1.50 (s, 9H), 1.30 (s, 9H).

SO1-136 (4a)

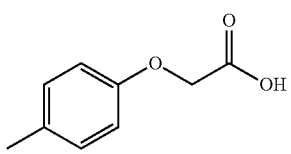

Chemical Formula: $C_9H_{10}O_3$
Exact Mass: 166.06
Molecular Weight: 166.17 p-Tolyloxy-acetic acid (SO1-136) (4a): A solution of ethyl 2-(p-tolyloxy)acetate (3a) (0.4 g, 2.4 mmol) an 10 ml NaOH (1M) and 10 ml ethanol was refluxed overnight. Ethanol was evaporated and aqueous solution was acidified with conc. HCl, the product was precipitated, filtered off and washed with water to give the pure compound SO1-136 4a as a white solid (0.34 g, 94%). $^1$H NMR (400 MHz, DMSO) δ 12.94 (s, 1H), 7.05 (d, J=8.6 Hz, 2H), 6.76 (d, J=8.6 Hz, 2H), 4.59 (s, 2H), 2.20 (s, 3H).

SO1-161 (4b)

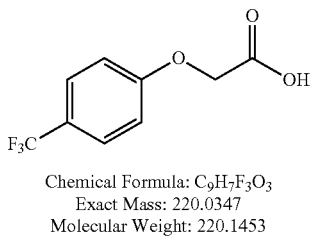 [SMILES: O=C(O)COc1ccc(C(F)(F)F)cc1]

Chemical Formula: $C_9H_7F_3O_3$
Exact Mass: 220.0347
Molecular Weight: 220.1453

2-(4-Trifluoromethyl)phenoxy)acetic acid (SO1-161) (4b): This compound was synthesized using the same protocol for SO1-136 4a except using ethyl 2-(4-trifluoromethyl)phenoxy)acetate (3b) (2.70 g, 10.9 mmol), NaOH (1 M) (10 ml) and THF (10 ml). SO1-161 4b was isolated as a white solid. (2.35 g, 98%). $^1$H NMR (400 MHz, DMSO) δ 13.14 (s, 1H), 7.64 (d, J=9.0 Hz, 2H), 7.08 (d, J=8.5 Hz, 2H), 4.78 (s, 2H).

SO1-174 (4d)

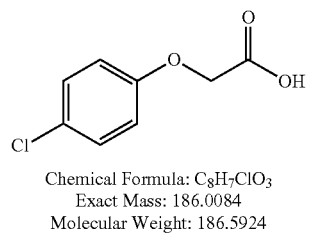 [SMILES: O=C(O)COc1ccc(Cl)cc1]

Chemical Formula: $C_8H_7ClO_3$
Exact Mass: 186.0084
Molecular Weight: 186.5924

2-(4-Chlorophenoxy)acetic acid (SO1-174) (4d): This compound was synthesized using the same protocol for SO1-136 4a except using ethyl 2-(4-chloromethyl)phenoxy)acetate (3d) (1.00 g, 4.66 mmol), NaOH (1 M) (10 ml) and THF (10 ml). SO1-161 4c was isolated as a white solid. (0.79 g, 91%). $^1$H NMR (400 MHz, DMSO) δ 13.03 (s, 1H), 7.31 (d, J=9.1 Hz, 2H), 6.92 (d, J=9.1 Hz, 2H), 4.67 (s, 2H).

SO2-042 (4e)

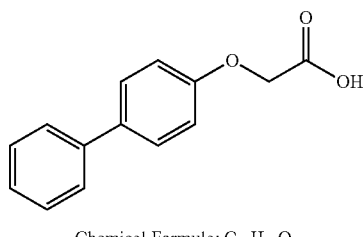

Chemical Formula: $C_{14}H_{12}O_3$
Exact Mass: 228.0786
Molecular Weight: 228.2433

2-(Biphenyl-4-yloxy)acetic acid (SO2-042) (4e): This compound was synthesized using the same protocol for SO1-136 4a except using ethyl 2-(biphenyl-4-yloxy)acetate (3e) (500 mg, 1.95 mmol), NaOH (1 M) (10 ml) and THF (10 ml). SO2-042 4e was isolated as a white solid. (410 mg, 92%). $^1$H NMR (400 MHz, DMSO) δ 7.58 (dd, J=8.0, 5.9 Hz, 4H), 7.41 (t, J=7.7 Hz, 2H), 7.29 (t, J=7.4 Hz, 1H), 6.98 (d, J=8.8 Hz, 2H), 4.70 (s, 2H).

SO2-041 (4g)

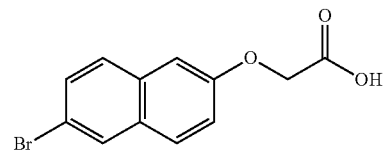

Chemical Formula: $C_{12}H_9BrO_3$
Exact Mass: 279.9735
Molecular Weight: 281.1021 ethyl 2-(6-bromonaphthalen-2-yloxy)acetate 2-(6-Bromonapthalen-2-yloxy)acetic acid (SO2-041) (4g): This compound was synthesized using the same protocol for SO1-136 4a except using ethyl 2-(6-bromonapthalen-2-yloxy)acetate (3g) (500 mg, 1.62 mmol), NaOH (1 M) (10 ml) and THF (10 ml). SO2-041 4g was isolated as a white solid. (401 mg, 88%). $^1$H NMR (400 MHz, DMSO) δ 8.09 (brs, 1H), 7.82 (d, J=9.0 Hz, 1H), 7.74 (d, J=8.8 Hz, 1H), 7.54 (dd, J=8.7, 1.4 Hz, 1H), 7.28 (brs, 1H), 7.23 (dd, J=8.9, 2.3 Hz, 1H), 4.78 (s, 2H).

SO2-056 (4h)

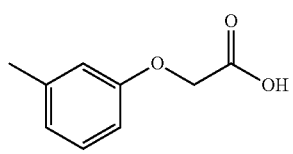

Chemical Formula: $C_9H_{10}O_3$
Exact Mass: 166.0630
Molecular Weight: 166.1739

2-(m-Tolyloxy)acetic acid (SO2-056) (4h): This compound was synthesized using the same protocol for SO1-136 4a except using ethyl 2-(m-tolyloxy)acetate (3h) (500 mg, 2.57 mmol), NaOH (1 M) (10 ml) and THF (10 ml). SO2-056 4h was isolated as a white solid. (384 mg, 90%). $^1$H NMR (400 MHz, DMSO) δ 7.13 (t, J=7.8 Hz, 1H), 6.76-6.65 (m, 3H), 4.61 (s, 2H).

SO2-047 (4j)

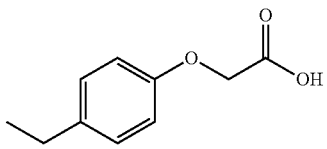

Chemical Formula: $C_{10}H_{12}O_3$
Exact Mass: 180.0786
Molecular Weight: 180.2005

2-(4-Ethylphenoxy)acetic acid (SO2-047) (4j): This compound was synthesized using the same protocol for SO1-136 4a except using ethyl 2-(4-ethylphenoxy)acetate (3j) (500 mg, 2.40 mmol), NaOH (1 M) (10 ml) and THF (10 ml). SO2-047 4j was isolated as a white solid. (394 mg, 91%). $^1$H NMR (400 MHz, DMSO) δ 7.09 (d, J=8.7 Hz, 2H), 6.79 (d, J=8.7 Hz, 2H), 2.62-2.38 (m, 2H), 1.12 (t, J=7.6 Hz, 3H).
SO2-182 (4k)

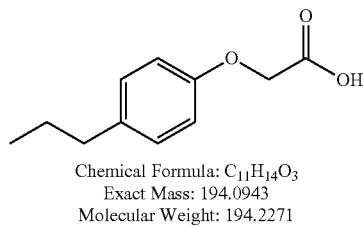

Chemical Formula: C₁₁H₁₄O₃
Exact Mass: 194.0943
Molecular Weight: 194.2271

2-(4-Propylphenoxy)acetic acid (SO2-182) (4k): A solution of tert-Butyl 2-(4-propylphenoxy)acetate (3k) (300 mg, 1.19 mmol) in dichloromethane (5 ml) and trifluoroacetic acid (5 ml) was stirred for 2 h at rt. Acetone (5 ml) was added to the reaction mixture. Excess trifluoroacetic acid and dichloromethane were evaporated to provide the pure acid SO2-182 4k as a pale yellow solid. (208 mg, 90%) ¹H NMR 400 MHz, DMSO) δ 7.06 (d, J=8.5 Hz, 2H), 6.78 (d, J=8.6 Hz, 2H), 4.59 (s, 2H), 2.48-2.41 (m, 2H), 1.56-1.47 (m, 2H), 0.84 (t, J=7.3 Hz, 3H).
SO3-024 (4l)

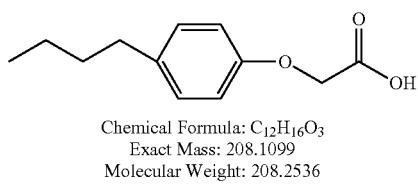

Chemical Formula: C₁₂H₁₆O₃
Exact Mass: 208.1099
Molecular Weight: 208.2536

2-(4-Butylphenoxy)acetic acid (SO3-024) (4l): This compound was synthesized using the same protocol for SO2-182 4k except using tert-Butyl 2-(4-butylphenoxy)acetate (3l) (300 mg, 1.13 mmol) in dichloromethane (5 ml) and trifluoroacetic acid (5 ml). SO3-024 4l was isolated as a white solid. (212 mg, 90%). ¹H NMR (400 MHz, DMSO) δ 7.03 (d, J=8.4 Hz, 1H), 6.74 (d, J=8.4 Hz, 1H), 4.47 (s, 1H), 2.53-2.39 (m, 2H), 1.55-1.38 (m, 1H), 1.24 (dd, J=14.8, 7.4 Hz, 1H), 0.85 (t, J=7.3 Hz, 1H).
SO3-046 (4m)

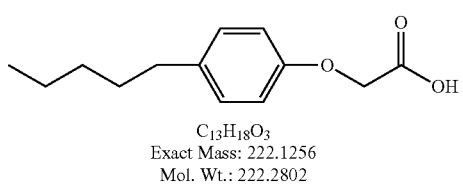 [SMILES: CCCCCc1ccc(OCC(=O)O)cc1]

C₁₃H₁₈O₃
Exact Mass: 222.1256
Mol. Wt.: 222.2802

2-(4-Pentylphenoxy)acetic acid (SO3-046) (4m): This compound was synthesized using the same protocol for SO2-182 4k except using tert-Butyl 2-(4-pentylphenoxy)acetate (3m) (166 mg, 0.60 mmol) in dichloromethane (5 ml) and trifluoroacetic acid (5 ml). SO3-046 4m was isolated as a white solid. (123 mg, 93%).
SO3-044 (4n)

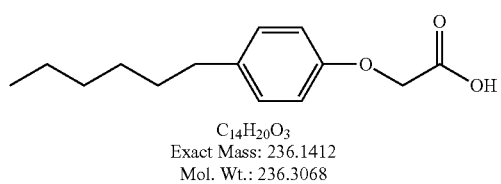 [SMILES: CCCCCCc1ccc(OCC(=O)O)cc1]

C₁₄H₂₀O₃
Exact Mass: 236.1412
Mol. Wt.: 236.3068

2-(4-Hexylphenoxy)acetic acid (SO3-044) (4n): This compound was synthesized using the same protocol for SO2-182 4k except using tert-Butyl 2-(4-hexylphenoxy)acetate (3n) (280 mg, 0.96 mmol) in dichloromethane (5 ml) and trifluoroacetic acid (5 ml). SO3-044 4n was isolated as a white solid. (222 mg, 98%).
¹H NMR (400 MHz, DMSO) δ 7.05 (d, J=8.6 Hz, 2H), 6.76 (d, J=8.6 Hz, 2H), 4.56 (s, 2H), 2.53-2.35 (m, 2H), 1.57-1.39 (m, 2H), 1.28-1.17 (m, 6H), 0.82 (t, J=6.7 Hz, 3H).
SO3-059 (4o)

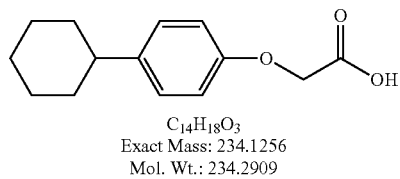 [SMILES: O=C(O)COc1ccc(C2CCCCC2)cc1]

C₁₄H₁₈O₃
Exact Mass: 234.1256
Mol. Wt.: 234.2909

2-(4-Cyclohexylphenoxy)acetic acid (SO3-059) (4o): This compound was synthesized using the same protocol for SO2-182 4k except using tert-Butyl 2-(4-cyclohexylphenoxy)acetate (3o) (1.00 g, 3.44 mmol) in dichloromethane (10 ml) and trifluoroacetic acid (10 ml). SO3-059 4o was isolated as a white solid. (0.75 g, 94%). ¹H NMR (400 MHz, CD₃OD) δ 7.11 (d, J=8.5 Hz, 2H), 6.83 (d, J=8.8 Hz, 2H), 4.60 (s, 2H), 2.49-2.37 (m, 1H), 1.87-1.69 (m, 6H), 1.49-1.22 (m, 4H).
SO3-073 (4p)

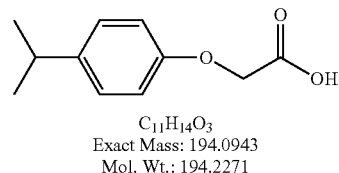

C₁₁H₁₄O₃
Exact Mass: 194.0943
Mol. Wt.: 194.2271

2-(4-Isopropylphenoxy)acetic acid (SO3-073) (4p): This compound was synthesized using the same protocol for SO2-182 4k except using tert-Butyl 2-(4-isopropylphenoxy)acetate (3p) (700 mg, 2.80 mmol) in dichloromethane (5 ml) and trifluoroacetic acid (5 ml). SO3-073 4p was isolated as a pale yellow solid (506 mg, 93%). ¹H NMR (400 MHz, CDCl₃) δ 7.17 (d, J=8.4 Hz, 2H), 6.86 (d, J=8.8 Hz, 2H), 4.67 (s, 2H), 2.92-2.81 (m, 1H), 1.22 (d, J=6.9 Hz, 6H).
SO3-087 (4q)

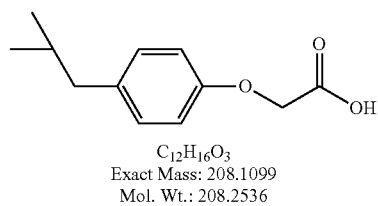

C₁₂H₁₆O₃
Exact Mass: 208.1099
Mol. Wt.: 208.2536

2-(4-Isobutylphenoxy)acetic acid (SO3-087) (4q): This compound was synthesized using the same protocol for SO2-182 4k except using tert-Butyl 2-(4-isobutylphenoxy)acetate (3q) (250 mg, 0.95 mmol) in dichloromethane (5 ml) and trifluoroacetic acid (5 ml). SO3-087 4q was isolated as a white solid (188 mg, 95%). $^1$H NMR (400 MHz, CDCl$_3$) δ 7.02 (d, J=8.4 Hz, 2H), 6.79 (d, J=8.5 Hz, 2H), 5.69 (s, 1H), 2.42 (d, J=7.2 Hz, 2H), 1.98-1.69 (m, 1H), 0.91 (d, J=6.6 Hz, 6H).

SO3-077 (4r)

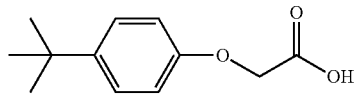

C$_{12}$H$_{16}$O$_3$
Exact Mass: 208.1099
Mol. Wt.: 208.2536

2-(4-Tert-butylphenoxy)acetic acid (SO3-077) (4r): This compound was synthesized using the same protocol for SO2-182 4k except using tert-Butyl 2-(4-tert-butylphenoxy) acetate (3r) (500 mg, 1.89 mmol) in dichloromethane (5 ml) and trifluoroacetic acid (5 ml). SO3-077 4r was isolated as a pale brown solid (358 mg, 91%). $^1$H NMR (400 MHz, CDCl$_3$) δ 9.68 (s, 1H), 7.33 (d, J=8.8 Hz, 2H), 6.87 (d, J=8.8 Hz, 2H), 4.68 (s, 2H), 1.30 (s, 9H).

SO1-140 (5a)

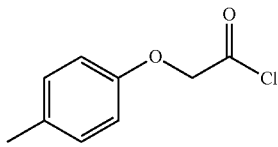

Chemical Formula: C$_9$H$_9$ClO$_2$
Exact Mass: 184.0291
Molecular Weight: 184.6196 p-Tolyloxy-acetyl chloride (SO1-140) (5a): To a solution of p-tolyoxy-acetic acid (4a) (300 mg, 1.81 mmol) in 20 ml benzene thionyl chloride (5 mL) was added and the mixture was refluxed for 3 h till a clear solution was formed. Excess thionyl chloride and benzene were evaporated to give the pure compound SO1-140 5a as colorless liquid (313 mg, 94%). $^1$H NMR (400 MHz, CDCl$_3$) δ 7.11 (dd, J=8.7, 0.6 Hz, 1H), 6.80 (d, J=8.7 Hz, 1H), 4.92 (d, J=3.4 Hz, 1H), 2.30 (s, 3H).

SO1-162 (5b)

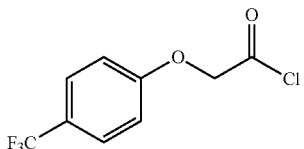

Chemical Formula: C$_9$H$_6$ClF$_3$O$_2$
Exact Mass: 238.0008
Molecular Weight: 238.5909

2-(4-Trifluoromethyl)phenoxy)acetyl chloride (SO1-162) (5b): This compound was synthesized using the same protocol for SO1-140 5a except using 2-(4-trifluoromethyl) phenoxy)acetic acid (4b) (1.00 g, 4.54 mmol), SOCl$_2$ (5 ml) and benzene (5 ml). SO1-162 was isolated as colorless liquid (996 mg, 92%). $^1$H NMR (400 MHz, CDCl$_3$) δ 7.59 (d, J=8.8 Hz, 2H), 6.97 (d, J=8.7 Hz, 2H), 5.00 (s, 2H).

SO1-178 (5d)

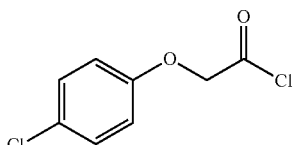

Chemical Formula: C$_8$H$_6$Cl$_2$O$_2$
Exact Mass: 203.9745
Molecular Weight: 205.0380

2-(4-Chlorophenoxy)acetyl chloride (SO1-178) (5d): This compound was synthesized using the same protocol for SO1-140 5a except using 2-(4-chlorophenoxy)acetic acid (4d) (1.00 g, 5.36 mmol), SOCl$_2$ (10 ml) and benzene (10 ml). SO1-178 5d was isolated as yellow solid (930 mg, 91%). $^1$H NMR (400 MHz, CDCl$_3$) δ 7.28 (d, J=8.8 Hz, 2H), 6.84 (d, J=8.9 Hz, 2H), 4.93 (s, 2H).

SO2-043 (5e)

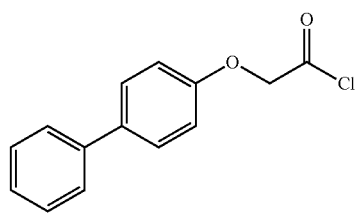

Chemical Formula: C$_{14}$H$_{11}$ClO$_2$
Exact Mass: 246.0448
Molecular Weight: 246.6889

2-(Biphenyl-4-yloxy)acetyl chloride (SO2-043) (5e): This compound was synthesized using the same protocol for SO1-140 5a except using 2-(biphenyl-4-yloxy)acetic acid (4e) (410 mg, 1.80 mmol), SOCl$_2$ (10 ml) and benzene (10 ml). SO2-043 5e was isolated as yellow liquid (417 mg, 94%). $^1$H NMR (400 MHz, CDCl$_3$) δ 7.57-7.52 (m, 4H), 7.43 (dd, J=8.2, 7.0 Hz, 2H), 7.33 (t, J=7.4 Hz, 1H), 6.97 (d, J=8.9 Hz, 2H), 4.99 (s, 2H).

SO2-029 (5f)

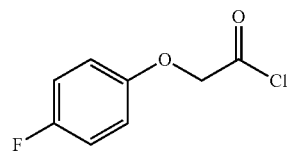

C$_8$H$_6$ClFO$_2$
Exact Mass: 188.0040
Mol. Wt.: 188.5834

2-(4-Fluoro-phenoxy)acetyl chloride (SO2-029) (5f): This compound was synthesized using the same protocol for SO1-140 5a except using (4-fluoro-phenoxy)-acetic acid (1.00 g, 5.88 mmol), SOCl$_2$ (10 ml) and benzene (10 ml). SO2-029 5f was isolated as yellow solid (1.04 g, 94%).

SO2-044 (5g)

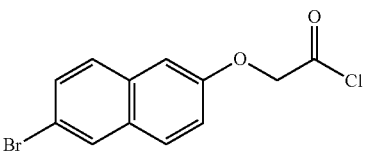

Chemical Formula: C$_{12}$H$_8$BrClO$_2$
Exact Mass: 297.9396
Molecular Weight: 299.5477

2-(6-Bromonapthalen-2-yloxy)acetyl chloride (SO2-044) (5g): This compound was synthesized using the same protocol for SO1-140 5a except using 2-(6-bromonapthalen-2-yloxy)acetic acid (4g) (500 mg, 1.78 mmol), SOCl$_2$ (10 ml) and benzene (10 ml). SO2-044 5g was isolated as yellow liquid (507 mg, 95%). $^1$H NMR (400 MHz, CDCl$_3$) δ 7.93 (d, J=1.7 Hz, 1H), 7.69 (d, J=9.0 Hz, 1H), 7.59 (d, J=8.7 Hz, 1H), 7.53 (dd, J=8.7, 1.9 Hz, 1H), 7.21 (dd, J=9.0, 2.4 Hz, 1H), 7.03 (d, J=2.3 Hz, 1H), 5.05 (s, 2H).

SO2-057 (5h)

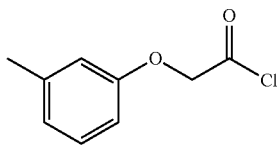

Chemical Formula: C$_9$H$_9$ClO$_2$
Exact Mass: 184.0291
Molecular Weight: 184.6196

2-(m-Tolyloxy)acetyl chloride (SO2-057) (5h): This compound was synthesized using the same protocol for SO1-140 5a except using 2-(m-tolyloxy)acetic acid (4h) (750 mg, 4.51 mmol), SOCl$_2$ (10 ml) and benzene (10 ml). SO2-057 5h was isolated as yellow liquid (758 mg, 91%). $^1$H NMR (400 MHz, CDCl$_3$) δ 7.20 (t, J=7.9 Hz, 1H), 6.88 (d, J=7.5 Hz, 1H), 6.74-6.65 (m, 2H), 4.93 (s, 2H).

SO2-072 (5i)

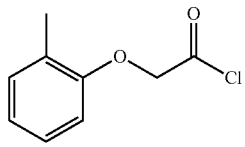

Chemical Formula: C$_9$H$_9$ClO$_2$
Exact Mass: 184.0291
Molecular Weight: 184.6196

2-(o-Tolyloxy)acetyl chloride (SO2-072) (5i): This compound was synthesized using the same protocol for SO1-140 5a except using ethyl 2-(o-tolyloxy)acetic acid (500 mg, 3.01 mmol), SOCl$_2$ (10 ml) and benzene (10 ml). SO2-072 5i was isolated as yellow liquid (511 mg, 92%). $^1$H NMR (400 MHz, CDCl$_3$) δ 7.26 (t, J=2.8 Hz, 1H), 7.10 (d, J=8.3 Hz, 1H), 6.83 (d, J=8.5 Hz, 2H), 4.64 (s, 2H).

SO2-048 (5j)

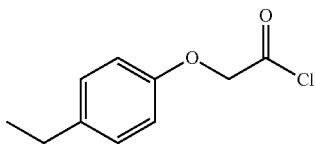

Chemical Formula: C$_{10}$H$_{11}$ClO$_2$
Exact Mass: 198.0448
Molecular Weight: 198.6461

2-(4-Ethylphenoxy)acetyl chloride (SO2-048) (5j): This compound was synthesized using the same protocol for SO1-140 5a except using 2-(4-ethylphenoxy)acetic acid (4j) (300 mg, 1.66 mmol), SOCl$_2$ (5 ml) and benzene (5 ml). SO2-048 5j was isolated as yellow liquid (313 mg, 95%). $^1$H NMR (400 MHz, CDCl$_3$) δ 7.15 (d, J=8.7 Hz, 1H), 6.84 (d, J=8.7 Hz, 1H), 4.92 (s, 2H), 2.62 (q, J=7.6 Hz, 2H), 1.23 (dd, J=7.6 Hz, 3H).

SO2-183 (5k)

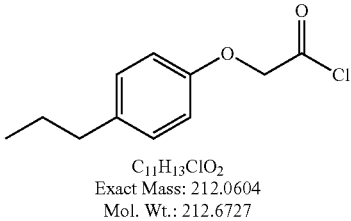

C$_{11}$H$_{13}$ClO$_2$
Exact Mass: 212.0604
Mol. Wt.: 212.6727

(4-Propylphenoxy)-acetyl chloride (SO2-183) (5k): This compound was synthesized using the same protocol for SO1-140 5a except using 2-(4-propylphenoxy)acetic acid (4k) (200 mg, 1.03 mmol), SOCl$_2$ (5 ml) and benzene (5 ml). SO2-183 5k was isolated as a viscous yellow liquid. (208 mg, 95%). $^1$H NMR (400 MHz, CDCl$_3$) δ 7.13 (d, J=8.3 Hz, 2H), 6.83 (d, J=8.3 Hz, 2H), 4.93 (s, 2H), 2.55 (t, J=7.6 Hz, 2H), 1.70-1.55 (m, 2H), 0.94 (t, J=7.3 Hz, 3H).

SO3-025 (5l)

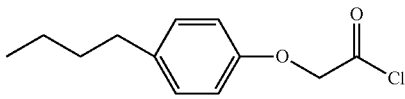

Chemical Formula: C$_{12}$H$_{15}$ClO$_2$
Exact Mass: 226.0761
Molecular Weight: 226.6993

2-(4-Butylphenoxy)acetyl chloride (SO3-025) (5l): This compound was synthesized using the same protocol for SO1-140 5a except 2-(4-butylphenoxy)acetic acid (4l) (200 mg, 0.96 mmol), SOCl$_2$ (5 ml) and benzene (5 ml). SO3-125 5l was isolated as a viscous yellow liquid. (207 mg, 95%). $^1$H NMR (400 MHz, cdcl$_3$) δ 7.12 (d, J=8.0 Hz, 1H), 6.82 (d, J=8.1 Hz, 1H), 4.92 (s, 1H), 2.56 (t, J=7.6 Hz, 1H), 1.60-1.51 (m, 1H), 1.34 (dd, J=14.7, 7.3 Hz, 1H), 0.93 (t, J=7.3 Hz, 2H).

SO3-049 (5m)

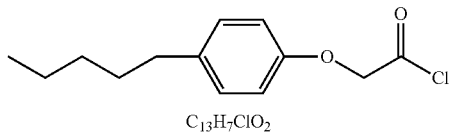

C$_{13}$H$_7$ClO$_2$
Exact Mass: 240.0917
Mol. Wt.: 240.7259

2-(4-Pentylphenoxy)acetyl chloride (SO3-049) (5m): This compound was synthesized using the same protocol for SO1-140 5a except using 2-(4-pentylphenoxy)acetic acid (4m) (120 mg, 0.54 mmol), SOCl$_2$ (5 ml) and benzene (5 ml). SO3-049 5m was isolated as a viscous yellow liquid. (120 mg, 92%). $^1$H NMR (400 MHz, CDCl$_3$) δ 7.12 (d, J=8.6 Hz, 2H), 6.81 (d, J=8.6 Hz, 2H), 4.92 (s, 2H), 2.59-2.50 (m, 2H), 1.63-1.51 (m, 2H), 1.39-1.23 (m, 4H), 0.89 (t, J=6.9 Hz, 3H).

SO3-048 (5n)

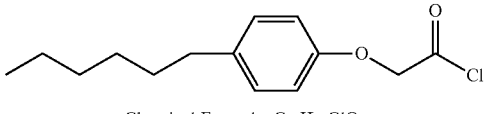

Chemical Formula: C$_{14}$H$_{19}$ClO$_2$
Exact Mass: 254.1074
Molecular Weight: 254.7525

2-(4-Hexylphenoxy)acetyl chloride (SO3-049) (5n): This compound was synthesized using the same protocol for SO1-140 5a except using 2-(4-hexylphenoxy)acetic acid (4n) (220 mg, 0.93 mmol) SOCl$_2$ (5 ml) and benzene (5 ml). SO3-048 5n was isolated as a viscous yellow liquid. (227 mg, 96%). $^1$H NMR (400 MHz, cdcl$_3$) δ 7.10 (d, J=8.5 Hz, 2H), 6.80 (dd, J=8.6, 2.6 Hz, 2H), 4.91 (s, 2H), 2.53 (t, J=7.7 Hz, 2H), 1.61-1.49 (m, 2H), 1.36-1.20 (m, 6H), 0.91-0.81 (m, 3H).

SO3-064 (5o)

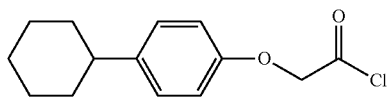

C$_{14}$H$_{17}$ClO$_2$
Exact Mass: 252.9017
Mol. Wt.: 252.7366

2-(4-Cyclohexylphenoxy)acetyl chloride (SO3-049) (5o): This compound was synthesized using the same protocol for SO1-140 5a except using 2-(4-cyclohexylphenoxy)acetic acid (4o) (200 mg, 0.85 mmol), SOCl$_2$ (5 ml) and benzene (5 ml). SO3-064 5o was isolated as a viscous yellow liquid. (198 mg, 92%). $^1$H NMR (400 MHz, CDC$_3$) δ 7.15 (d, J=8.7 Hz, 2H), 0.82 (d, J=8.8 Hz, 2H), 4.92 (s, 2H), 2.51-2.40 (m, 1H), 1.88-1.68 (m, 6H), 1.43-1.20 (m, 4H).

SO3-076 (5p)

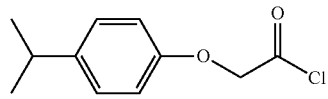

C$_{11}$H$_{13}$ClO$_2$
Exact Mass: 212.0604
Mol. Wt.: 212.6727

2-(4-Isopropylphenoxy)acetyl chloride (SO3-076) (5p): This compound was synthesized using the same protocol for SO1-140 5a except using 2-(4-isopropylphenoxy)acetic acid (4p) (260 mg, 1.34 mmol SOCl$_2$ (5 ml) and benzene (5 ml). SO3-076 5p was isolated as a viscous yellow liquid. (280 mg, 94%). $^1$H NMR (400 MHz, CDCl$_3$) δ 7.18 (d, J=8.5 Hz, 2H), 6.84 (d, J=8.7 Hz, 2H), 4.93 (s, 2H), 2.94-2.86 (m, 1H), 1.24 (d, J=6.9 Hz, 6H).

SO3-088 (5q)

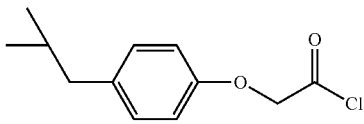

C$_{12}$H$_{15}$ClO$_2$
Exact Mass: 226.0761
Mol. Wt.: 226.6993

2-(4-Isobutylphenoxy)acetyl chloride (SO3-088) (5q): This compound was synthesized using the same protocol for SO1-140 5a except using 2-(4-isobutylphenoxy)acetic acid (4q) (127 mg, 0.61 mmol), SOCl$_2$ (5 ml) and benzene (5 ml). SO3-088 5q was isolated as a viscous yellow liquid. (131 mg, 95%). $^1$H NMR (400 MHz, CDCl$_3$) δ 7.08 (d, J=8.6 Hz, 2H), 6.81 (d, J=8.6 Hz, 2H), 4.93 (s, 2H), 2.42 (d, J=7.2 Hz, 1H), 1.89-1.69 (m, 1H), 0.89 (d, J=6.6 Hz, 6H).

SO3-078 (5r)

C$_{12}$H$_{15}$ClO$_2$
Exact Mass: 226.0761
Mol. Wt.: 226.6993

2-(4-Tert-butylphenoxy)acetyl chloride (SO3-078): This compound was synthesized using the same protocol for SO1-140 5a except using 2-(4-tert-butylphenoxy)acetic acid (4r) (200 mg, 0.96 mmol), SOCl$_2$ (5 ml) and benzene (5 ml). SO3-078 5r was isolated as a viscous yellow liquid. (207 mg, 95%). $^1$H NMR (400 MHz, CDCl$_3$) δ 7.34 (d, J=9.0 Hz, 2H), 6.84 (d, J=9.0 Hz, 2H), 4.94 (s, 2H), 1.31 (s, 9H).

SO2-169 (5s)

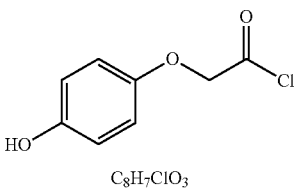

C$_8$H$_7$ClO$_3$
Exact Mass: 186.0084
Mol. Wt.: 186.5924

2-(4-Hydroxyphenoxy)acetyl chloride (SO2-169) (5s): This compound was synthesized using the same protocol for SO1-140 5a except using (4-hydroxy-phenoxy)-acetic acid (4s) (300 mg, 1.78 mmol), SOCl$_2$ (5 ml) and benzene (5 ml). SO2-169 5s was isolated as a viscous yellow liquid. (302 mg, 91%). $^1$H NMR (400 MHz, CDCl$_3$) δ 7.24 (d, J=8.6 Hz, 2H), 6.95 (d, J=8.6 Hz, 2H), 4.95 (s, 2H).

SO3-090 (7c)

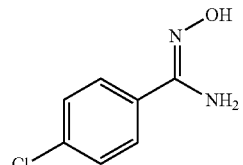

Chemical Formula: C$_7$H$_7$ClN$_2$O
Exact Mass: 170.0247
Molecular Weight: 170.5963

4-Chloro-N-hydroxy-benzamidine (SO3-090) (7c): 4-chlorobenzonitrile (1.00 g, 7.30 mmol) and hydroxylamine hydrochloride (1.02 g, 14.60 mmol) were dissolved in 7 ml of water. A solution of sodium carbonate (15.48 g, 14.60 mmol) in water (5.0 ml) was cautiously added, and the resulting solution was stirred and heated at 70° C. for 14 h. The solution was cooled to rt, saturated with sodium chloride and extracted with (4×15 ml) EtAc. The solution was dried (MgSO$_4$) and the solvent was evaporated to give the pure compound SO3-090 7c as a white solid (1.02 g, 82%). $^1$H NMR (400 MHz, CD$_3$OD) δ 7.62 (d, J=8.6 Hz, 2H), 7.39 (d, J=8.5 Hz, 2H). LC-MS (ESI+) m/z 171.04 (M+H)$^+$;

HRMS (ESI+ve) m/z calculated for $C_9H_9Cl_2N_2O_2$ (M+H)$^+$ 171.0320. found 171.0321.

SO3-099 (7e)

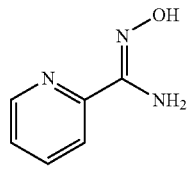

Chemical Formula: $C_6H_7N_3O$
Exact Mass: 137.0589
Molecular Weight: 137.1393

N-Hydroxy-pyridine-2-carboxamidine (SO3-099) (7e): This compound was synthesized using the same protocol for SO3-090 7c except using 2-cyanopyridine (1.24 g, 12 mmol), hydroxylamine hydrochloride (1.66 g, 24 mmol) in 12 ml water and sodium carbonate (2.54 g, 24 mmol) in 9 ml water. The compound SO3-099 7e was isolated as a white solid (1.5 g, 93%). $^1$H NMR (400 MHz, CD$_3$OD) δ 8.55 (ddd, J=4.9, 1.6, 1.0 Hz, 1H), 7.86 (dd, J=5.1, 4.0 Hz, 1H), 7.77 (ddd, J=8.0, 7.5, 1.7 Hz, 1H), 7.37 (ddd, J=7.4, 4.9, 1.2 Hz, 1H).

SO3-005 (7f)

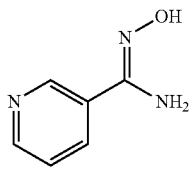

Chemical Formula: $C_6H_7N_3O$
Exact Mass: 137.0589
Molecular Weight: 137.1393

N-Hydroxy-nicotinamidine (SO3-005) (7f): This compound was synthesized using the same protocol for SO3-090 7c except using 3-cyanopyridine (0.62 g, 6.0 mmol), hydroxylamine hydrochloride (0.83 g, 12 mmol) in 6 ml of water and A solution of sodium carbonate (1.27 g, 12 mmol) in water (4.5 ml). SO3-005 7f was isolated as a white solid. (507 mg, 62%). $^1$H NMR (400 MHz, CD$_3$OD) δ 8.80 (dd, J=2.2, 0.7 Hz, 1H), 8.55 (dd, J=4.9, 1.6 Hz, 1H), 8.09-8.04 (m, 1H), 7.45 (ddd, J=8.0, 4.9, 0.7 Hz, 1H).

$^1$H NMR (400 MHz, DMSO) δ 9.82 (s, 1H), 8.84 (dd, J=2.2, 0.8 Hz, 1H), 8.54 (dd, J=4.8, 1.6 Hz, 1H), 8.01-7.97 (m, 1H), 7.39 (ddd, J=8.0, 4.8, 0.8 Hz, 1H). LC-MS (ESI+) m/z 138.06 (M+H)$^+$; HRMS (ESI+ve) m/z calculated for $C_6H_8N_3O$ (M+H)$^+$138.0662. found 138.0659.

SO3-100 (7g)

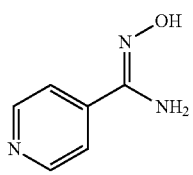

Chemical Formula: $C_6H_7N_3O$
Exact Mass: 137.0589
Molecular Weight: 137.1393

N-Hydroxy-isonicotinamidine (SO3-100) (7g) This compound was synthesized using the same protocol for SO3-090 7c except using 4-cyanopyridine (1.24 g, 12 mmol), hydroxylamine hydrochloride (1.66 g, 24 mmol) in 12 ml water and sodium carbonate (2.54 g, 24 mmol) in 9 ml water. The compound SO3-100 7g was isolated as a white solid (1.4 g, 87%). $^1$H NMR (400 MHz, CD$_3$OD) δ 8.55 (d, J=6.3 Hz, 2H), 7.68 (d, J=6.3 Hz, 2H).

SO3-068 (7h)

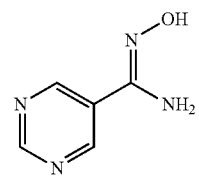

Chemical Formula: $C_5H_6N_4O$
Exact Mass: 138.0542
Molecular Weight: 138.1273

N-Hydroxy-pyrimidine-5-carboxamidine (SO3-068) (7h): This compound was synthesized using the same protocol for SO3-090 7c except using pyrimidine-5-carbonitrile (0.167 g, 1.60 mmol), hydroxylamine hydrochloride (0.22 g, 3.20 mmol) in 1.6 ml water and sodium carbonate (0.34 g, 3.20 mmol) in 1.2 ml water. The compound SO3-068 7h was isolated as a white solid (0.12 g, 55%). $^1$H NMR (400 MHz, CD$_3$OD) δ 9.16 (s, 1H), 9.03-9.01 (m, 2H).

SO3-092 (7i)

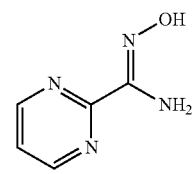

Chemical Formula: $C_5H_6N_4O$
Exact Mass: 138.0542
Molecular Weight: 138.1273

N-Hydroxy-pyrimidine-2-carboxamidine (SO3-092) (7i): This compound was synthesized using the same protocol for SO3-090 7c except using pyrimidin-2-carbonitrile (1.67 g, 16 mmol), hydroxylamine hydrochloride (2.20 g, 32 mmol) in 16 ml water and sodium carbonate (3.39 g, 32 mmol) in 12 ml water. The compound SO3-092 7i was isolated as a white solid (1.70 g, 77%). $^1$H NMR (400 MHz, DMSO) δ 10.16 (s, 1H), 8.82 (d, J=4.9 Hz, 2H), 7.48 (s, 1H), 5.82 (s, 2H).

SO3-045 (7j)

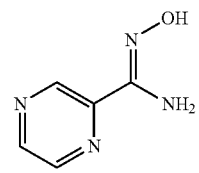

Chemical Formula: $C_5H_6N_4O$
Exact Mass: 138.0542
Molecular Weight: 138.1273

N-Hydroxy-pyrazine-2-carboxamidine (SO3-045) (7j): This compound was synthesized using the same protocol for SO3-090 7c except using pyrazine-2-carbonitrile (0.50 g, 4.80 mmol), hydroxylamine hydrochloride (0.66 g, 9.60 mmol) in 4.8 ml water and sodium carbonate (1.02 g, 9.60 mmol) 3.6 ml water. The compound SO3-045 7j was isolated as a white solid (0.54 g, 82%). ¹H NMR (400 MHz, DMSO) δ 10.22 (s, 1H), 9.03 (d, J=1.4 Hz, 1H), 8.64-8.58 (m, 2H), 5.94 (s, 2H).

SO3-004 (8a)

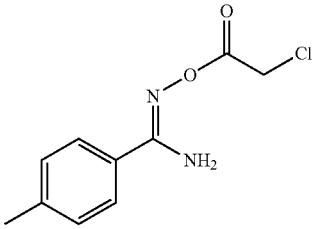

Chemical Formula: $C_{10}H_{11}ClN_2O_2$
Exact Mass: 226.0509
Molecular Weight: 226.6595

(Z)—N'-(2-chloroacetoxy)-4-methylbenzimidamide (SO3-004) (8a): To a solution of N-hydroxy-4-methylbenzamidine (0.50 g, 3.30 mmol) in acetone (20 ml) chloroacetyl chloride (0.37 g, 3.30 mmol) was added slowly and the mixture was stirred at rt for 30 min. Acetone was evaporated and the residue was washed with sodium bicarbonate solution (5 ml) and water (10 ml). The compound SO3-004 8a was dried and obtained as a white solid. (0.70 g, 88%). ¹H NMR (400 MHz, DMSO) δ 7.05 (d, J=8.6 Hz, 2H), 6.76 (d, J=8.6 Hz, 2H), 4.58 (s, 2H), 2.20 (s, 3H).

SO3-085 (8b)

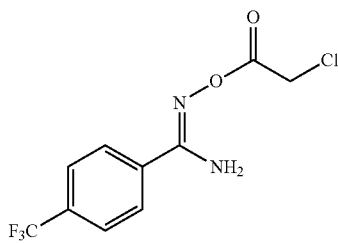

Chemical Formula: $C_{10}H_8ClF_3N_2O_2$
Exact Mass: 280.0226
Molecular Weight: 280.6309

(Z)—N'-(2-chloroacetoxy)-4-(trifluoromethyl)benzimidamide (SO3-085) (8b): This compound was synthesized using the same protocol for SO3-004 8a except using 4-trifluoromethyl-N-hydroxy-benzamidine (100 mg, 4.89 mmol) and chloroacetyl chloride (55 mg, 4.89 mmol). The compound SO3-085 8b was isolated as a yellow solid (120 mg, 88%). ¹H NMR (400 MHz, CD₃OD) δ 7.92 (d, J=8.2 Hz, 2H), 7.76 (d, J=8.2 Hz, 2H), 4.40 (s, 2H). LC-MS (ESI+) m/z 281.03 (M+H)⁺; HRMS (ESI+ve) m/z calculated for $C_{10}H_9ClF_3N_2O_2$ (M+Na)⁺303.0119. found 303.0117.

SO2-053 (8c)

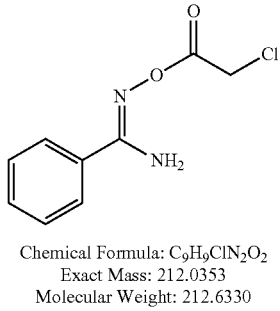 [SMILES: N/C(=N\OC(=O)CCl)c1ccccc1]

Chemical Formula: $C_9H_9ClN_2O_2$
Exact Mass: 212.0353
Molecular Weight: 212.6330

(Z)—N'-(2-chloroacetoxy)benzimidamide (SO2-053) (8c): This compound was synthesized using the same protocol for SO3-004 8a except using N-hydroxy-benzamidine (7c) (100 mg, 0.73 mmol) and chloroacetyl chloride (83 mg, 0.73 mmol). The compound SO2-053 8c was isolated as a white solid (136 mg, 87%). ¹H NMR (400 MHz, CD₃OD) δ 7.76-7.69 (m, 2H), 7.56-7.40 (m, 3H), 4.39 (s, 2H).

SO3-091 (8d)

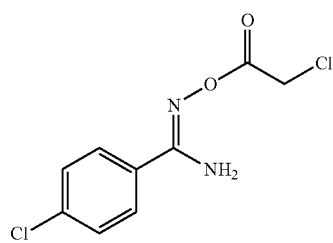

Chemical Formula: $C_9H_8Cl_2N_2O_2$
Exact Mass: 245.9963
Molecular Weight: 247.0780

(Z)—N'-(2-chloroacetoxy)-4-chlorobenzimidamide (SO3-091) (8d): This compound was synthesized using the same protocol for SO3-004 8a except using 4-chloro-N-hydroxy-benzamidine (220 mg, 12.89 mmol) and chloroacetyl chloride (146 mg, 4.89 mmol). The compound SO3-091 8d was isolated as a yellow solid (260 mg, 81%). ¹H NMR (400 MHz, CD₃OD) δ 7.71 (d, J=7.6 Hz, 1H), 7.45 (d, J=7.8 Hz, 1H), 4.38 (s, 1H). LC-MS (ESI+) m/z 246.99 (M+H)⁺; HRMS (ESI+ve) m/z calculated for $C_9H_8Cl_2N_2O_2Na$ (M+Na)⁺268.9855. found 268.99855.

SO3-097 (8e)

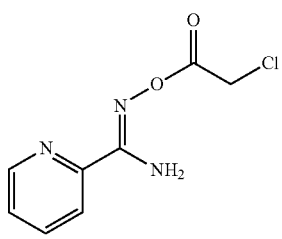

Chemical Formula: $C_8H_8ClN_3O_2$
Exact Mass: 213.0305
Molecular Weight: 213.6210

(Z)—N'-(2-chloroacetoxy)picolinimidamide (SO3-097) (8e): This compound was synthesized using the same protocol for SO3-004 except using (Z)—N'-hydroxypicolinimidamide (7e) (130 mg, 0.95 mmol) and chloroacetyl chloride (107 mg, 0.95 mmol). The compound SO3-097 8e was isolated as a white solid (185 mg, 91%). ¹H NMR (400 MHz, CD₃OD) δ 8.63 (d, J=4.3 Hz, 1H), 8.08 (d, J=8.0 Hz, 1H), 7.87 (td, J=7.8, 1.7 Hz, 1H), 7.49 (ddd, J=7.5, 4.8, 1.0 Hz, 1H), 4.43 (s, 2H).

SO2-098 (8f)

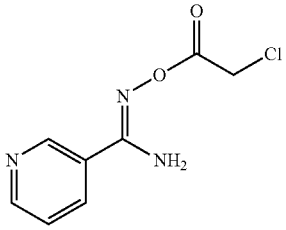

Chemical Formula: $C_8H_8ClN_3O_2$
Exact Mass: 213.0305
Molecular Weight: 213.6210

(Z)—N'-(2-chloroacetoxy)nicotinimidamide (SO2-098) (8f): This compound was synthesized using the same protocol for SO3-004 8a except using N-hydroxy-nicotinamidine (7f) (125 mg, 0.91 mmol) and chloroacetyl chloride (136 mg, 1.20 mmol). The compound SO2-098 8f was isolated as a yellow solid (161 mg, 83%). $^1$H NMR (400 MHz, CD$_3$OD) δ 8.91 (dd, J=2.2, 0.8 Hz, 1H), 8.67 (dd, J=5.0, 1.6 Hz, 1H), 8.20 (ddd, J=8.0, 2.2, 1.6 Hz, 1H), 7.60-7.44 (m, 1H), 4.40 (s, 2H). LC-MS (ESI+) m/z 214.03 (M+H)$^+$; HRMS (ESI+ve) m/z calculated for C$_8$H$_9$ClN$_3$O$_2$ (M+H)$^+$214.0378. found 214.0389.

SO3-098 (8g)

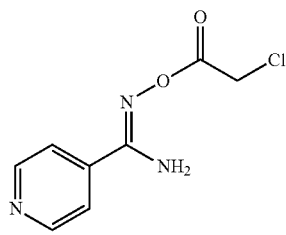

Chemical Formula: C$_8$H$_8$ClN$_3$O$_2$
Exact Mass: 213.0305
Molecular Weight: 213.6210

(Z)—N'-(2-chloroacetoxy)isonicotinimidamide (SO3-098) (8g): This compound was synthesized using the same protocol for SO3-004 8a except using (Z)—N'-(2-chloroacetoxy)picolinimidamide (7g) (200 mg, 1.46 mmol) and chloro acetyl chloride (165 mg, 1.46 mmol). The compound SO3-098 8g was isolated as a yellow solid (274 mg, 88%). $^1$H NMR (400 MHz, CD$_3$OD) δ 8.55 (d, J=4.9 Hz, 2H), 7.68 (d, J=5.2 Hz, 2H), 4.19 (s, 2H). LC-MS (ESI+) m/z 214.04 (M+H)$^+$; HRMS (ESI+ve) m/z calculated for C$_8$H$_9$ClN$_3$O$_2$ (M+Na)$^+$236.0197. found 236.0186.

SO3-069 (8h)

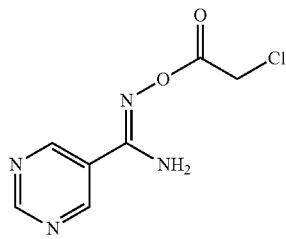

Chemical Formula: C$_7$H$_7$ClN$_4$O$_2$
Exact Mass: 214.0258
Molecular Weight: 214.6091

(Z)—N'-(2-chloroacetoxy)pyrimidine-5-carboximidamide (SO3-069) (8h): This compound was synthesized using the same protocol for SO3-004 8a except using N-hydroxy-pyrimidine-5-carboxamidine (7h) (110 mg, 0.80 mmol) and chloroacetyl chloride (90 mg, 0.80 mmol). The compound SO3-069 8h was isolated as a white solid (1.58 g, 92%). $^1$H NMR (400 MHz, CD$_3$OD) δ 9.26 (s, 1H), 9.11 (s, 2H), 4.41 (s, 2H).

SO3-093 (8i)

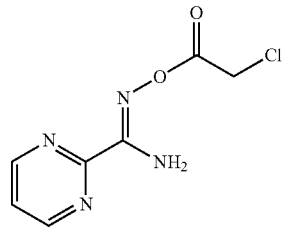

Chemical Formula: C$_7$H$_7$ClN$_4$O$_2$
Exact Mass: 214.0258
Molecular Weight: 214.6091

(Z)—N'-(2-chloroacetoxy)pyrimidine-2-carboximidamide (SO3-093) (8i): This compound was synthesized using the same protocol for SO3-004 8a except using N-hydroxy-pyrimidine-2-carboxamidine (7i) (80 mg, 5.79 mmol) and chloroacetyl chloride (65 mg, 5.79 mmol). The compound SO3-093 8i was isolated as a white solid (115 mg, 90%). $^1$H NMR (400 MHz, CD$_3$OD) δ 9.03 (d, J=4.9 Hz, 2H), 7.78 (d, J=4.9 Hz, 1H), 4.19 (s, 2H).

SO3-047 (8j)

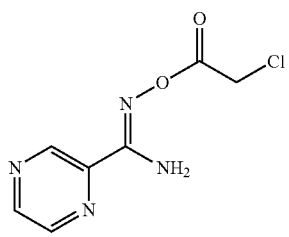

Chemical Formula: C$_7$H$_7$ClN$_4$O$_2$
Exact Mass: 214.0258
Molecular Weight: 214.6091

(Z)—N'-(2-chloroacetoxy)pyrazine-2-carboximidamide (SO3-047) (8j): This compound was synthesized using the same protocol for SO3-004 8a except using (Z)—N'-hydroxypyrazine-2-carboximidamide (7j) (0.54 g, 3.90 mmol) and chloroacetyl chloride (0.44 g, 3.90 mmol). The compound SO3-047 8j was isolated as a brown solid (0.76 g, 85%). $^1$H NMR (400 MHz, CD$_3$OD) δ 9.27 (d, J=1.2 Hz, 1H), 8.73-8.66 (m, 2H), 4.44 (s, 2H). LC-MS (ESI+) m/z 232.04 (M+NH4)$^+$; HRMS (ESI+ve) m/z calculated for C$_7$H$_7$ClN$_4$O$_2$(M+Na)$^+$237.0150. found 237.01401.

SO1-141 (9a)

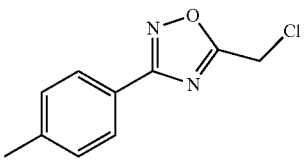

Chemical Formula: C$_{10}$H$_9$ClN$_2$O
Exact Mass: 208.0403
Molecular Weight: 208.6443

5-Chloromethyl-3-p-tolyl-[1,2,4]oxadiazole (SO1-141) (9a): (Z)—N'-(2-chloropropanoyloxy)benzimidamide (8a)

(400 mg, 1.76 mmol) was refluxed in toluene (20 ml) along with 4A° molecular sieves for 2 hours. The reaction mixture was concentrated under vacuum to provide a crude residue. The crude residue was triturated with diethyl ether to afford 5-(chloromethyl)-3-phenyl-1,2,4-oxadiazole (9a) as a pale yellow solid. (323 mg, 82%). $^1$H NMR (400 MHz, CDCl$_3$) δ 7.95 (d, J=8.2 Hz, 2H), 7.27 (dd, J=7.9, 0.5 Hz, 2H), 4.72 (s, 2H), 2.40 (s, 3H).
SO1-149-b2 (9b)

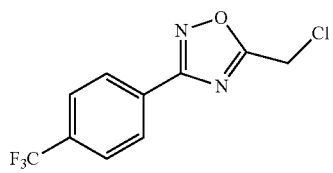

Chemical Formula: C$_{10}$H$_6$ClF$_3$N$_2$O
Exact Mass: 262.0121
Molecular Weight: 262.6156

5-Chloromethyl-3-(4-trifluoromethylphenyl)[1,2,4]oxadiazole (SO1-149) (9b): This compound was synthesized using the same protocol for SO1-141 9a except using (Z)—N'-(2-chloroacetoxy)-4-(trifluoromethyl)benzimidamide (8b) (150 mg, 0.53 mmol) The compound SO1-149-b2 9b was isolated as a white solid (128 mg, 91%). $^1$H NMR (400 MHz, CD$_3$OD) δ 7.92 (d, J=8.1 Hz, 2H), 7.76 (d, J=8.3 Hz, 2H), 4.71 (s, 2H).
SO1-167 (9c)

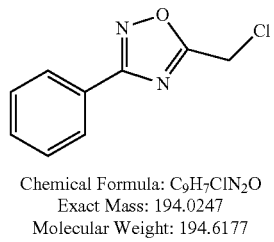 [SMILES: ClCc1nc(-c2ccccc2)no1]

Chemical Formula: C$_9$H$_7$ClN$_2$O
Exact Mass: 194.0247
Molecular Weight: 194.6177

5-Chloromethyl-3-phenyl-[1,2,4]oxadiazole (SO1-167) (9c): This compound was synthesized using the same protocol for SO1-141 9a except using (Z)—N'-(2-chloroacetoxy)benzimidamide (8c) (300 mg, 1.33 mmol) was refluxed in toluene (20 ml) The compound 5-chloromethyl-3-phenyl-[1,2,4]oxadiazole (9c) was isolated as a yellow solid. (238 mg, 92%). $^1$H NMR (400 MHz, CDCl$_3$) δ 8.06 (d, J=8.0 Hz, 2H), 7.52-7.40 (m, 2H), 4.74 (s, 2H).
SO1-153-b2 (9d)

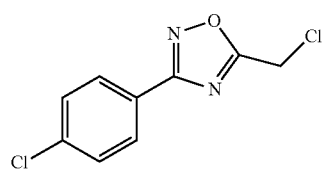

Chemical Formula: C$_9$H$_6$Cl$_2$N$_2$O
Exact Mass: 227.9857
Molecular Weight: 229.0627

5-Chloromethyl-3-(4-chloro-phenyl)-[1,2,4]oxadiazole (SO1-153-b2) (9d): This compound was synthesized using the same protocol for SO1-141 9a except using (Z)—N'-(2-chloroacetoxy)-4-chlorobenzimidamide (8d) (200 mg, 0.81 mmol) The compound SO1-153-b2 (9d) was isolated as a white solid (154 mg, 83%). $^1$H NMR (400 MHz, CDCl$_3$) δ 8.03 (d, J=8.7 Hz, 2H), 7.47 (d, J=8.7 Hz, 2H), 4.75 (s, 2H).
SO2-065 (9e)

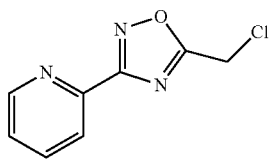

Chemical Formula: C$_8$H$_6$ClN$_3$O
Exact Mass: 195.0199
Molecular Weight: 195.6057

5-(Chloromethyl)-3-(pyridin-2-yl)-1,2,4-oxadiazole (SO2-065) (9e): This compound was synthesized using the same protocol for SO1-141 9a except using (Z)—N'-(2-chloroacetoxy)picolinimidamide (8e) (100 mg, 0.47 mmol) The compound SO2-065 9e was isolated as a white solid (86 mg, 94%). $^1$H NMR (400 MHz, CDCl$_3$) δ 8.81 (ddd, J=4.8, 1.6, 1.0 Hz, 1H), 8.14 (dt, J=7.9, 1.1 Hz, 1H), 7.87 (td, J=7.8, 1.8 Hz, 1H), 7.46 (ddd, J=7.7, 4.8, 1.2 Hz, 1H), 4.79 (s, 2H). LC-MS (ESI+) m/z 196.03 (M+H)$^+$; HRMS (ESI+ve) m/z calculated for C$_8$H$_7$ClN$_3$O (M+H)$^+$ 196.0272. found 196.0264.
SO2-055 (9f)

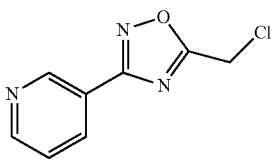

Chemical Formula: C$_8$H$_6$ClN$_3$O
Exact Mass: 195.0199
Molecular Weight: 195.6057

5-(Chloromethyl)-3-(pyridin-3-yl)-1,2,4-oxadiazole (SO2-055) (9f): This compound was synthesized using the same protocol for SO1-141 9a except using (Z)—N'-(2-chloroacetoxy)nicotinimidamide (80 (100 mg, 0.47 mmol) The compound SO2-055 9f was isolated as a yellow solid (83 mg, 90%). $^1$H NMR (400 MHz, CDCl$_3$) δ 9.25 (dd, J=2.2, 0.9 Hz, 1H), 8.70 (dd, J=4.9, 1.7 Hz, 1H), 8.38-8.24 (m, 1H), 7.38 (ddd, J=8.0, 4.9, 0.9 Hz, 1H). LC-MS (ESI+) m/z 196.03 (M+H)$^+$; HRMS (ESI+ve) m/z calculated for C$_8$H$_7$ClN$_3$O (M+H)$^+$ 196.0272. found 196.0269.
SO2-063 (9g)

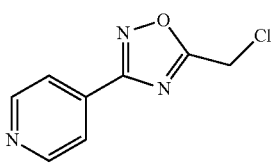

Chemical Formula: C$_8$H$_6$ClN$_3$O
Exact Mass: 195.0199
Molecular Weight: 195.6057

5-(Chloromethyl)-3-(pyridin-4-yl)-1,2,4-oxadiazole (SO2-063) (9g): This compound was synthesized using the same protocol for SO1-141 9a except using (Z)—N'-(2-chloroacetoxy)isonicotinimidamide (8g) (100 mg, 0.47 mmol) The compound SO2-063 9g was isolated as a yellow solid (77 mg, 84%). ¹H NMR (400 MHz, CDCl₃) δ 8.79 (dd, J=5.3, 0.7 Hz, 2H), 7.94 (d, J=6.1 Hz, 2H), 4.77 (s, 2H).
SO3-055 (28)

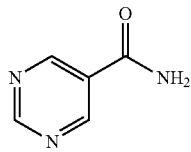

Chemical Formula: C₅H₅N₃O
Exact Mass: 123.0433
Molecular Weight: 123.1127

Pyrimidine-5-carboxamide (SO3-055): A mixture of pyrimidine-5-carboxylic acid ethyl ester (1.57 g, 10.32 mmol) and NH₄OH (1.2 ml) were heated in a sealed tube at 50° C. for 14 h. The solid precipitated was filtered off (300 mg) and filtrate then concentrated and the residue was stirred in ethanol/ethyl acetate (v/v 1/4, 13 ml) at rt for 2 h. The white precipitate was collected by filtration and dried to give the final compound SO3-055 as a white solid. (525 mg, 65%). ¹H NMR (400 MHz, DMSO) δ 9.29 (s, 1H), 9.15 (s, 2H), 8.31 (brs, 1H), 7.82 (brs, 1H).
SO3-067 (29)

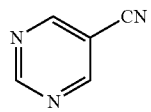

Chemical Formula: C₅H₃N₃
Exact Mass: 105.0327
Molecular Weight: 105.0974

Pyrimidine-5-carbonitrile (SO3-067): To a suspension of pyrimidine-5-carboxamide (SO3-055) (262 mg, 2.12 mmol) and triethyl amine (481 mg, 4.24 mmol) in anhydrous dichoromethane (15 ml) was slowly added a solution of trifluoroacetic anhydride (0.36 ml in 4 ml dichloromethane) at 0° C. The reaction mixture was stirred at 0° C. to RT for 2 h. and quenched with water (2 ml) and washed with NaOH (1 N, 5 ml) and brine (2×5 ml). Organic solvent was dried (MgSO₄) and evaporated at less than 30° C. to provide SO3-067 as a pale yellow solid. (174 mg, 78%). ¹H NMR (400 MHz, DMSO) δ 9.44 (s, 1H), 9.31 (s, 2H).
SO3-070 (9h)

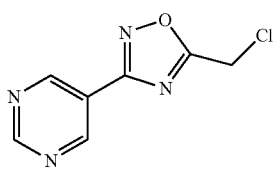

Chemical Formula: C₇H₅ClN₄O
Exact Mass: 196.0152
Molecular Weight: 196.5938

5-(Chloromethyl)-3-(pyrimidin-5-yl)-1,2,4-oxadiazole (SO3-070) (9h): This compound was synthesized using the same protocol for SO1-141 9a except using (Z)—N'-(2-chloroacetoxy)pyrimidine-5-carboximidamide (8h) (140 mg, 0.65 mmol) The compound SO3-070 9h was isolated as a yellow solid (112 mg, 87%). ¹H NMR (400 MHz, CDCl₃) δ 9.61-9.17 (m, 3H), 4.78 (s, 2H).
SO3-094 (9i)

Chemical Formula: C₇H₅ClN₄O
Exact Mass: 196.0152
Molecular Weight: 196.5938

5-(Chloromethyl)-3-(pyrimidin-2-yl)-1,2,4-oxadiazole (SO3-094) (9i): This compound was synthesized using the same protocol for SO1-141 9a except using (Z)—N'-(2-chloroacetoxy)pyrimidine-2-carboximidamide (8i) (500 mg, 2.33 mmol) The compound SO3-094 9i was isolated as a white solid (389 mg, 85%). ¹H NMR (400 MHz, CDCl₃) δ 8.96 (d, J=4.9 Hz, 2H), 7.47 (t, J=4.9 Hz, 1H), 4.80 (s, 2H). LC-MS (ESI+) m/z 197.03 (M+H)⁺; HRMS (ESI+ve) m/z calculated for C₇H₆ClN₄O (M+H)⁺197.0225. found 197.0224.
SO3-052 (9j)

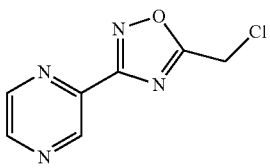

Chemical Formula: C₇H₅ClN₄O
Exact Mass: 196.0152
Molecular Weight: 196.5938

5-(Chloromethyl)-3-(pyrazin-2-yl)-1,2,4-oxadiazole (SO3-052) (9j): This compound was synthesized using the same protocol for SO1-141 9a except using (Z)—N'-(2-chloroacetoxy)pyrazine-2-carboximidamide (8j) (200 mg, 0.93 mmol) The compound SO3-052 9j was isolated as a white solid (150 mg, 82%). ¹H NMR (400 MHz, CDCl₃) δ 9.32 (d, J=1.5 Hz, 1H), 8.72 (dd, J=2.4, 1.6 Hz, 1H), 8.70 (d, J=2.5 Hz, 1H), 7.20 (s, 1H), 4.75 (s, 2H).
LC-MS (ESI+) m/z 197.02 (M+H)⁺; HRMS (ESI+ve) m/z calculated for C₇H₆ClN₄O (M+H)⁺196.0225. found 196.0223.
SO1-142 (10a)

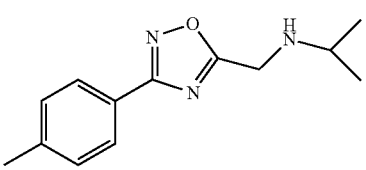

Chemical Formula: C₁₃H₁₇N₃O
Exact Mass: 231.1372
Molecular Weight: 231.2936

Isopropyl-(3-p-tolyl-[1,2,4]oxadiazol-5-ylmethyl)-amine (SO1-142) (10a): To a solution of 5-chloromethyl-3-p-tolyl-

[1,2,4]oxadiazole (9a) (300 mg, 1.44 mmol) in 20 mL acetonitrile was added diisopropyl amine (0.17 g, 2.88 mmol) and potassium carbonate (994 mg, 7.2 mmol) and the mixture was refluxed for 30 min. Acetonitrile was evaporated and the residue was dissolved in ethyl acetate and washed with water. Organic solvent was dried (MgSO$_4$) and evaporated to give the pure compound SO1-142 10a as a white solid (303 mg, 91%). $^1$H NMR (400 MHz, CDCl$_3$) δ 7.94 (d, J=8.2 Hz, 2H), 7.25 (dd, J=7.8, 0.7 Hz, 2H), 4.08 (s, 2H), 2.92 (hept, J=6.2 Hz, 1H), 2.38 (s, 3H), 1.10 (d, J=6.2 Hz, 6H).

SO1-155 (10b)

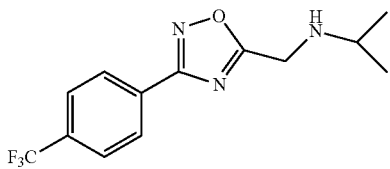

Chemical Formula: C$_{13}$H$_{13}$F$_3$N$_3$O
Exact Mass: 285.1089
Molecular Weight: 285.2650

Isopropyl-(3-(4-trifluoromethyl-phenyl)-[1,2,4]oxadiazol-5-ylmethyl)-amine (SO1-155) (10b): This compound was synthesized using the same protocol for SO1-142 10a except using 5-chloromethyl-3-(4-trifluoromethylphenyl)-[1,2,4]oxadiazole (9b) (100 mg, 0.38 mmol), isopropyl amine (45 mg, 0.76 mmol) and potassium carbonate (262 mg, 1.90 mmol). The compound SO1-155 10b was isolated as a viscous yellow liquid (997 mg, 92%). $^1$H NMR (400 MHz, CDCl$_3$) δ 8.21 (dd, J=8.8, 0.7 Hz, 2H), 7.74 (dd, J=8.7, 0.6 Hz, 2H), 4.14 (s, 2H), 2.93 (hept, J=6.2 Hz, 1H), 1.13 (d, J=6.2 Hz, 6H).

SO1-168 (10c)

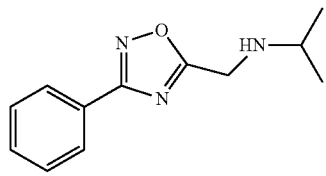

Chemical Formula: C$_{12}$H$_{15}$N$_3$O
Exact Mass: 217.1215
Molecular Weight: 217.2670

Isopropyl-(3-phenyl-[1,2,4]oxadiazol-5-ylmethyl)-amine (SO1-168) (10c): This compound was synthesized using the same protocol for SO1-142 10a except using 5-chloromethyl-3-(4-trifluoromethylphenyl)-[1,2,4]oxadiazole (9c) (100 mg, 0.38 mmol), isopropyl amine (45 mg, 0.76 mmol) and potassium carbonate (262 mg, 1.90 mmol). The compound SO1-168 10c was isolated as a white solid (349 mg, 98%). $^1$H NMR (400 MHz, CDCl$_3$) δ 8.15-8.00 (m, 2H), 7.59-7.32 (m, 3H), 4.10 (s, 2H), 2.90 (hept, J=6.2 Hz, 1H), 1.10 (d, J=6.2 Hz, 6H). LC-MS (ESI+) m/z 218.13 (M+H)$^+$; HRMS (ESI+ve) m/z calculated for C$_{12}$H$_{16}$N$_3$O (M+H)$^+$ 218.1288. found 218.1286.

SO1-156 (10d)

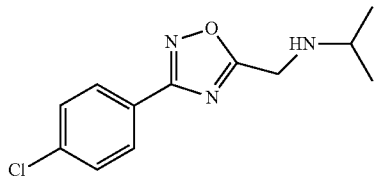

Chemical Formula: C$_{12}$H$_{14}$ClN$_3$O
Exact Mass: 251.0825
Molecular Weight: 251.7121

[3-(4-Chloro-phenyl)-[1,2,4]oxadiazol-5-yl)methyl]isopropyl-amine SO1-156 (10d): This compound was synthesized using the same protocol for SO1-142 10a except using 5-chloromethyl-3-(4-chloro-phenyl)-[1,2,4]oxadiazole (9d) (290 mg, 1.27 mmol), isopropyl amine (150 mg, 2.53 mmol) and potassium carbonate (283 mg, 6.35 mmol). The pure compound 10d was isolated as a pale yellow solid. (75 mg, 84%). $^1$H NMR (400 MHz, CDCl$_3$) δ 7.99 (d, J=8.6 Hz, 2H), 7.42 (d, J=8.5 Hz, 2H), 4.09 (s, 2H), 2.89 (hept, J=6.2 Hz, 1H), 1.10 (d, J=6.2 Hz, 6H).

LC-MS (ESI+) m/z 252.08 (M+H)$^+$; HRMS (ESI+ve) m/z calculated for C$_{12}$H$_{15}$ClN$_3$O (M+H)$^+$ 252.0898. found 252.0887.

LC-MS (ESI+) m/z 286.13 (M+H)$^+$; HRMS (ESI+ve) m/z calculated for C$_{13}$H$_{15}$ClF$_3$N$_3$O (M+H)$^+$ 286.1162. found 286.1156.

SO2-071 (10e)

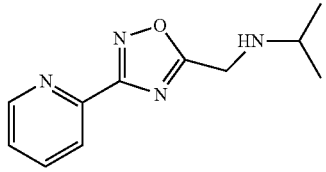

Chemical Formula: C$_{11}$H$_{14}$N$_4$O
Exact Mass: 218.1168
Molecular Weight: 218.2551

N-((3-(pyridin-2-yl)-1,2,4-oxadiazol-5-yl)methyl)propan-2-amine (SO2-071) (10e): This compound was synthesized using the same protocol for SO1-142 10a except using 5-(chloromethyl)-3-(pyridin-2-yl)-1,2,4-oxadiazole (9e) (75 mg, 0.38 mmol), isopropyl amine (34 mg, 0.58 mmol) and potassium carbonate (262 mg, 1.90 mmol). The compound SO2-071 10e was isolated as a yellow solid (75 mg, 89%). $^1$H NMR (400 MHz, CDCl$_3$) δ 8.80 (ddd, J=4.8, 1.7, 0.9 Hz, 1H), 8.13 (d, J=7.9 Hz, 1H), 7.85 (td, J=7.8, 1.8 Hz, 1H), 7.43 (ddd, J=7.6, 4.8, 1.2 Hz, 1H), 4.15 (s, 2H), 2.91 (hept, J=6.2 Hz, 1H), 1.11 (d, J=6.2 Hz, 6H).

LC-MS (ESI+) m/z 219.13 (M+H)⁺; HRMS (ESI+ve) m/z calculated for $C_{11}H_{15}N_4O$ (M+H)⁺219.1240. found 219.1244.

SO2-060 (10f)

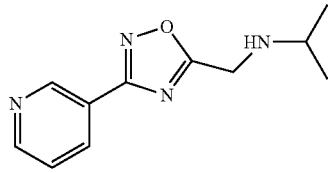

Chemical Formula: $C_{11}H_{14}N_4O$
Exact Mass: 218.1168
Molecular Weight: 218.2551

N-((3-(pyridin-3-yl)-1,2,4-oxadiazol-5-yl)methyl)propan-2-amine (SO2-060) (10f: This compound was synthesized using the same protocol for SO1-142 10a except using 5-(chloromethyl)-3-(pyridin-3-yl)-1,2,4-oxadiazole (90 (80 mg, 0.41 mmol), isopropyl amine (48 mg, 0.82 mmol) and potassium carbonate (283 mg, 2.05 mmol). The pure compound SO2-060 10f was isolated as a pale yellow solid. (75 mg, 84%). ¹H NMR (400 MHz, CDCl₃) δ 9.33-9.25 (m, 1H), 8.73 (dd, J=4.9, 1.7 Hz, 1H), 8.34 (dt, J=8.0, 1.9 Hz, 1H), 7.41 (ddd, J=8.0, 4.9, 0.8 Hz, 1H), 4.13 (s, 2H), 2.91 (hept, J=6.2 Hz, 1H), 1.12 (d, J=6.2 Hz, 6H). LC-MS (ESI+) m/z 219.13 (M+H)⁺; HRMS (ESI+ve) m/z calculated for $C_{11}H_{15}N_4O$ (M+H)⁺219.1240. found 219.1241.

SO2-064 (10g)

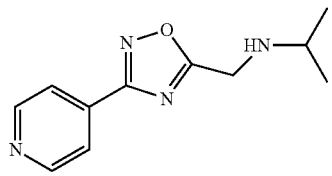

Chemical Formula: $C_{11}H_{14}N_4O$
Exact Mass: 218.1168
Molecular Weight: 218.2551

N-((3-(pyridin-4-yl)-1,2,4-oxadiazol-5-yl)methyl)propan-2-amine (SO2-064) (10g): This compound was synthesized using the same protocol for SO1-142 10a except using 5-(chloromethyl)-3-(pyridin-4-yl)-1,2,4-oxadiazole (9g) (26 mg, 0.13 mmol), isopropyl amine (15 mg, 0.26 mmol) and potassium carbonate (90 mg, 0.65 mmol). The compound SO2-064 10g was isolated as a pale yellow solid (23 mg, 81%). ¹H NMR (400 MHz, CDCl₃) δ 8.75 (d, J=6.0 Hz, 2H), 7.92 (d, J=6.1 Hz, 2H), 4.12 (s, 2H), 2.91 (hept, J=6.2 Hz, 1H), 1.10 (d, J=6.2 Hz, 6H).

LC-MS (ESI+) m/z 219.12 (M+H)⁺; HRMS (ESI+ve) m/z calculated for $C_{11}H_{15}N_4O$ (M+H)⁺219.1240. found 219.1251.

SO3-071 (10h)

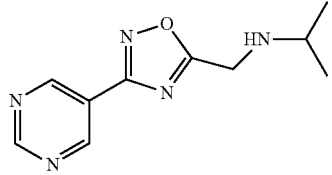

Chemical Formula: $C_{10}H_{13}N_5O$
Exact Mass: 219.1120
Molecular Weight: 219.2431

N-((3-(pyrimidin-5-yl)-1,2,4-oxadiazol-5-yl)methyl)propan-2-amine (SO2-071) (10h): This compound was synthesized using the same protocol for SO1-142 10a except using 5-(chloromethyl)-3-(pyrimidin-5-yl)-1,2,4-oxadiazole (9h) (80 mg, 0.41 mmol), isopropyl amine (49 mg, 0.82 mmol) and potassium carbonate (283 mg, 2.05 mmol). The compound SO3-071 10h was isolated as a yellow solid (289 mg, 88%). ¹H NMR (400 MHz, CDCl₃) δ 9.33 (d, J=0.7 Hz, 2H), 9.29 (s, 1H), 4.10 (d, J=0.6 Hz, 2H), 2.86 (hept, J=6.2 Hz, 1H), 1.07 (dd, J=6.2, 0.7 Hz, 6H). LC-MS (ESI+) m/z 220.13 (M+H)⁺; HRMS (ESI+ve) m/z calculated for $C_{10}H_{14}N_5O$ (M+H)⁺220.1193. found 220.1213.

SO3-095 (10i)

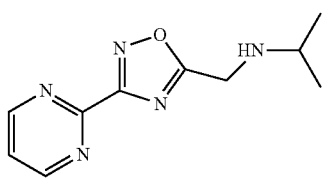

Chemical Formula: $C_{10}H_{13}N_5O$
Exact Mass: 219.1120
Molecular Weight: 219.2431

N-((3-(pyrimidin-2-yl)-1,2,4-oxadiazol-5-yl)methyl)propan-2-amine (SO3-095) (10i): This compound was synthesized using the same protocol for SO1-142 10a except using 5-(chloromethyl)-3-(pyrimidin-2-yl)-1,2,4-oxadiazole (9i) (300 mg, 1.53 mmol), isopropyl amine (180 mg, 3.05 mmol) and potassium carbonate (1058 mg, 7.65 mmol). The compound SO3-095 10i was isolated as a yellow solid (289 mg, 86%). ¹H NMR (400 MHz, CDCl₃) δ 8.89 (d, J=4.9 Hz, 2H), 7.40 (t, J=4.9 Hz, 1H), 4.12 (s, 2H), 2.81 (hept, J=6.2 Hz, 1H), 1.03 (d, J=6.2 Hz, 6H). LC-MS (ESI+) m/z 220.11 (M+H)⁺; HRMS (ESI+ve) m/z calculated for $C_{10}H_{14}N_5O$ (M+H)⁺220.1193. found 220.1193.

SO3-053 (10j)

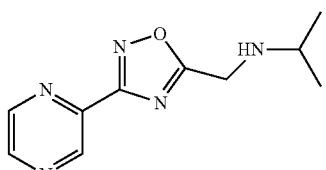

Chemical Formula: $C_{10}H_{13}N_5O$
Exact Mass: 219.1120
Molecular Weight: 219.2431

N-((3-(pyrazin-2-yl)-1,2,4-oxadiazol-5-yl)methyl)propan-2-amine (SO2-071) (10j): This compound was synthesized using the same protocol for SO1-142 10a except using 5-(chloromethyl)-3-(pyrazin-2-yl)-1,2,4-oxadiazole (9j) (150 mg, 0.76 mmol), isopropyl amine (90 mg, 1.52 mmol) and potassium carbonate (524 mg, 3.80 mmol). The compound SO2-071 10j was isolated as a yellow viscous liquid (150 mg, 90%). ¹H NMR (400 MHz, CDCl₃) δ 9.37 (d, J=1.4 Hz, 1H), 8.87-8.54 (m, 2H), 4.18 (s, 2H), 2.91 (hept, J=6.2 Hz, 1H), 1.12 (d, J=6.2 Hz, 6H). LC-MS (ESI+) m/z 220.13 (M+H)+; HRMS (ESI+ve) m/z calculated for C10H14N5O (M+H)+220.1193. found 220.1198.
SO1-183 (10k)

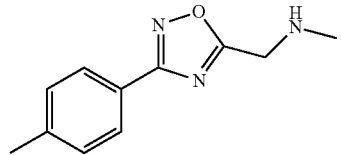

Chemical Formula: C11H13N3O
Exact Mass: 203.1059
Molecular Weight: 203.2404

Methyl-(3-p-tolyl-[1,2,4]oxadiazol-5-ylmethyl)-amine (SO1-183) (10k): This compound was synthesized using the same protocol for SO1-142 10a except using 5-chloromethyl-3-p-tolyl-[1,2,4]oxadiazole (8a) (85 mg, 0.41 mmol) and methyl amine (1 ml from 40% solution in water) and potassium carbonate (282 mg, 2.04 mmol). The compound SO1-183 10k was obtained as a yellow viscous liquid (90 mg, 95%).

$^1$H NMR (400 MHz, CDCl$_3$) δ 7.97 (d, J=8.2 Hz, 2H), 7.29 (d, J=7.9 Hz, 2H), 4.07 (s, 2H), 2.55 (s, 3H), 2.41 (s, 3H).

LC-MS (ESI+) m/z 204.12 (M+H)+; HRMS (ESI+ve) m/z calculated for C11H14N3O (M+H)+204.1131. found 204.1141.

SO2-008 (10l)

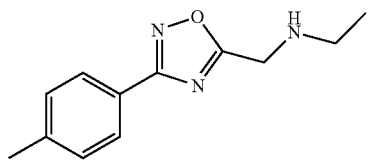

Chemical Formula: C12H15N3O
Exact Mass: 217.1215
Molecular Weight: 217.2670

Ethyl-(3-p-tolyl-[1,2,4]oxadiazol-5-ylmethyl)-amine (SO2-008) (10l): This compound was synthesized using the same protocol for SO1-142 10a except using 5-chloromethyl-3-p-tolyl-[1,2,4]oxadiazole (8a) (80 mg, 0.38 mmol) and ethyl amine (1 ml from 40% solution in water) and potassium carbonate (265 mg, 1.92 mmol). The compound SO2-008 10l was obtained as a yellow viscous liquid (73 mg, 88%). $^1$H NMR (400 MHz, CDCl$_3$) δ 7.96 (d, J=8.2 Hz, 2H), 7.28 (d, J=8.2 Hz, 2H), 4.11 (s, 2H), 2.77 (q, J=7.1 Hz, 2H), 2.41 (s, 3H), 1.16 (t, J=7.1 Hz, 3H). LC-MS (ESI+) m/z 218.13 (M+H)+; HRMS (ESI+ve) m/z calculated for C12H16N3O (M+H)+218.1288. found 218.1290.

SO1-154 (10 m)

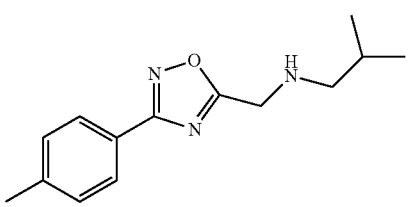

Chemical Formula: C14H19N3O
Exact Mass: 245.1528
Molecular Weight: 245.3202

Isobutyl-(3-p-tolyl-[1,2,4]oxadiazol-5-ylmethyl)-amine (SO1-154) (10m): This compound was synthesized using the same protocol for SO1-142 10a except using 5-chloromethyl-3-p-tolyl-[1,2,4]oxadiazole (8a) (100 mg, 0.48 mmol) and isobutyl amine (70 mg, 0.96 mmol) and potassium carbonate (331 mg, 2.40 mmol). The compound SO1-154 10m was obtained as a white solid (110 mg, 92%). $^1$H NMR (400 MHz, CDCl$_3$) δ 7.96 (d, J=8.1 Hz, 2H), 7.27 (d, J=7.8 Hz, 2H), 4.08 (s, 2H), 2.50 (d, J=6.8 Hz, 2H), 2.39 (s, 3H), 1.83-1.69 (m, 1H), 0.92 (d, J=6.7 Hz, 6H).

SO2-005 (10n)

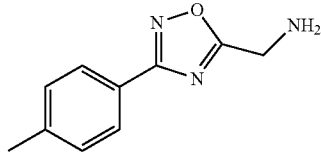

Chemical Formula: C10H11N3O
Exact Mass: 189.0902
Molecular Weight: 189.2138

C-(3-p-Tolyl-[1,2,4]oxadiazol-5-yl)-methylamine (SO2-005) (10n): A solution of 2-(3-p-tolyl-)-[1,2,4]oxadiazol-5-ylmethyl)-isoindole-1,3-dione (120 mg, 0.38 mmol) and hydrazine (20 mg, 0.45 mmol) were refluxed in 20 ml ethanol. The reaction was monitored by TLC and completed in 30 min. Ethanol was evaporated and the residue was dissolved in EtAc and washed with 1M NaOH solution (5×10 ml) and water (2×10 ml). Organic solvent was dried (MgSO$_4$) and evaporated to give the pure compound SO2-005 10n as a yellow solid (55 mg, 77%).

$^1$H NMR (400 MHz, CDCl$_3$) δ 7.89 (d, J=8.2 Hz, 2H), 7.21 (dd, J=8.0, 0.4 Hz, 2H), 4.07 (s, 2H), 2.34 (s, 3H).

SO2-067 (10o)

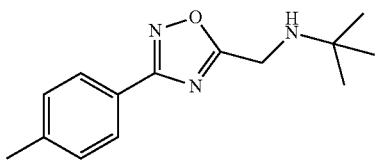

Chemical Formula: C14H19N3O
Exact Mass: 245.1528
Molecular Weight: 245.3202

Tert-butyl-(3-p-tolyl-[1,2,4]oxadiazol-5-ylmethyl)-amine (SO2-067) (10o): This compound was synthesized using the same protocol for SO1-142 10a except using 5-chloromethyl-3-p-tolyl-[1,2,4]oxadiazole (8a) (88 mg, 0.43 mmol) and tert-buyl amine (37 mg, 0.51 mmol) and potassium carbonate (298 mg, 2.15 mmol). The compound SO2-067 10o was obtained as a yellow viscous liquid (833 mg, 79%).

$^1$H NMR (400 MHz, CDCl$_3$) δ 7.97 (d, J=8.2 Hz, 2H), 7.28 (dd, J=8.5, 0.5 Hz, 2H), 4.07 (s, 2H), 2.41 (s, 3H), 1.19 (s, 9H). LC-MS (ESI+) m/z 246.15 (M+H)+; HRMS (ESI+ve) m/z calculated for C14H19N3O (M+H)+246.1601. found 246.1593.

SO3-082 (10p)

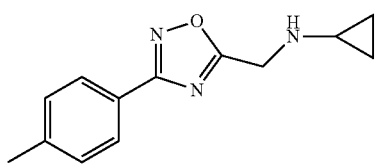 [SMILES: Cc1ccc(-c2noc(CNC3CC3)n2)cc1]

Cyclopropyl-(3-p-tolyl-[1,2,4]oxadiazol-5-ylmethyl)-amine (SO3-082) (10p): This compound was synthesized using the same protocol for SO1-142 10a except using 5-chloromethyl-3-p-tolyl-[1,2,4]oxadiazole (8a) (100 mg, 0.48 mmol) and cyclopropyl amine (55 mg, 0.96 mmol) and potassium carbonate (350 mg, 2.40 mmol). The compound SO3-082 10p was obtained as a yellow viscous liquid (1024 mg, 93%).

$^1$H NMR (400 MHz, CDCl$_3$) δ 7.97 (d, J=8.2 Hz, 2H), 7.28 (dd, J=7.9, 0.6 Hz, 2H), 4.14 (s, 2H), 2.41 (s, 3H), 2.33-2.17 (m, 1H), 0.61-0.33 (m, 4H). LC-MS (ESI+) m/z 230.13 (M+H)$^+$; HRMS (ESI+ve) m/z calculated for C$_{13}$H$_{16}$ClN$_3$O (M+H)$^+$230.1288. found 230.1285.

SO2-004 (30)

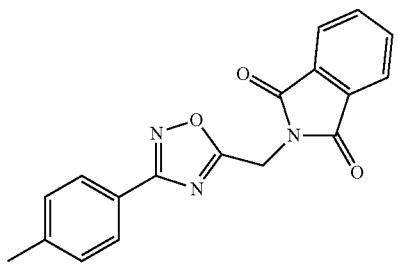

Chemical Formula: C$_{18}$H$_{13}$N$_3$O$_3$
Exact Mass: 319.0957
Molecular Weight: 319.3141

2-(3-p-Tolyl-)-[1,2,4]oxadiazol-5-ylmethyl)-isoindole-1,3-dione (SO2-004): A solution of 5-Chloromethyl-3-p-tolyl-[1,2,4]oxadiazole (100 mg, 0.48 mmol), phthalimide (70 mg, 0.48 mmol) and potassium carbonate (330 mg, 2.3 mmol) were refluxed in acetonitrile (15 ml) for 1 h. Acetonitrile was evaporated and the residue was dissolved in ethyl acetate and washed with water, the solvent was dried (MgSO$_4$) and evaporated to give the pure compound as a white solid (140 mg, 91%). $^1$H NMR (400 MHz, CDCl$_3$) δ 7.96-7.90 (m, 2H), 7.89 (d, J=8.2 Hz, 2H), 7.81-7.77 (m, 1H), 7.23 (d, J=8.0 Hz, 2H), 5.16 (s, 2H), 2.38 (s, 3H). LC-MS (ESI+) m/z 320.10 (M+H)$^+$; HRMS (ESI+ve) m/z calculated for C$_{18}$H$_{14}$N$_3$O$_3$ (M+H)$^+$320.1030. found 320.1041.

SO2-085 (24)

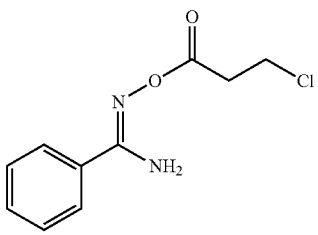

Chemical Formula: C$_{10}$H$_{11}$ClN$_2$O$_2$
Exact Mass: 226.0509
Molecular Weight: 226.6595

(Z)—N'-(2-chloropropanoyloxy)benzimidamide (SO2-085) (24): To a solution of oxime (300 mg, 2.20 mmol) in dichloromethane (15 ml) at 0° C. was added chloroacetyl chloride (249 mg, 2.20 mmol) dropwise and the mixture was warmed up to rt and stirred for 14 h. The mixture was extracted with saturated sodium bicarbonate (2×15 ml) and water (15 ml) and dried (MgSO$_4$) and evaporated to give the colorless viscous compound SO2-085 (24). (446 mg, 76%). $^1$H NMR (400 MHz, CDCl$_3$) δ 7.69 (dd, J=8.3, 1.3 Hz, 2H), 7.49-7.46 (m, 1H), 7.45-7.37 (m, 2H), 3.85 (t, J=6.7 Hz, 2H), 3.01 (t, J=6.7 Hz, 2H).

SO2-086 (25)

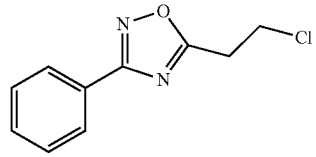

Chemical Formula: C$_{10}$H$_9$ClN$_2$O
Exact Mass: 208.0403
Molecular Weight: 208.6443

5-(2-Chloro-ethyl)-3-phenyl)-[1,2,4]oxadiazole (SO2-086) (25): This compound was synthesized using the same protocol for SO1-141 9a except using (Z)—N'-(2-chloroacetoxy)-4-(trifluoromethyl)benzimidamide (24) (400 mg, 1.50 mmol) The compound SO2-086 25 was isolated as a viscous colorless liquid (254 mg, 81%). $^1$H NMR (400 MHz, CDCl$_3$) δ 8.08 (dd, J=7.9, 1.8 Hz, 2H), 7.54-7.45 (m, 3H), 3.99 (t, J=6.9 Hz, 2H), 3.43 (t, J=6.9 Hz, 2H).

SO2-088 (26)

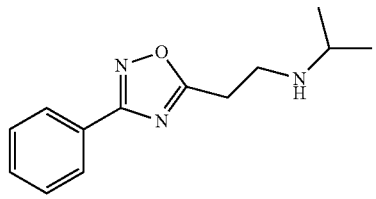

Chemical Formula: C$_{13}$H$_{17}$N$_3$O
Exact Mass: 231.1372
Molecular Weight: 231.2936

Isopropyl-[2-(3-phenyl)-[1,2,4]oxadiazol5-yl)-ethyl]-amine (SO2-088) (26): This compound was synthesized using the same protocol for SO1-142 10a except using 5-(2-chloro-ethyl)-3-phenyl)-[1,2,4]oxadiazole (25) (100 mg, 0.48 mmol), isopropyl amine (42 mg, 0.72 mmol) and potassium carbonate (331 mg, 2.40 mmol). The compound SO2-088 (26) was isolated as a brown viscous liquid (955 mg, 86%). $^1$H NMR (400 MHz, CDCl$_3$) δ 8.00 (dd, J=8.0, 1.8 Hz, 2H), 7.55-7.34 (m, 3H), 3.09-3.07 (m, 4H), 2.84 (hept, J=6.2 Hz, 1H), 1.03 (d, J=6.3 Hz, 6H).

SO2-135 (13a)

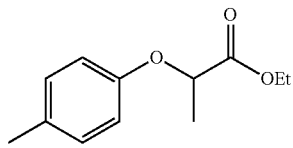

C$_{12}$H$_{16}$O$_3$
Exact Mass: 208.1099
Mol. Wt.: 208.2536

2-p-Tolyloxy-propionic acid ethyl ester (SO2-135) (13a): This compound was synthesized using the same protocol for SO1-133 5a except using p-cresol (1.00 g, 9.24 mmol), 2-bromo-propionic acid ethyl ester (1.81 g, 10.00 mmol) and potassium carbonate (6.35 g, 46.00 mmol). SO2-135 13a was isolated as a yellow viscous liquid (150 mg, 78%). $^1$H NMR (400 MHz, CDCl$_3$) δ 7.06 (dd, J=8.7, 0.6 Hz, 2H), 6.77 (d, J=8.6 Hz, 2H), 4.70 (q, J=6.8 Hz, 1H), 4.21 (q, J=7.1 Hz, 2H), 2.27 (s, 3H), 1.60 (d, J=6.8 Hz, 3H), 1.25 (t, J=7.1 Hz, 3H).

SO3-101 (13b)

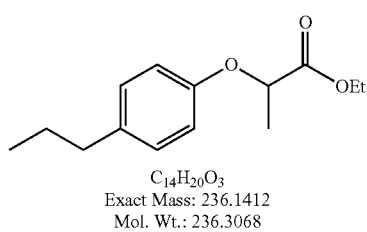 [SMILES: CCCc1ccc(OC(C)C(=O)OCC)cc1]

C$_{14}$H$_{20}$O$_3$
Exact Mass: 236.1412
Mol. Wt.: 236.3068

2-(4-Propyl-phenoxy)-propionic acid ethyl ester (SO3-101) (13b): This compound was synthesized using the same protocol for SO1-133 5a except using p-cresol (1.00 g, 7.34 mmol), 2-bromo-propionic acid ethyl ester (1.46 g, 8.08 mmol) and potassium carbonate (5.06 g, 36.70 mmol). SO3-10113b was isolated as a colorless viscous liquid (141 mg, 81%). $^1$H NMR (400 MHz, CDCl$_3$) δ 7.06 (d, J=8.5 Hz, 2H), 6.79 (d, J=8.6 Hz, 2H), 4.70 (q, J=6.8 Hz, 1H), 4.21 (q, J=7.1 Hz, 2H), 2.50 (t, J=7.4 Hz, 2H), 2.46-2.36 (m, 2H), 1.65-1.53 (m, 2H), 1.60 (d, J=6.8 Hz, 3H), 1.24 (t, J=7.1 Hz, 2H), 0.91 (t, J=7.3 Hz, 3H).

SO2-138 (14a)

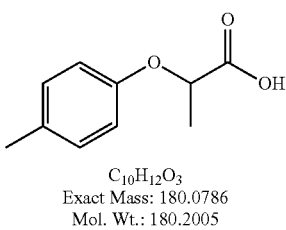

C$_{10}$H$_{12}$O$_3$
Exact Mass: 180.0786
Mol. Wt.: 180.2005

2-p-Tolyloxy-propionic acid (SO2-138) (14a): This compound was synthesized using the same protocol for SO1-136 except using 2-p-tolyloxy-propionic acid ethyl ester (13a) (500 mg, 2.40 mmol), NaOH (1 M) (10 ml) and THF (10 ml). SO2-138 14a was isolated as a yellow solid. (368 mg, 85%). $^1$H NMR (400 MHz, CDCl$_3$) δ 7.09 (d, J=8.5 Hz, 2H), 6.80 (d, J=8.6 Hz, 2H), 4.76 (q, J=6.9 Hz, 1H), 2.29 (s, 3H), 1.65 (d, J=6.9 Hz, 3H).

SO3-006 (14b)

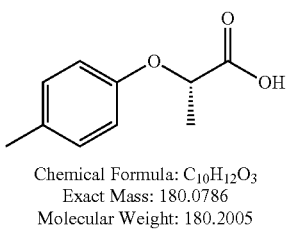

Chemical Formula: C$_{10}$H$_{12}$O$_3$
Exact Mass: 180.0786
Molecular Weight: 180.2005

(S)-2-(p-tolyloxy)propanoic acid (SO3-006) (14b): NaH (60% suspension, 60 mg, 1.50 mmol) was added to a solution of (S)-bromopropionic acid (231 mg, 1.50 mmol) in THF (10 ml). In a separate vessel NaH (60% suspension, 120 mg, 3.00 mmol) was added to a solution of p-cresol (324 mg, 3.00 mmol). The phenolate solution was calculated into the 2-bromopropionate solution, and stirred at room temperature for 0.5 h. The reaction was quenched with NaOH solution (20 ml, 2 N NaOH), and kept stirring at room temperature for another hour. The reaction was acidified with HCl (2M) up to pH=1, and extracted with Et$_2$O (3×25 ml). The Et$_2$O extract was dried over anhydrous (MgSO$_4$) and concentrated. The residue was purified by column chromatography to yield the acid SO3-006 14b as a white solid. (144 mg, 62%).

$^1$H NMR (400 MHz, CDCl$_3$) δ 7.09 (d, J=8.6 Hz, 2H), 6.80 (d, J=8.6 Hz, 2H), 4.76 (q, J=6.9 Hz, 1H), 2.29 (s, 3H), 1.64 (d, J=6.9 Hz, 3H).

SO3-062 (14c)

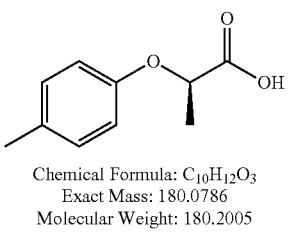

Chemical Formula: C$_{10}$H$_{12}$O$_3$
Exact Mass: 180.0786
Molecular Weight: 180.2005

(R)-2-(p-tolyloxy)propanoic acid (SO3-062) (14c): NaH (60% suspension, 60 mg, 1.50 mmol) was added to a solution of (R)-bromopropionic acid (231 mg, 1.50 mmol) in THF (10 ml). In a separate vessel NaH (60% suspension, 120 mg, 3.00 mmol) was added to a solution of p-cresol (324 mg, 3.00 mmol). The phenolate solution was calculated into the 2-bromopropionate solution, and stirred at room temperature for 5 h. The reaction was quenched with NaOH solution (20 ml, 2 M NaOH), and kept stirring at room temperature for another hour. The reaction was acidified with HCl (2M) up to pH=1, and extracted with Et$_2$O (3×25 ml). The Et$_2$O extract was dried over anhydrous (MgSO$_4$) and concentrated. The residue was purified by column chromatography to yield the acid SO3-062 14c as a white solid. (230 mg, 85%). $^1$H NMR (400 MHz, CDCl$_3$) δ 7.09 (d, J=8.6 Hz, 2H), 6.80 (d, J=8.5 Hz, 2H), 4.76 (q, J=6.8 Hz, 1H), 2.29 (s, 3H), 1.64 (d, J=6.9 Hz, 3H).

SO3-103 (14d)

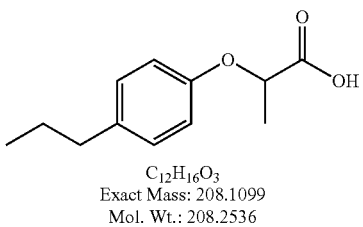

C$_{12}$H$_{16}$O$_3$
Exact Mass: 208.1099
Mol. Wt.: 208.2536

2-(4-Propyl-phenoxy)-propionic acid (SO3-103) (14d): This compound was synthesized using the same protocol for SO1-136 except using 2-(4-propyl-phenoxy)-propionic acid ethyl ester (13b) (200 mg, 0.85 mmol), NaOH (1 M) (10 ml) and THF (10 ml). SO3-103 14d was isolated as a yellow solid. (155 mg, 88%). $^1$H NMR (400 MHz, CDCl$_3$) δ 7.09 (d, J=8.6 Hz, 2H), 6.82 (d, J=8.7 Hz, 2H), 4.76 (q, J=6.9 Hz, 1H), 2.52 (t, J=7.3 Hz, 2H), 1.65 (d, J=6.9 Hz, 3H), 1.63-1.54 (m, 2H), 0.93 (dd, J=8.2, 6.4 Hz, 3H).

SO3-102 (14e)

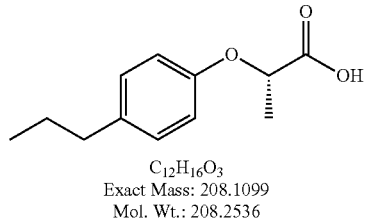

C₁₂H₁₆O₃
Exact Mass: 208.1099
Mol. Wt.: 208.2536

(S)-2-(4-Propyl-phenoxy)-propanoic acid (SO3-102) (14e): NaH (60% suspension, 26 mg, 0.65 mmol) was added to a solution of (S)-bromopropionic acid (100 mg, 0.65 mmol) in THF (10 ml). In a separate vessel NaH (60% suspension, 52 mg, 1.30 mmol) was added to a solution of p-propylphenol (1.77 g, 1.30 mmol). The phenolate solution was calculated into the 2-bromopropionate solution, and stirred at room temperature for 0.5 h. The reaction was quenched with NaOH solution (20 ml, 2 M NaOH), and kept stirring at room temperature for another hour. The reaction was acidified with HCl (2M) up to pH=1, and extracted with Et₂O (3×25 ml). The Et₂O extract was dried over anhydrous (MgSO₄) and concentrated. The residue was purified by column chromatography to yield the acid SO3-102 14e as a viscous yellow liquid. (112 mg, 83%). ¹H NMR (400 MHz, CDCl₃) δ 7.09 (d, J=8.7 Hz, 2H), 6.81 (d, J=8.7 Hz, 2H), 4.76 (q, J=6.9 Hz, 1H), 2.52 (t, J=7.3 Hz, 2H), 1.64 (d, J=6.9 Hz, 3H), 1.64-1.53 (m, 2H), 0.92 (t, J=7.3 Hz, 3H).

SO3-104 (14f)

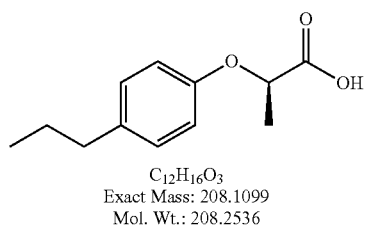

C₁₂H₁₆O₃
Exact Mass: 208.1099
Mol. Wt.: 208.2536

(R)-2-(4-Propyl-phenoxy)-propanoic acid (SO3-104) (14f): NaH (60% suspension, 130 mg, 3.27 mmol) was added to a solution of (R)-bromopropionoc acid (500 mg, 3.27 mmol) in THF (10 ml). In a separate vessel NaH (60% suspension, 260 mg, 6.54 mmol) was added to a solution of p-cresol (900 mg, 6.54 mmol). The phenolate solution was calculated into the 2-bromopropionate solution, and stirred at room temperature for 0.5 h. The reaction was quenched with NaOH solution (20 ml, 2 M NaOH), and kept stirring at room temperature for another hour. The reaction was acidified with HCl (2M) up to pH=1, and extracted with Et₂O (3×25 ml). The Et₂O extract was dried over anhydrous (MgSO₄) and concentrated. The residue was purified by column chromatography to yield the acid SO3-104 14f as a viscous yellow liquid. (640 mg, 94%). ¹H NMR (400 MHz, CDCl₃) δ 7.09 (d, J=8.7 Hz, 2H), 6.82 (d, J=8.7 Hz, 2H), 4.76 (q, J=6.9 Hz, 1H), 2.52 (t, J=7.3 Hz, 2H), 1.65 (d, J=6.9 Hz, 3H), 1.64-1.55 (m, 2H), 0.92 (t, J=7.3 Hz, 3H).

SO2-142 (15a)

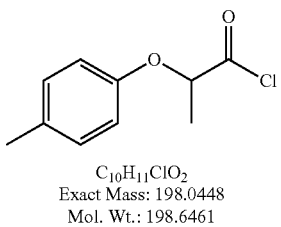

C₁₀H₁₁ClO₂
Exact Mass: 198.0448
Mol. Wt.: 198.6461

2-(p-tolyloxy)propanoyl chloride (SO2-142): This compound was synthesized using the same protocol for SO1-140 5a except using 2-p-tolyloxy-propionic acid (14a) (300 mg, 1.66 mmol), SOCl₂ (10 ml) and benzene (10 ml). SO2-142 (15a) was isolated as yellow liquid (317 mg, 96%). ¹H NMR (400 MHz, CDCl₃) δ 7.11 (d, J=8.6 Hz, 2H), 6.79 (d, J=8.6 Hz, 2H), 4.92 (q, J=6.8 Hz, 1H), 2.30 (s, 3H), 1.74 (d, J=6.8 Hz, 3H).

SO3-015 (15b)

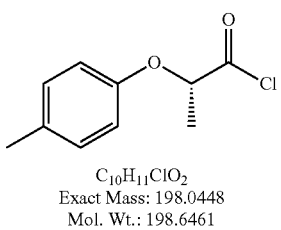

C₁₀H₁₁ClO₂
Exact Mass: 198.0448
Mol. Wt.: 198.6461

(S)-2-(p-tolyloxy)propanoyl chloride (SO3-015) (15b): This compound was synthesized using the same protocol for SO1-140 5a except using (S)-2-(p-tolyloxy)propanoic acid (130 mg, 0.72 mmol), SOCl₂ (10 ml) and benzene (10 ml). SO3-015 15b was isolated as yellow liquid (133 mg, 93%). ¹H NMR (400 MHz, CDCl₃) δ 7.09 (d, J=8.5 Hz, 2H), 6.77 (d, J=8.6 Hz, 2H), 4.90 (q, J=6.8 Hz, 1H), 2.29 (s, 3H), 1.73 (d, J=6.8 Hz, 3H).

SO3-063 (15c)

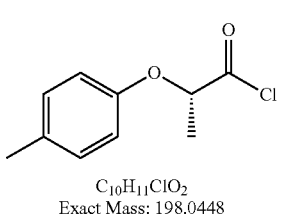

C₁₀H₁₁ClO₂
Exact Mass: 198.0448
Mol. Wt.: 198.6461

(R)-2-(p-tolyloxy)propanoyl chloride (SO3-015) (15c): This compound was synthesized using the same protocol for SO1-140 5a except using (R)-2-(p-tolyloxy)propanoic acid (14c) (130 mg, 0.72 mmol), SOCl₂ (10 ml) and benzene (10 ml). SO3-063 15c was isolated as yellow liquid (139 mg, 97%). ¹H NMR (400 MHz, CDCl₃) δ 7.10 (d, J=8.5 Hz, 2H), 6.78 (d, J=8.6 Hz, 2H), 4.91 (q, J=6.8 Hz, 1H), 2.29 (s, 3H), 1.73 (d, J=6.8 Hz, 3H).

SO3-105 (15d)

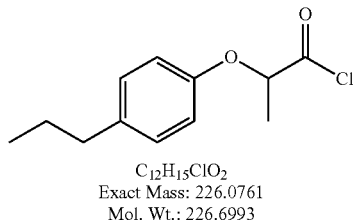

C₁₂H₁₅ClO₂
Exact Mass: 226.0761
Mol. Wt.: 226.6993

2-(4-Propylphenoxy)propanoyl chloride (SO3-105) (15d): This compound was synthesized using the same protocol for SO1-140 5a except using 2-(4-propyl-phenoxy)-propionic acid (14d) (150 mg, 0.72 mmol), SOCl₂ (10 ml) and benzene (10 ml). SO3-105 15d was isolated as greenish yellow liquid (157 mg, 96%). ¹H NMR (400 MHz, CDCl₃) δ 7.11 (d, J=8.6 Hz, 2H), 6.80 (d, J=8.6 Hz, 2H), 4.92 (q, J=6.8 Hz, 1H), 2.54 (t, J=7.4 Hz, 2H), 1.74 (d, J=6.8 Hz, 2H), 1.71-1.51 (m, 2H), 0.93 (t, J=7.3 Hz, 3H).

SO3-108 (15e)

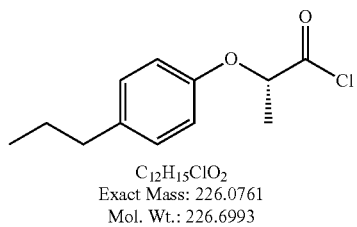

C₁₂H₁₅ClO₂
Exact Mass: 226.0761
Mol. Wt.: 226.6993

(S)-2-(4-Propylphenoxy)propanoyl chloride (SO3-108) (15e): This compound was synthesized using the same protocol for SO1-140 5a except using (S)-2-(4-propyl-phenoxy)-propionic acid (14e) (300 mg, 1.44 mmol), SOCl₂ (10 ml) and benzene (10 ml). SO3-108 15e was isolated as yellow liquid (304 mg, 93%). ¹H NMR (400 MHz, CDCl₃) δ 7.11 (d, J=8.6 Hz, 1H), 6.80 (d, J=8.6 Hz, 1H), 4.92 (q, J=6.8 Hz, 1H), 2.53 (t, J=7.4 Hz, 2H), 1.74 (d, J=6.8 Hz, 3H), 1.67-1.51 (m, 2H), 0.93 (t, J=7.3 Hz, 3H).

SO3-107 (15f)

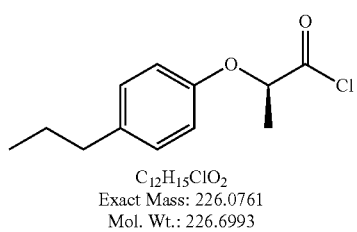

C₁₂H₁₅ClO₂
Exact Mass: 226.0761
Mol. Wt.: 226.6993

(R)-2-(4-Propyl-phenoxy)-propionyl chloride (SO3-107) (15f): This compound was synthesized using the same protocol for SO1-140 5a except using (R)-2-(4-propyl-phenoxy)-propionic acid (14f) (300 mg, 1.44 mmol), SOCl₂ (10 ml) and benzene (10 ml). SO3-107 15f was isolated as yellow liquid (311 mg, 95%). ¹H NMR (400 MHz, CDCl₃) δ 7.11 (d, J=8.7 Hz, 2H), 6.80 (d, J=8.7 Hz, 2H), 4.91 (q, J=6.8 Hz, 1H), 2.53 (t, J=7.3 Hz, 2H), 1.74 (d, J=6.8 Hz, 3H), 1.68-1.53 (m, 2H), 0.92 (t, J=7.3 Hz, 3H).

SO2-026 (22a)

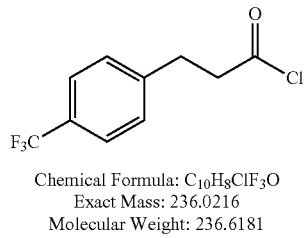 [SMILES: O=C(Cl)CCc1ccc(C(F)(F)F)cc1]

Chemical Formula: C₁₀H₈ClF₃O
Exact Mass: 236.0216
Molecular Weight: 236.6181

3-(4-(Trifluoromethyl)phenyl)propanoyl chloride (SO2-026) (22a): This compound was synthesized using the same protocol for SO1-140 except using 3-(4-(trifluoromethyl)phenyl)propanoic acid (700 mg, 3.21 mmol), SOCl₂ (10 ml) and benzene (10 ml). SO2-026 22a was isolated as yellow liquid (714 mg, 94%). ¹H NMR (400 MHz, CDCl₃) δ 7.58 (d, J=8.1 Hz, 2H), 7.33 (d, J=8.0 Hz, 2H), 3.24 (t, J=7.3 Hz, 2H), 3.08 (t, J=7.3 Hz, 2H).

SO3-028 (22b)

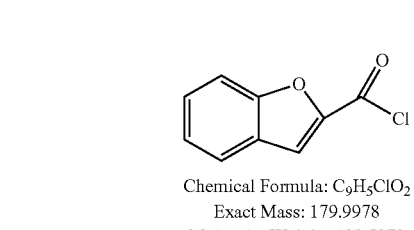

Chemical Formula: C₉H₅ClO₂
Exact Mass: 179.9978
Molecular Weight: 180.5878

Benzofuran-2-carbonyl chloride (SO3-028) (22b): This compound was synthesized using the same protocol for SO1-140 except using benzofuran-2-carbonic acid (300 mg, 1.85 mmol), SOCl₂ (5 ml) and benzene (5 ml). SO3-028 22b was isolated as yellow liquid (314 mg, 94%). ¹H NMR (400 MHz, CDCl₃) δ 7.85 (d, J=0.9 Hz, 1H), 7.76 (d, J=8.0 Hz, 1H), 7.65-7.51 (m, 2H), 7.37 (ddd, J=8.1, 6.8, 1.3 Hz, 1H).

SO2-066 (19)

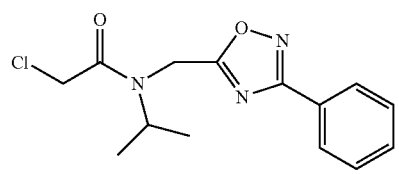

Chemical Formula: C₁₄H₁₆ClN₃O₂
Exact Mass: 293.0931
Molecular Weight: 293.7487

N-Isopropyl-2-chloro-N-((3-phenyl-1,2,4-oxadiazol-5-yl)methyl)acetamide SO2-066 (19): To a solution of 10c (80 mg, 0.36 mmol) and triethyl amine 970 mg, 0.72 mmol) in THF (4 ml) was added chloroacetyl chloride (50 mg, 0.44 mmol) in THF (1 ml) slowly. The reaction was monitored by TLC and completed in 15 min. THF was evaporated and the residue was dissolved in EtOAc (15 ml) and washed with 4M HCl (2×15 ml) and water (2×15 ml). Organic solvent was dried (MgSO₄) and evaporated. The compound was purified by column chromatography (EtOAc:hexane gradient elution) to obtain SO2-066 (19) as a viscous colorless liquid (84 mg, 80%).

HPLC 100% ($R_t$=5.54 min, 60% $CH_3CN$ in 0.1% TFA water 30 min); $^1$H NMR (400 MHz, $CDCl_3$) δ 8.09-8.00 (m, 2H), 7.53-7.41 (m, 3H), 4.79 (s, 2H), 4.70 (s, 2H) [δ 4.79 minor isomer shown]), 4.33-4.24 (m, 1H) [δ 4.90-4.79 minor isomer shown]), 4.20 (s, 2H), 1.34 (d, J=6.6 Hz, 6H), [δ 1.15 minor isomer shown]). LC-MS (ESI+) m/z 294.10 (M+H)$^+$316.09 (M+Na)$^+$; HRMS (ESI+ve) m/z calculated for $C_{14}H_{17}N_3O_3$ (M+H)$^+$294.1004. found 294.1005.

SO2-059 (31)

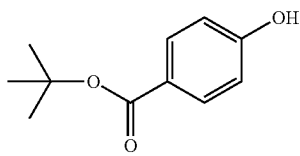

Chemical Formula: $C_{11}H_{14}O_3$
Exact Mass: 194.0943
Molecular Weight: 194.2271 tert-Butyl 4-hydroxybenzoate (SO2-059) (31): Hydroxy benzoic acid (1.50 g, 10.86 mmol), tert-butanol (13.34 g, 18 mmol), DBU (0.19 ml, 1.20 mmol) and DCC (2.5 g, 12.00 mmol) were mixed in DCM (40 ml) and vigorously stirred for 18 h. After evaporation to dryness, DCM (50 ml) was added to the residue and the resulting heterogeneous solution was filtered. The solution was washed with sat. $K_2CO_3$ (2×50 ml) and sat. NaCl (50 ml). The solvent was dried ($MgSO_4$) and evaporated and purified by column chromatography (EtOAc:hexane gradient elution) to obtain SO2-059 31 as a crystalline white compound. (1.1 g, 55%). $^1$H NMR (400 MHz, $cdcl_3$) δ 7.89 (d, J=8.8 Hz, 1H), 6.84 (d, J=8.9 Hz, 1H), 5.29 (s, 1H), 1.57 (s, 9H).

SO1-143 (1)

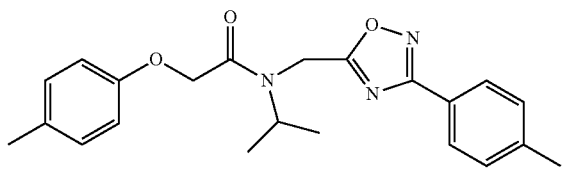

Chemical Formula: $C_{22}H_{25}N_3O_3$
Exact Mass: 379.1896
Molecular Weight: 379.4522

N-Isopropyl-N-((3-p-tolyl-1,2,4-oxadiazol-5-yl)methyl)-2-(p-tolyloxy)acetamide (SO1-143) (1): To a solution of isopropyl-(3-p-tolyl-[1,2,4]oxadiazol-5-ylmethyl)-amine (10a) (180 mg, 0.81 mmol) and triethyl amine (160 mg, 1.6 mmol) in THF (15 ml) at room temperature was added p-tolyloxy-acetyl chloride (5a) (300 mg, 0.17 mmol) in THF (3 ml) dropwise. As the acyl chloride was added, a precipitate was formed and the reaction was completed in 10 min. The THF was evaporated and the residue was dissolved in EtOAc (20 ml), washed with 4M HCl (2×15 ml) and water (15 ml). Organic phase was dried ($MgSO_4$) and evaporated and the product obtained was purified by column chromatography (Sift, EtOAc:hexane gradient elution) to obtain 1 as a white solid (270 mg, 88%). M.p. 142.1-143.4° C.

HPLC 100% ($R_t$=11.8 min, 60% $CH_3CN$ in 0.1% TFA water 30 min); The $^1$H NMR showed 3:1 ratio of atropisomers: $^1$H NMR (400 MHz, $CDCl_3$) δ 7.91 (d, J=8.0 Hz, 2H [δ 7.93 minor isomer shown]), 7.30-7.25 (m, 2H), 7.09 (d, J=8.3 Hz, 2H [δ 7.05 minor isomer shown]), 6.87 (d, J=8.5 Hz, 1H [δ 6.82 minor isomer shown]), 4.78 (s, 1H [δ 4.84 minor isomer shown]), 4.70 (s, 1H [δ 4.83 minor isomer shown]), 4.45-4.39 (m, 1H), 2.42 (s, 1H [δ 2.41 minor isomer shown]), 2.28 (s, 1H [δ 2.25 minor isomer shown]), 1.30 (d, J=6.6 Hz, 6H [δ 1.15 minor isomer shown]);
$^1$H NMR (400 MHz, $d_6$-DMSO) δ 7.84 (d, J=8.2 Hz, 2H [δ 7.87 minor isomer shown]), 7.36 (d, J=7.9 Hz, 2H [δ 7.37 minor isomer]), 7.01 (d, J=8.6 Hz, 2H), 6.78 (d, J=8.6 Hz, 2H [δ 6.75 minor isomer shown]), 4.88 (s, 2H [δ 4.98 minor isomer shown]), 4.71 (s, 2H [δ 4.82 minor isomer shown]), 4.31-4.21 (m, 1H [δ 4.62-4.52 minor isomer shown]), 2.37 (s, 3H), 2.18 (s, 3H), 1.26 (d, J=6.6 Hz, 6H [δ 1.06 minor isomer shown]); $^{13}$C NMR (100 MHz, $CDCl_3$) δ 176.40 [δ 176.54 minor isomer shown], 168.51 [δ 168.56 minor isomer shown], 156.01 [δ 155.81 minor isomer shown], 141.68, 131.23 [δ 131.25 minor isomer shown], 130.29 [δ 130.24 minor isomer shown], 129.68 [δ 129.84 minor isomer shown], 127.65, 124.08 114.68 [δ 114.64 minor isomer shown], 67.99 [δ 68.74 minor isomer shown], 48.96 [δ 46.96 minor isomer shown], 37.20 [δ 38.40 minor isomer shown], 21.49 [δ 19.97 minor isomer shown], 20.81, 20.73.

Anal. Calcd for $C_{22}H_{25}N_3O_3$: C, 69.64; H, 6.64; N, 11.07. Found: C, 69.51; H, 6.74; N, 11.13.

LC-MS (ESI+) m/z 380.24 (M+H)$^+$; HRMS (ESI+ve) m/z calculated for $C_{22}H_{26}N_3O_3$ (M+H)$^+$380.1969. found 380.1966.

SO1-176 (11a)

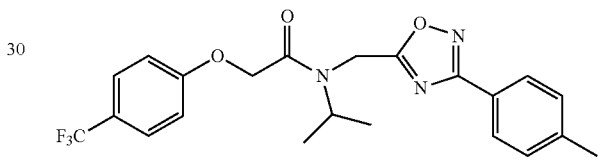

Chemical Formula: $C_{22}H_{22}F_3N_3O_3$
Exact Mass: 433.1613
Molecular Weight: 433.4236

N-Isopropyl-N-((3-p-tolyl-1,2,4-oxadiazol-5-yl)methyl)-2-(4-(trifluoromethyl)phenoxy)acetamide (SO1-176) (11a): This compound was synthesized using the same protocol for 1 (SO1-143) except using 2-(4-trifluoromethyl-phenoxy)-acetyl chloride (5b) (190 mg, 0.78 mmol) and isopropyl-(3-p-tolyl-[1,2,4]oxadiazol-5-ylmethyl)-amine (10a) (120 mg, 0.52 mmol) and triethyl amine (100 mg, 1 mmol). The compound 11a (SO1-176) was isolated as a white solid (190 mg, 87%). M.p. 76.6-78.5° C.

HPLC 99.87% ($R_t$=14.8 min, 60% $CH_3CN$ in 0.1% TFA water 30 min); The $^1$H NMR showed 3:1 ratio of atropisomers: $^1$H NMR (400 MHz, $CDCl_3$) δ 7.88 (d, J=8.1 Hz, 2H), 7.54 (d, J=8.7 Hz, 2H [δ 7.51 minor isomer shown]), 7.27-7.23 (d, J=7.9 Hz, 2H [δ 7.29 minor isomer shown]), 7.04 (d, J=8.5 Hz, 2H), 4.88 (s, 2H [δ 4.94 minor isomer shown]), 4.71 (s, 2H [δ 4.76 minor isomer shown]), 4.38-4.34 (m, 1H), 2.41 (s, 3H [δ 2.43 minor isomer shown]), 1.32 (d, J=6.6 Hz, 6H [δ 1.16 minor isomer shown]); $^{13}$C NMR (100 MHz, $CDCl_3$) δ 176.16 [δ 176.23 minor isomer shown], 168.57 [δ 167.84 minor isomer shown], 167.80 [δ 167.87 minor isomer shown], 160.48, 141.86 [δ 142.43 minor isomer shown], 129.73 127.58, 127.29 (q, J=3.67 Hz), 124.47 (q, J=270 Hz), 124.11 (q, J=32.5 Hz), 123.88 [δ 123.86 minor isomer shown], 114.96 [δ 114.90 minor isomer shown], 114.82, 67.48 [δ 67.90 minor isomer shown], 49.00 [δ 47.05 minor isomer shown], 37.23 [δ 38.35 minor isomer shown], 21.45 [δ 19.96 minor isomer shown], 21.81; $^{19}$F NMR (376 MHz, $CDCl_3$) δ −62.02 [δ −62.06 minor isomer shown].

LC-MS (ESI+) m/z 434.18 (M+H)+; HRMS (ESI+ve) m/z calculated for $C_{22}H_{23}F_3N_3O_3$ (M+H)+434.1686. found 434.1711.

SO1-171 (11b)

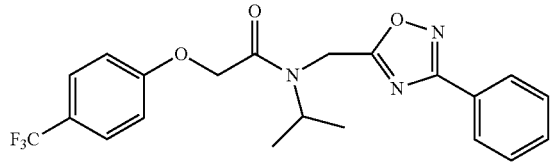

Chemical Formula: $C_{21}H_{20}F_3N_3O_3$
Exact Mass: 419.1457
Molecular Weight: 419.3970

N-Isopropyl-N-((3-phenyl-1,2,4-oxadiazol-5-yl)methyl)-2-(4-(trifluoromethyl)phenoxy)acetamide (SO1-171) (11b): This compound was synthesized using the same protocol for 1 (SO1-143) except using 2-(4-trifluoromethyl-phenoxy)-acetyl chloride (5b) (240 mg, 0.92 mmol) and isopropyl-(3-phenyl)-[1,2,4]oxadiazol-5-ylmethyl)-amine (10c) (100 mg, 0.46 mmol) and triethyl amine (90 mg, 0.92 mmol). The compound 11b (SO1-171) was isolated as a white solid (170 mg, 89%). M.p. 97.9-99.3° C.

HPLC 100% ($R_t$=10.4 min, 60% $CH_3CN$ in 0.1% TFA water 30 min); The $^1$H NMR showed 2.5:1 ratio of atropisomers: $^1$H NMR (400 MHz, CDCl$_3$) δ 8.00 (dd, J=8.0 Hz, 1.6 Hz, 2H), 7.62-7.37 (m, 3H), 7.05 (d, J=8.8 Hz, 2H), 4.88 (s, 2H [δ 4.94 minor isomer shown]), 4.72 (s, 2H [δ 4.79 minor isomer shown]), 4.39-4.35 (m, 1H), 1.32 (d, J=6.6 Hz, 6H [δ 1.16 minor isomer shown]); $^{13}$C NMR (100 MHz, CDCl$_3$) δ 176.36 [δ 176.47 minor isomer shown], 168.58 [δ 168.54 minor isomer shown], 167.66 [δ 166.71 minor isomer shown], 160.50 [δ 160.47 minor isomer shown], 131.47 [δ 131.92 minor isomer shown], 130.34, 129.00 [δ 129.20 minor isomer shown], 127.65, 127.29 (q, J=3.74 Hz), 126.78, 126.17, 124.46 (q, J=270 Hz), 124.14 (q, J=32.7 Hz), 114.97 [δ 114.75 minor isomer shown], 114.90, 67.56 [δ 68.07 minor isomer shown], 65.33, 48.96 [δ 47.07 minor isomer shown], 37.21 [δ 38.41 minor isomer shown], 21.48 [δ 19.98 minor isomer shown]; $^{19}$F NMR (376 MHz, CDCl$_3$) δ −62.03 [δ −62.07 minor isomer shown].

LC-MS (ESI+) m/z 420.16 (M+H)+; HRMS (ESI+ve) m/z calculated for $C_{21}H_{21}F_3N_3O_3$ (M+H)+420.1530. found 420.1547.

SO1-170 (11c)

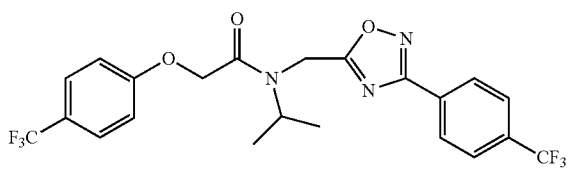

Chemical Formula: $C_{22}H_{19}F_6N_3O_3$
Exact Mass: 487.1331
Molecular Weight: 487.3950

N-Isopropyl-2-(4-(trifluoromethyl)phenoxy)-N-((3-(4-(trifluoromethyl)phenyl)-1,2,4-oxadiazol-5-yl)methyl)acetamide (SO1-170) (11c): This compound was synthesized using the same protocol for 1 (SO1-143) except using 2-(4-trifluoromethyl-phenoxy)-acetyl chloride (5b) (180 mg, 0.70 mmol) and isopropyl-[3-(4-trifluoromethyl-phenyl)-[1,2,4]oxadiazol-5-ylmethyl]-amine (10b) (100 mg, 0.35 mmol) and triethyl amine (71 mg, 0.70 mmol). The compound 11c (SO1-170) was isolated as a white solid (160 mg, 92%). M.p. 92-94.5° C.

HPLC 95% ($R_t$=19.0 min, 60% $CH_3CN$ in 0.1% TFA water 30 min); The $^1$H NMR showed 4:1 ratio of atropisomers: $^1$H NMR (400 MHz, CDCl$_3$) δ 8.11 (d, J=8.3 Hz, 2H), 7.72 (d, J=8.3 Hz, 2H), 7.54 (d, J=8.8 Hz, 2H [δ 7.49 minor isomer shown]), 7.04 (d, J=8.7 Hz, 2H [δ 6.97 minor isomer shown]), 4.88 (s, 2H [δ 4.91 minor isomer shown]), 4.72 (s, 2H [δ 4.84 minor isomer shown]), 4.42-4.38 (m, 1H), 1.34 (d, J=6.6 Hz, 6H [δ 1.17 minor isomer shown]); $^{13}$C NMR (100 MHz, CDCl$_3$) δ 176.91, 167.87 [δ 167.60 minor isomer shown], 160.42 [δ 160.02 minor isomer shown], 133.18 (q, J=33 Hz), 130.16, 128.01 [δ 128.12 minor isomer shown], 127.32 (q, J=3.59 Hz), 126.03 (q, J=3.81 Hz), 124.41 (q, J=270 Hz), 124.23 (q, J=32.59 Hz), 123.94 (q, J=270 Hz), 114.94 [δ 114.90 minor isomer shown], 114.83, 67.51 [δ 64.80 minor isomer shown], 49.08, 37.30, 29.94, 21.50 [δ 19.97 minor isomer shown]; $^{19}$F NMR (376 MHz, CDCl$_3$) δ −62.07 [δ −62.02 minor isomer shown], −62.13 [δ −62.14 minor isomer shown], −62.45 [δ −62.52 minor isomer shown], LC-MS (ESI+) m/z 488.14 (M+H)+; HRMS (ESI+ve) m/z calculated for $C_{22}H_{20}F_6N_3O_3$ (M+H)+488.1403. found 488.1419.

SO1-169 (11d)

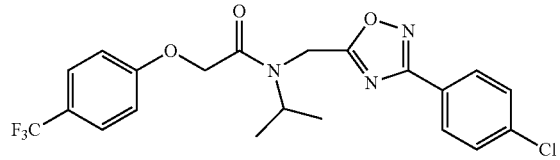

Chemical Formula: $C_{21}H_{19}ClF_3N_3O_3$
Exact Mass: 453.1067
Molecular Weight: 453.8421

N-((3-(4-chlorophenyl)-1,2,4-oxadiazol-5-yl)methyl)-N-isopropyl-2-(4-(trifluoromethyl)phenoxy)acetamide (SO1-169) (11d): This compound was synthesized using the same protocol for 1 (SO1-143) 1 except using 2-(4-trifluoromethyl-phenoxy)-acetyl chloride (5b) (200 mg, 0.80 mmol) and [3-(4-chloro-phenyl)-[1,2,4]oxadiazol-5-ylmethyl)-isopropyl-amine (10d) (100 mg, 0.4 mmol) and triethyl amine (80 mg, 0.79 mmol). The compound 11d (SO1-169) was isolated as a white solid (140 mg, 85%). M.p. 111.4-113.9° C.

HPLC 100% ($R_t$=16.5 min, 60% $CH_3CN$ in 0.1% TFA water 30 min); The $^1$H NMR showed 3.4:1 ratio of atropisomers: $^1$H NMR (400 MHz, CDCl$_3$) δ 7.93 (d, J=8.6 Hz, 2H), 7.54 (d, J=8.7 Hz, 2H [δ 7.50 minor isomer shown]), 7.43 (d, J=8.6 Hz, 2H [δ 7.46 minor isomer shown]), 7.04 (d, J=8.6 Hz, 2H [δ 6.99 minor isomer shown]), 4.88 (s, 2H [δ 4.92 minor isomer shown]), 4.70 (s, 2H [δ 4.80 minor isomer shown]), 4.41-4.35 (m, 1H), 1.32 (d, J=6.6 Hz, 6H [δ 1.16 minor isomer shown]); $^{13}$C NMR (100 MHz, CDCl$_3$) δ 176.60 [δ 176.74 minor isomer shown], 167.81 [δ 167.70 minor isomer shown], 160.46 [δ 160.40 minor isomer shown], 137.61, 129.54, 129.35, 128.96, 127.31 (q, J=3.7 Hz), 125.28, 124.45 (q, J=270 Hz), 124.17 (q, J=32 Hz), 114.95 [δ 114.87 minor isomer shown], 68.25, 67.54 [δ 68.25 minor isomer shown], 49.00 [δ 47.16 minor isomer shown], 38.50, 37.25 [δ 38.50 minor isomer shown], 21.50, [δ 19.98 minor isomer shown]; $^{19}$F NMR (376 MHz, CDCl$_3$) δ −62.03 [δ −62.08 minor isomer shown].

LC-MS (ESI+) m/z 454.12 (M+H)+; HRMS (ESI+ve) m/z calculated for $C_{21}H_{20}ClF_3N_3O_3$ (M+H)+454.1140. found 454.1149.

SO2-002 (11e)

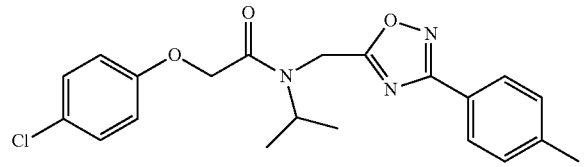

Chemical Formula: $C_{21}H_{22}ClN_3O_3$
Exact Mass: 399.1350
Molecular Weight: 399.8707

2-(4-Chlorophenoxy)-N-isopropyl-N-((3-p-tolyl-1,2,4-oxadiazol-5-yl)methyl)acetamide (SO2-002) (11e): This compound was synthesized using the same protocol for 1 (SO1-143) except using 2-(4-chlorophenoxy)acetyl chloride (5d) (130 mg, 0.65 mmol) and isopropyl-(3-p-tolyl-[1,2,4]oxadiazol-5-ylmethyl)-amine (10a) (100 mg, 0.43 mmol) and triethyl amine (90 mg, 0.86 mmol). The compound 11e (SO2-002) was obtained as a white solid (150 mg, 88%). M.p. 133.1-136.5° C.

HPLC 98.5% ($R_t$=12.5 min, 60% $CH_3CN$ in 0.1% TFA water 30 min); The $^1H$ NMR showed 3:1 ratio of atropisomers: $^1H$ NMR (400 MHz, $CDCl_3$) δ 7.88 (d, J=8.3 Hz, 2H [δ 7.91 minor isomer shown]), 7.26 (J=8.6 Hz, 2H [δ 7.29 minor isomer shown]), 7.23 (J=9.0 Hz, 2H [δ 7.20 minor isomer shown]), 6.86 (d, J=9.0 Hz, 2H [δ 6.87 minor isomer shown]), 4.81 (s, 2H [δ 4.86 minor isomer shown]), 4.70 (s, 2H [δ 4.79 minor isomer shown]), 4.42-4.35 (m, 1H), 2.41 (s, 3H), 1.30 (d, J=6.6 Hz, 6H [δ 1.15 minor isomer shown]); $^{13}C$ NMR (100 MHz, $CDCl_3$) δ 176.22 [δ 176.34 minor isomer shown], 168.57, 168.01, 156.75, 141.75 [δ 142.36 minor isomer shown], 129.90, 129.74 [δ 129.72 minor isomer shown], 129.67, 127.61 [δ 126.90 minor isomer shown], 123.98 [δ 123.42 minor isomer shown], 116.24 [δ 116.17 minor isomer shown], 67.95 [δ 68.47 minor isomer shown], 48.93 [δ 46.97 minor isomer shown], 37.17 [δ 38.37 minor isomer shown], 21.47 [δ 19.98 minor isomer shown], 21.82.

LC-MS (ESI+) m/z 400.15 (M+H)+; HRMS (ESI+ve) m/z calculated for $C_{21}H_{23}ClN_3O_3$ (M+H)+400.1423. found 400.1448.

SO1-180 (11f)

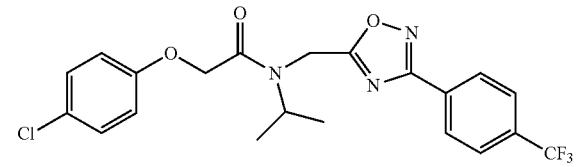

Chemical Formula: $C_{21}H_{19}ClF_3N_3O_3$
Exact Mass: 453.1067
Molecular Weight: 453.8421

2-(4-Chlorophenoxy)-N-isopropyl-N-((3-(4-(trifluoromethyl)phenyl)-1,2,4-oxadiazol-5-yl)methyl)acetamide (SO1-180) (11f): This compound was synthesized using the same protocol for 1 (SO1-143) except using 2-(4-chlorophenoxy)acetyl chloride (5d) (110 mg, 0.53 mmol) and isopropyl-[3-(4-trifluoromethyl-phenyl)-[1,2,4]oxadiazol-5-ylmethyl)-amine (10b) (100 mg, 0.35 mmol) and triethyl amine (71 mg, 0.70 mmol). The compound 11f (SO1-180) was isolated as a white solid (130 mg, 81%). M.p. 106.4-108.9° C.

HPLC 99.8% ($R_t$=17.1 min, 60% $CH_3CN$ in 0.1% TFA water 30 min); The $^1H$ NMR showed 4:1 ratio of atropisomers: $^1H$ NMR (400 MHz, $CDCl_3$) δ 8.10 (d, J=8.1 Hz, 2H), 7.73 (d, J=8.2 Hz, 2H), 7.23 (d, J=9.0 Hz, 2H [δ 7.18 minor isomer shown]), 6.91 (d, J=9.0 Hz, 2H [δ 6.83 minor isomer shown]), 4.81 (s, 2H [δ 4.85 minor isomer shown]), 4.70 (s, 2H [δ 4.83 minor isomer shown]), 4.45-4.39 (m, 1H), 1.32 (d, J=6.6 Hz, 6H [δ 1.16 minor isomer shown]); $^{13}C$ NMR (100 MHz, $CDCl_3$) δ 177.00, 168.16 [δ 167.64 minor isomer shown], 156.68, 133.11 (q, J=32.6 Hz), 129.76 [δ 130.18 minor isomer shown], 128.04, 126.96, 126.08 (q, J=3.8 Hz), 123.96 (q, J=270 Hz), 116.20 [δ 116.08 minor isomer shown], 67.91 [δ 68.88 minor isomer shown], 49.01 [δ 47.09 minor isomer shown], 37.24 [δ 38.52 minor isomer shown], 21.50 [δ 19.88 minor isomer shown]; $^{19}F$ NMR (376 MHz, $CDCl_3$) δ -63.40 [δ -63.46 minor isomer shown]. LC-MS (ESI+) m/z 454.11 (M+H)+; HRMS (ESI+ve) m/z calculated for $C_{21}H_{20}ClF_3N_3O_3$ (M+H)+454.1140. found 454.1142.

SO1-179 (11g)

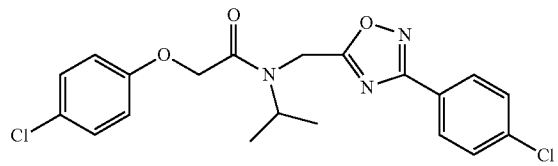

Chemical Formula: $C_{20}H_{19}Cl_2N_3O_3$
Exact Mass: 419.0803
Molecular Weight: 420.2892

2-(4-Chlorophenoxy)-N-((3-(4-chlorophenyl)-1,2,4-oxadiazol-5-yl)methyl)-N-isopropylacetamide (SO1-179) (11g): This compound was synthesized using the same protocol for 1 (SO1-143) except using 2-(4-chlorophenoxy)acetyl chloride (5d) (120 mg, 0.60 mmol) and [3-(4-chlorophenyl)-[1,2,4]oxadiazol-5-ylmethyl)-isopropyl-amine (10d) (100 mg, 0.40 mmol) and triethyl amine (80 mg, 0.79 mmol). The compound 11g (SO1-179) was obtained as a white solid (140 mg, 91%). M.p. 133.4-135.8° C.

HPLC 99.9% ($R_t$=15.5 min, 60% $CH_3CN$ in 0.1% TFA water 30 min); The $^1H$ NMR showed 4.4:1 ratio of atropisomers: $^1H$ NMR (400 MHz, $CDCl_3$) δ 7.92 (d, J=8.7 Hz, 2H), 7.44 (d, J=8.6 Hz, 2H), 7.23 (d, J=9.0 Hz, 2H [δ 7.19 minor isomer shown]), 6.91 (d, J=9.1 Hz, 2H [δ 6.84 minor isomer shown]), 4.80 (s, 2H [δ 4.83 minor isomer shown]), 4.69 (s, 2H [δ 4.81 minor isomer shown]), 4.40-4.37 (m, 1H), 1.30 (d, J=6.6 Hz, 6H [δ 1.15 minor isomer shown]); $^{13}C$ NMR (100 MHz, $CDCl_3$) δ 176.66 [δ 176.83 minor isomer shown], 168.10 [δ 167.78 minor isomer shown], 156.69, 137.56, 129.75, 129.36 [δ 129.54 minor isomer shown], 128.99, 126.93, 125.29, 116.20 [δ 116.11 minor isomer shown], 67.90 [δ 68.68 minor isomer shown], 48.96, 37.20, 21.49 [δ 19.98 minor isomer shown].

LC-MS (ESI+) m/z 420.08 (M+H)+; HRMS (ESI+ve) m/z calculated for $C_{20}H_{20}Cl_2N_3O_3$ (M+H)+420.0876. found 420.0891.

SO1-181 (11h)

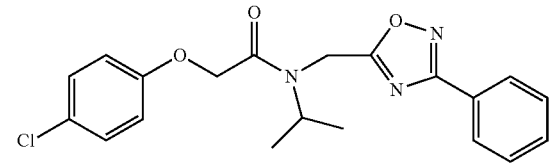

Chemical Formula: $C_{20}H_{20}ClN_3O_3$
Exact Mass: 385.1193
Molecular Weight: 385.8441

2-(4-Chlorophenoxy)-N-isopropyl-N-((3-phenyl-1,2,4-oxadiazol-5-yl)methyl)acetamide (SO1-181) (11h): This compound was synthesized using the same protocol for 1 (SO1-143) except using 2-(4-chlorophenoxy)acetyl chloride (5d) (200 mg, 0.96 mmol) and isopropyl-(3-phenyl)-[1,2,4]oxadiazol-5-ylmethyl)-amine (10c) (120 mg, 0.48 mmol) and triethyl amine (100 mg, 0.95 mmol). The compound 11h (SO1-181) was obtained as a white solid (150 mg, 82%). M.p. 108.3-109.5° C.

HPLC 99.8% ($R_t$=9.5 min, 60% $CH_3CN$ in 0.1% TFA water 30 min); The $^1$H NMR showed 3:1 ratio of atropisomers: $^1$H NMR (400 MHz, $CDCl_3$) δ 7.99 (dd, J=7.9, 1.7 Hz, 2H [δ 8.02 minor isomer shown]), 7.56-7.41 (m, 3H), 7.23 (d, J=9.0 Hz, 2H [δ 7.19 minor isomer shown]), 6.91 (d, J=9.0 Hz, 2H [δ 6.87 minor isomer shown]), 4.80 (s, 2H [δ 4.85 minor isomer shown]), 4.70 (s, 2H), 4.43-4.36 (m, 1H), 1.30 (d, J=6.6 Hz, 6H [δ 1.15 minor isomer shown]); $^{13}$C NMR (100 MHz, $CDCl_3$) δ 176.42, 168.56, 168.08, 156.73, 131.44 [δ 131.87 minor isomer shown], 129.75 [δ 129.68 minor isomer shown], 129.75 [δ 129.02 minor isomer shown], 127.69, 126.91, 126.79, 116.23 [δ 116.16 minor isomer shown], 67.92 [δ 68.52 minor isomer shown], 48.97 [δ 47.07 minor isomer shown], 37.19 [δ 38.43 minor isomer shown], 21.47 [δ 19.98 minor isomer shown].

LC-MS (ESI+) m/z 386.14 (M+H)$^+$; HRMS (ESI+ve) m/z calculated for $C_{20}H_{21}ClN_3O_3$ (M+H)$^+$386.1266. found 386.1269.

SO1-160 (11i)

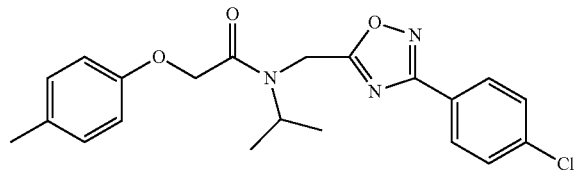

Chemical Formula: $C_{21}H_{22}ClN_3O_3$
Exact Mass: 399.1350
Molecular Weight: 399.8707

N-((3-(4-chlorophenyl)-1,2,4-oxadiazol-5-yl)methyl)-N-isopropyl-2-(p-tolyloxy)acetamide (SO1-160) (11i): This compound was synthesized using the same protocol for 1 (SO1-143) except using p-tolyloxy-acetyl chloride (5a) (110 mg, 0.60 mmol) and [3-(4-chloro-phenyl)-[1,2,4]oxadiazol-5-ylmethyl)-isopropyl-amine (10d) (100 mg, 0.4 mmol) and triethyl amine (80 mg, 0.80 mmol). The compound 11i (SO1-160) was isolated as a white solid (140 mg, 85%). M.p. 133.5-134.3° C.

HPLC 99.7% ($R_t$=21.0 min, 60% $CH_3CN$ in 0.1% TFA water 30 min); The $^1$H NMR showed 3.6:1 ratio of atropisomers: $^1$H NMR (400 MHz, $CDCl_3$) δ 7.95 (d, J=8.6 Hz, 2H), 7.43 (d, J=8.6 Hz, 2H [δ 7.45 minor isomer shown]), 7.08 (d, J=8.3 Hz, 2H [δ 7.03 minor isomer shown]), 6.87 (d, J=8.6 Hz, 2H [δ 6.79 minor isomer shown]), 4.78 (s, 2H [δ 4.86 minor isomer shown]), 4.69 (s, 2H [δ 4.81 minor isomer shown]), 4.46-4.40 (m, 1H), 2.28 (s, 3H [δ 2.25 minor isomer shown]), 1.30 (d, J=6.6 Hz, 6H [δ 1.15 minor isomer shown]); $^{13}$C NMR (101 MHz, $CDCl_3$) δ 176.85, [δ 176.00 minor isomer shown], 168.56 [δ 167.78 minor isomer shown], 156.26, 137.34, 131.26, 130.28 [δ 130.24 minor isomer shown], 129.30 [δ 129.45 minor isomer shown], 129.04, 125.42, 114.67 [δ 114.59 minor isomer shown], 67.98 [δ 68.95 minor isomer shown], 48.96 [δ 47.05 minor isomer shown], 37.22 [δ 38.48 minor isomer shown], 21.50, 20.74 [δ 19.99 minor isomer shown].

LC-MS (ESI+) m/z 400.14 (M+H)$^+$; HRMS (ESI+ve) m/z calculated for $C_{21}H_{23}ClN_3O_3$ (M+H)$^+$400.1423. found 400.1423.

SO2-011 (11j)

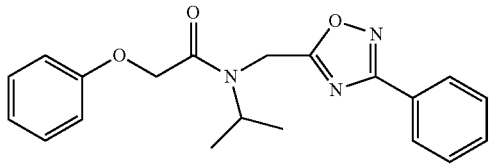

Chemical Formula: $C_{20}H_{21}N_3O_3$
Exact Mass: 351.1583
Molecular Weight: 351.3990

N-Isopropyl-2-phenoxy-N-((3-phenyl-1,2,4-oxadiazol-5-yl)methyl)acetamide (SO2-011) (11j): This compound was synthesized using the same protocol for 1 (SO1-143) except using phenoxyacetyl chloride (5c) (47 mg, 0.27 mmol) and isopropyl-(3-phenyl)-[1,2,4]oxadiazol-5-ylmethyl)-amine (10c) (50 mg, 0.27 mmol) and triethyl amine (47 mg, 0.46 mmol). The compound 11j (SO2-011) was obtained as a white solid (60 mg, 76%). M.p. 77.9-79.0° C.

HPLC 94.37% ($R_t$=11.6 min, 60% $CH_3CN$ in 0.1% TFA water 30 min); The $^1$H NMR showed 4:1 ratio of atropisomers: $^1$H NMR (400 MHz, $CDCl_3$) δ 8.02 (dd, J=8.1, 1.6 Hz, 2H), 7.59-7.40 (m, 3H), 7.36-7.22 (m, 2H), 7.03-6.95 (m, 3H), 4.83 (s, 2H [δ 4.88 minor isomer shown]), 4.72 (s, 2H [δ 4.86 minor isomer shown]), 4.46-4.40 (m, 1H), 1.31 (d, J=6.6 Hz, 6H [δ 1.16 minor isomer shown]); $^{13}$C NMR (100 MHz, $CDCl_3$) δ 176.53 [δ 176.65 minor isomer shown], 168.72 [δ 168.80 minor isomer shown], 168.53, 158.01 [δ 157.85 minor isomer shown], 156.40 131.44 [δ 131.81 minor isomer shown], 129.88 [δ 129.82 minor isomer shown], 129.79, 129.00 [δ 129.17 minor isomer shown], 127.73 [δ 127.69 minor isomer shown], 127.04, 126.78, 122.00, 116.21, 114.86 [δ 114.81 minor isomer shown], 67.66 [δ 68.34 minor isomer shown], 49.09 [δ 47.12 minor isomer shown], 37.28 [δ 38.45 minor isomer shown], 21.43 [δ 19.95 minor isomer shown].

LC-MS (ESI+) m/z 352.17 (M+H)$^+$; HRMS (ESI+ve) m/z calculated for $C_{20}H_{22}N_3O_3$ (M+H)$^+$352.1656. found 352.1662.

SO2-006 (11k)

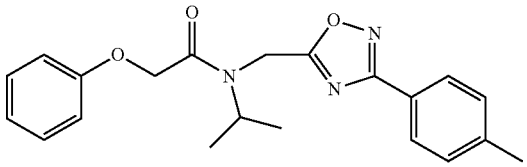

Chemical Formula: $C_{21}H_{23}N_3O_3$
Exact Mass: 365.1739
Molecular Weight: 365.4256

N-Isopropyl-2-phenoxy-N-((3-p-tolyl-1,2,4-oxadiazol-5-yl)methyl)acetamide (SO2-006) (11k): This compound was synthesized using the same protocol for 1 (SO1-143) except using phenoxyacetyl chloride (5c) (80 mg, 0.46 mmol) and isopropyl-(3-p-tolyl-[1,2,4]oxadiazol-5-ylmethyl)-amine (10a) (89 mg, 0.39 mmol) and triethyl amine (78 mg, 0.77 mmol). The compound 11k (SO2-006) was obtained as a white solid (100 mg, 78%). M.p. 97.8-99.5° C.

HPLC 99.8% ($R_t$=8.5 min, 60% $CH_3CN$ in 0.1% TFA water 30 min); The $^1$H NMR showed 3:1 ratio of atropisomers: $^1$H NMR (400 MHz, $CDCl_3$) δ 7.90 (d, J=8.2 Hz, 2H [δ 7.93 minor isomer shown]), 7.34-7.22 (m, 4H), 7.00-6.94

(m, 3H), 4.82 (s, 2H [δ 4.87 minor isomer shown]), 4.71 (s, 2H [δ 4.83 minor isomer shown]), 4.45-4.39 (m, 1H), 2.41 (s, 3H [δ 2.42 minor isomer shown]), 1.30 (d, J=6.6 Hz, 6H [δ 1.15 minor isomer shown]); $^{13}$C NMR (100 MHz, CDCl$_3$) δ 176.49 [δ 176.50 minor isomer shown], 168.34 [δ 168.55 minor isomer shown], 141.68 [δ 142.23 minor isomer shown], 129.86 [δ 129.81 minor isomer shown], 129.68, 127.65, 124.01, 121.95, 114.86 [δ 114.83 minor isomer shown], 68.49, 67.81 [δ 68.49 minor isomer shown], 48.96 [δ 46.89 minor isomer shown], 37.21 [δ 38.37 minor isomer shown], 21.48 [δ 19.98 minor isomer shown].

LC-MS (ESI+) m/z 366.19 (M+H)$^+$; HRMS (ESI+ve) m/z calculated for C$_{21}$H$_{24}$N$_3$O$_3$ (M+H)$^+$366.1812. found 366.1816.

SO2-010 (11l)

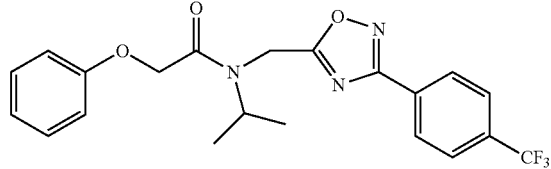

Chemical Formula: C$_{21}$H$_{20}$F$_3$N$_3$O$_3$
Exact Mass: 419.1457
Molecular Weight: 419.3970

N-Isopropyl-2-phenoxy-N-((3-(4-(trifluoromethyl)phenyl)-1,2,4-oxadiazol-5-yl)methyl)acetamide (SO2-010) (11l): This compound was synthesized using the same protocol for 1 (SO1-143) except using phenoxyacetyl chloride (5c) (70 mg, 0.42 mmol) and isopropyl-[3-(4-trifluoromethyl-phenyl)-[1,2,4]oxadiazol-5-ylmethyl)-amine (10b) (80 mg, 0.28 mmol) and triethyl amine (57 mg, 0.56 mmol). The compound 11l (SO2-010) was obtained as a white solid (95 mg, 81%). M.p. 122.8-123.8° C.

HPLC 100% (R$_t$=11.6 min, 60% CH$_3$CN in 0.1% TFA water 30 min); The $^1$H NMR showed 4.5:1 ratio of atropisomers: $^1$H NMR (400 MHz, CDCl$_3$) δ 8.13 (d, J=8.1 Hz, 2H [δ 8.15 minor isomer shown]), 7.72 (d, J=8.2 Hz, 2H [δ 7.75 minor isomer shown]), 7.35-7.26 (m, 2H), 7.03-6.94 (m, 3H [δ 6.90 minor isomer shown]), 4.83 (s, 2H [δ 4.89 minor isomer shown]), 4.72 (s, 2H [δ 4.86 minor isomer shown]), 4.48-4.43 (m, 1H), 1.32 (d, J=6.6 Hz, 6H [δ 1.16 minor isomer shown]); $^{13}$C NMR (100 MHz, CDCl$_3$) δ 177.15 [δ 177.39 minor isomer shown], 168.45 [δ 167.58 minor isomer shown], 158.04, 133.07 (q, J=32.6 Hz), 130.29 [δ 130.27 minor isomer shown], 129.87 [δ 129.83 minor isomer shown], 128.09, 125.97 (q, J=3.7 Hz), 123.99 (q, J=271 Hz), 121.99 [δ 122.07 minor isomer shown], 114.83 [δ 114.75 minor isomer shown], 67.75 [δ 68.75 minor isomer shown], 49.01 [δ 47.05 minor isomer shown], 37.27 [δ 38.58 minor isomer shown], 21.50 [δ 19.98 minor isomer shown]; $^{19}$F NMR (376 MHz, CDCl$_3$) δ -63.37, [δ -63.43 minor isomer shown].

LC-MS (ESI+) m/z 420.15 (M+H)$^+$; HRMS (ESI+ve) m/z calculated for C$_{21}$H$_{21}$F$_3$N$_3$O$_3$ (M+H)$^+$420.1530. found 420.1530.

SO1-172 (11m)

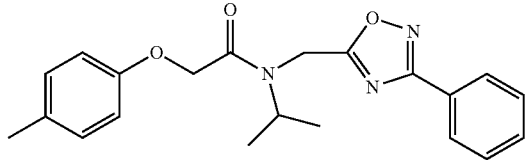

Chemical Formula: C$_{21}$H$_{23}$N$_3$O$_3$
Exact Mass: 365.1739
Molecular Weight: 365.4256

N-isopropyl-N-((3-phenyl-1,2,4-oxadiazol-5-yl)methyl)-2-(p-tolyloxy)acetamide (SO1-172) (11m): This compound was synthesized using the same protocol for 1 (SO1-143) except using p-tolyloxy-acetyl chloride (5a) (130 mg, 0.69 mmol) and isopropyl-(3-phenyl)-[1,2,4]oxadiazol-5-ylmethyl)-amine (10c) (100 mg, 0.46 mmol) and triethyl amine (93 mg, 0.92 mmol). The compound 11m (SO1-172) was isolated as a white solid (150 mg, 91%). M.p. 134.7-136.5° C.

HPLC 97% (R$_t$=8.5 min, 60% CH$_3$CN in 0.1% TFA water 30 min); The $^1$H NMR showed 3:1 ratio of atropisomers: $^1$H NMR (400 MHz, CDCl$_3$) δ 8.02 (dd, J=8.0, 1.6 Hz, 2H), 7.55-7.41 (m, 3H), 7.08 (d, J=8.3 Hz, 2H [δ 7.04 minor isomer shown]), 6.87 (d, J=8.6 Hz, 2H [δ 6.81 minor isomer shown]), 4.78 (s, 2H [δ 4.85 minor isomer shown]), 4.71 (s, 2H [δ 4.83 minor isomer shown]), 4.45-4.40 (m, 1H), 2.28 (s, 3H [δ 2.25 minor isomer shown]), 1.30 (d, J=6.6 Hz, 6H [δ 1.15 minor isomer shown]); $^{13}$C NMR (100 MHz, CDCl$_3$) δ 176.62, 168.53, 156.00, 131.74, 131.37 [δ 131.74 minor isomer shown], 131.22 [δ 131.25 minor isomer shown], 130.28 [δ 130.24 minor isomer shown], 128.97 [δ 129.13 minor isomer shown], 127.73, 126.89, 114.68 [δ 114.62 minor isomer shown], 67.97 [δ 68.75 minor isomer shown], 48.93 [δ 46.94 minor isomer shown], 37.20 [δ 38.44 minor isomer shown], 21.48, [δ 19.98 minor isomer shown], 20.74.

LC-MS (ESI+) m/z 366.18 (M+H)$^+$; HRMS (ESI+ve) m/z calculated for C$_{21}$H$_{24}$N$_3$O$_3$ (M+H)$^+$366.1812. found 366.1828.

SO1-159 (11n)

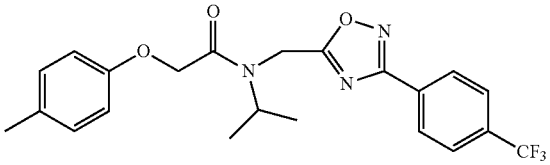

Chemical Formula: C$_{22}$H$_{22}$F$_3$N$_3$O$_3$
Exact Mass: 433.1613
Molecular Weight: 433.4236

N-Isopropyl-2-(p-tolyloxy)-N-((3-(4-(trifluoromethyl)phenyl)-1,2,4-oxadiazol-5-yl)methyl)acetamide (SO1-159) (11n): This compound was synthesized using the same protocol for 1 (SO1-143) except using p-tolyloxy-acetyl chloride (5a) (130 mg, 0.70 mmol) and isopropyl-[3-(4-trifluoromethyl-phenyl)-[1,2,4]oxadiazol-5-ylmethyl)-amine (10b) (100 mg, 0.35 mmol) and triethyl amine (71 mg, 0.70 mmol). The compound 11n (SO1-159) was isolated as a white solid (130 mg, 84%). mp 146.9-148.6° C.

HPLC 99% (R$_t$=16.1 min, 60% CH$_3$CN in 0.1% TFA water 30 min); The $^1$H NMR showed 4:1 ratio of atropisomers: $^1$H NMR (400 MHz, CDCl$_3$) δ 8.14 (d, J=8.1 Hz, 2H), 7.72 (d, J=8.2 Hz, 2H), 7.08 (d, J=8.3 Hz, 2H [δ 7.02 minor isomer shown]), 6.87 (d, J=8.6 Hz, 2H [δ 6.77 minor isomer shown]), 4.79 (s, 2H [δ 4.89 minor isomer shown]), 4.70 (s, 2H [δ 4.81 minor isomer shown]), 4.48-4.42 (m, 1H), 2.28 (s, 3H [δ 2.23 minor isomer shown]), 1.31 (d, J=6.6 Hz, 6H [δ 1.16 minor isomer shown]); $^{13}$C NMR (100 MHz, CDCl$_3$) δ 177.20 [δ 178.43 minor isomer shown], 168.62, [δ 167.54 minor isomer shown], 155.98 [δ 155.73 minor isomer shown], 131.27 [δ 131.37 minor isomer shown], 130.29 [δ 130.24 minor isomer shown], 128.09, 126.88 (q, J=28 Hz), 125.97 (q, J=4.1 Hz), 125.68 (q, J=262.26 Hz), 114.65 [δ 114.54 minor isomer shown], 67.94 [δ 68.85 minor isomer shown], 48.97, 37.26, 21.50, 20.74 [δ 19.62 minor isomer shown]; $^{19}$F NMR (376 MHz, CDCl$_3$) δ -63.39 [δ -63.45 minor isomer shown].

LC-MS (ESI+) m/z 434.18 (M+H)⁺; HRMS (ESI+ve) m/z calculated for $C_{22}H_{23}F_3N_3O_3$ (M+H)⁺434.1686. found 434.1693.

SO2-058 (11o)

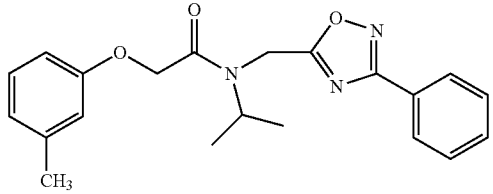

Chemical Formula: $C_{21}H_{23}N_3O_3$
Exact Mass: 365.1739
Molecular Weight: 365.4256

N-isopropyl-N-((3-phenyl-1,2,4-oxadiazol-5-yl)methyl)-2-(m-tolyloxy)acetamide (SO2-058) (11o): This compound was synthesized using the same protocol for 1 (SO1-143) except using m-tolyloxy-acetyl chloride (5h) (76 mg, 0.41 mmol) and isopropyl-(3-phenyl-[1,2,4]oxadiazol-5-ylmethyl)-amine (10c) (60 mg, 0.30 mmol) and triethyl amine (60 mg, 0.60 mmol). The compound 110 (SO2-058) was obtained as a colorless viscous compound (83 mg, 76%).

HPLC 98.5% ($R_f$=8.6 min, 60% $CH_3CN$ in 0.1% TFA water 30 min); The ¹H NMR showed 3:1 ratio of atropisomers: ¹H NMR (400 MHz, CDCl₃) δ 8.01 (dd, J=8.0, 1.5 Hz, 2H [δ 8.08 minor isomer shown]), 7.58-7.37 (m, 4H), 7.17 (t, J=7.6 Hz, 1H), 6.87-6.65 (m, 2H), 4.79 (s, 2H [δ 4.85 minor isomer shown]), 4.71 (s, 2H [δ 4.84 minor isomer shown]), 4.46-4.40 (m, 1H), 2.31 (s, 3H [δ 2.25 minor isomer shown]), 1.31 (d, J=6.6 Hz, 6H [δ 1.16 minor isomer shown]); ¹³C NMR (100 MHz, CDCl₃) δ 176.58, 168.43 [δ 168.56 minor isomer shown], 158.09, 139.99, 131.74, 131.36 [δ 131.74 minor isomer shown], 129.58 [δ 129.53 minor isomer shown], 128.96 [δ 129.13 minor isomer shown], 127.72, 126.90, 122.80 [δ 122.84 minor isomer shown], 115.64 [δ 115.74 minor isomer shown], 111.70 [δ 111.46 minor isomer shown], 67.79 [δ 68.59 minor isomer shown], 48.97 [δ 46.97 minor isomer shown], 37.22 [δ 38.52 minor isomer shown], 21.49 [δ 19.98 minor isomer shown], 21.76.

LC-MS (ESI+) m/z 366.19 HRMS (ESI+ve) m/z calculated for $C_{21}H_{24}N_3O_3$ (M+H)⁺366.1812. found 366.1817.

SO2-073 (11p)

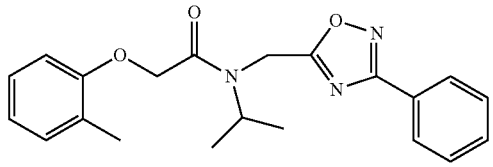

Chemical Formula: $C_{21}H_{23}N_3O_3$
Exact Mass: 365.1739
Molecular Weight: 365.4256

N-Isopropyl-N-((3-phenyl-1,2,4-oxadiazol-5-yl)methyl)-2-(o-tolyloxy)acetamide (SO2-073) (11p): This compound was synthesized using the same protocol for 1 (SO1-143) except using o-tolyloxy-acetyl chloride (5i) (54 mg, 0.28 mmol) and isopropyl-(3-phenyl-[1,2,4]oxadiazol-5-ylmethyl)-amine (10c) (50 mg, 0.23 mmol) and triethyl amine (57 mg, 0.56 mmol). The compound SO2-073 11p was obtained as a colorless viscos compound (71 mg, 85%). M.p. 129.1-130° C.

HPLC 98.0% ($R_f$=9.5 min, 60% $CH_3CN$ in 0.1% TFA water 30 min); The ¹H NMR showed 3:1 ratio of atropisomers: ¹H NMR (400 MHz, CDCl₃) δ 7.95 (dd, J=7.9, 1.6 Hz, 2H), 7.47-7.33 (m, 3H), 7.11-7.03 (m, 1H), 6.86-6.78 (m, 2H), 4.75 (s, 2H [δ 4.81 minor isomer shown]), 4.65 (s, 2H), 4.48-4.38 (m, 1H), 2.22 (s, 3H [δ 2.14 minor isomer shown]), 1.24 (d, J=6.6 Hz, 6H [δ 1.09 minor isomer shown]); ¹³C NMR (100 MHz, CDCl₃) δ 176.68, 176.57 [δ 176.68 minor isomer shown], 168.57, 168.50, 156.23, 131.38 [δ 131.77 minor isomer shown], 131.18, 128.98 [δ 129.15 minor isomer shown], 127.73, 127.25, 126.87, 126.84, 121.61 [δ 121.69 minor isomer shown], 111.28 [δ 111.63 minor isomer shown], 68.01 [δ 68.86 minor isomer shown], 48.94, 48.90, 37.22 [δ 38.26 minor isomer shown], 21.51 [δ 20.07 minor isomer shown], 16.62.

LC-MS (ESI+) m/z 366.14 (M+H)⁺; HRMS (ESI+ve) m/z calculated for $C_{21}H_{24}N_3O_3$ (M+H)⁺366.1812. found 366.1821.

SO2-045 (11q)

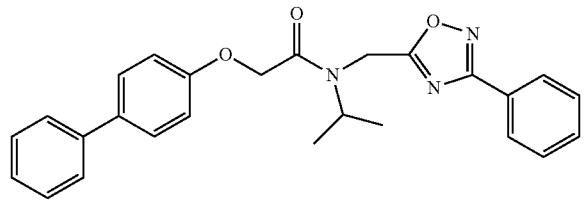

Chemical Formula: $C_{26}H_{25}N_3O_3$
Exact Mass: 427.1896
Molecular Weight: 427.4950

2-(Biphenyl-4-yloxy)-N-isopropyl-N-((3-phenyl-1,2,4-oxadiazol-5-yl)methyl)acetamide (SO2-045) (11q): This compound was synthesized using the same protocol for 1 (SO1-143) except using 2-(biphenyl-4-yloxy)acetyl chloride (5e) (120 mg, 0.47 mmol) and isopropyl-(3-phenyl)-[1,2,4]oxadiazol-5-ylmethyl)-amine (10c) (85 mg, 0.39 mmol) and triethyl amine (79 mg, 0.78 mmol). The compound 11q (SO2-045) was obtained as a white solid (145 mg, 87%). M.p. 147.8-148.7° C.

HPLC 99.6% ($R_f$=14.6 min, 60% $CH_3CN$ in 0.1% TFA water 30 min); The ¹H NMR showed 3:1 ratio of atropisomers: ¹H NMR (400 MHz, CDCl₃) δ 8.02 (dd, J=8.2, 1.4 Hz, 2H), 7.55-7.36 (m, 9H), 7.31 (t, J=7.4 Hz, 1H), 7.05 (d, J=8.8 Hz, 2H [δ 7.00 minor isomer shown]), 4.87 (s, 2H [δ 4.91 minor isomer shown]), 4.73 (s, 2H), 4.48-4.42 (m, 1H), 1.33 (d, J=6.6 Hz, 6H [δ 1.17 minor isomer shown]); ¹³C NMR (100 MHz, CDCl₃) δ 176.55 [δ 176.69 minor isomer shown], 168.58, 168.30, 157.63 [δ 157.49 minor isomer shown], 140.78, 135.04, 131.36 [δ 131.77 minor isomer shown], 128.98, 128.94 [δ 129.16 minor isomer shown], 128.53, 127.71, 127.04, 127.01 [δ 126.88 minor isomer shown], 115.17 [δ 115.10 minor isomer shown], 68.62, 67.86 [δ 68.62 minor isomer shown], 48.98 [δ 47.02 minor isomer shown], 37.22 [δ 38.50 minor isomer shown], 21.51 [δ 20.00 minor isomer shown].

LC-MS (ESI+) m/z 428.21 (M+H)⁺; HRMS (ESI+ve) m/z calculated for $C_{26}H_{26}N_3O_3$ (M+H)⁺428.1969. found 428.1968.

SO2-046 (11r)

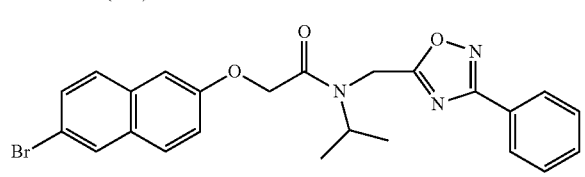

Chemical Formula: $C_{24}H_{22}BrN_3O_3$
Exact Mass: 479.0845
Molecular Weight: 480.3538

2-(6-Bromonaphthalen-2-yloxy)-N-isopropyl-N-((3-phenyl-1,2,4-oxadiazol-5-yl)methyl)acetamide (SO2-046) (11r): This compound was synthesized using the same protocol for 1 (SO1-143) except using 2-(6-bromonapthalen-2-yloxy)acetyl chloride (5g) (140 mg, 0.47 mmol) and isopropyl-(3-phenyl)-[1,2,4]oxadiazol-5-ylmethyl)-amine (10c) (85 mg, 0.39 mmol) and triethyl amine (79 mg, 0.78 mmol). The compound 11r (SO2-046) was obtained as a white solid (140 mg, 75%). M.p. 97.7-98.4° C.

HPLC 98.1% ($R_t$=19.6 min, 60% $CH_3CN$ in 0.1% TFA water 30 min); The $^1H$ NMR showed 3:1 ratio of atropisomers: $^1H$ NMR (400 MHz, $CDCl_3$) δ 7.93-7.91 (m, 3H), 7.67 (d, J=9.0 Hz, 1H), 7.56 (d, J=8.9 Hz, 1H), 7.53-7.36 (m, 4H), 7.24 (dd, J=9.0, 2.6 Hz, 1H), 7.19 (d, J=2.3 Hz, 1H), 4.93 (s, 2H [δ 4.98 minor isomer shown]), 4.72 (s, 2H [δ 4.86 minor isomer shown]), 4.52-4.46 (m, 1H), 1.33 (d, J=6.6 Hz, 6H [δ 1.18 minor isomer shown]); $^{13}C$ NMR (100 MHz, $CDCl_3$) δ 176.47, 168.14 [δ 168.59 minor isomer shown], 156.26, 133.02, 131.36 [δ 131.80 minor isomer shown], 130.63, 130.00 [δ 129.94 minor isomer shown], 129.82, 129.03 [δ 129.14 minor isomer shown], 128.94, 127.63 [δ 127.68 minor isomer shown], 126.75, 119.65 [δ 119.49 minor isomer shown], 117.90, 107.72, 67.89 [δ 68.50 minor isomer shown], 49.03 [δ 47.10 minor isomer shown], 37.23 [δ 38.65 minor isomer shown], 29.94, 21.53 [δ 19.99 minor isomer shown].

LC-MS (ESI+) m/z 480.09 (M+H)$^+$; HRMS (ESI+ve) m/z calculated for $C_{24}H_{23}BrN_3O_3$ (M+H)$^+$480.0917. found 480.0914.

SO2-030 (11s)

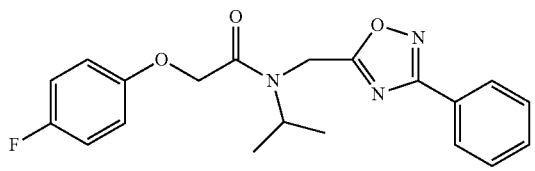

Chemical Formula: $C_{20}H_{20}FN_3O_3$
Exact Mass: 369.1489
Molecular Weight: 369.3895

2-(4-Fluorophenoxy)-N-isopropyl-N-((3-phenyl-1,2,4-oxadiazol-5-yl)methyl)acetamide (SO2-030) (11s): This compound was synthesized using the same protocol for 1 (SO1-143) except using 2-(4-fluorophenoxy)acetyl chloride (5f) (100 mg, 0.53 mmol) and isopropyl-(3-phenyl)-[1,2,4]oxadiazol-5-ylmethyl)-amine (10c) (90 mg, 0.42 mmol) and triethyl amine (1.07 mg, 1.06 mmol). The compound 11s (SO2-030) was obtained as a white solid (160 mg, 82%). M.p. 83.0-85.5° C.

HPLC 99.46% ($R_t$=16.00 min, 50% $CH_3CN$ in 0.1% TFA water 30 min); The $^1H$ NMR showed 3:1 ratio of atropisomers: $^1H$ NMR (400 MHz, $CDCl_3$) δ 8.00 (dd, J=8.1, 1.6 Hz, 2H [δ 8.04 minor isomer shown]), 7.56-7.41 (m, 3H), 7.02-6.88 (m, 4H), 4.80 (s, 2H [δ 4.85 minor isomer shown]), 4.72 (s, 2H [δ 4.83 minor isomer shown]), 4.44-4.38 (m, 1H), 1.31 (d, J=6.7 Hz, 6H [δ 1.16 minor isomer shown]); $^{13}C$ NMR (100 MHz, $CDCl_3$) δ 176.49 [δ 177.63 minor isomer shown], 168.82 [δ 168.56 minor isomer shown], 159.17 [δ 156.79 minor isomer shown], 154.25 [δ 154.23 minor isomer shown], 131.44 [δ 131.86 minor isomer shown], 129.00 [δ 129.19 minor isomer shown], 127.64 (d, J=272 Hz), 127.69, 126.82, 116.36 [δ 116.29 minor isomer shown], 116.11 (d, J=40.9 Hz) 116.01 [δ 115.92 minor isomer shown], 68.30 [δ 68.92 minor isomer shown], 48.91 [δ 46.94 minor isomer shown], 37.18 [δ 38.39 minor isomer shown], 21.46 [δ 19.97 minor isomer shown]; $^{19}F$ NMR (376 MHz, $CDCl_3$) δ -123.13.

LC-MS (ESI+) m/z 370.15 (M+H)$^+$; HRMS (ESI+ve) m/z calculated for $C_{20}H_{21}FN_3O_3$ (M+H)$^+$370.1562. found 370.1567.

SO2-089 (11t)

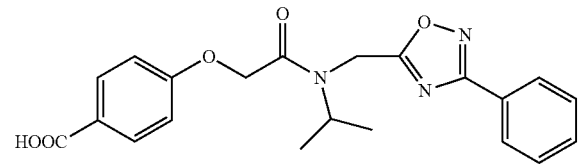

Chemical Formula: $C_{21}H_{21}N_3O_5$
Exact Mass: 395.1481
Molecular Weight: 395.4085

4-(2-(Isopropyl((3-phenyl-1,2,4-oxadiazol-5-yl)methyl)amino)-2-oxoethoxy)benzoic acid (SO2-089) (11t): A solution of 11aq (SO2-068) (50 mg, 0.11 mmol) in trifluoroacetic acid (3 ml) and dichloromethane (5 ml) were stirred 2 h at rt. Acetone (5 ml) was added to the reaction mixture and the solvents were evaporated under vacuo to give the pure compound 11t (SO2-089) as a white compound. (41 mg, 95%). M.p. 211.3-213.8° C.

HPLC 100% ($R_t$=14.8 min, 40% MeOH in 0.1% TFA water 30 min); The $^1H$ NMR showed 3:1 ratio of atropisomers: $^1H$ NMR (400 MHz, DMSO) δ 12.58 (brs, 1H), 7.97-7.90 (m, 2H [δ 8.03-7.98 minor isomer shown]), 7.82 (d, J=8.8 Hz, 2H), 7.64-7.47 (m, 2H), 6.96 (d, J=8.8 Hz, 2H), 5.09 (s, 2H [δ 5.02 minor isomer shown]), 4.75 (s, 2H [δ 5.00 minor isomer shown]), 4.63 (s, 1H), 4.32-4.20 (m, 1H [δ 4.66-4.60 minor isomer shown]), 1.28 (d, J=6.5 Hz, 6H [δ 1.07 minor isomer shown]). $^{13}C$ NMR (100 MHz, $CDCl_3$) δ 176.32, 171.41, 168.58, 167.80, 162.38, 132.70 [δ 132.63 minor isomer shown], 131.48 [δ 131.94 minor isomer shown], 129.22, 129.01 [δ 129.22 minor isomer shown], 127.68 [δ 126.71 minor isomer shown], 122.97 [δ 122.90 minor isomer shown], 114.71 [δ 114.68 minor isomer shown], 67.46 [δ 67.96 minor isomer shown], 49.07 [δ 47.24 minor isomer shown], 37.24 [δ 38.43 minor isomer shown], 21.46 [δ 19.96 minor isomer shown].

LC-MS (ESI+) m/z 396.15 (M+H)$^+$; HRMS (ESI+ve) m/z calculated for $C_{21}H_{22}N_3O_5$ (M+H)$^+$396.1554. found 396.1566.

SO2-170 (11u)

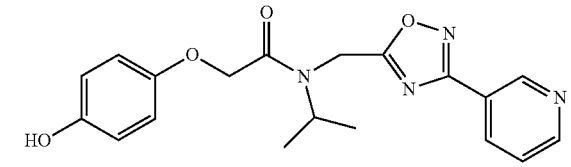

Chemical Formula: $C_{19}H_{20}N_4O_4$
Exact Mass: 368.1485
Molecular Weight: 368.3865

2-(4-Hydroxyphenoxy)-N-isopropyl-N-((pyridine-3-yl)-1,2,4-oxadiazol-5-yl)methyl)acetamide (SO2-170) (11u): This compound was synthesized using the same protocol for 11x (SO2-076) except using 2-(4-hydroxyphenoxy)acetyl chloride (5s) (62 mg, 0.33 mmol) and of N-((3-pyridin-3-yl)-1,2,4-oxadiazol-5-yl)methyl)propan-2-amine (10f) (60 mg, 0.27 mmol) and triethyl amine (55 mg, 0.54 mmol). The compound 11u (SO2-170) was isolated as a white solid. (83 mg, 83%). mp 140.0-142.4° C.

HPLC 100% ($R_t$=5.47 min, 45% MeOH in 0.1% TFA water 20 min); The $^1H$ NMR showed 5:1 ratio of atropisomers: $^1H$ NMR (400 MHz, $CDCl_3$) δ 9.23 (s, 1H), 9.11 (s, 1H [δ 9.23 minor isomer shown]), 8.70 (dd, J=4.8, 1.4 Hz, 1H [δ 8.74 minor isomer shown]), 8.30 (dt, J=8.0, 1.9 Hz, 1H), 7.43 (dd, J=7.9, 4.8 Hz, 1H), 6.88 (d, J=9.1 Hz, 2H), 6.80 (d, J=9.1 Hz, 2H), 4.78 (s, 2H [δ 4.88 minor isomer shown]), 4.69 (s, 2H), 4.60-4.52 (m, 1H), 1.29 (d, J=6.6 Hz, 6H [δ 1.16 minor isomer shown]); $^{13}$C NMR (100 MHz, CDCl$_3$) δ 177.39, 169.00, 166.13, 152.05, 151.05, 148.10, 135.85, 124.36, 116.41 19 [δ 117.00 minor isomer shown], 115.97, 68.37, 48.88, 37.08, 21.49 19 [δ 19.99 minor isomer shown].

LC-MS (ESI+) m/z 369.15 (M+H)$^+$; HRMS (ESI+ve) m/z calculated for C$_{19}$H$_{21}$N$_4$O$_4$ (M+H)$^+$369.1557. found 369.1571.

SO2-171 (11v)

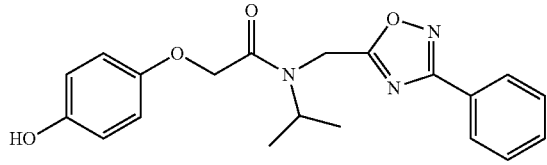

Chemical Formula: C$_{20}$H$_{21}$N$_3$O$_4$
Exact Mass: 367.1532
Molecular Weight: 367.3984

2-(4-hydroxyphenoxy)-N-isopropyl-N-((3-phenyl-1,2,4-oxadiazol-5-yl)methyl)acetamide (SO2-171) (11v): This compound was synthesized using the same protocol same protocol for 1 (SO1-143) except using 2-(4-hydroxyphenoxy)acetyl chloride (5s) (52 mg, 0.23 mmol) and isopropyl-(3-phenyl)-[1,2,4]oxadiazol-5-ylmethyl)-amine (10c) (52 mg, 0.28 mmol) and triethyl amine (47 mg, 0.46 mmol). The compound 11v (SO2-171) was obtained as a white solid (68 mg, 80%). M.p. 155.5-158.5° C.

HPLC 100% (R$_t$=13.1 min, 40% CH$_3$CN in 0.1% TFA water 20 min); The $^1$H NMR showed 3:1 ratio of atropisomers: $^1$H NMR (400 MHz, CDCl$_3$) δ 8.04 (d, J=8.2 Hz, 1H), 8.01 (dd, J=7.8, 1.7 Hz, 2H [δ 8.04 minor isomer shown]), 7.54-7.43 (m, 3H), 6.85 (d, J=9.0 Hz, 2H [δ 6.80 minor isomer shown]), 6.73 (d, J=9.0 Hz, 2H [δ 6.70 minor isomer shown]), 4.75 (s, 2H [δ 4.85 minor isomer shown]), 4.71 (s, 2H [δ 4.80 minor isomer shown]), 4.48-4.41 (m, 1H), 1.30 (d, J=6.6 Hz, 6H [δ 1.15 minor isomer shown]). $^{13}$C NMR (101 MHz, DMSO) δ 178.76 [δ 178.92 minor isomer shown], 168.67, 168.57 [δ 168.67 minor isomer shown], 168.12 [δ 168.25 minor isomer shown], 152.16 [δ 152.02 minor isomer shown], 151.45, 150.38, 132.27 [δ 132.45 minor isomer shown], 129.97 [δ 130.02 minor isomer shown], 127.61 [δ 127.69 minor isomer shown], 126.78 [δ 126.55 minor isomer shown], 116.30, 116.21 [δ 116.13 minor isomer shown], 116.16 [δ 115.91 minor isomer shown], 67.33 [δ 67.42 minor isomer shown], 48.31, 40.79, 40.58, 40.37, 40.16, 39.95, 39.74, 39.53, 37.77, 21.34 [δ 19.94 minor isomer shown].

LC-MS (ESI+) m/z 368.16 (M+H)$^+$; HRMS (ESI+ve) m/z calculated for C$_{20}$H$_{22}$N$_3$O$_4$ (M+H)$^+$368.1605. found 368.1615.

SO2-075 (11w)

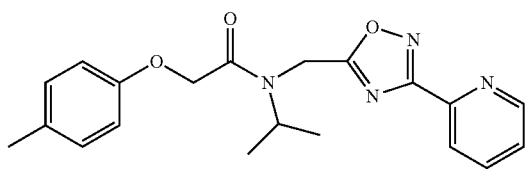

Chemical Formula: C$_{20}$H$_{22}$N$_4$O$_3$
Exact Mass: 366.1692
Molecular Weight: 366.4137

N-Isopropyl-N-((3-(pyridin-2-yl)-1,2,4-oxadizaol-5-yl)methyl)-2-(p-tolyloxy)acetamide (SO2-075) (11w): This compound was synthesized using the same protocol for 11x (SO2-076) except using p-tolyloxy-acetyl chloride (5a) (42 mg, 0.24 mmol) and N-((3-pyridin-2-yl)-1,2,4-oxadiazol-5-yl)methyl)propan-2-amine (10e) (42 mg, 0.20 mmol) and triethyl amine (38 mg, 0.38 mmol). The compound 11w (SO2-075) was obtained as a white compound (52 mg, 75%). M.p. 125.7-126.9° C.

HPLC 96.2% (R$_t$=15.7 min, 40% CH$_3$CN in 0.1% TFA water 30 min); The $^1$H NMR showed 3:1 ratio of atropisomers: $^1$H NMR (400 MHz, CDCl$_3$) δ 8.79 (d, J=4.7 Hz, 1H), 8.06 (d, J=7.9 Hz, 1H), 7.82 (td, J=7.8, 1.7 Hz, 1H), 7.42 (dd, J=6.7, 4.9 Hz, 1H), 7.09 (d, J=8.4 Hz, 2H [δ 7.03 minor isomer shown]), 6.87 (d, J=8.5 Hz, 2H [δ 6.80 minor isomer shown]), 4.79 (s, 2H [δ 4.93 minor isomer shown]), 4.77 (s, 2H [δ 4.81 minor isomer shown]), 4.49-4.38 (m, 1H), 2.29 (s, 3H [δ 2.24 minor isomer shown]), 1.29 (d, J=6.6 Hz, 6H [δ 1.16 minor isomer shown]); $^{13}$C NMR (100 MHz, CDCl$_3$) δ 177.38, 168.57 [δ 168.37 minor isomer shown], 155.96, 150.60 [δ 150.73 minor isomer shown], 146.46, 137.19, 131.25, 130.30, 125.72, 123.51, 114.66, 67.98 [δ 68.99 minor isomer shown], 49.01, 37.24, 21.44 [δ 19.95 minor isomer shown], 20.72. LC-MS (ESI+) m/z 367.17 (M+H)$^+$; HRMS (ESI+ve) m/z calculated for C$_{20}$H$_{23}$N$_4$O$_3$ (M+H)$^+$ 367.1765. found 367.1774.

SO2-076 (11x)

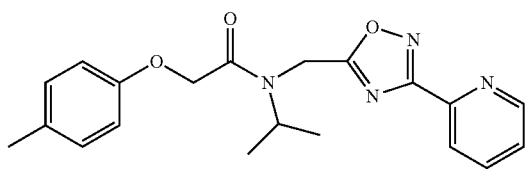

Chemical Formula: C$_{20}$H$_{22}$N$_4$O$_3$
Exact Mass: 366.1692
Molecular Weight: 366.4137

N-isopropyl-N-((3-(pyridin-3-yl)-1,2,4-oxadiazol-5-yl)methyl)-2-(p-tolyloxy)acetamide N-Isopropyl-N-((3-(pyridin-3-yl)-1,2,4-oxadizaol-5-yl)methyl)-2-(p-tolyloxy)acetamide 11x (SO2-076): To a solution of N-((3-(pyridin-3-yl)-1,2,4-oxadiazol-5-yl)methyl)propan-2-amine (11f) (50 mg, 0.23 mmol) and triethyl amine (47 mg, 0.46 mmol) in THF (10 ml) at rt was added p-tolyloxy-acetyl chloride (5a) (51 mg, 0.27 mmol) in THF (1 ml) dropwise. As the acyl chloride was added, a precipitate was formed and the reaction was completed in 10 min. The THF was evaporated and the residue purified by column chromatography (EtOAc:hexane gradient elution) to obtain 11x as a white solid (69 mg, 82%). M.p. 126.5-128.3° C.

HPLC 98.3% (R$_t$=10.6 min, 35% CH$_3$CN in 0.1% TFA water 30 min); The $^1$H NMR showed 4:1 ratio of atropisomers: $^1$H NMR (400 MHz, CDCl$_3$) δ 9.24 (s, 1H), 8.72 (dd, J=4.8, 1.2 Hz, 1H [δ 8.75 minor isomer shown]), 8.27 (dt, J=7.9, 1.6 Hz, 1H), 7.39 (dd, J=8.0, 4.9 Hz, 1H [δ 7.43 minor isomer shown]), 7.08 (d, J=8.6 Hz, 2H [δ 7.02 minor isomer shown]), 6.86 (d, J=8.5 Hz, 2H [δ 6.77 minor isomer shown]), 4.78 (s, 2H [δ 4.88 minor isomer shown]), 4.70 (s, 2H [δ 4.78 minor isomer shown]), 4.49-4.39 (m, 1H), 2.27 (s, 3H [δ 2.22 minor isomer shown]), 1.31 (d, J=6.6 Hz, 6H [δ 1.16 minor isomer shown]); $^{13}$C NMR (100 MHz, CDCl$_3$) $^{13}$C NMR (100 MHz, CDCl$_3$) δ 177.23, 168.60, 166.65, 155.94 [δ 155.72 minor isomer shown], 152.24 [δ 152.52 minor isomer shown], 148.92 [δ 148.87 minor isomer shown], 134.97, 131.30, 130.28, 123.79 [δ 123.86 minor isomer shown], 123.20, 114.64 [δ 114.53 minor isomer shown], 67.91 [δ 69.02 minor isomer shown], 48.99, 48.96, 37.27 [δ 38.66 minor isomer shown], 21.52 [δ 19.99 minor isomer shown], 20.72. LC-MS (ESI+) m/z 367.17 (M+H)⁺; HRMS (ESI+ve) m/z calculated for C₂₀H₂₃N₄O₃ (M+H)⁺ 367.1765. found 367.1774.

SO2-069 (11y)

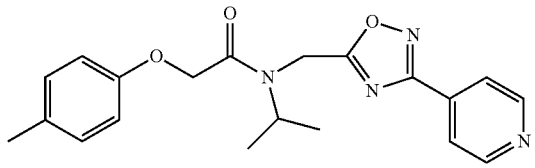

Chemical Formula: C₂₀H₂₂N₄O₃
Exact Mass: 366.1692
Molecular Weight: 366.4137

N-Isopropyl-N-((3-(pyridin-4-yl)-1,2,4-oxadizaol-5-yl)methyl)-2-(p-tolyloxy)acetamide (SO2-069) (11y): This compound was synthesized using the same protocol for 11x (SO2-076) except using p-tolyloxy-acetyl chloride (5a) (21 mg, 0.12 mmol) and N-((3-pyridin-4-yl)-1,2,4-oxadiazol-5-yl)methyl)propan-2-amine (21 mg, 0.10 mmol) (10g) and triethyl amine (19 mg, 0.19 mmol). The compound fly (SO2-069) was obtained as a white compound (27 mg, 78%). M.p. 150.6-151.7° C.

HPLC 96.6% (R$_f$=14.7 min, 30% CH₃CN in 0.1% TFA water 30 min); The ¹H NMR showed 3:1 ratio of atropisomers: ¹H NMR (400 MHz, CDCl₃) δ 8.75 (d, J=4.8 Hz, 2H), 7.87 (d, J=4.6 Hz, 2H), 7.09 (d, J=8.1 Hz, 2H [δ 7.02 minor isomer shown]), 6.87 (d, J=8.5 Hz, 2H [δ 6.76 minor isomer shown]), 4.80 (s, 2H [δ 4.90 minor isomer shown]), 4.70 (s, 2H [δ 4.79 minor isomer shown]), 4.51-4.40 (m, 1H), 2.29 (s, 3H [δ 2.23 minor isomer shown]), 1.32 (d, J=6.6 Hz, 6H [δ 1.16 minor isomer shown]); ¹³C NMR (100 MHz, CDCl₃) δ 177.57, 168.65, 167.05, 155.94, 150.79 [δ 150.91 minor isomer shown], 134.35, 131.30, 130.29, 121.57, 114.64 [δ 114.50 minor isomer shown], 67.91 [δ 69.08 minor isomer shown], 49.01, 48.97, 37.27 [δ 38.61 minor isomer shown], 29.94, 21.52 [δ 19.98 minor isomer shown], 20.72.

LC-MS (ESI+) m/z 367.18 (M+H)⁺; HRMS (ESI+ve) m/z calculated for C₂₀H₂₃N₄O₃ (M+H)⁺367.1765. found 367.1780.

SO2-179 (11z)

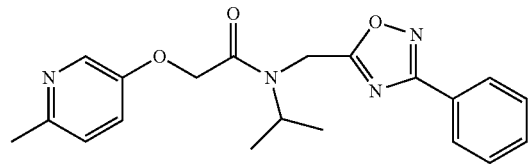

Chemical Formula: C₂₀H₂₂N₄O₃
Exact Mass: 366.1692
Molecular Weight: 366.4137

N-Isopropyl-2-(60methylpyridin-3-yloxy)-N-((3-phenyl-1,2,4-oxadiazol-5-yl)methyl)acetamide (SO2-179) (11z): A solution of 6-methylpyridin-3-ol (80 mg, 0.73 mmol), N-isopropyl-2-chloro-N-((3-phenyl-1,2,4-oxodiazol-5-yl)methyl) acetamide (19) (220 mg, 0.733 mmol) and potassium carbonate (510 mg, 3.665 mmol) in acetonitrile (25 ml) were refluxed for 14 h. The solvent was evaporated, the residue was dissolved in ethyl acetate (20 ml) and washed with water (2×20 ml). Solvent was dried (MgSO₄), evaporated and the compound was purified by column chromatography (EtOAc:hexane gradient elution) to obtain a white solid (199 mg, 72%). M.p 130.3-132.2° C.

HPLC 97.26% (R$_f$=8.3 min, 30% CH₃CN in 0.1% TFA water 30 min); ¹H NMR (400 MHz, CDCl₃) δ 8.27 (d, J=2.9 Hz, 1H [δ 8.26 minor isomer shown]), 8.00 (dd, J=7.9, 1.6 Hz, 1H [δ 8.04 minor isomer shown]), 7.54-7.43 (m, 4H), 7.20 (d, J=8.5 Hz, 1H), 4.93 (s, 2H [δ 5.01 minor isomer shown]), 4.89-4.80 (m, 1H), 4.72 (s, 2H [δ 4.78 minor isomer shown]), 4.33-4.21 (m, 1H [δ 4.89-4.80 minor isomer shown]), 1.35 (d, J=6.6 Hz, 6H [δ 1.16 minor isomer shown]); ¹³C NMR (100 MHz, CDCl₃) δ 176.25, 168.58, 166.98, 153.61, 149.71, 131.50 [δ 131.94 minor isomer shown], 129.26 [δ 129.04 minor isomer shown], 127.69, 126.73, 125.54, 67.68, 48.90 [δ 47.05 minor isomer shown], 47.05, 37.21, 29.93, 21.51 [δ 19.99 minor isomer shown].

LC-MS (ESI+) m/z 367.18 (M+H)⁺; HRMS (ESI+ve) m/z calculated for C₂₀H₂₃N₄O₃(M+H)⁺367.1765. found 367.1759.

SO2-050 (11aa)

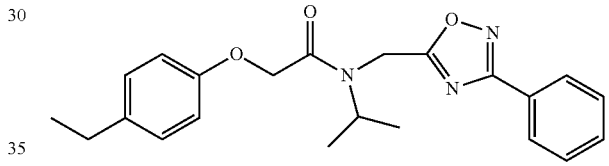

Chemical Formula: C₂₂H₂₅N₃O₃
Exact Mass: 379.1896
Molecular Weight: 379.4522

2-(4-Ethylphenoxy)-N-isopropyl-N-((3-phenyl-1,2,4-oxadiazol-5-yl)methyl)acetamide (SO2-050) (11aa): This compound was synthesized using the same protocol for 1 (SO1-143) except using 2-(4-ethylphenoxy)acetyl chloride (5j) (90 mg, 0.47 mmol) and isopropyl-(3-phenyl)-[1,2,4]oxadiazol-5-ylmethyl)-amine (10c) (85 mg, 0.39 mmol) and triethyl amine (79 mg, 0.78 mmol). The compound 11aa (SO2-050) was obtained as a white solid (120 mg, 83%). mp 106.7-109.2° C.

HPLC 95.49% (R$_f$=11.5 min, 60% CH₃CN in 0.1% TFA water 30 min); The ¹H NMR showed 2:1 ratio of atropisomers: ¹H NMR (400 MHz, CDCl₃) δ 8.03 (dd, J=7.9, 1.4 Hz, 2H), 7.55-7.38 (m, 3H), 7.11 (d, J=8.4 Hz, 2H [δ 7.07 minor isomer shown]), 6.90 (d, J=8.5 Hz, 2H [δ 6.84 minor isomer shown]), 4.79 (s, 2H [δ 4.86 minor isomer shown]), 4.71 (s, 2H [δ 4.83 minor isomer shown]), 4.46-4.40 (m, 1H), 2.59 (q, J=7.5 Hz, 2H [δ 2.55 minor isomer shown]), 1.31 (d, J=6.6 Hz, 6H [δ 1.16 minor isomer shown]), 1.20 (t, J=7.6 Hz, 3H); ¹³C NMR (100 MHz, CDCl₃) δ 176.62 [δ 176.77 minor isomer shown], 168.56 [δ 168.66 minor isomer shown], 156.14 [δ 155.94 minor isomer shown], 137.73, 131.38 [δ 131.75 minor isomer shown], 129.11, 128.98, 127.73 [δ 126.90 minor isomer shown], 114.72 [δ 114.76 minor isomer shown], 114.65, 67.97 [δ 68.74 minor isomer shown], 48.98, 37.23 [δ 38.44 minor isomer shown], 28.21, 21.48 [δ 19.99 minor isomer shown], 16.01.

LC-MS (ESI+) m/z 380.21 (M+H)+; HRMS (ESI+ve) m/z calculated for C22H26N3O3 (M+H)+380.1969. found 380.1979.

SO2-103 (11ab)

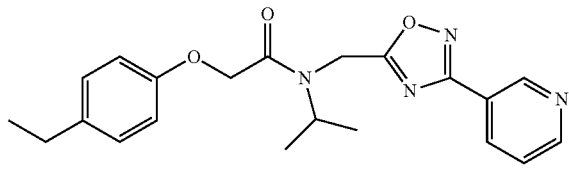

Chemical Formula: C21H24N4O3
Exact Mass: 380.1848
Molecular Weight: 380.4403

2-(4-Ethylphenoxy)-N-isopropyl-N-((3-pyridin-3-yl)1,2,4-oxadiazol-5-yl)methylacetamide (SO2-103) (11ab): This compound was synthesized using the same protocol for 11x (SO2-076) except using 2-(4-ethylphenoxy)acetylchloride (5j) (49 mg, 0.25 mmol) and of N-((3-pyridin-3-yl)-1,2,4-oxadiazol-5-yl)methyl)propan-2-amine (10f) (45 mg, 0.21 mmol) and triethyl amine (43 mg, 0.42 mmol). The compound 11ab (SO2-103) was isolated as a white solid. (65 mg, 81%). M.p. 104.4-106.3° C.

HPLC 95.94% ($R_t$=5.4 min, 50% CH3CN in 0.1% TFA water 30 min); The $^1$H NMR showed 4:1 ratio of atropisomers: $^1$H NMR (400 MHz, CDCl3) δ 9.21 (s, 1H), 8.67 (brs, 1H), 8.23 (d, J=7.7 Hz, 1H), 7.42-7.29 (m, 1H), 7.04 (d, J=8.5 Hz, 2H [δ 6.98 minor isomer shown]), 6.82 (d, J=8.5 Hz, 2H [δ 6.73 minor isomer shown]), 4.72 (s, 2H [δ 4.82 minor isomer shown]), 4.64 (s, 2H [δ 4.74 minor isomer shown]), 4.40-4.32 (m, 1H), 2.51 (q, J=7.6 Hz, 2H, [δ 2.47 minor isomer shown]), 1.25 (d, J=6.6 Hz, 6H [δ 1.16 minor isomer shown]), 1.11 (t, J=7.3 Hz, 3H); $^{13}$C NMR (100 MHz, CDCl3) δ 177.26, 168.59, 166.65, 156.09, 152.11, 148.82, 137.79, 135.02, 129.10, 114.68 [δ 114.57 minor isomer shown], 67.97 [δ 69.01 minor isomer shown], 49.00, [δ 46.98 minor isomer shown], 37.29 [δ 38.61 minor isomer shown], 28.19 [δ 29.93 minor isomer shown], 21.49 [δ 19.99 minor isomer shown], 16.00.

LC-MS (ESI+) m/z 381.21 (M+H)+; HRMS (ESI+ve) m/z calculated for C21H25N4O3(M+H)+381.1921. found 381.1941.

SO3-030 (11ac)

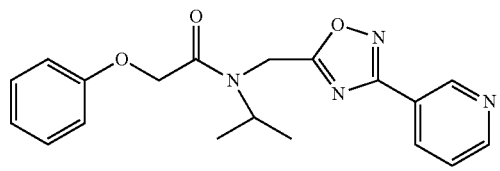

Chemical Formula: C19H20N4O3
Exact Mass: 352.1535
Molecular Weight: 352.3871

N-Isopropyl-2-phenoxy-N-((3-(pyridine-3-yl)-1,2,4-oxadiazol-5-yl)methyl)acetamide (SO3-030) (11ac): This compound was synthesized using the same protocol for 11x (SO2-076) except using phenoxyacetyl chloride (5c) (55 mg, 0.32 mmol) and N-((3-pyridin-3-yl)-1,2,4-oxadiazol-5-yl)methyl)propan-2-amine (10f) (59 mg, 0.27 mmol) and triethyl amine (55 mg, 0.54 mmol). The compound 11ac (SO3-030) was obtained as a white compound (81 mg, 85%). mp 83.0-85.5° C.

HPLC 97.50% ($R_t$=11.4 min, 30% CH3CN in 0.1% TFA water 30 min); The $^1$H NMR showed 4:1 ratio of atropisomers: $^1$H NMR (400 MHz, CDCl3) δ 9.25 (s, 1H), 8.74 (brs, 1H), 8.29 (d, J=8.0 Hz, 1H), 7.45-7.39 (m, 1H), 7.33-7.22 (m, 2H), 7.02-6.87 (m, 3H), 4.82 (s, 2H [δ 4.89 minor isomer shown]), 4.71 (s, 2H [δ 4.84 minor isomer shown]), 4.51-4.37 (m, 1H), 1.32 (d, J=6.6 Hz, 6H [δ 1.16 minor isomer shown]); $^{13}$C NMR (100 MHz, CDCl3) δ 177.21 [δ 177.41 minor isomer shown]), 168.43, 166.62, 158.01 [δ 157.83 minor isomer shown], 152.20 [δ 152.53 minor isomer shown], 148.85, 134.99, 129.85, 123.83 [δ 123.19 minor isomer shown], 121.98, 114.81 [δ 114.71 minor isomer shown], 67.65 [δ 68.66 minor isomer shown], 48.97 [δ 47.08 minor isomer shown]), 38.62, 37.28 21.49 [δ 19.97 minor isomer shown].

LC-MS (ESI+) m/z 353.16 (M+H)+; HRMS (ESI+ve) m/z calculated for C19H21N4O3(M+H)+353.1608. found 353.1614.

SO2-184 (11ad)

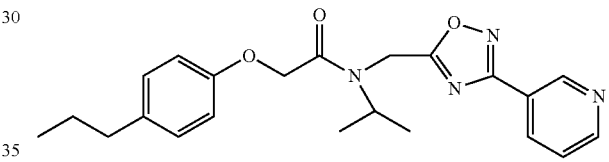

Chemical Formula: C22H26N4O3
Exact Mass: 394.2005
Molecular Weight: 394.4668

N-Isopropyl-2-(4-propylphenoxy)-N-((3-pyridin-3-yl)-1,2,4-oxadiazol-5-yl)methyl)acetamide (SO2-184) (11ad): This compound was synthesized using the same protocol for 11x (SO2-076) except using 2-(4-propylphenoxy)acetyl chloride (5k) (84 mg, 0.39 mmol) and N-((3-pyridin-3-yl)-1,2,4-oxadiazol-5-yl)methyl)propan-2-amine (10f) (72 mg, 0.33 mmol) and triethyl amine (67 mg, 0.66 mmol). The compound 11ad (SO2-184) was obtained as a white compound (100 mg, 84%). M.p. 95.1-98.0° C.

HPLC 97.74% ($R_t$=11.6 min, 50% CH3CN in 0.1% TFA water 20 min); The $^1$H NMR showed 4:1 ratio of atropisomers: $^1$H NMR (400 MHz, CDCl3) δ 9.26 (s, 1H), 8.73 (d, J=3.8 Hz, 1H), 8.29 (dt, J=8.0 Hz, J=2.0 Hz, 1H), 7.40 (dd, J=8.0, 4.9 Hz, 1H), 7.09 (d, J=8.6 Hz, 2H [δ 7.03 minor isomer shown]), 6.88 (d, J=8.6 Hz, 2H [δ 6.79 minor isomer shown]), 4.81 (s, 1H), 4.79 (s, 2H [δ 4.89 minor isomer shown]), 4.71 (s, 2H [δ 4.79 minor isomer shown]), 4.48-4.38 (m, 1H), 2.51 (t, J=7.7 Hz, 2H [δ 2.47 minor isomer shown]), 1.63-1.52 (m, 2H), 1.32 (d, J=6.6 Hz, 6H [δ 1.16 minor isomer shown]), 0.91 (t, J=7.3 Hz, 3H [δ 0.89 minor isomer shown]); $^{13}$C NMR (100 MHz, CDCl3) δ 177.38, 168.61, 166.44 [δ 166.79 minor isomer shown], 156.09 [δ 155.85 minor isomer shown], 151.55 [δ 151.20 minor isomer shown], 148.29 [δ 148.57 minor isomer shown], 136.25 [δ 136.32 minor isomer shown], 135.55 [δ 135.24 minor isomer shown], 129.70, 124.09 [δ 123.57 minor isomer shown], 114.58, 114.48, 67.86 [δ 69.00 minor isomer shown], 49.01 [δ 47.02 minor isomer shown], 37.35 [δ 38.66 minor isomer shown], 29.94, 24.93, 21.52 [δ 19.99 minor isomer shown], 14.02.

LC-MS (ESI+) m/z 395.21 (M+H)+; HRMS (ESI+ve) m/z calculated for C22H27N4O3 (M+H)+395.2078. found 395.2080.

SO3-026 (11ae)

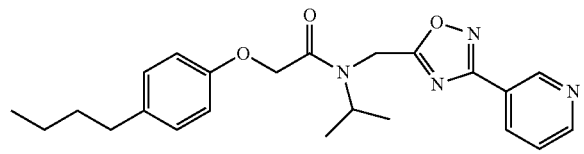

Chemical Formula: C23H28N4O3
Exact Mass: 408.2161
Molecular Weight: 408.4934

2-(4-Butylphenoxy)-N-isopropyl-N-((3-(pyridine-3-yl)-1,2,4-oxadiazol-5-yl)methyl)acetamide (SO3-026) (11ae): This compound was synthesized using the same protocol for 11x (SO2-076) except using 2-(4-butylphenoxy)acetyl chloride (5l) (76 mg, 0.36 mmol) and N-((3-pyridin-3-yl)-1,2,4-oxadiazol-5-yl)methyl)propan-2-amine (10l (61 mg, 0.28 mmol) and triethyl amine (57 mg, 0.56 mmol). The compound 11ae (SO3-026) was obtained as a white compound (94 mg, 82%). M.p. 94.5-95.2° C.

HPLC 97.51% (R$_f$=10.2 min, 60% CH3CN in 0.1% TFA water 30 min); The 1H NMR showed 4:1 ratio of atropisomers: 1H NMR (400 MHz, CDCl3) δ 9.29 (s, 1H [δ 9.26 minor isomer shown]), 8.80-8.73 (m, 1H), 8.44 (d, J=7.5 Hz, 1H [δ 8.33 minor isomer shown]), 7.56-7.52 (m, 1H [δ 7.50 minor isomer shown]), 7.09 (d, J=8.6 Hz, 2H [δ 7.02 minor isomer shown]), 6.87 (d, J=8.6 Hz, 2H [δ 6.78 minor isomer shown]), 4.78 (s, 2H [δ 4.90 minor isomer shown]), 4.70 (s, 2H [δ 4.80 minor isomer shown]), 4.47-4.40 (m, 1H), 2.54 (t, J=7.3 Hz, 2H [δ 2.48 minor isomer shown]), 1.59-1.46 (m, 2H), 1.36-1.29 (m, 2H), 1.32 (d, J=6.6 Hz, 6H [δ 1.16 minor isomer shown]), 0.91 (t, J=7.3 Hz, 3H); 13C NMR (100 MHz, CDCl3) δ 177.23, 168.58, 166.66, 156.07, 152.24 [δ 152.54 minor isomer shown], 148.93, 136.46, 134.97, 129.64, 123.80, 123.21, 114.59 [δ 114.50 minor isomer shown], 67.91, 48.97, 37.29, 34.95, 34.03, 22.53, 21.50 [δ 19.99 minor isomer shown], 14.20.

LC-MS (ESI+) m/z 409.23 (M+H)+; HRMS (ESI+ve) m/z calculated for C23H29N4O3(M+H)+409.2234. found 409.2238.

SO3-050 (11af)

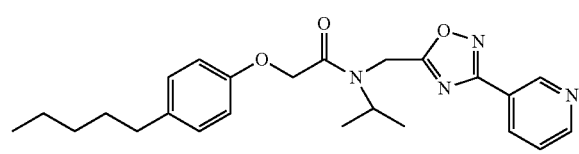

Chemical Formula: C24H30N4O3
Exact Mass: 422.2318
Molecular Weight: 422.5200

N-Isopropyl-2-(4-pentylphenoxy)-N-((3-pyridin-3-yl)-1,2,4-oxadiazol-5-yl)methyl)acetamide (SO3-050) (11af): This compound was synthesized using the same protocol for 11x (SO2-076) except using 2-(4-pentylphenoxy)acetyl chloride (5m) (77 mg, 0.32 mmol) and N-((3-pyridin-3-yl)-1,2,4-oxadiazol-5-yl)methyl)propan-2-amine (10f) (59 mg, 0.27 mmol) and triethyl amine (55 mg, 0.54 mmol). The compound 11af (SO3-050) was obtained as a white compound (95 mg, 83%). M.p. 93.0-95.9° C.

HPLC 96.51% (R$_f$=17.1 min, 70% MeOH in 0.1% TFA water 20 min); 1H NMR (400 MHz, CDCl3) δ 9.19 (s, 1H [δ 9.24 minor isomer shown]), 8.67 (dd, J=4.9, 1.6 Hz, 1H), 8.28-8.19 (m, 1H), 7.43-7.28 (m, 1H), 7.02 (d, J=8.4 Hz, 2H [δ 6.95 minor isomer shown]), 6.81 (d, J=8.5 Hz, 2H [δ 6.72 minor isomer shown]), 4.72 (s, 2H [δ 4.83 minor isomer shown]), 4.64 (s, 2H [δ 4.74 minor isomer shown]), 4.41-4.32 (m, 1H), 2.46 (t, J=7.8 Hz, 2H [δ 2.41 minor isomer shown]), 1.55-1.39 (m, 2H), 1.33-1.05 (m, 4H), 1.25 (d, J=6.7 Hz, 6H [δ 1.09 minor isomer shown]), 0.81 (t, J=6.6 Hz, 3H); 13C NMR (100 MHz, CDCl3) δ 177.29 [δ 177.50 minor isomer shown], 168.62, 166.79, 166.56 [δ 166.79 minor isomer shown], 156.07 [δ 155.82 minor isomer shown], 152.19, 151.88 [δ 152.19 minor isomer shown], 148.60, 136.51 [δ 136.33 minor isomer shown], 135.25, 129.63 [δ 129.59 minor isomer shown], 123.97, 114.60 [δ 114.50 minor isomer shown], 67.90 [δ 69.04 minor isomer shown], 49.00 [δ 47.08 minor isomer shown], 37.30 [δ 38.65 minor isomer shown], 35.24, 31.69, 31.57 [δ 29.93 minor isomer shown], 22.77, 21.51 [δ 19.99 minor isomer shown], 14.29.

LC-MS (ESI+) m/z 423.24 (M+H)+; HRMS (ESI+ve) m/z calculated for C24H31N4O3(M+H)+423.2391. found 423.2393.

SO3-051 (11ag)

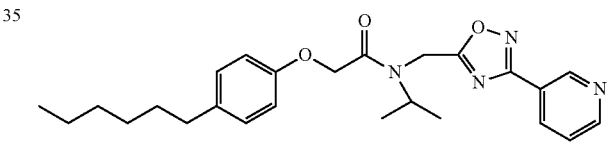

Chemical Formula: C25H32N4O3
Exact Mass: 436.2474
Molecular Weight: 436.5466

2-(4-Hexylphenoxy)-N-isopropyl-N-((3-(pyridine-3-yl)-1,2,4-oxadiazol-5-yl)methyl)acetamide (SO3-051) (11ag): This compound was synthesized using the same protocol for 11x (SO2-076) except using 2-(4-hexylphenoxy)acetyl chloride (5n) (97 mg, 0.38 mmol) and N-((3-pyridin-3-yl)-1,2,4-oxadiazol-5-yl)methyl)propan-2-amine (10g (69 mg, 0.32 mmol) and triethyl amine (65 mg, 0.64 mmol). The compound 11ag (SO3-051) was obtained as a white compound (120 mg, 87%). M.p. 94.4-96.1° C.

HPLC 93.76% (R$_f$=7.7 min, 80% MeOH in 0.1% TFA water 20 min); The 1H NMR showed 4:1 ratio of atropisomers: 1H NMR (400 MHz, CDCl3) δ 9.28 (s, 1H), 8.75 (brs, 1H), 8.33 (d, J=7.9 Hz, 1H), 7.50-7.40 (m, 1H), 7.09 (d, J=8.6 Hz, 2H [δ 7.03 minor isomer shown]), 7.87 (d, J=8.7 Hz, 2H [δ 6.79 minor isomer shown]), 4.79 (s, 2H [δ 4.90 minor isomer shown]), 4.71 (s, 2H [δ 4.81 minor isomer shown]), 4.49-4.36 (m, 1H), 2.53 (t, J=7.8 Hz, 2H), 1.60-1.48 (m, 2H), 1.35-1.22 (m, 6H), 1.32 (d, J=6.6 Hz, 6H [δ 1.16 minor isomer shown]), 0.91-0.83 (m, 3H); 13C NMR (100 MHz, CDCl3) δ 177.34, 168.59, 166.52, 156.06, 151.72 [δ 152.30 minor isomer shown], 148.48 [δ 148.68 minor isomer shown], 136.52, 135.38, 129.63 [δ 129.59 minor isomer shown], 114.60, 114.50, 67.91 [δ 69.02 minor isomer shown], 48.99, 37.31 [δ 38.64 minor isomer shown], 35.28, 31.96, 31.86, 29.18, 22.85, 21.52 [δ 19.99 minor isomer shown], 14.35.

LC-MS (ESI+) m/z 437.24 (M+H)+; HRMS (ESI+ve) m/z calculated for C$_{25}$H$_{33}$N$_4$O$_3$(M+H)+437.2547. found 437.2548.

SO3-066 (11ah)

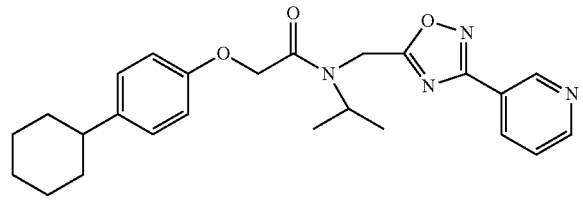

Chemical Formula: C$_{25}$H$_{30}$N$_4$O$_3$
Exact Mass: 434.2318
Molecular Weight: 434.5307

N-Isopropyl-2-(4-cyclohexylphenoxy)-N-((3-pyridin-3-yl)-1,2,4-oxadiazol-5-yl)methyl)acetamide (SO3-066) (11ah): This compound was synthesized using the same protocol for 11x (SO2-076) except using 2-(4-cyclohexylphenoxy)acetyl chloride (5o) (79 mg, 0.31 mmol) and N-((3-pyridin-3-yl)-1,2,4-oxadiazol-5-yl)methyl)propan-2-amine (10f) (57 mg, 0.26 mmol) and triethyl amine (53 mg, 0.52 mmol). The compound 11ah (SO3-054) was obtained as a sticky solid (88 mg, 78%).

HPLC 97.00% (R$_t$=17.0 min, 70% MeOH in 0.1% TFA water 30 min); $^1$H NMR (400 MHz, CDCl$_3$) δ 9.27 (s, 1H), 8.74 (d, J=3.8 Hz, 1H), 8.30 (d, J=8.0 Hz, 1H), 7.48-7.36 (m, 1H), 7.12 (d, J=8.7 Hz, 2H [δ 7.06 minor isomer shown]), 6.88 (d, J=8.7 Hz, 2H [δ 6.80 minor isomer shown]), 4.78 (s, 2H [δ 4.89 minor isomer shown]), 4.71 (s, 2H [δ 4.81 minor isomer shown]), 4.46-4.39 (m, 1H), 2.48-2.37 (m, 1H), 1.87-1.67 (m, 6H), 1.42-1.28 (m, 4H), 1.32 (d, J=6.6 Hz, 6H [δ 1.17 minor isomer shown]); $^{13}$C NMR (100 MHz, CDCl$_3$) δ 177.26 [δ 177.47 minor isomer shown], 168.57, 166.88, 166.66 [δ 166.88 minor isomer shown], 156.11 [δ 155.86 minor isomer shown], 152.20 [δ 152.49 minor isomer shown], 148.91 [δ 148.86 minor isomer shown], 141.82, 141.75, 134.96, 128.03, 123.86, 114.60 [δ 114.50 minor isomer shown], 67.88 [δ 69.03 minor isomer shown], 48.98 [δ 47.07 minor isomer shown], 43.88, 37.30 [δ 38.66 minor isomer shown], 34.85, 27.13 [δ 29.93 minor isomer shown], 26.36, 21.51 [δ 19.99 minor isomer shown].

LC-MS (ESI+) m/z 435.24 (M+H)+; HRMS (ESI+ve) m/z calculated for C$_{25}$H$_{31}$N$_4$O$_3$(M+H)+435.2391. found 435.2395.

SO3-080 (11ai)

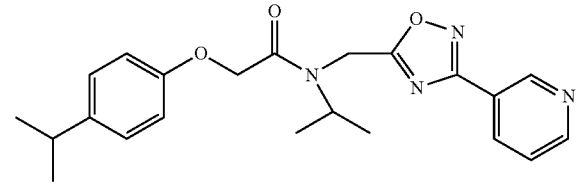

Chemical Formula: C$_{22}$H$_{26}$N$_4$O$_3$
Exact Mass: 394.2005
Molecular Weight: 394.4668

N-Isopropyl-2-(4-isopropylphenoxy)-N-((3-(pyridin-3-yl)-1,2,4-oxadiazol-5-yl)methyl)acetamide (SO3-080) (11ai): This compound was synthesized using the same protocol for 11x (SO2-076) except using 2-(4-isopropylphenoxy)acetyl chloride (5p) (62 mg, 0.29 mmol) and N-((3-pyridin-3-yl)-1,2,4-oxadiazol-5-yl)methyl)propan-2-amine (10f) (53 mg, 0.24 mmol) and triethyl amine (49 mg, 0.48 mmol). The compound 11ai (SO3-080) was obtained as a sticky solid (77 mg, 81%).

HPLC 99.09% (R$_t$=6.7 min, 50% CH$_3$CN in 0.1% TFA water 20 min); $^1$H NMR (400 MHz, CDCl$_3$) δ 9.27 (s, 1H), 8.73 (d, J=4.1 Hz, 1H), 8.30 (dt, J=8.0, 1.8 Hz, 1H), 7.40 (dd, J=7.7, 5.0 Hz, 1H), 7.14 (d, J=8.6 Hz, 2H [δ 7.08 minor isomer shown]), 6.89 (d, J=8.7 Hz, 2H [δ 6.81 minor isomer shown]), 4.79 (s, 2H [δ 4.89 minor isomer shown]), 4.71 (s, 2H [δ 4.81 minor isomer shown]), 4.47-4.39 (m, 1H), 2.90-2.76 (m, 1H), 1.32 (d, J=6.6 Hz, 6H [δ 1.17 minor isomer shown]), 1.20 (d, J=6.9 Hz, 6H); $^{13}$C NMR (100 MHz, CDCl$_3$) δ 177.26 [δ 177.47 minor isomer shown], 168.56, 166.65 [δ 166.88 minor isomer shown], 156.11 [δ 155.88 minor isomer shown], 152.22 [δ 152.52 minor isomer shown], 148.91, 142.44, 134.96, 127.66, 123.81 [δ 123.25 minor isomer shown], 114.64 [δ 114.53 minor isomer shown], 67.89 [δ 69.01 minor isomer shown], 48.98 [δ 47.06 minor isomer shown], 38.65, 37.30, 33.49, 29.93, 24.37, 21.50 [δ 19.99 minor isomer shown].

LC-MS (ESI+) m/z 395.22 (M+H)+; HRMS (ESI+ve) m/z calculated for C$_{22}$H$_{27}$N$_4$O$_3$(M+H)+395.2078. found 395.2074.

SO3-079 (11aj)

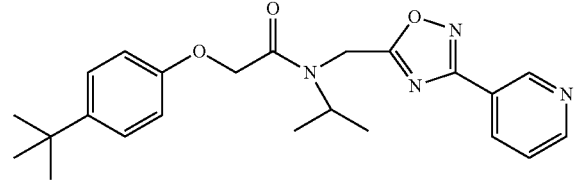

Chemical Formula: C$_{23}$H$_{28}$N$_4$O$_3$
Exact Mass: 408.2161
Molecular Weight: 408.4934

N-Isopropyl-2-(4-tert-butylphenoxy)-N-((3-(pyridin-3-yl)-1,2,4-oxadiazol-5-yl)methyl)acetamide (SO3-079) (11aj): This compound was synthesized using the same protocol for 11x (SO2-076) except using 2-(4-tert-butylphenoxy)acetyl chloride (5r) (62 mg, 0.27 mmol) and N-((3-pyridin-3-yl)-1,2,4-oxadiazol-5-yl)methyl)propan-2-amine (10f) (50 mg, 0.23 mmol) and triethyl amine (47 mg, 0.46 mmol). The compound 11aj (SO3-079) was obtained as a sticky colorless solid (78 mg, 83%).

HPLC 97.96% (R$_t$=9.1 min, 50% CH$_3$CN in 0.1% TFA water 20 min); $^1$H NMR (400 MHz, CDCl$_3$) δ 9.28 (s, 1H), 8.73 (brs, 1H), 8.31 (d, J=8.0 Hz, 1H), 7.40 (dd, J=7.7, 4.9 Hz, 1H), 7.29 (d, J=8.7 Hz, 2H [δ 7.24 minor isomer shown]), 6.89 (d, J=8.7 Hz, 2H [δ 6.81 minor isomer shown]), 4.79 (s, 2H [δ 4.89 minor isomer shown]), 4.71 (s, 2H [δ 4.83 minor isomer shown]), 4.43-4.33 (m, 1H), 1.32 (d, J=6.6 Hz, 6H [δ 1.16 minor isomer shown]), 1.27 (s, 9H); $^{13}$C NMR (100 MHz, CDCl$_3$) δ 177.27 [δ 177.48 minor isomer shown], 168.62, 168.53, 166.64 [δ 166.86 minor isomer shown], 155.76 [δ 155.53 minor isomer shown], 152.23 [δ 152.52 minor isomer shown], 148.89, 144.69, 134.97, 126.64 [δ 126.60 minor isomer shown], 123.87 [δ 123.26 minor isomer shown], 114.26 [δ 114.15 minor isomer shown], 67.75 [δ 68.86 minor isomer shown], 48.98 [δ 47.00 minor isomer shown], 38.62, 37.32 [δ 38.62 minor isomer shown], 34.35, 31.70 [δ 31.67 minor isomer shown], 31.67, 29.94, 21.52 [δ 20.01 minor isomer shown].

LC-MS (ESI+) m/z 409.21 (M+H)⁺; HRMS (ESI+ve) m/z calculated for C₂₃H₂₉N₄O₃(M+H)⁺409.2234. found 409.2233.

SO3-089 (11ak)

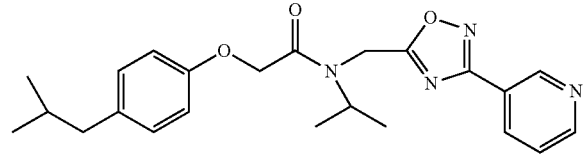

Chemical Formula: C₂₃H₂₈N₄O₃
Exact Mass: 408.2161
Molecular Weight: 408.4934

N-Isopropyl-2-(4-isobutylphenoxy)-N-((3-(pyridin-3-yl)-1,2,4-oxadiazol-5-yl)methyl)acetamide (SO3-089) (11ak): This compound was synthesized using the same protocol for 11x (SO2-076) except using 2-(4-isobutylphenoxy)acetyl chloride (5q) (74 mg, 0.33 mmol) and N-((3-(pyridin-3-yl)-1,2,4-oxadiazol-5-yl)methyl)propan-2-amine (10f) (60 mg, 0.27 mmol) and triethyl amine (55 mg, 0.54 mmol). The compound 11ak (SO3-089) was obtained as a white solid (97 mg, 88%). M.p. 121.5-123.7° C.

HPLC 98.31% ($R_f$=10.8 min, 50% CH₃CN in 0.1% TFA water 20 min); ¹H NMR (400 MHz, CDCl₃) δ 9.27 (s, 1H), 8.74 (brs, 1H), 8.29 (d, J=7.8 Hz, 1H), 7.45-7.39 (m, 1H), 7.05 (d, J=8.3 Hz, 2H [δ 7.00 minor isomer shown]), 6.87 (d, J=8.6 Hz, 2H [δ 6.79 minor isomer shown]), 4.79 (s, 2H [δ 4.90 minor isomer shown]), 4.71 (s, 2H [δ 4.81 minor isomer shown]), 4.50-4.40 (m, 1H), 2.40 (d, J=7.2 Hz, 2H [δ 2.36 minor isomer shown]), 2.36 (d, J=7.1 Hz, 1H), 1.86-1.70 (m, 1H), 1.32 (d, J=6.6 Hz, 6H [δ 1.16 minor isomer shown]), 0.87 (d, J=6.6 Hz, 6H [δ 0.85 minor isomer shown]); ¹³C NMR (100 MHz, CDCl₃) δ 177.24, 168.59 [δ 166.72 minor isomer shown], 166.72, 156.15, 155.89, 152.14, 148.89, 135.26, 134.93, 130.35, 67.93 [δ 69.06 minor isomer shown], 48.98 [δ 47.06 minor isomer shown], 44.73, 37.30 [δ 38.65 minor isomer shown], 30.53 [δ 29.93 minor isomer shown], 22.52, 21.51 [δ 19.98 minor isomer shown].

LC-MS (ESI+) m/z 409.23 (M+H)⁺; HRMS (ESI+ve) m/z calculated for C₂₃H₂₉N₄O₃(M+H)⁺409.2234. found 409.2231.

SO3-074 (11al)

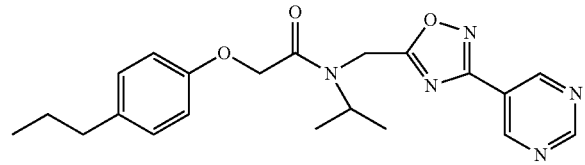

Chemical Formula: C₂₁H₂₅N₅O₃
Exact Mass: 395.1957
Molecular Weight: 395.4549

N-Isopropyl-2-(4-propylphenoxy)-N-((3-(pyrimidin-2-yl)-1,2,4-oxadiazol-5-yl)methyl)acetamide (SO3-074) (11al): This compound was synthesized using the same protocol for 11x (SO2-076) except using 2-(4-propylphenoxy)acetyl chloride (5k) (47 mg, 0.22 mmol) and N-((3-pyrimidin-2-yl)-1,2,4-oxadiazol-5-yl)methyl)propan-2-amine (10h) (40 mg, 0.18 mmol) and triethyl amine (37 mg, 0.26 mmol). The compound 11al (SO3-074) was obtained as a white solid (58 mg, 81%). M.p. 92.7-94.0° C.

HPLC 97.18% ($R_f$=12.1 min, 50% CH₃CN in 0.1% TFA water 20 min); ¹H NMR (400 MHz, CDCl₃) δ 9.41-9.26 (m, 3H), 7.09 (d, J=8.5 Hz, 2H [δ 7.01 minor isomer shown]), 6.87 (d, J=8.6 Hz, 2H [δ 6.75 minor isomer shown]), 4.79 (s, 2H [δ 4.92 minor isomer shown]), 4.71 (s, 2H), 4.49-4.41 (m, 1H), 2.52 (t, J=7.6 Hz, 2H [δ 2.45 minor isomer shown]), 1.64-1.47 (m, 2H), 1.32 (d, J=6.8 Hz, 6H [δ 1.17 minor isomer shown]), 0.91 (t, J=7.6 Hz, 3H); ¹³C NMR (100 MHz, CDCl₃) δ 177.87, 168.67, 164.52, 160.62 [δ 160.82 minor isomer shown], 155.72 [δ 156.04 minor isomer shown], 136.33, 129.71, 121.78, 114.54 [δ 114.40 minor isomer shown], 67.83, 49.03, 49.00, 37.34 [δ 38.87 minor isomer shown], 24.92, 21.53 [δ 20.05 minor isomer shown], 14.02.

LC-MS (ESI+) m/z 396.20 (M+H)⁺; HRMS (ESI+ve) m/z calculated for C₂₁H₂₆N₅O₃(M+H)⁺396.2030. found 396.2031.

SO3-057 (11am)

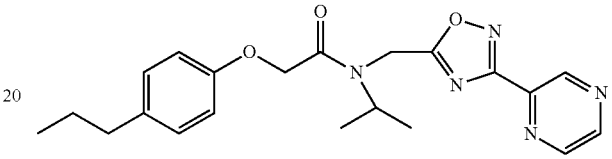

Chemical Formula: C₂₁H₂₅N₅O₃
Exact Mass: 395.1957
Molecular Weight: 395.4549

N-Isopropyl-2-(4-propylphenoxy)-N-((3-(pyrazin-2-yl)-1,2,4-oxadiazol-5-yl)methyl)acetamide (SO3-057) (11am): This compound was synthesized using the same protocol for 11x (SO2-076) except using 2-(4-propylphenoxy)acetyl chloride (80 mg, 0.38 mmol) and N-((3-pyrazin-2-yl)-1,2,4-oxadiazol-5-yl)methyl)propan-2-amine (10j) (69 mg, 0.30 mmol) and triethyl amine (61 mg, 0.60 mmol). The compound 11am (SO3-057) was obtained as a sticky solid (100 mg, 85%).

HPLC 97.25% ($R_f$=11.1 min, 50% MeOH in 0.1% TFA water 30 min); ¹H NMR (400 MHz, CDCl₃) δ 9.29 (d, J=1.4 Hz, 1H [δ 9.26 minor isomer shown]), 8.75-8.67 (m, 2H), 7.08 (d, J=8.6 Hz, 2H [δ 7.01 minor isomer shown]), 6.86 (d, J=8.6 Hz, 2H [δ 6.77 minor isomer shown]), 6.77 (d, J=8.5 Hz, 1H), 4.78 (s, 2H [δ 4.94 minor isomer shown]), 4.76 (s, 1H [δ 4.79 minor isomer shown]), 4.49-4.33 (m, 1H), 2.50 (t, J=7.8 Hz, 2H [δ 2.45 minor isomer shown]), 1.63-1.49 (m, 2H), 1.30 (d, J=6.6 Hz, 6H [δ 1.15 minor isomer shown]), 0.90 (t, J=7.3 Hz, 3H); ¹³C NMR (100 MHz, CDCl₃) δ 178.00, 168.64, 166.65 [δ 166.86 minor isomer shown], 156.08 [δ 155.82 minor isomer shown], 146.96, [δ 146.67 minor isomer shown], 145.02 [δ 145.09 minor isomer shown], 144.62, 142.47, 136.29, 129.72 [δ 129.67 minor isomer shown], 114.58 [δ 114.50 minor isomer shown], 67.92 [δ 69.16 minor isomer shown], 49.02 [δ 47.08 minor isomer shown], 37.35 [δ 38.85 minor isomer shown], 29.93, 24.92, 21.49 [δ 19.96 minor isomer shown], 14.02.

LC-MS (ESI+) m/z 396.19 (M+H)⁺; HRMS (ESI+ve) m/z calculated for C₂₁H₂₆N₅O₃(M+H)⁺396.2030. found 396.2028.

SO3-054 (11an)

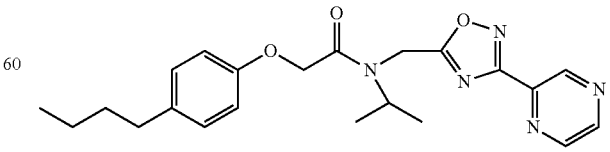

Chemical Formula: C₂₂H₂₇N₅O₃
Exact Mass: 409.2114
Molecular Weight: 409.4815

2(-4-Butylphenoxy)-N-isopropyl-N-((3-(pyrazin-2-yl)-1,2,4-oxadiazol-5-yl)methylecetamide (SO3-054) (11an): This compound was synthesized using the same protocol for 11x (SO2-076) except using 2-(4-butylphenoxy)acetyl chloride (5l) (50 mg, 0.24 mmol) and N-((3-pyrazin-2-yl)-1,2,4-oxadiazol-5-yl)methyl)propan-2-amine (10j) (43 mg, 0.20 mmol) and triethyl amine (41 mg, 0.40 mmol). The compound 11an (SO3-054) was obtained as a greenish sticky solid (64 mg, 78%).

HPLC 97.97% ($R_f$=9.7 min, 70% MeOH in 0.1% TFA water 30 min); $^1$H NMR (400 MHz, CDCl$_3$) δ 9.30 (d, J=1.4 Hz, 1H), 9.27 (s, 1H), 8.77-8.66 (m, 1H), 7.09 (d, J=8.6 Hz, 2H, [δ 7.02 minor isomer shown]), 6.87 (d, J=8.6 Hz, 2H, [δ 6.78 minor isomer shown]), 4.80 (s, 2H, [δ 4.95 minor isomer shown]), 4.76 (s, 2H [δ 4.80 minor isomer shown]), 4.48-4.37 (m, 1H), 2.53 (t, J=7.7 Hz, 2H), 1.58-1.48 (m, 2H), 1.37-1.26 (m, 2H), 1.30 (d, J=6.7 Hz, 6H, [δ 1.16 minor isomer shown]), 0.90 (t, J=7.3 Hz, 3H); $^{13}$C NMR (100 MHz, CDCl$_3$) δ 178.00, 168.64, 166.64, 156.05 [δ 155.78 minor isomer shown], 146.65 [δ 146.94 minor isomer shown], 145.00 [δ 145.08 minor isomer shown], 144.61, 142.47 [δ 142.08 minor isomer shown], 136.49 [δ 136.57 minor isomer shown], 129.65 [δ 129.80 minor isomer shown], 114.60 [δ 114.53 minor isomer shown], 67.93 [δ 69.17 minor isomer shown], 49.01 [δ 47.13 minor isomer shown], 37.34 [δ 38.85 minor isomer shown], 34.94, 34.00, 31.15, 29.92, 22.52 [δ 21.11 minor isomer shown], 21.47 [δ 19.95 minor isomer shown], 14.17.

LC-MS (ESI+) m/z 410.222 (M+H)$^+$; HRMS (ESI+ve) m/z calculated for C$_{22}$H$_{28}$N$_5$O$_3$(M+H)$^+$410.2187. found 410.2185.

SO3-096 (11ao)

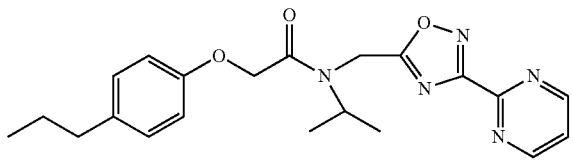

Chemical Formula: C$_{21}$H$_{25}$N$_5$O$_3$
Exact Mass: 395.1957
Molecular Weight: 395.4549

N-Isopropyl-2-(4-propylphenoxy)-N-((3-(pyrimidin-2-yl)-1,2,4-oxadiazol-5-yl)methyl)acetamide (SO3-096) (11ao): This compound was synthesized using the same protocol for 11x (SO2-076) except using 2-(4-propylhenoxy)acetyl chloride (5k) (47 mg, 0.22 mmol) and N-((3-pyrimidin-2-yl)-1,2,4-oxadiazol-5-yl)methyl)propan-2-amine (10i) (40 mg, 0.18 mmol) and triethyl amine (37 mg, 0.36 mmol). The compound SO3-096 11ao was obtained as a colorless sticky solid (97 mg, 88%).

HPLC 97.92% ($R_f$=7.1 min, 50% CH$_3$CN in 0.1% TFA water 20 min); $^1$H NMR (400 MHz, CDCl$_3$) δ 8.96 (d, J=4.9 Hz, 2H), 7.45 (t, J=4.9 Hz, 1H, [δ 7.48 minor isomer shown]), 7.10 (d, J=8.6 Hz, 2H [δ 7.04 minor isomer shown]), 6.88 (d, J=8.7 Hz, 2H [δ 6.81 minor isomer shown]), 4.83 (s, 2H [δ 4.99 minor isomer shown]), 4.80 (s, 2H [δ 4.81 minor isomer shown]), 4.50-4.25 (m, 1H) 2.52 (t, J=7.7 Hz, 2H [δ 2.48 minor isomer shown]), 1.66-1.51 (m, 2H [δ 1.46-1.38 minor isomer shown]), 1.28 (d, J=6.6 Hz, 2H [δ 1.14 minor isomer shown]), 0.92 (t, J=7.3 Hz, 3H); $^{13}$C NMR (100 MHz, CDCl$_3$) δ 168.62 [δ 167.85 minor isomer shown], 158.19, 156.27, 156.09, 136.24, 129.73, 122.37, 114.59, 67.97 [δ 69.02 minor isomer shown], 49.02 [δ 47.00 minor isomer shown], 37.36 [δ 38.85 minor isomer shown], 37.34, 24.93 [δ 29.93 minor isomer shown], 21.42 [δ 19.90 minor isomer shown], 14.02.

LC-MS (ESI+) m/z 396.19 (M+H)$^+$; HRMS (ESI+ve) m/z calculated for C$_{21}$H$_{26}$N$_5$O$_3$(M+H)$^+$396.2030. found 396.2025.

SO3-126 (11ap)

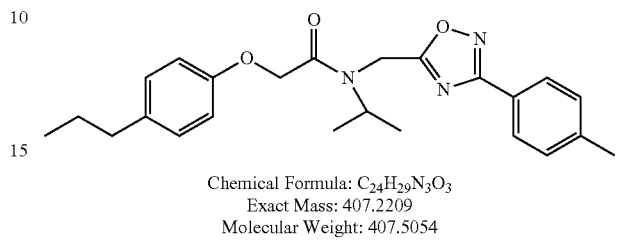

Chemical Formula: C$_{24}$H$_{29}$N$_3$O$_3$
Exact Mass: 407.2209
Molecular Weight: 407.5054

N-Isopropyl-2-(4-propylphenoxy)-N-((3-p-tolyl-1,2,4-oxadiazol-5-yl)methyl)acetamide (SO3-126) (11ap): This compound was synthesized using the same protocol for 1 (SO1-143) except using 2-(4-propylphenoxy)acetyl chloride (5k) (130 mg, 0.61 mmol) and N-((3-p-tolyl-1,2,4-oxadiazol-5-yl)methyl)propan-2-amine (10a) (128 mg, 0.55 mmol) and triethyl amine (112.3 mg, 11.10 mmol). The compound 11ap (SO3-126) was obtained as a white (195 mg, 87%). mp 121.7-122.3° C.

HPLC 99.33% ($R_f$=11.1 min, 45% MeOH in 0.1% TFA water 30 min); $^1$H NMR (400 MHz, CDCl$_3$) δ 7.90 (d, J=8.2 Hz, 2H), 7.29-7.20 (m, 2H), 7.07 (d, J=8.6 Hz, 2H [δ 7.03 minor isomer shown]), 6.87 (d, J=8.6 Hz, 2H [δ 6.82 minor isomer shown]), 4.77 (s, 2H [δ 4.83 minor isomer shown]), 4.69 (s, 2H [δ 4.82 minor isomer shown]), 4.45-4.34 (m, 1H), 2.54-2.46 (m, 2H), 2.40 (d, J=3.8 Hz, 3H [δ 2.39 minor isomer shown]), 1.62-1.53 (m, 2H), 1.29 (d, J=6.6 Hz, 6H [δ 1.13 minor isomer shown]), 0.91 (t, J=7.3 Hz, 3H); $^{13}$C NMR (100 MHz, CDCl$_3$) δ 176.43 [δ 176.57 minor isomer shown], 168.50 [δ 168.56 minor isomer shown], 156.18 [δ 155.99 minor isomer shown], 141.66 [δ 142.14 minor isomer shown], 136.16, 129.69 [δ 129.83 minor isomer shown], 127.65, 124.09 [δ 123.58 minor isomer shown], 114.64 [δ 114.59 minor isomer shown], 67.99 [δ 68.74 minor isomer shown], 48.94 [δ 46.89 minor isomer shown], 37.37 [δ 38.41 minor isomer shown], 37.22, 24.92, 21.82, 21.47 [δ 19.98 minor isomer shown], 14.03.

LC-MS (ESI+) m/z 408.24 (M+H)$^+$; HRMS (ESI+ve) m/z calculated for C$_{24}$H$_{30}$N$_3$O$_3$(M+H)$^+$408.2282. found 409.2279.

SO2-068 11aq

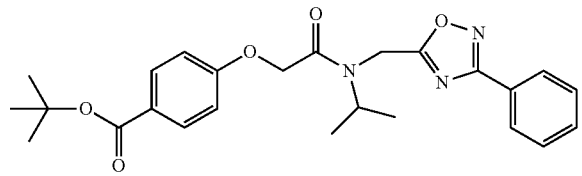

Chemical Formula: C$_{25}$H$_{29}$N$_3$O$_5$
Exact Mass: 451.2107
Molecular Weight: 451.5149 tert-Butyl 4-(2-(isopropyl((3-phenyl-1,2,4-oxadiazol-5-yl)methyl)amino)-2-oxoethoxy)benzoate (SO2-068) (11aq): A solution of tert-Butyl 4-hydroxybenzoate (28) (26 mg, 0.14 mmol), N-isopropyl-2-chloro-N-((3-phenyl-1,2,4-oxodiazol-5-yl)methyl)acetamide (19) (40 mg, 0.14 mmol) and potassium carbonate (97 mg, 0.7 mmol) in acetonitrile (20 ml) were refluxed overnight. Acetonitile was evaporated and the residue was dissolved in ethyl acetate (20 ml) and washed with water (20 ml×2). Organic solvent was dried (MgSO$_4$) and the product was purified by column chromatography (EtOAc:hexane gradient elution) to obtain 11aq as a white solid (50 mg, 80%). M.p. 143.0-144.4° C.

HPLC 99.7% ($R_t$=14.1 min, 60% CH$_3$CN in 0.1% TFA water 30 min); The $^1$H NMR showed 3:1 ratio of atropisomers: $^1$H NMR (400 MHz, CDCl$_3$) δ 7.97 (d, J=8.8 Hz, 2H [δ 8.01 minor isomer shown]), 7.92 (d, J=8.8 Hz, 2H [δ 7.88 minor isomer shown]), 7.50-7.38 (m, 3H), 6.96 (d, J=8.9 Hz, 2H [δ 6.93 minor isomer shown]), 4.86 (s, 2H [δ 4.91 minor isomer shown]), 4.69 (s, 2H [δ 4.78 minor isomer shown]), 4.41-4.31 (m, 1H), 1.55 (s, 9H), 1.29 (d, J=6.6 Hz, 6H [δ 1.14 minor isomer shown]). $^{13}$C NMR (100 MHz, CDCl$_3$) δ 176.37 [δ 176.47 minor isomer shown], 168.57, 167.84 [δ 167.93 minor isomer shown], 165.83, 165.64, 161.35, 159.73, 131.87, 131.75 [δ 131.68 minor isomer shown], 131.43, 129.00 [δ 129.19 minor isomer shown], 127.69, 126.75, 125.77, 124.71, 115.17, 114.35 [δ 114.30 minor isomer shown], 80.98 [δ 80.81 minor isomer shown], 77.56, 77.44, 77.35, 77.24, 77.03, 76.92, 76.71, 67.56 [δ 68.11 minor isomer shown], 49.02 (47.15), 37.22 [δ 38.41 minor isomer shown], 28.48 [δ 29.93 minor isomer shown], 28.46, 21.48 [δ 19.98 minor isomer shown].

LC-MS (ESI+) m/z 469.26 (M+NH$_4$)$^+$; HRMS (ESI+ve) m/z calculated for C$_{25}$H$_{30}$N$_3$O$_5$ (M+H)$^+$452.2180. found 452.2191.

SO1-157 (12a)

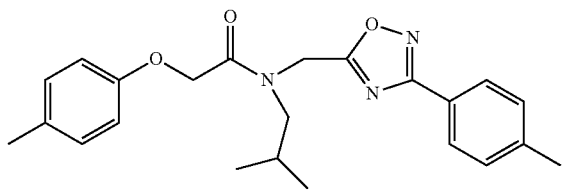

Chemical Formula: C$_{23}$H$_{27}$N$_3$O$_3$
Exact Mass: 393.2052
Molecular Weight: 393.4788

N-Isobutyl-N-((3-p-tolyl-1,2,4-oxadiazol-5-yl)methyl)-2-(p-tolyloxy)acetamide (SO1-157) (12a): This compound was synthesized using the same protocol for 1 (SO1-143) except using p-tolyloxy-acetyl chloride (5a) (160 mg, 0.87 mmol) and isobutyl-(3-p-tolyl-[1,2,4]oxadiazol-5-ylmethyl)-amine (10m) (110 mg, 0.43 mmol) and triethyl amine (88 mg, 0.87 mmol). The compound 12a (SO1-157) was isolated as a white solid (130 mg, 87%). M.p. 78.4-79.8° C.

HPLC 99.27% ($R_t$=11.8 min, 60% CH$_3$CN in 0.1% TFA water 30 min); The $^1$H NMR showed 1.5:1 ratio of atropisomers: $^1$H NMR (400 MHz, CDCl$_3$) δ 7.92 (d, J=8.2 Hz, 2H), 7.30-7.25 (m, 2H), 7.08 (d, J=8.3 Hz, 2H [δ 7.04 minor isomer shown]), 6.86 (d, J=8.6 Hz, 2H [δ 6.81 minor isomer shown]), 4.85 (s, 2H [δ 4.93 minor isomer shown]), 4.79 (s, 2H [δ 4.86 minor isomer shown]), 3.36 (d, J=7.7 Hz, 2H [δ 3.34 minor isomer shown]), 2.41 (s, 3H [δ 2.42 minor isomer shown]), 2.27 (s, 3H [δ 2.24 minor isomer shown]), 2.06-1.94 (m, 1H), 1.01 (d, J=6.6 Hz, 6H [δ 0.86 minor isomer shown]); $^{13}$C NMR (100 MHz, CDCl$_3$) δ 175.43 [δ 175.48 minor isomer shown], 169.22 [δ 169.08 minor isomer shown], 168.61 [δ 168.79 minor isomer shown], 156.04 [δ 155.63 minor isomer shown], 141.82 [δ 142.15 minor isomer shown], 131.21 [δ 131.33 minor isomer shown], 130.24, 129.74 [δ 129.84 minor isomer shown], 127.66 [δ 127.67 minor isomer shown], 123.92 [δ 123.53 minor isomer shown], 114.82 [δ 114.54 minor isomer shown], 67.23 [δ 68.55 minor isomer shown], 55.50 [δ 54.51 minor isomer shown], 42.10 [δ 43.59 minor isomer shown], 27.73 [δ 26.86 minor isomer shown], 21.85, [δ 20.75 minor isomer shown], 20.28 [δ 20.15 minor isomer shown].

LC-MS (ESI+) m/z 394.20 (M+H)$^+$; HRMS (ESI+ve) m/z calculated for C$_{23}$H$_{28}$N$_3$O$_3$ (M+H)$^+$394.2125. found 394.2127.

SO2-012 (12b)

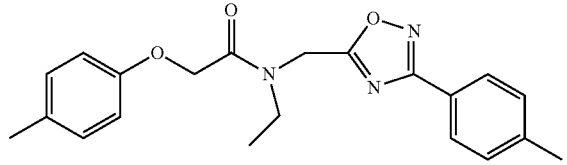

Chemical Formula: C$_{21}$H$_{23}$N$_3$O$_3$
Exact Mass: 365.1739
Molecular Weight: 365.4256

N-Ethyl-N-((3-p-tolyl-1,2,4-oxadiazol-5-yl)methyl)-2-(p-tolyloxy)acetamide (SO2-012) (12b): This compound was synthesized using the same protocol for 1 (SO1-143) except using p-tolyloxy-acetyl chloride (5a) (54 mg, 0.28 mmol) and ethyl-(3-p-tolyl-[1,2,4]oxadiazol-5-ylmethyl)-amine (10l) (50 mg, 0.23 mmol) and triethyl amine (47 mg, 0.46 mmol). The compound 12b (SO2-012) was obtained as a white solid (70 mg, 82%). M.p. 83.4-84.0° C.

HPLC 99.6% ($R_t$=9.0 min, 60% CH$_3$CN in 0.1% TFA water 30 min); The $^1$H NMR showed 2:1 ratio of atropisomers: $^1$H NMR (400 MHz, CDCl$_3$) δ 7.93 (d, J=8.1 Hz, 2H [δ 7.91 minor isomer shown]), 7.27 (d, J=8.7 Hz, 2H [δ 7.29 minor isomer shown]), 7.10 (d, J=8.2 Hz, 2H [δ 7.03 minor isomer shown]), 6.87 (d, J=8.6 Hz, 2H [δ 6.79 minor isomer shown]), 4.84 (s, 2H [δ 4.91 minor isomer shown]), 4.78 (s, 2H [δ 4.82 minor isomer shown]), 3.63 (q, J=7.1 Hz, 2H [δ 3.59 minor isomer shown]), 2.41 (s, 3H [δ 2.42 minor isomer shown]), 2.29 (s, 3H [δ 2.24 minor isomer shown]), 1.29 (t, J=7.1 Hz, 3H [δ 1.16 minor isomer shown]); $^{13}$C NMR (100 MHz, CDCl$_3$) δ 175.56 [δ 175.49 minor isomer shown], 168.86 [δ 168.80 minor isomer shown], 168.66 [δ 168.48 minor isomer shown], 156.00 [δ 155.65 minor isomer shown], 141.85 [δ 142.12 minor isomer shown], 131.27 [δ 131.32 minor isomer shown], 130.30 [δ 130.27 minor isomer shown], 130.25 129.75 [δ 129.82 minor isomer shown], 127.66, 123.89 [δ 123.56 minor isomer shown], 114.72 [δ 114.52 minor isomer shown], 67.61 [δ 68.52 minor isomer shown], 43.31 [δ 42.97 minor isomer shown], 41.30 [δ 42.72 minor isomer shown], 21.83, 20.74 [δ 20.68 minor isomer shown], 14.14 [δ 12.56 minor isomer shown].

LC-MS (ESI+) m/z 366.19 (M+H)$^+$; HRMS (ESI+ve) m/z calculated for C$_{21}$H$_{24}$N$_3$O$_3$ (M+H)$^+$366.1812. found 366.1810.

SO1-184 (12c)

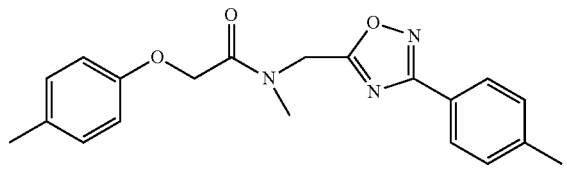

Chemical Formula: C$_{20}$H$_{21}$N$_3$O$_3$
Exact Mass: 351.1583
Molecular Weight: 351.3990

N-Methyl-N-((3-p-tolyl-1,2,4-oxadiazol-5-yl)methyl)-2-(p-tolyloxy)acetamide (SO1-184) (12c): This compound was synthesized using the same protocol for SO1-143 1 except using p-tolyloxy-acetyl chloride (5a) (81 mg, 0.44 mmol) and methyl-(3-p-tolyl-[1,2,4]oxadiazol-5-ylmethyl)-amine (10k) (60 mg, 0.30 mmol) and triethyl amine (60 mg, 0.59 mmol). The compound 12c (SO1-184) was obtained as a white solid (100 mg, 95%). M.p. 99.1-100.9° C.

HPLC 96% ($R_f$=7.4 min, 60% $CH_3CN$ in 0.1% TFA water 30 min); The $^1$H NMR showed 2:1 ratio of atropisomers: $^1$H NMR (400 MHz, $CDCl_3$) δ 7.93 (d, J=8.3 Hz, 2H [δ 7.90 minor isomer shown]), 7.30-7.26 (d, J=7.9 Hz, 2H), 7.14-7.07 (d, J=8.1 Hz, 2H [δ 7.03 minor isomer shown]), 6.87 (d, J=8.6 Hz, 2H [δ 6.78 minor isomer shown]), 4.88 (s, 2H [δ 4.94 minor isomer shown]), 4.78 (s, 2H [δ 4.82 minor isomer shown]), 3.28 (s, 3H [δ 3.12 minor isomer shown]), 2.42 (s, 3H), 2.28 (s, 3H [δ 2.23 minor isomer shown]); $^{13}$C NMR (100 MHz, $CDCl_3$) δ 175.13 [δ 175.03 minor isomer shown], 169.08 [δ 168.92 minor isomer shown], 168.80 [δ 168.68 minor isomer shown], 155.58 [δ 155.89 minor isomer shown], 141.91 [δ 142.12 minor isomer shown], 131.32 [δ 131.38 minor isomer shown], 130.29, 129.82, 129.77, 127.65, 123.82 [δ 123.54 minor isomer shown], 114.76, [δ 114.44 minor isomer shown], 67.57 [δ 68.37 minor isomer shown], 67.53 [δ 67.49 minor isomer shown], 43.98 [δ 45.45 minor isomer shown], 35.78, 35.76, 35.22, 21.85 [δ 21.83 minor isomer shown], 20.75 [δ 20.74 minor isomer shown].

LC-MS (ESI+) m/z 352.17 (M+H)$^+$; HRMS (ESI+ve) m/z calculated for $C_{21}H_{22}N_3O_3$ (M+H)$^+$352.1656. found 352.1678.

SO2-007 (12d)

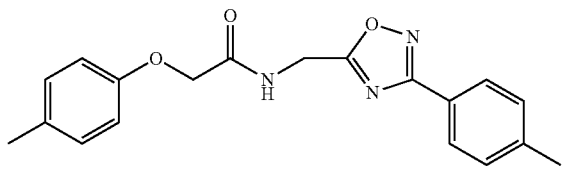

Chemical Formula: $C_{19}H_{19}N_3O_3$
Exact Mass: 337.1426
Molecular Weight: 337.3725

N-((3-p-tolyl-1,2,4-oxadiazol-5-yl)methyl)-2-(p-tolyloxy)acetamide (SO2-007) (12d): This compound was synthesized using the same protocol for 1 (SO1-143) except using
p-tolyloxy-acetyl chloride (5a) (60 mg, 0.32 mmol) and C-(3-p-tolyl-[1,2,4]oxadiazol-5-yl)-methylamine (10n) (50 mg, 0.26 mmol) and triethyl amine (50 mg, 0.53 mmol). The compound 12d (SO2-007) was obtained as a white solid (70 mg, 79%). M.p. 113.7-115.5° C.

HPLC 99.9% ($R_f$=6.5 min, 60% $CH_3CN$ in 0.1% TFA water 30 min); $^1$H NMR (400 MHz, $CDCl_3$) δ 7.94 (d, J=8.2 Hz, 2H), 7.28 (d, J=8.0 Hz, 2H), 7.13 (d, J=8.2 Hz, 2H), 6.87 (d, J=8.6 Hz, 2H), 4.84 (d, J=5.9 Hz, 2H), 4.59 (s, 2H), 2.42 (s, 3H), 2.31 (s, 3H); $^{13}$C NMR (100 MHz, $CDCl_3$) δ 175.46, 169.14, 168.66, 155.20, 142.02, 131.98, 130.49, 129.82, 127.64, 123.67, 114.82, 67.74, 67.70, 67.66, 35.46, 21.85, 20.77.

LC-MS (ESI+) m/z 360.14 (M+Na)$^+$; HRMS (ESI+ve) m/z calculated for $C_{19}H_{20}N_3O_3$ (M+H)$^+$338.1499. found 338.1505.

SO2-070 (12e)

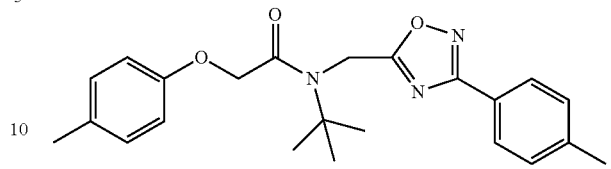

Chemical Formula: $C_{23}H_{27}N_3O_3$
Exact Mass: 393.2052
Molecular Weight: 393.4788

N-Tert-butyl-N-((3-p-tolyl-1,2,4-oxadiazol-5-yl)methyl-2-(p-tolyloxy)acetamide (SO2-070) (12e): This compound was synthesized using the same protocol for 1 (SO1-143) except using p-tolyloxy-acetyl chloride (5a) (76 mg, 0.41 mmol) and tert-butyl-(3-p-tolyl-[1,2,4]oxadiazol-5-ylmethyl)-amine (10o) (45 mg, 0.18 mmol) and triethyl amine (36 mg, 0.22 mmol). The compound 12e (SO2-070) was obtained as a white compound (53 mg, 75%). mp 150.6-151.7° C.

HPLC 97.7% ($R_f$=18.3 min, 60% $CH_3CN$ in 0.1% TFA water 30 min); $^1$H NMR (400 MHz, $CDCl_3$) δ 7.92 (d, J=8.2 Hz, 2H), 7.32-7.27 (m, 2H), 7.07-6.99 (m, 2H), 6.79 (d, J=8.6 Hz, 2H), 4.95 (s, 2H), 4.76 (s, 2H), 2.42 (s, 3H), 2.24 (s, 3H), 1.47 (s, 9H). $^{13}$C NMR (100 MHz, $CDCl_3$) δ 176.97, 169.45, 168.78, 155.88, 142.11, 131.07, 130.17, 129.81, 127.66, 123.62, 114.55, 77.58, 77.26, 76.94, 69.89, 69.81, 59.15, 40.71, 40.64, 29.94, 28.47, 21.88, 21.83, 20.72, 20.68.

LC-MS (ESI+) m/z 294.21 (M+H)$^+$; HRMS (ESI+ve) m/z calculated for $C_{23}H_{28}N_3O_3$ (M+H)$^+$394.2125. found 394.2120.

SO3-084 (12f)

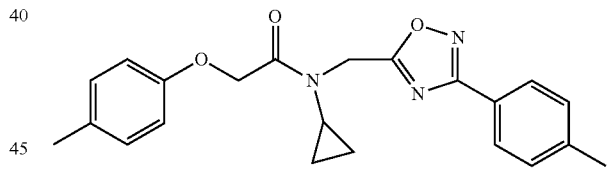

Chemical Formula: $C_{22}H_{23}N_3O_3$
Exact Mass: 377.1739
Molecular Weight: 377.4363

N-Cyclopropyl-N-((3-p-tolyl-1,2,4-oxadiazol-5-yl)methyl)-2-(p-tolyloxy)acetamide (SO3-084) (12f): This compound was synthesized using the same protocol for 1 (SO1-143) except using p-tolyloxy-acetyl chloride (5a) (72 mg, 0.39 mmol) and cyclopropyl-(3-p-tolyl-[1,2,4]oxadiazol-5-ylmethyl)-amine (10p) (75 mg, 0.33 mmol) and triethyl amine (67 mg, 0.66 mmol). The compound 12f (SO3-084) was isolated as a white solid (116 mg, 79%). M.p. 113.8-115.2° C.

HPLC 94.78% ($R_f$=6.2 min, 70% MeOH in 0.1% TFA water 20 min); $^1$H NMR (400 MHz, $CDCl_3$) δ 7.93 (d, J=8.0 Hz, 2H), 7.31-7.23 (m, 2H), 7.06 (d, J=8.2 Hz, 2H), 6.86 (d, J=8.3 Hz, 2H), 4.97 (s, 2H), 4.88 (s, 2H), 3.10-3.02 (m, 1H), 2.42 (s, 3H), 2.26 (s, 3H), 1.05-0.91 (m, 4H); $^{13}$C NMR (100 MHz, $CDCl_3$) δ 175.92, 171.51, 168.61, 156.24, 141.86, 131.02, 130.19, 129.75, 127.65, 123.91, 114.81, 77.58, 77.26, 76.94, 67.14, 43.44, 29.96, 21.82, 20.72, 9.29.

LC-MS (ESI+) m/z 378.18 (M+H)+; HRMS (ESI+ve) m/z calculated for C22H24N4O3(M+H)+378.1812. found 378.1796.

SO2-145 (16a)

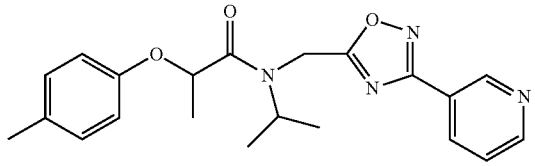

Chemical Formula: C21H24N4O3
Exact Mass: 380.1848
Molecular Weight: 380.4403

2-(4-Ethylphenoxy)-N-isopropyl-N-((3-pyridin-3-yl)1,2,4-oxadiazol-5-yl)methylacetamide (SO2-145) (16a): This compound was synthesized using the same protocol for 11x (SO2-076) except using 2-(p-tolyloxy)propanoyl chloride (15a) (34 mg, 0.17 mmol) and of N-((3-pyridin-3-yl)-1,2,4-oxadiazol-5-yl)methyl)propan-2-amine (10f) (31 mg, 0.14 mmol) and triethyl amine (28 mg, 0.28 mmol). The compound 16a (SO2-145) was isolated as a yellow solid. (40 mg, 75%). M.p. 87.9-89.4° C.

Chiral HPLC 47.44% (S isomer) 49.08% (R isomer) [$R_t$=63.27 min (S isomer) $R_t$=65.88 min, 0.5% isopropanol in hexane 120 min)]; HPLC 96.31% ($R_t$=14.9 min, 35% CH3CN in 0.1% TFA water 30 min); The $^1$H NMR showed 7:1 ratio of atropisomers: $^1$H NMR (400 MHz, CDCl3) δ 9.25 (s, 1H [δ 9.32 minor isomer shown], [δ 9.18 minor isomer shown]), 8.73 (dd, J=4.8, 1.4 Hz, 1H), 8.29 (dt, J=7.9, 2.1 Hz, 1H [δ 8.36 minor isomer shown] [δ 8.20 minor isomer shown]), 7.57 (ddd, J=7.8, 4.8, 0.6 Hz, 1H), 6.83 (d, J=8.5 Hz, 2H [δ 6.70 minor isomer shown]), 5.00 (q, J=6.8 Hz, 1H), 4.81-4.72 (m, 1H), 4.67 (d, $J_{BA}$=16.76 Hz, 1H [δ 4.97 minor isomer shown]), 4.61 (d, $J_{AB}$=16.68 Hz, 1H [δ 4.83 minor isomer shown]), 2.28 (s, 3H [δ 2.15 minor isomer shown]), 1.67 (s, 3H [δ 1.62 minor isomer shown]), 1.31 (s, 3H [δ 1.19 minor isomer shown]), 1.12 (s, 3H [δ 1.15 minor isomer shown]); $^{13}$C NMR (100 MHz, CDCl3) δ 177.41, 171.86 [δ 171.53 minor isomer shown], 166.58 [δ 166.65 minor isomer shown], 155.37, 152.19 [δ 152.38 minor isomer shown], 148.92, 134.94 [δ 134.88 minor isomer shown], 131.13 [δ 131.39 minor isomer shown], 130.33 [δ 130.20 minor isomer shown], 123.78 [δ 123.30 minor isomer shown], 115.30, 114.98 [δ 115.30 minor isomer shown], 74.69 [δ 75.11 minor isomer shown], 48.19 [δ 47.92 minor isomer shown], 37.64 [δ 39.03 minor isomer shown], 29.93 [δ 29.59 minor isomer shown], 29.59, 21.44 [δ 19.93 minor isomer shown], 21.35 [δ 19.86 minor isomer shown], 20.73 [δ 20.58 minor isomer shown], 18.19 [δ 18.00 minor isomer shown].

LC-MS (ESI+) m/z 381.19 (M+H)+; HRMS (ESI+ve) m/z calculated for C21H25N4O3(M+H)+381.1921. found 381.1924.

SO3-019 (16b)

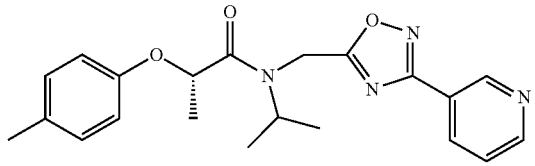

Chemical Formula: C21H24N4O3
Exact Mass: 380.1848
Molecular Weight: 380.4403

(S)—N-Isopropyl-N-((3-(pyridine-3-yl)-1,2,4-oxadiazol-5-yl)methyl)-2-(p-tolyloxy)propanamide (SO3-019) (16b):

This compound was synthesized using the same protocol for 11x (SO2-076) except using (S)-2-(p-tolyloxy)propanoyl chloride (15b) (34 mg, 0.17 mmol) and N-((3-pyridin-3-yl)-1,2,4-oxadiazol-5-yl)methyl)propan-2-amine (10f) (31 mg, 0.14 mmol) and triethyl amine (29 mg, 0.28 mmol). The compound 16b (SO3-019) was obtained as a sticky compound (41 mg, 77%).

Chiral HPLC 91.18% ($R_t$=61.67 min, 0.5% isopropanol in hexane 120 min); HPLC 94.66% ($R_t$=14.3 min, 35% CH3CN in 0.1% TFA water 20 min); The $^1$H NMR showed 7:1 ratio of atropisomers: $^1$H NMR (400 MHz, CDCl3) δ 9.19 (s, 1H [δ 9.25 minor isomer shown], [δ 9.12 minor isomer shown]), 8.67 (brs, 1H), 8.22 (dt, J=7.8 Hz, 1.8 Hz, 1H [δ 8.29 minor isomer shown], [δ 8.14 minor isomer shown]), 7.34 (dd, J=7.9, 4.9 Hz, 1H), 7.00 (d, J=8.5 Hz, 2H [δ 6.88 minor isomer shown]), 6.76 (d, J=8.6 Hz, 2H [δ 6.63 minor isomer shown]), 4.93 (q, J=6.8 Hz, 1H), 4.74-4.65 (m, 1H), 4.60 (d, $J_{AB}$=16.72 Hz, 1H [δ 4.89 minor isomer shown]), 4.54 (d, $J_{BA}$=16.72 Hz, 1H [δ 4.76 minor isomer shown]), 2.21 (s, 3H [δ 2.20 minor isomer shown] [δ 2.07 minor isomer shown]), 1.60 (d, J=6.8 Hz, 3H [δ 1.66 minor isomer shown], [δ 1.55 minor isomer shown]), 1.24 (d, J=6.7 Hz, 3H [δ 1.13 minor isomer shown]), 1.12-1.07 (m, 1H), 1.05 (d, J=6.6 Hz, 3H [δ 1.09 minor isomer shown]); $^{13}$C NMR (101 MHz, CDCl3) δ 177.47, 171.91, 166.46, 155.35 [δ 155.67 minor isomer shown], 151.75, 148.49, 135.29, 131.13 [δ 131.38 minor isomer shown], [δ 130.94 minor isomer shown], 130.33 [δ 130.22 minor isomer shown], 114.96 [δ 115.19 minor isomer shown], [δ 115.27 minor isomer shown], 74.66 [δ 74.58 minor isomer shown], 48.26 [δ 48.18 minor isomer shown], 37.64 [δ 37.71 minor isomer shown] [δ 37.58 minor isomer shown] 29.93, 21.43 [δ 20.75 minor isomer shown], 21.34 [δ 20.71 minor isomer shown], 18.18 [δ 18.87 minor isomer shown] [δ 18.02 minor isomer shown].

LC-MS (ESI+) m/z 381.20 (M+H)+; HRMS (ESI+ve) m/z calculated for C21H25N4O3 (M+H)+381.1921. found 381.1921.

SO3-065 (16c)

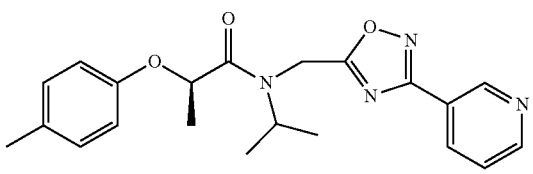

Chemical Formula: C21H24N4O3
Exact Mass: 380.1848
Molecular Weight: 380.4403

(R)—N-Isopropyl-N-((3-(pyridine-3-yl)-1,2,4-oxadiazol-5-yl)methyl)-2-(p-tolyloxy)propanamide (SO3-065): This compound was synthesized using the same protocol for 11x (SO2-076) except using (R)-2-(p-tolyloxy)propanoyl chloride (15c) (68 mg, 0.34 mmol) and N-((3-pyridin-3-yl)-1,2,4-oxadiazol-5-yl)methyl)propan-2-amine (10f) (62 mg, 0.28 mmol) and triethyl amine (57 mg, 0.56 mmol). The compound 16c (SO3-065) was obtained as a sticky compound (91 mg, 85%).

Chiral HPLC 97.85% ($R_t$=67.90 min, 0.5% isopropanol in hexane 120 min); HPLC 97.58% ($R_t$=9.7 min, 35% CH3CN in 0.1% TFA water 30 min); The $^1$H NMR showed 7:1 ratio of atropisomers: $^1$H NMR (400 MHz, CDCl3) δ 9.27 (s, 1H), 8.75 (brs, 1H), 8.29 (d, J=7.9 Hz, 1H [δ 8.20 minor isomer shown]), 7.46-7.39 (m, 1H), 7.06 (d, J=8.3 Hz, 1H [δ 6.94 minor isomer shown]), 6.82 (d, J=8.6 Hz, 1H [δ 6.69 minor isomer shown]), 5.00 (q, J=6.8 Hz, 1H), 4.81-4.71 (m, 1H), 4.66 (d, J$_{AB}$=16.76 Hz, 1H [δ 4.96 minor isomer shown]), 4.60 (d, J$_{BA}$=16.72 Hz, 1H [δ 4.82 minor isomer shown]), 2.27 (s, 3H [δ 2.14 minor isomer shown]), 1.66 (d, J=6.8 Hz, 2H [δ 1.61 minor isomer shown]), 1.30 (d, J=6.7 Hz, 3H [δ 1.18 minor isomer shown]), 1.12 (d, J=6.9 Hz, 1H [δ 1.15 minor isomer shown]); $^{13}$C NMR (101 MHz, CDCl$_3$) δ 177.42, 171.86 [δ 171.54 minor isomer shown], 166.56 [δ 166.53 minor isomer shown], 155.36 [δ 154.88 minor isomer shown], 152.16 [δ 152.35 minor isomer shown], 148.88 [δ 148.80 minor isomer shown], 134.96 [δ 134.91 minor isomer shown], 131.12 [δ 131.37 minor isomer shown], 130.32 [δ 130.19 minor isomer shown], 123.81 [δ 123.29 minor isomer shown], 114.96 [δ 115.28 minor isomer shown], 74.66 [δ 74.60 minor isomer shown], 48.23 [δ 48.17 minor isomer shown], 37.63 [δ 39.03 minor isomer shown], 29.93, 21.44 [δ 20.74 minor isomer shown], [δ 19.93 minor isomer shown] 21.34 [δ 20.72 minor isomer shown] [δ 19.85 minor isomer shown], 18.19 [δ 18.01 minor isomer shown].

LC-MS (ESI+) m/z 381.20 (M+H)$^+$; HRMS (ESI+ve) m/z calculated for C$_{21}$H$_{25}$N$_4$O$_3$(M+H)$^+$381.1921. found 381.1922.

SO3-106 (16d)

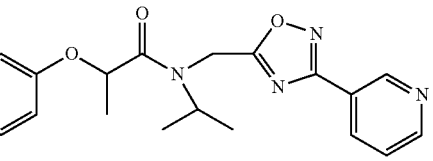

Chemical Formula: C$_{22}$H$_{28}$N$_4$O$_3$
Exact Mass: 408.2161
Molecular Weight: 408.4934

N-Isopropyl-2-(4-propylphenoxy)-N-((3-(pyridine-3-yl)-1,2,4-oxadiazol-5-yl)methyl)propanamide (SO3-106) (16d): This compound was synthesized using the same protocol for 11x (SO2-076) except using 2-(4-propylphenoxy)propanoyl chloride (15d) (71 mg, 0.31 mmol) and N-((3-pyrimidin-3-yl)-1,2,4-oxadiazol-5-yl)methyl)propan-2-amine (10f) (62 mg, 0.28 mmol) and triethyl amine (57 mg, 0.56 mmol). The compound 16d (SO3-106) was obtained as a pale yellow solid (92 mg, 80%). M.p. 93.9-96.0. ° C.

Chiral HPLC 50.07% (S isomer) 49.94% (R isomer) [R$_t$=58.38 min (S isomer) R$_t$=70.87 min, 0.5% isopropanol in hexane 120 min)]; HPLC 97.29% (R$_t$=9.2 min, 50% CH$_3$CN in 0.1% TFA water 30 min); The $^1$H NMR showed 7:1 ratio of atropisomers: $^1$H NMR (400 MHz, CDCl$_3$) δ 9.27 (s, 1H), 8.74 (brs, 1H), 8.29 (dt, J=8.0 Hz, 1.8 Hz, 1H [δ 8.21 minor isomer shown]), 7.41 (dd, J=7.8 Hz, 4.9 Hz, 1H), 7.07 (d, J=8.6 Hz, 2H [δ 6.96 minor isomer shown]), 6.84 (d, J=8.7 Hz, 2H [δ 6.72 minor isomer shown]), 5.01 (q, J=6.8 Hz, 1H), 4.80-4.70 (m, 1H), 4.66 (d, J$_{AB}$=16.84 Hz, 1H, [δ 4.96 minor isomer shown]), 4.62 (d, J$_{BA}$=16.80 Hz, 1H [δ 4.84 minor isomer shown]), 2.51 (t, J=7.6 Hz, 2H [δ 2.38 minor isomer shown]), 1.66 (d, J=6.8 Hz, 3H), 1.64-1.51 (m, 2H [δ 1.53-1.44 minor isomer shown]), 1.31 (d, J=6.7 Hz, 3H [δ 1.18 minor isomer shown]), 1.12 (d, J=6.9 Hz, 3H [δ 1.15 minor isomer shown]), 1.12 (d, J=6.6 Hz, 2H), 0.90 (t, J=7.3 Hz, 3H, 4.64 (s, 1H [δ 0.95 minor isomer shown], [δ 0.86 minor isomer shown]); $^{13}$C NMR (100 MHz, CDCl$_3$) δ 177.43, 171.84 [δ 171.51 minor isomer shown], 166.56, 155.52 [δ 155.01 minor isomer shown], 152.10 [δ 152.35 minor isomer shown], 148.83, 136.04 [δ 136.31 minor isomer shown], 134.94, 129.72 [δ 129.92 minor isomer shown], [δ 129.59 minor isomer shown], 123.85, 114.92 [δ 115.24 minor isomer shown], [δ 114.62 minor isomer shown], 74.55 [δ 75.03 minor isomer shown], 48.20 [δ 47.87 minor isomer shown], 47.87, 37.64 [δ 39.02 minor isomer shown], 37.33 [δ 37.21 minor isomer shown], 24.88 [δ 24.78 minor isomer shown], 21.44 [δ 21.17 minor isomer shown], [δ 19.92 minor isomer shown], 21.33 [δ 21.02 minor isomer shown], [δ 19.84 minor isomer shown], 18.21 [δ 18.00 minor isomer shown], 13.99.

LC-MS (ESI+) m/z 409.23 (M+H)$^+$; HRMS (ESI+ve) m/z calculated for C$_{23}$H$_{29}$N$_4$O$_3$(M+H)$^+$409.2234. found 409.2238.

SO3-110 (16e)

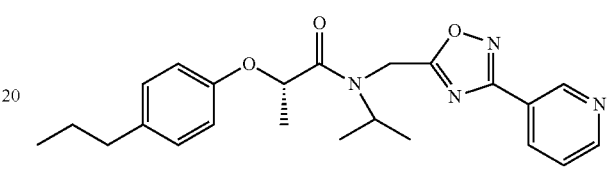

Chemical Formula: C$_{23}$H$_{28}$N$_4$O$_3$
Exact Mass: 408.2161
Molecular Weight: 408.4934

(S)—N-Isopropyl-2-(4-propylphenoxy)-N-((3-(pyridine-3-yl)-1,2,4-oxadiazol-5-yl)methyl)propanamide (SO3-110) (16e): This compound was synthesized using the same protocol for 11x (SO2-076) except using (S)-2-(4-propylphenoxy)acetyl chloride (15e) (62 mg, 0.23 mmol) and N-((3-pyrimidin-3-yl)-1,2,4-oxadiazol-5-yl)methyl)propan-2-amine (10f) (50 mg, 0.23 mmol) and triethyl amine (47 mg, 0.46 mmol). The compound 16e (SO3-110) was obtained as a pale yellow solid (79 mg, 84%). M.p. 76.7-78.8° C.

Chiral HPLC 90.58% (R$_t$=56.67 min, 0.5% isopropanol in hexane 120 min); HPLC 96.01% (R$_t$=18.7 min, 45% MeOH in 0.1% TFA water 30 min); The $^1$H NMR showed 7:1 ratio of atropisomers: $^1$H NMR (400 MHz, CDCl$_3$) δ 9.25 (s, 1H [δ 9.30 minor isomer shown]), [δ 9.21 minor isomer shown]), 8.72 (dd, J=4.9, 1.7 Hz, 1H), 8.28 (dt, J=8.0 Hz, J=2.0 Hz, [δ 8.34 minor isomer shown]), [δ 8.21 minor isomer shown]), 7.40 (ddd, J=8.0, 4.9, 0.8 Hz, 1H), 7.06 (d, J=8.7 Hz, 2H [δ 6.95 minor isomer shown]), 6.83 (d, J=8.7 Hz, 2H [δ 6.71 minor isomer shown]), 5.00 (q, J=6.7 Hz, 2H), 4.79-4.67 (m, 1H), 4.66 (d, J$_{AB}$=16.84 Hz, 1H [δ 4.96 minor isomer shown]), 4.61 (d, J$_{BA}$=16.68 Hz, 1H [δ 4.83 minor isomer shown]), 2.50 (t, J=7.6 Hz, 2H [δ 2.38 minor isomer shown]), 1.65 (d, J=6.8 Hz, 3H), 1.63-1.52 (m, 2H [δ 1.52-1.43 minor isomer shown]), 1.30 (d, J=6.7 Hz, 3H [δ 1.36 minor isomer shown], [δ 1.25 minor isomer shown]), 1.11 (d, J=6.6 Hz, 3H [δ 1.08 minor isomer shown], [δ 1.04 minor isomer shown]), 0.90 (t, J=7.3 Hz, 3H [δ 0.95 minor isomer shown], [δ 0.85 minor isomer shown]); $^{13}$C NMR (100 MHz, CDCl$_3$) δ 177.44, 171.82 [δ 171.51 minor isomer shown], [δ 172.48 minor isomer shown], 166.54 [δ 166.63 minor isomer shown], 155.52 [δ 155.02 minor isomer shown], 152.15 [δ 152.36 minor isomer shown], 148.85 [δ 148.78 minor isomer shown], 136.00 [δ 136.26 minor isomer shown] [δ 136.08 minor isomer shown], 134.89 [δ 134.96 minor isomer shown] [δ 134.86 minor isomer shown], 129.70, [δ 129.90 minor isomer shown], [δ 129.56 minor isomer shown], 123.78 [δ 123.89 minor isomer shown], [δ 123.82 minor isomer shown], 123.28, 114.92 [δ 114.63 minor isomer shown], [δ 115.24 minor isomer shown], 74.47 [δ 74.95 minor isomer shown], [δ 73.99 minor isomer shown], 48.20 [δ 48.58 minor isomer shown], [δ 47.88 minor isomer shown], 37.62 [δ 39.04 minor isomer shown], 37.31 [δ 37.19 minor isomer shown], 24.86 [δ 24.76 minor isomer shown], 21.42 [δ 21.16 minor isomer shown]), [δ 19.90 minor isomer shown]), 21.30 [δ 21.00 minor isomer shown]), [δ 19.82 minor isomer shown], 18.20 [δ 18.32 minor isomer shown]), [δ 17.99 minor isomer shown], 13.97 [δ 13.94 minor isomer shown];

LC-MS (ESI+) m/z 409.23 (M+H)$^+$; HRMS (ESI+ve) m/z calculated for C$_{23}$H$_{29}$N$_4$O$_3$(M+H)$^+$409.2234. found 409.2250.

SO3-109 (16f)

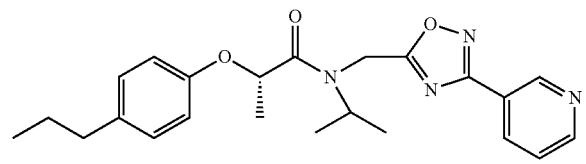

Chemical Formula: C$_{23}$H$_{28}$N$_4$O$_3$
Exact Mass: 408.2161
Molecular Weight: 408.4934

(R)—N-Isopropyl-2-(4-propylphenoxy)-N-((3-(pyridine-3-yl)-1,2,4-oxadiazol-5-yl)methyl)propanamide (SO3-109) (16f): This compound was synthesized using the same protocol for 11x (SO2-076) except using (S)-2-(4-propyl-phenoxy)acetyl chloride (15f) (62 mg, 0.23 mmol) and N-((3-pyrimidin-3-yl)-1,2,4-oxadiazol-5-yl)methyl)propan-2-amine (10f) (50 mg, 0.23 mmol) and triethyl amine (47 mg, 0.46 mmol). The compound 16f (SO3-109) was obtained as a pale yellow solid (77 mg, 82%). M.p. 75.5-76.8° C.

Chiral HPLC 98.02% (R$_t$=81.55 min, 0.5% isopropanol in hexane 120 min); HPLC 96.38% (R$_t$=18.5 min, 45% MeOH in 0.1% TFA water 30 min); The $^1$H NMR showed 7:1 ratio of atropisomers: $^1$H NMR (400 MHz, CDCl$_3$) δ 9.26 (s, 1H [δ 9.31 minor isomer shown]), [δ 9.19 minor isomer shown]), 8.73 (dd, J=4.9, 1.6 Hz, 1H), 8.29 (dt, J=8.1 Hz, J=1.9 Hz, [δ 8.35 minor isomer shown]), [δ 8.21 minor isomer shown]), 7.40 (ddd, J=8.0, 4.9, 0.8 Hz, 1H), 7.07 (d, J=8.7 Hz, 2H [δ 6.95 minor isomer shown]), 6.84 (d, J=8.7 Hz, 2H [δ 6.72 minor isomer shown]), 5.01 (q, J=6.7 Hz, 1H), 4.79-4.71 (m, 1H), 4.66 (d, J$_{AB}$=16.80 Hz, 1H [δ 4.96 minor isomer shown]), 4.62 (d, J$_{BA}$=16.80 Hz, 1H [δ 4.84 minor isomer shown]), 2.51 (t, J=7.6 Hz, 2H [δ 2.39 minor isomer shown]), 1.66 (d, J=6.8 Hz, 3H), 1.64-1.53 (m, 2H), 1.31 (d, J=6.7 Hz, 3H [δ 1.25 minor isomer shown]), 1.12 (d, J=6.6 Hz, 3H [δ 1.08 minor isomer shown]), [δ 1.04 minor isomer shown]), 0.90 (t, J=7.3 Hz, 3H); [δ 0.95 minor isomer shown]), [δ 0.86 minor isomer shown]), $^{13}$C NMR (100 MHz, CDCl$_3$) δ 177.42, 171.86 57 [δ 171.50 minor isomer shown], 166.57, 155.52 [δ 155.01 minor isomer shown], 152.37, 152.16 [δ 152.37 minor isomer shown], 148.89 [δ 148.81 minor isomer shown], 136.05 [δ 136.32 minor isomer shown], 134.92 [δ 134.88 minor isomer shown], 129.72, [δ 129.59 minor isomer shown], [δ 129.92 minor isomer shown], 123.79 [δ 123.33 minor isomer shown], 114.93 [δ 115.25 minor isomer shown] [δ 114.63 minor isomer shown], 74.57 [δ 75.05 minor isomer shown], 48.20 [δ 47.88 minor isomer shown], 37.64, 37.33 [δ 37.21 minor isomer shown], 24.88 [δ 24.78 minor isomer shown], 21.44 [δ 21.17 minor isomer shown], [δ 19.92 minor isomer shown], 21.33 [δ 21.02 minor isomer shown], [δ 19.84 minor isomer shown], 18.21 [δ 18.00 minor isomer shown], 13.98.

LC-MS (ESI+) m/z 409.23 (M+H)$^+$; HRMS (ESI+ve) m/z calculated for C$_{23}$H$_{29}$N$_4$O$_3$(M+H)$^+$409.2234. found 409.2242.

SO2-024 (18)

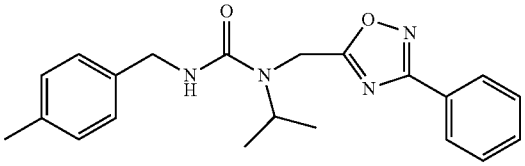

Chemical Formula: C$_{21}$H$_{24}$N$_4$O$_2$
Exact Mass: 364.1899
Molecular Weight: 364.4409

1-Isopropyl-3-(4-methylbenzyl)-1-((3-phenyl-1,2,4-oxadiazol-5-yl)methyl)urea (SO2-024) (18): A solution of isopropyl-(3-phenyl)-[1,2,4]oxadiazol-5-ylmethyl)-amine (10c) (70 mg, 0.32 mmol), 1-isocyanatomethyl-4-methylbenzene (47 mg, 0.32 mmol) and triethyl amine (39 mg, 0.39 mmol) were refluxed in benzene overnight. Benzene was evaporated and the residue was dissolved in ethyl acetate (20 ml) and washed with 4M HCl (3×10 ml) and water (2×20 ml). Organic solvent was dried (MgSO$_4$) and evaporated, the compound 18 was purified by column chromatography (EtOAc:hexane gradient elution) to obtain 18 (SO2-024) as a white solid (90 mg, 78%). M.p. 87.6-89.1. ° C.

HPLC 96.26% (R$_t$=14.98 min, 50% CH$_3$CN in 0.1% TFA water 30 min); $^1$H NMR (400 MHz, CDCl$_3$) δ 7.96 (dd, J=8.3, 1.4 Hz, 2H), 7.56-7.49 (m, 1H), 7.49-7.39 (m, 2H), 7.24 (d, J=8.0 Hz, 2H), 7.13 (d, J=7.8 Hz, 2H), 5.52 (apparent t, 1H), 4.63 (s, 2H), 4.43 (d, J=4.7 Hz, 2H), 4.40-4.34 (m, 1H), 2.33 (s, 3H), 1.22 (d, J=6.8 Hz, 6H); $^{13}$C NMR (100 MHz, CDCl$_3$) δ 177.63, 168.47, 158.01, 137.13, 136.32, 131.58, 129.52, 129.03, 128.03, 127.71, 126.53, 77.62, 77.31, 76.99, 47.12, 45.27, 37.62, 21.36, 20.96.

LC-MS (ESI+) m/z 365.20 (M+H)$^+$; HRMS (ESI+ve) m/z calculated for C$_{21}$H$_{25}$N$_4$O$_2$ (M+H)$^+$365.1972. found 365.1988.

SO2-090 (20)

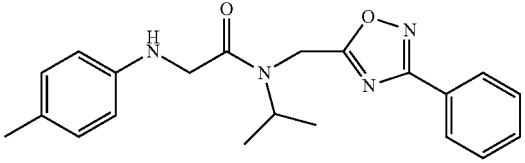

Chemical Formula: C$_{21}$H$_{24}$N$_4$O$_2$
Exact Mass: 364.1899
Molecular Weight: 364.4409

N-Isopropyl-N-((3-phenyl-1,2,4-oxadiazol-5-yl)methyl)-2-(p-tolylamino)acetamide (SO2-090) (20): A solution of p-toluidine (19 mg, 0.18 mmol), N-isopropyl-2-chloro-N-((3-phenyl-1,2,4-oxodiazol-5-yl)methyl)acetamide (19) (66 mg, 0.2 mmol) and sodium acetate (18 mg, 0.22 mmol) in ethanol (20 ml) were refluxed for 15 h. Ethanol was evaporated and the product was purified by column chromatography (EtOAc:hexane gradient elution) to obtain 20 (SO2-090) as a yellow-brown sticky solid (51 mg, 78%).

HPLC 96.59% ($R_t$=12.2 min, 45% $CH_3CN$ in 0.1% TFA water 30 min); The $^1H$ NMR showed 4:1 ratio of atropisomers: $^1H$ NMR (400 MHz, $CDCl_3$) δ 8.06 (dd, J=8.0, 1.7 Hz, 2H), 7.54-7.41 (m, 3H), 7.01 (d, J=8.1 Hz, 2H), 6.59 (d, J=8.3 Hz, 2H), 4.76 (s, 2H [δ 4.71 minor isomer shown]), 4.29-4.16 (m, 1H [δ 4.98-4.90 minor isomer shown]), 4.05 (s, 2H), 2.25 (s, 3H [δ 2.23 minor isomer shown]), 1.34 (d, J=6.6 Hz, 6H [δ 1.18 minor isomer shown]); $^{13}C$ NMR (100 MHz, $CDCl_3$) δ 176.66 [δ 176.22 minor isomer shown], 169.91 [δ 169.69 minor isomer shown], 168.65 [δ 168.92 minor isomer shown], 145.14, 131.43 [δ 131.83 minor isomer shown], 130.01 [δ 130.14 minor isomer shown], 129.00 [δ 129.18 minor isomer shown], 127.74 [δ 127.33 minor isomer shown], 126.82, 113.51 [δ 113.65 minor isomer shown], 47.98 [δ 49.59 minor isomer shown], 46.18 [δ 46.74 minor isomer shown], 37.25 [δ 37.44 minor isomer shown], 21.46 [δ 20.14 minor isomer shown], 20.65 [δ 19.96 minor isomer shown].

LC-MS (ESI+) m/z 365.19 (M+H)$^+$; HRMS (ESI+ve) m/z calculated for $C_{21}H_{25}N_4O_2$(M+H)$^+$365.1972. found 365.1981.

SO2-027 (23a)

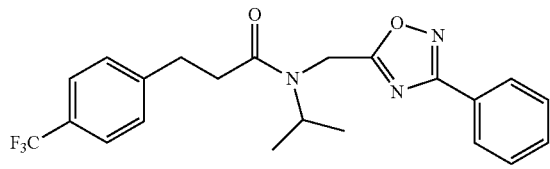

Chemical Formula: $C_{22}H_{22}F_3N_3O_2$
Exact Mass: 417.1664
Molecular Weight: 417.4242

N-Isopropyl-N-((3-phenyl-1,2,4-oxadiazol-5-yl)methyl)-3-(4-(trifluoromethyl)phenyl)propanamide (SO2-027) (23a): This compound was synthesized using the same protocol for 1 (SO1-143) except using 3-(4-trifluoromethyl) phenyl)propanoyl chloride (22a) (130 mg, 0.55 mmol) and isopropyl-(3-phenyl)-[1,2,4]oxadiazol-5-ylmethyl)-amine (10c) (100 mg, 0.46 mmol) and triethyl amine (90 mg, 0.92 mmol). The compound 23a (SO2-027) was obtained as a white solid (168 mg, 88%). mp 96.1-97.7° C.

HPLC 97.9% ($R_t$=5.27 min, 60% $CH_3CN$ in 0.1% TFA water 30 min); The $^1H$ NMR showed 3:1 ratio of atropisomers: $^1H$ NMR (400 MHz, $CDCl_3$) δ 8.06 (dd, J=7.9, 1.7 Hz, 2H), 7.63-7.42 (m, 5H), 7.37 (d, J=8.1 Hz, 2H [δ 7.33 minor isomer shown]), 4.61 (s, 2H [δ 4.61 minor isomer shown]), 4.25-4.18 (m, 1H [δ 4.97 minor isomer shown]), 3.08 (t, J=7.6 Hz, 2H [δ 3.02 minor isomer shown]), 2.79 (t, J=7.7 Hz, 2H [δ 2.71 minor isomer shown]), 1.24 (d, J=6.7 Hz, 6H [δ 1.12 minor isomer shown]); $^{13}C$ NMR (100 MHz, $CDCl_3$) δ 177.07 [δ 176.66 minor isomer shown], 172.02, 171.92 [δ 172.02 minor isomer shown], 168.58, 145.48, 131.40 [δ 131.84 minor isomer shown], 129.19, 129.07, 129.00 [δ 128.88 minor isomer shown], 127.70 [δ 127.67 minor isomer shown], 126.94, 125.64 (q, J=3.76 Hz), 124.50 (q, J=271 Hz), 48.78 [δ 45.82 minor isomer shown], 37.16 [δ 38.72 minor isomer shown], 34.81 [δ 35.30 minor isomer shown], 31.09 [δ 31.17 minor isomer shown], 21.33 [δ 20.20 minor isomer shown]; $^{19}F$ NMR (376 MHz, $CDCl_3$) δ −62.75, [δ −62.78 minor isomer shown].

LC-MS (ESI+) m/z 418.18 (M+H)$^+$; HRMS (ESI+ve) m/z calculated for $C_{22}H_{23}F_3N_3O_2$ (M+H)$^+$418.1737. found 418.1745.

SO3-029 (23b)

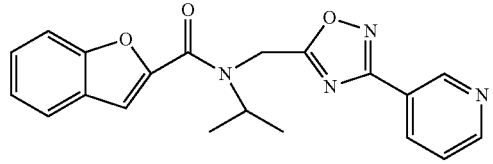

Chemical Formula: $C_{20}H_{18}N_4O_3$
Exact Mass: 362.1379
Molecular Weight: 362.3819

Benzofuran-2-carboxylic acid isopropyl-(3-pyridin-3-yl-[1,2,4]oxadiazol-5-yl)methyl)-amide (SO3-029) (23b): This compound was synthesized using the same protocol for SO2-076 11x except using benzofuran-2-carbonyl chloride (22b) (64 mg, 0.35 mmol) and N-((3-pyridin-2-yl)-1,2,4-oxadizaol-5-yl)methyl)propan-2-amine (10f) (64 mg, 0.29 mmol) and triethyl amine (59 mg, 0.58 mmol). The compound 23b (SO3-029) was obtained as a sticky colorless compound (103 mg, 82%).

HPLC 94.48% ($R_t$=4.1 min, 70% MeOH in 0.1% TFA water 20 min); $^1H$ NMR (400 MHz, $CDCl_3$) δ 9.27 (s, 1H), 8.71 (d, J=4.0 Hz, 1H), 8.32 (d, J=7.9 Hz, 1H), 7.63 (d, J=7.7 Hz, 1H), 7.46-7.32 (m, 3H [δ 7.57-7.46 minor isomer shown]), 7.31-7.25 (m, 2H), 5.03-4.93 (m, 1H), 4.89 (s, 2H), 1.37 (d, J=3.1 Hz, 6H [δ 7.50 minor isomer shown]). $^{13}C$ NMR (101 MHz, $CDCl_3$) δ 166.69 50 [δ 161.31 minor isomer shown], 154.93, 152.05, 148.69, 135.19, 127.05 50 [δ 126.98 minor isomer shown], 123.98 [δ 123.95 minor isomer shown], 122.63 [δ 123.26 minor isomer shown] 113.13, 112.13, 49.89, 41.68, 38.21, 22.78, 21.66.

LC-MS (ESI+) m/z 363.16 (M+H)$^+$; HRMS (ESI+ve) m/z calculated for $C_{20}H_{19}N_4O_3$(M+H)$^+$363.1452. found 363.1455.

SO2-091 (27)

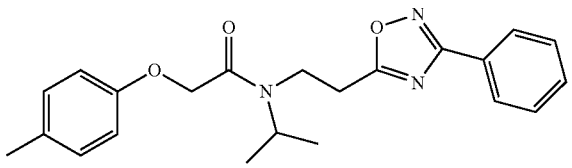

Chemical Formula: $C_{22}H_{25}N_3O_3$
Exact Mass: 379.1896
Molecular Weight: 379.4522

N-Isopropyl-N-(2-(3-phenyl-1,2,4-oxadiazol-5-yl)ethyl)-2-(p-tolyloxy)acetamide (SO2-091) (24): This compound was synthesized using the same protocol for SO1-143 1 except using p-tolyloxy-acetyl chloride (5a) (56 mg, 0.30 mmol) and N-(2-(3-phenyl-1,2,4-oxadiazol-5-yl)ethyl)propan-2-amine (26) (58 mg, 0.25 mmol) and triethyl amine (51 mg, 0.50 mmol). The compound 24 (SO2-091) was isolated as a sticky solid (86 mg, 87%).

HPLC 97.51% ($R_t$=22.7 min, 50% $CH_3CN$ in 0.1% TFA water 30 min); The $^1H$ NMR showed 3:1 ratio of atropisomers: $^1H$ NMR (400 MHz, $CDCl_3$) δ 8.07-8.02 (m, 2H), 7.52-7.40 (m, 3H), 7.09 (d, J=8.4 Hz, 2H), 6.85 (d, J=8.6 Hz, 2H), 4.69 (s, 2H), 4.31-4.18 (m, 2H [δ 4.55-4.44 minor isomer shown]), 3.72 (t, J=7.4 Hz, 2H [δ 3.89 minor isomer shown]), 3.28 (t, J=7.4 Hz, 2H), 2.28 (s, 3H [δ 2.26 minor isomer shown]), 1.28 (d, J=6.7 Hz, 6H [δ 1.20 minor isomer shown]); $^{13}$C NMR (100 MHz, CDCl$_3$) δ 177.76, 168.50, 168.40, 155.99, 131.37 [δ 131.18 minor isomer shown], 130.29, 129.05, 127.66 [δ 126.99 minor isomer shown], 114.59 [δ 114.67 minor isomer shown], 68.31 [δ 68.99 minor isomer shown], 48.80 [δ 47.87 minor isomer shown], 38.56 [δ 41.31 minor isomer shown], 26.18 [δ 28.64 minor isomer shown], 21.36, [δ 20.45 minor isomer shown]. 20.72.

LC-MS (ESI+) m/z 380.20 (M+H)$^+$; HRMS (ESI+ve) m/z calculated for C$_{22}$H$_{26}$N$_3$O$_3$(M+H)$^+$380.1969. found 380.1965.

SO2-075

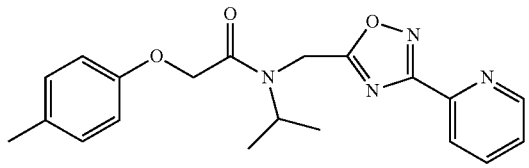

Chemical Formula: C$_{20}$H$_{22}$N$_4$O$_3$
Exact Mass: 366.17
Molecular Weight: 366.41

N-isopropyl-N-((3-pyridin-2-yl)-1,2,4-oxadiazol-5-yl)methyl-2-(p-tolyloxy)acetamide (SO2-75): This compound was synthesized using the same protocol shown for SO1-143 except using p-tolyloxy-acetyl chloride (42 mg, 0.24 mmol), N-((3-(pyridine-2-yl)-1,2,4-oxadiazol-5-yl)methyl)propan-2-amine (42 mg, 0.19 mmol) and triethylamine (38 mg, 0.54 mmol). The required compound SO2-075 (52 mg, 75%) was obtained as a white solid. HPLC 95.31% (R$_t$=9.03, 60% CH$_3$CN in 0.1% TFA water 30 min); The $^1$H NMR showed 3:1 ratio of atropisomers: $^1$H NMR (400 MHz, CDCl$_3$) δ 8.73 (s, 1H), 7.99 (d, J=7.8 Hz, 1H), 7.76 (td, J=7.8, 1.6 Hz, 1H), 7.39-7.31 (m, 1H), 7.03 (dd, J=8.5, 3.8 Hz, 2H [δ 6.96 minor isomer shown]), 6.80 (d, J=8.6 Hz, 2H [δ 6.73 minor isomer shown]), 4.72 (s, 2H [δ 4.85 minor isomer shown]), 4.70 (s, 2H [δ 4.74 minor isomer shown])), 4.40-4.31 (m, 1H), 2.21 (s, 3H [δ 2.17 minor isomer shown]), 1.22 (d, J=6.6 Hz, 6H [δ 1.08 minor isomer shown]). LC-MS (ES+) 366 (M+H)$^+$ HRMS (ESI+ve) m/z calculated for C$_{21}$H$_{24}$N$_3$O$_3$ (M+H)$^+$366.1812. found 366.1821. LC-MS (ES+) 367 (M+H)$^+$ HRMS (ESI+ve) m/z calculated for C$_{20}$H$_{23}$N$_4$O$_3$ (M+H)$^+$367.1765. found 367.1774.

SO2-076

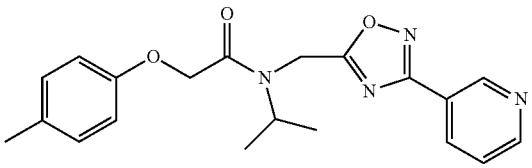

Chemical Formula: C$_{20}$H$_{22}$N$_4$O$_3$
Exact Mass: 366.17
Molecular Weight: 366.41

N-Isopropyl-N-((3-(pyridine-3-yl)-1,2,4-oxadiazol-5-yl)methyl)-2-(p-tolyoxy)acetamide (SO2-076): This compound was synthesized using the same protocol shown for SO1-143 except using p-tolyloxy-acetyl chloride (42 mg, 0.24 mmol), N-((3-(pyridine-3-yl)-1,2,4-oxadiazol-5-yl)propan-2-amine (42 mg, 0.19 mmol) and triethylamine (38 mg, 0.54 mmol). The required compound SO2-076 (52 mg, 75%) was obtained as a white solid.

HPLC 99.43% (R$_t$=9.03, 60% CH$_3$CN in 0.1% TFA water 30 min); The $^1$H NMR showed 3:1 ratio of atropisomers: $^1$H NMR (400 MHz, CDCl$_3$) δ 9.25 (s, 1H), 8.73 (brs, 1H), 8.28 (d, J=7.7 Hz, 1H), 7.39 (d, J=5.1 Hz, 1H), 7.08 (d, J=7.7 Hz, 2H [δ 7.02 minor isomer shown]), 6.87 (d, J=7.5 Hz, 2H [δ 6.78 minor isomer shown]), 4.79 (s, 2H[δ 4.89 minor isomer shown]), 4.71 (s, 2H[δ 4.80 minor isomer shown]), 2.28 (s, 3H[δ 2.23 minor isomer shown]), 1.32 (d, J=6.6 Hz, 6H[δ 1.17 minor isomer shown]).

LC-MS (ES+) 366 (M+H)$^+$ HRMS (ESI+ve) m/z calculated for C$_{21}$H$_{24}$N$_3$O$_3$ (M+H)$^+$366.1812. found 366.1821. LC-MS (ES+) 367 (M+H)$^+$ HRMS (ESI+ve) m/z calculated for C$_{20}$H$_{23}$N$_4$O$_3$ (M+H)$^+$367.1765. found 367.1774.

SO2-065

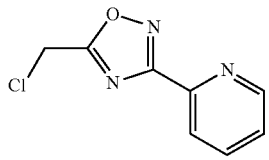

Chemical Formula: C$_8$H$_6$ClN$_3$O
Exact Mass: 195.02
Molecular Weight: 195.61

5-(Chloromethyl)-3-(pyridine-2-yl)-1,2,4-oxadiazole (SO2-065): To a solution of N-hydroxypicolinimidamide (0.2 g, 1.5 mmol) in DCM (20 ml) and chloroacetyl chloride (0.2 g, 1.8 mmol) at 0° C., diisopropylethylamine (0.23 g, 1.8 mmol) was added (dropwise). The mixture was warmed up to r.t. and stirred for 24 h. and organic solvent was evaporated and the residue was refluxed overnight in toluene (20 mL) to complete the cyclization. The product obtained was purified using SiO$_2$ chromatography (EtOAc:hexane gradient elution). The required compound SO2-065 (0.24 g, 81%) was obtained as a white solid.

$^1$H NMR (400 MHz, CDCl$_3$) δ 8.81 (ddd, J=4.8, 1.6, 1.0 Hz, 1H), 8.14 (d, J=7.9 Hz, 1H), 7.87 (ddd, J=7.9 Hz, 4.8, 1.8 Hz, 1H), 7.46 (ddd, J=7.7, 4.8, 1.2 Hz, 1H), 4.79 (s, 2H).

SO2-055

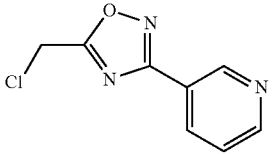

Chemical Formula: C$_8$H$_6$ClN$_3$O
Exact Mass: 195.02
Molecular Weight: 195.61

5-(Chloromethyl)-3-(pyridine-3-yl)-1,2,4-oxadiazole (SO2-055): This compound was synthesized using the same protocol shown for SO2-065 except using N-hydroxynicotinimidamide (0.3 g, 2 mmol), chloroacetyl chloride (0.29 g, 2.6 mmol) at 0° C., diisopropylethylamine (0.34 g, 2.6 mmol) The compound SO2-055 (0.29 g, 73%) was obtained as a yellow solid.

¹H NMR (400 MHz, CDCl₃) δ 9.25 (dd, J=2.2, 0.9 Hz, 1H), 8.70 (dd, J=4.9, 1.7 Hz, 1H), 8.34-8.24 (m, 1H), 7.38 (ddd, J=8.0, 4.9, 0.9 Hz, 1H), 4.71 (s, 2H).

SO2-071

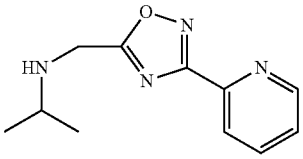

Chemical Formula: C₁₁H₁₄N₄O
Exact Mass: 218.12
Molecular Weight: 218.26

N-((3-(pyridine-2-yl)-1,2,4-oxadiazol-5-yl)methyl)propan-2-amine (SO2-071): This compound was synthesized using the same protocol shown for SO1-142 except using 5-(Chloromethyl)-3-(pyridine-2-yl)-1,2,4-oxadiazole (75 mg, 0.38 mmol), isopropylamine (34 mg, 0.58 mmol) and potassium carbonate (109 g, 1.9 mmol). The compound SO2-071 (75 mg, 89%) was obtained as a viscous liquid.

¹H NMR (400 MHz, CDCl₃) δ 8.80 (ddd, J=4.8, 1.7, 0.9 Hz, 1H), 8.13 (dt, J=7.9, 1.0 Hz, 1H), 7.85 (td, J=7.8, 1.8 Hz, 1H), 7.43 (ddd, J=7.6, 4.8, 1.2 Hz, 1H), 4.15 (s, 2H), 3.00-2.83 (m, 1H), 1.11 (d, J=6.2 Hz, 6H).

SO2-060

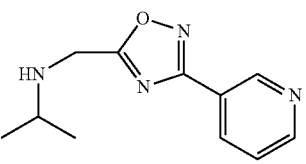

Chemical Formula: C₁₁H₁₄N₄O
Exact Mass: 218.12
Molecular Weight: 218.26

N-((3-(pyridine-3-yl)-1,2,4-oxadiazol-5-yl)propan-2-amine (SO2-060): This compound was synthesized using the same protocol shown for SO1-142 except using 5-(Chloromethyl)-3-(pyridine-3-yl)-1,2,4-oxadiazole (80 mg, 0.41 mmol), isopropylamine (48 mg, 8.18 mmol) and potassium carbonate (2.8 g, 2 mmol). The compound SO2-060 (75 mg, 84%) was obtained as a yellowish solid.

¹H NMR (400 MHz, CDCl₃)) δ 9.25 (d, J=1.4 Hz, 1H), 8.68 (dd, J=4.8, 1.6 Hz, 1H), 8.32-8.25 (m, 1H), 7.36 (ddd, J=7.9, 4.9, 0.8 Hz, 1H), 4.08 (s, 2H), 2.98-2.75 (m, 1H), 1.07 (d, J=6.2 Hz, 6H).

SO2-051 (10q)

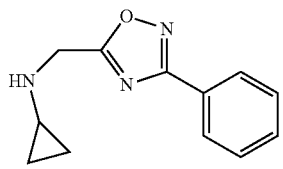

Chemical Formula: C₁₂H₁₃N₃O
Exact Mass: 215.11
Molecular Weight: 215.25

N-((3-phenyl-1,2,4-oxadiazol-5yl)methycyclopropanamine (SO2-051) (10q): This compound was synthesized using the same protocol for 10a (SO1-142) except using 5-Chloromethyl-3-phenyl-[1,2,4]oxadiazole (9c) (80 mg, 0.41 mmol) and cyclopropyl amine (50 mg, 0.82 mmol) and potassium carbonate (0.28 g, 2.1 mmol). The compound SO2-051 10q was obtained as a white solid (75 mg, 85%).

¹H NMR (400 MHz, CDCl₃) δ 8.13-7.96 (m, 2H), 7.53-7.34 (m, 3H), 4.09 (d, J=2.6 Hz, 2H), 2.32-2.14 (m, 1H), 0.57-0.29 (m, 4H).

SO2-054 (32)

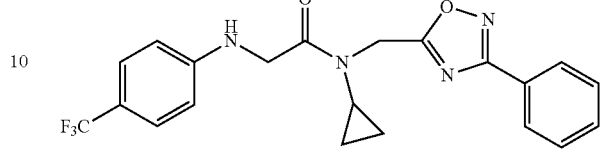

Chemical Formula: C₂₁H₁₈F₃N₃O₃
Exact Mass: 417.1300
Molecular Weight: 417.3811

N-cyclopropyl-N-((3-phenyl-1,2,4-oxadiazol-5-yl)methyl)-2-(4-(trifluoromethyl)phenoxy)acetamide (SO2-054) (32): This compound was synthesized using the same protocol for 1 (SO1-143) except using (4-trifluoromethylphenoxy)-acetyl chloride (5b) (140 mg, 0.52 mmol) and N-((3-phenyl-1,2,4-oxadiazol-5yl)methycyclopropanamine (10q) (75 mg, 0.35 mmol) and triethyl amine (71 mg, 0.70 mmol). The compound SO2-054 32 was obtained as a white solid (106 mg, 73%).

HPLC 97.4% (R_f=10.1 min, 60% CH₃CN in 0.1% TFA water 30 min); The ¹H NMR showed 4:1 ratio of atropisomers: ¹H NMR (400 MHz, CDCl₃) δ 8.04 (dd, J=8.1, 1.6 Hz, 2H), 7.62-7.39 (m, 5H), 7.02 (d, J=8.5 Hz, 2H), 5.07 (s, 2H [δ 4.73 minor isomer shown]), 4.89 (s, 2H [δ 4.71 minor isomer shown]), 3.11-3.06 (m, 1H [δ 3.42-3.37 minor isomer shown]), 1.08-0.94 (m, 4H [δ 1.22, 1.14 minor isomer shown]); HRMS (ESI+ve) m/z calculated for C₂₁H₁₉F₃N₃O₃ (M+H)⁺418.1373. found 418.1378.

SO3-010 (33)

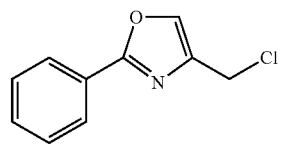

Chemical Formula: C₁₀H₈ClNO
Exact Mass: 193.0294
Molecular Weight: 193.6296

4-(Chloromethyl)-2-phenyloxazole (SO3-010) (33): To a solution of dichloroacetone (250 mg, 1.97 mmol) in toluene (5 ml) was added benzamide (120 mg, 0.99 mmol) and heated at 120° C. for 14 h. Toluene was evaporated and the compound was purified by column chromatography (gradient elution with EtOAc:Hexane). Compound 33 (SO3 010) was obtained as a viscous liquid. (141 mg, 74%). ¹H NMR (400 MHz, CDCl₃) δ 8.11-7.92 (m, 2H), 7.69 (s, 1H), 7.45 (d, J=2.6 Hz, 3H), 4.57 (s, 2H).

SO3-022 (34)

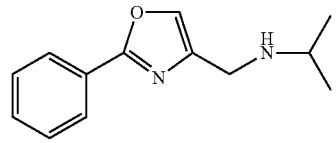

Chemical Formula: C₁₃H₁₆N₂O
Exact Mass: 216.1263
Molecular Weight: 216.2789

N-((2-phenyloxazol-4-yl)methyl)propan-2-amine (SO3-022) (34): A solution of 4-(chloromethyl)-2-phenyloxazole

(33) (SO3-010) (120 mg, 0.62 mmol), isopropyl amine (73 mg, 12.40 mmol) and potassium carbonate (428 mg, 31.00 mmol) in acetonitrile (20 ml) were refluxed for 4 h. Acetonitrile was evaporated and the residue was dissolved in ethyl acetate (20 ml) and washed with water (3×20 ml). Organic solvent was dried (MgSO$_4$) and evaporated to obtain SO3-022 34 as a brown viscous liquid. (121 mg, 90%). $^1$H NMR (400 MHz, CDCl$_3$) δ 8.06-7.86 (m, 2H), 7.54 (s, 1H), 7.37 (d, J=2.3 Hz, 3H), 3.72 (s, 2H), 2.91-2.82 (m, 1H), 1.07 (d, J=6.3 Hz, 6H).

SO3-023 (35)

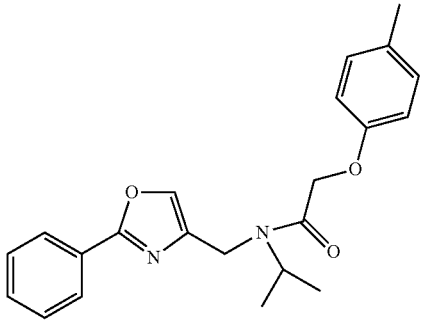

Chemical Formula: C$_{22}$H$_{24}$N$_2$O$_3$
Exact Mass: 364.1787
Molecular Weight: 364.4376

N-Isopropyl-N-((2-phenyloxazol-4-yl)methyl)-2-(p-tolyloxy)acetamide (SO3-023) (35): This compound was synthesized using the same protocol for 1 (SO1-143) except using p-tolyloxy-acetyl chloride (61 mg, 0.33 mmol) and N-((2-phenyloxazol-4-yl)methyl)propan-2-amine (SO3-022) (34) (60 mg, 0.28 mmol) and triethyl amine (57 mg, 0.56 mmol). The compound SO3-023 35 was isolated as a white solid (84 mg, 86%). mp 126.7-127.6° C.

HPLC 100% (R$_t$=8.4 min, 60% CH$_3$CN in 0.1% TFA water 30 min); $^1$H NMR (400 MHz, CDCl$_3$) δ 8.08-7.95 (m, 2H), 7.49 (s, 1H [δ 7.53 minor isomer shown]), 7.48-7.40 (m, 3H), 7.08 (d, J=8.2 Hz, 2H [δ 7.05 minor isomer shown]), 6.86 (d, J=8.6 Hz, 2H [δ 6.89 minor isomer shown]), 4.89 (s, 2H [δ 4.72 minor isomer shown]), 4.46 (s, 2H [δ 4.43 minor isomer shown]), 4.32-4.24 (m, 1H), 2.27 (s, 3H [δ 2.23 minor isomer shown]), 1.28 (d, J=6.6 Hz, 6H [δ 1.17 minor isomer shown]). $^{13}$C NMR (101 MHz, CDCl$_3$) δ 168.08 [δ 168.59 minor isomer shown], 160.80 [δ 162.37 minor isomer shown], 156.01 [δ 156.35 minor isomer shown], 140.29 [δ 137.54 minor isomer shown], 139.28 [δ 135.32 minor isomer shown], 131.18, 130.93, 130.65 [δ 130.82 minor isomer shown], 130.25 [δ 130.14 minor isomer shown], 128.99 [δ 129.06 minor isomer shown], 126.59 [δ 126.66 minor isomer shown], 114.69 [δ 114.86 minor isomer shown], 68.14 [δ 67.98 minor isomer shown], 48.94 [δ 47.07 minor isomer shown], 37.24 [δ 39.04 minor isomer shown], 21.71 [δ 20.43 minor isomer shown], 20.71.

LC-MS (ESI+) m/z 365.19 (M+H)$^+$; HRMS (ESI+ve) m/z calculated for C$_{22}$H$_{25}$N$_2$O$_3$ (M+H)$^+$365.1860. found 365.1872.

SO2-083 (36)

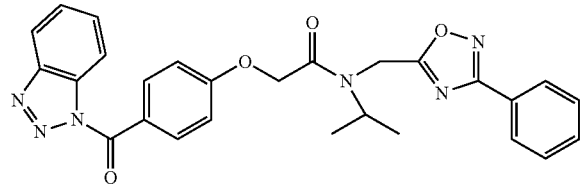

Chemical Formula: C$_{27}$H$_{24}$N$_6$O$_4$
Exact Mass: 496.1859
Molecular Weight: 496.5173

2-(4-(1H-benzo[d][1,2,3]triazole-1-carbonyl)phenoxy)-N-isopropyl-N-((3-phenyl-1,2,4-oxadiazol-5-yl)methyl)acetamide SO2-083 (36): To a solution of benzotriazole (130 mg, 1.09 mmol) in THF (10 ml) was added thionyl chloride (35 mg, 0.30 mmol) and the mixture was stirred at rt for 30 min. 4-(2-(Isopropyl((3-phenyl-1,2,4-oxadiazol-5-yl)methyl)amino)-2-oxoethoxy)benzoic acid (SO2-089) (11t) (108 mg, 0.27 mmol) in THF (3 ml) was added slowly and the mixture was stirred at rt for 5 h. THF was evaporated and the residue was dissolved in ethyl acetate (10 ml) and washed with 4M HCl (4×10 ml) and water (2×10 ml). Organic solvent was dried (MgSO$_4$) and evaporated to obtain the compound SO2-083 36 as a white solid (102 mg, 70%).

$^1$H NMR (400 MHz, CDCl$_3$) δ 8.37 (d, J=8.3 Hz, 1H), 8.28 (d, J=8.8 Hz, 2H), 8.17 (d, J=8.3 Hz, 1H), 8.09 (dd, J=7.8, 1.4 Hz, 1H), 8.00 (dd, J=6.5, 2.9 Hz, 1H), 7.70 (t, J=7.6 Hz, 1H), 7.57-7.48 (m, 2H), 7.44-7.39 (m, 2H), 7.14 (d, J=8.8 Hz, 2H), 4.96 (s, 2H [δ 5.03 minor isomer shown]), 4.74 (s, 2H [δ 4.82 minor isomer shown]), 4.44-4.33 (m, 1H), 1.35 (d, J=6.6 Hz, 6H [δ 1.18 minor isomer shown]).

SO2-104 (37)

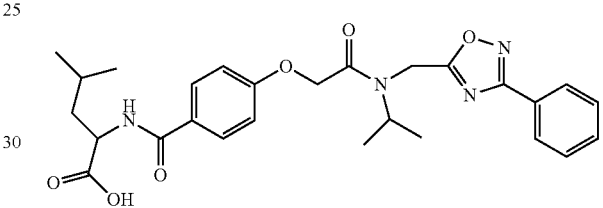

Chemical Formula: C$_{27}$H$_{32}$N$_4$O$_6$
Exact Mass: 508.2322
Molecular Weight: 508.5662

2-(4-(2-(Isopropyl((3-phenyl-1,2,4-oxadiazol-5-yl)methyl)amino)-2-oxoethoxy)benzamido)-4-methylpentanoic acid (SO2-104) (37): To a solution of leucine (24 mg, 0.18 mmol) and triethyl amine (18 mg, 0.18 mmol) in acetonitrile:water (5:2) at 0° C. was added 2-(4-(1H-benzo[d][1,2,3]triazole-1-carbonyl)phenoxy)-N-isopropyl-N-((3-phenyl-1,2,4-oxadiazol-5-yl)methyl)acetamide (SO2-083) (36) (60 mg, 0.12 mmol) and warmed up to rt and stirred for 1 h. Acetonitrile was evaporated and the residue was dissolved in ethyl acetate (15 ml) and washed with 4M HCl (3×15 ml) and water (2×15 ml). Organic solvent was dried (MgSO$_4$) and evaporated to give SO2-104 37 as a sticky solid. (44 mg, 72%).

HPLC 94.78% (R$_t$=7.5 min, 50% CH$_3$CN in 0.1% TFA water 30 min); The $^1$H NMR showed 3:1 ratio of atropisomers: $^1$H NMR (400 MHz, CDCl$_3$) δ 7.98 (d, J=7.4 Hz, 2H [δ 8.02 minor isomer shown]), 7.74 (d, J=8.8 Hz, 2H [δ 7.70 minor isomer shown]), 7.52-7.41 (m, 3H), 6.98 (d, J=8.8 Hz, 2H [δ 6.93 minor isomer shown]), 4.88 (s, 2H [δ 4.93 minor isomer shown]), 4.77-4.72 (m, 1H), 4.71 (s, 2H [δ 4.80 minor isomer shown]), 4.41-4.36 (m, 1H), 1.83-1.64 (m, 3H), 1.31 (d, J=6.6 Hz, 6H [δ 1.15 minor isomer shown]), 0.96 (d, J=5.9 Hz, 6H [δ 0.89 minor isomer shown]); $^{13}$C NMR (100 MHz, CDCl$_3$) δ 176.37, 176.30, 168.55, 167.96, 167.56, 160.95 [δ 160.90 minor isomer shown], 131.91, 131.51, 129.40 [δ 129.33 minor isomer shown], 129.03 [δ 129.22 minor isomer shown], 127.68, 127.06 [δ 127.01 minor isomer shown], 126.71, 114.83 [δ 114.77 minor isomer shown], 67.44 [δ 67.96 minor isomer shown], 51.65, 49.02 [δ 47.02 minor isomer shown], 41.27, 38.42, 37.25 [δ

38.42 minor isomer shown], 29.94, 25.19, 23.11, 22.14, 21.46 [δ 19.97 minor isomer shown].
LC-MS (ESI+) m/z 509.23 (M+H)⁺; HRMS (ESI+ve) m/z calculated for C₂₇H₃₃N₄O₆ (M+H)⁺509.2395. found 509.2381.
SO2-121 (38)

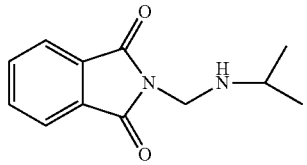

Chemical Formula: C₁₂H₁₄N₂O₂
Exact Mass: 218.1055
Molecular Weight: 218.2518

2-((Isopropylamino)methyl)isoindoline-1,3-dione (SO2-121) (38): This compound was synthesized using the same protocol for SO1-142 10a except using 2-(chloromethyl) isoindoline-1,3-dione (300 mg, 1.81 mmol), isopropyl amine (160 mg, 0.272 mmol) and potassium carbonate (125 mg, 9.05 mmol). The compound SO2-121 38 was isolated as a white solid (315 mg, 92%). ¹H NMR (400 MHz, CDCl₃) δ 7.24-7.21 (m, 4H), 4.09 (s, 2H), 2.90 (hept, J=6.3 Hz, 1H), 1.11 (d, J=6.3 Hz, 6H).
SO2-126 (39)

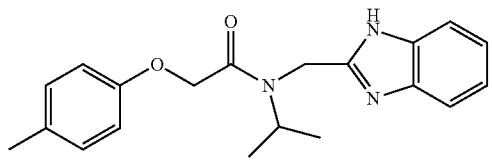

Chemical Formula: C₂₀H₂₃N₃O₂
Exact Mass: 337.1790
Molecular Weight: 337.4155

N-((1H-benzo[a']imidazol-2-yl)methyl-N-isopropyl-2-(p-tolyloxy)acetamide (SO2-126) (38): This compound was synthesized using the same protocol for SO1-143 except using p-tolyloxy-acetyl chloride (5a) (72 mg, 0.38 mmol) and N-((1H-benzo[a']imidazol-2-yl)methyl)propan-2-amine (38) (60 mg, 0.32 mmol) and triethyl amine (65 mg, 0.64 mmol). The compound SO2-126 39 was isolated as a white solid (95 mg, 88%). M.p. 143.0-145.2° C.
HPLC 98.95% (R₁=6.0 min, 50% CH₃CN in 0.1% TFA water 30 min); ¹H NMR (400 MHz, CDCl₃) δ 10.22 (s, 1H), 7.25-7.20 (m, 4H), 7.10 (d, J=8.5 Hz, 2H), 6.85 (d, J=8.6 Hz, 2H), 4.78 (s, 1H), 4.72 (s, 2H), 4.34-4.04 (m, 1H), 2.30 (s, 3H), 1.30 (d, J=6.6 Hz, 6H); ¹³C NMR (100 MHz, CDCl₃) δ 170.04, 155.78, 152.04, 131.53, 130.38, 123.09, 114.59, 77.57, 77.46, 77.26, 76.94, 67.47, 49.69, 39.49, 21.39, 20.73.
LC-MS (ESI+) m/z 338.19 (M+H)⁺; HRMS (ESI+ve) m/z calculated for C₂₀H₂₃N₃O₂(M+H)⁺338.1863. found 338.1866.
SO2-144 (40)

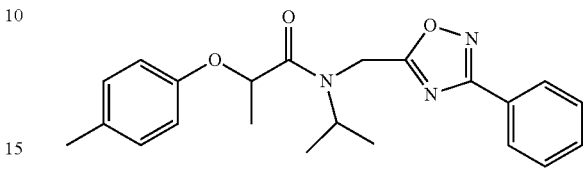

Chemical Formula: C₂₂H₂₅N₃O₃
Exact Mass: 379.1896
Molecular Weight: 379.4522

N-Isopropyl-N-((3-phenyl-1,2,4-oxadiazol-5-yl)methyl-2-(p-tolyl)propanamide (SO2-144) (40): This compound was synthesized using the same protocol for SO1-143 1 except using 2-(p-tolyloxy)propanoylchloride (5a) (19 mg, 0.98 mmol) and isopropyl-(3-phenyl)-[1,2,4]oxadiazol-5-ylmethyl)-amine (10c) (177 mg, 0.82 mmol) and triethyl amine (17 mg, 1.64 mmol). The compound SO2-144 40 was isolated as a white solid (23 mg, 74%). mp 109.0-110.0° C.
HPLC 99.77% (R₁=10.6 min, 60% CH₃CN in 0.1% TFA water 30 min); The ¹H NMR showed 3:1 ratio of atropisomers: ¹H NMR (400 MHz, CDCl₃) δ 8.03 (dd, J=8.0, 1.6 Hz, 2H [δ 7.99 minor isomer shown]), 7.53-7.42 (m, 3H), 7.07 (d, J=8.6 Hz, 2H [δ 6.98 minor isomer shown]), 6.84 (d, J=8.6 Hz, 2H [δ 6.80 minor isomer shown], [δ 6.78 minor isomer shown]), 5.00 (q, J=6.8 Hz, 1H), 4.82-4.70 (m, 1H), 4.67 (d, J_{AB}=16.72 Hz, 1H [δ 4.90 minor isomer shown]), 4.62 (d, J_{BA}=16.72 Hz, 1H [δ 4.83 minor isomer shown]), 2.28 (s, 3H, [δ 2.18 minor isomer shown]), 1.67 (d, J=6.8 Hz, 3H [δ 1.62 minor isomer shown], [δ 1.57 minor isomer shown]), 1.30 (d, J=6.7 Hz, 3H [δ 1.17 minor isomer shown]), 1.11 (d, J=6.6 Hz, 3H [δ 1.14 minor isomer shown]); ¹³C NMR (100 MHz, CDCl₃) δ 176.79, 171.79 [δ 171.44 minor isomer shown], 168.49, 155.44 [δ 154.92 minor isomer shown], 131.33 [δ 131.63 minor isomer shown], 131.04, 130.33 [δ 130.24 minor isomer shown], 128.95 [δ 129.07 minor isomer shown], 127.71 [δ 127.69 minor isomer shown], 127.00, 115.02 [δ 115.45 minor isomer shown], 74.80 [δ 74.66 minor isomer shown], 48.16 [δ 47.72 minor isomer shown], 37.57 [δ 38.83 minor isomer shown], 21.42 [δ 19.93 minor isomer shown], 21.34 [δ 19.88 minor isomer shown], 20.74 [δ 20.64 minor isomer shown], 18.25 [δ 17.92 minor isomer shown].
LC-MS (ESI+) m/z 380.21 (M+H)⁺; HRMS (ESI+ve) m/z calculated for C₂₂H₂₆N₃O₃ (M+H)⁺380.1969. found 380.1975.

SO2-030      4.62      HPLC > 99%

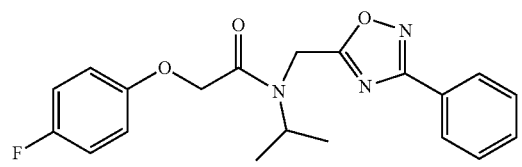

M.W. = 369.39

-continued
SO2-045  >10  HPLC = 99.6%
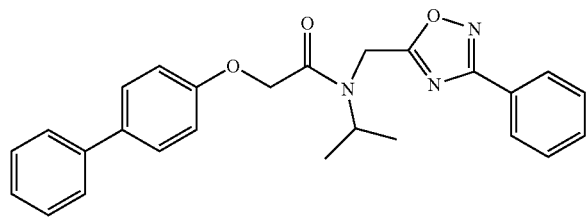
M.W. = 427.50
SO2-046  >10  HPLC = 99.25%
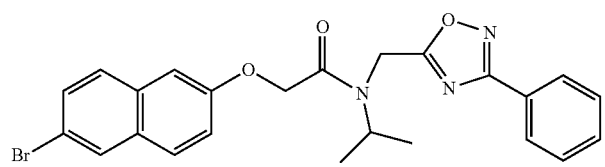
M.W. = 480.35
SO2-050  0.21  HPLC = 95.49%
0.28
0.245 ± 0.05
(n = 2)
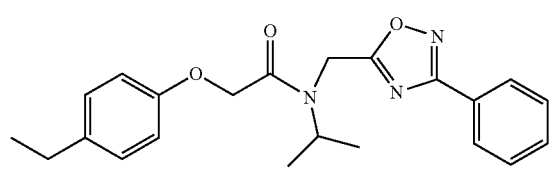
M.W. = 379.45
SO2-054  6.37
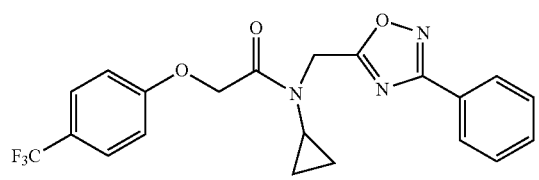
M.W. = 417.38
SO2-058  >10
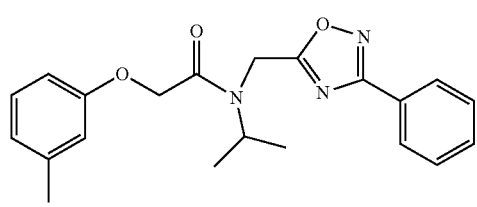
M.W. = 365.43
SO2-073  >10
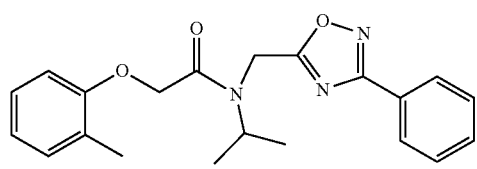
M.W. = 365.43

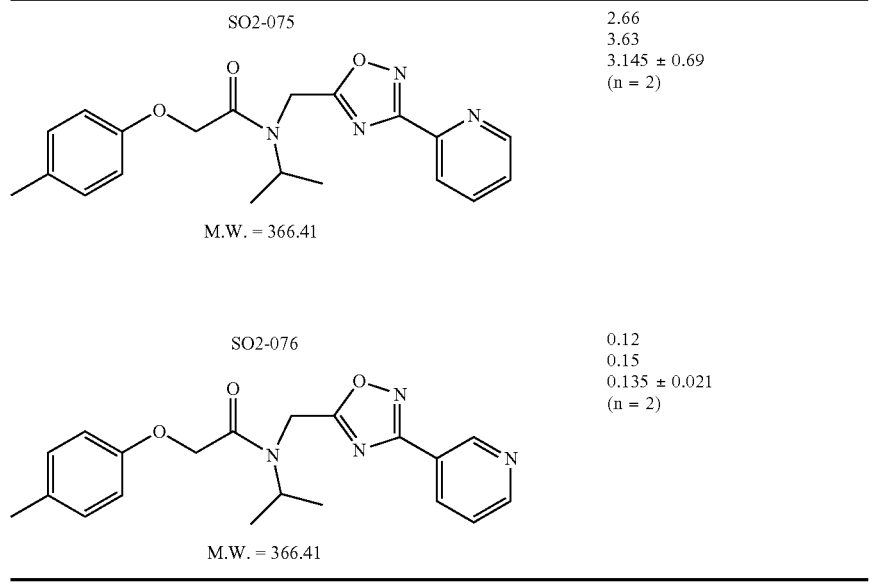

| | |
|---|---|
| SO2-075 M.W. = 366.41 | 2.66<br>3.63<br>3.145 ± 0.69<br>(n = 2) |
| SO2-076 M.W. = 366.41 | 0.12<br>0.15<br>0.135 ± 0.021<br>(n = 2) |

The modifications disclosed herein indicate that the activity is sensitive to changes around the amide moiety. Additionally, along with the modifications on the rings A and B, modifications on the oxadiazole ring will be used to improve the in vitro activity. The synthetic modifications also include introduction of a chiral center around the amide moiety to further characterize this class of compounds as proteasome inhibitors.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of proteasome inhibitors, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A compound of formula I:

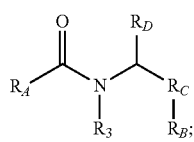

(I)

wherein $R_A$ is

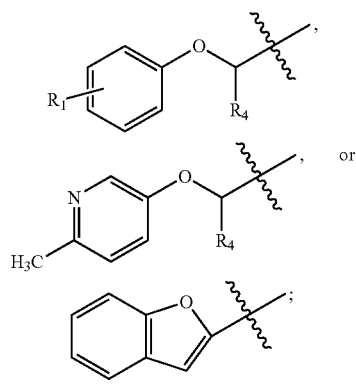

Wherein R1 is H, ethyl, isopropyl, propyl, isobutyl, Br, Ph, F, ortho-$CH_3$, meta-$CH_3$, para-$CH_3$, $CF_2H$, $CF_3$, F, Cl, Br, $NH_2$, CN, OX, OH, $C_6H_{16}$, $C_6H_{13}$, $C_5H_{11}$, $C_4H_9$, $C_3H_7$, or $NO_2$;

wherein $R_4$ is H, alkyl methyl, aryl methyl, OH, $OCH_3$, or $NH_2$;

where X is an aryl or alkyl;

wherein $R_3$ is H, isopropyl, or isobutyl;

wherein $R_B$ is

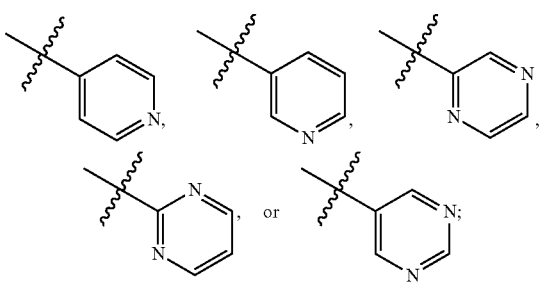

wherein $R_C$ is a heterocyclic aromatic five-member ring structure, wherein the heterocyclic aromatic five-member ring structure further comprises at least one heteroatom consisting of O, N, or S;

Wherein $R_D$ is H, alkyl, OH, or OX;

where X is an aryl or alkyl; and where $R_1$ and $R_3$ are not concurrently $R_1=CH_3$, ethyl, or $CH_2(CH_3)_2$, and $R_3=CH_2(CH_3)_2$.

2. The compound of claim 1, wherein $R_A$ is

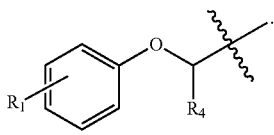

3. The compound of claim 2, wherein $R_1$ is para-$CH_3$, $CF_3$, Cl, $C_3H_7$, $C_4H_9$, propyl, or isobutyl.

4. The compound of claim 1, wherein $R_C$ is

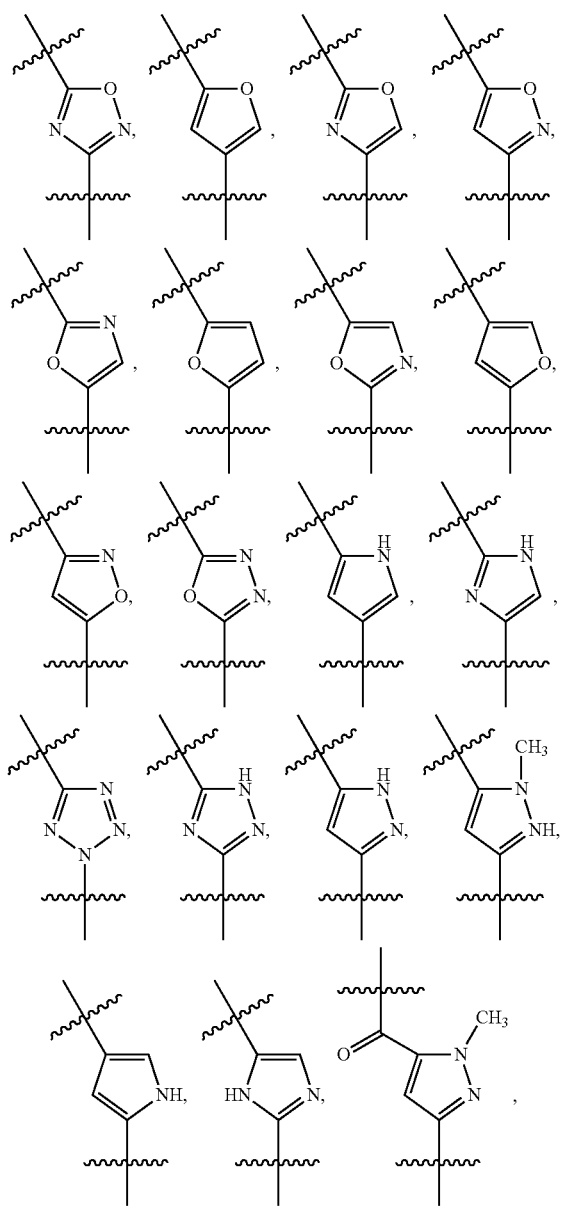

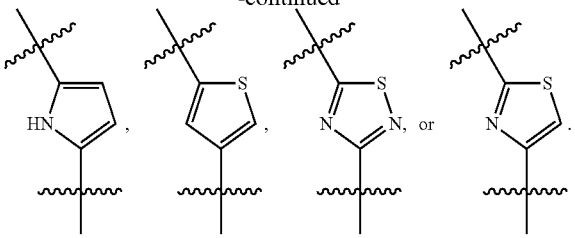

5. The compound of claim 3, further comprising:

wherein $R_1$ is para-$CH_3$, $CF_3$, or Cl;

wherein $R_3$ is $CH_2(CH_3)_2$, or $CH_2CH(CH_3)_2$;

wherein $R_4$ is H; and wherein $R_5$ is H.

6. The compound of claim 1, wherein the compound is an S-enantiomer.

7. A compound; comprising formula II:

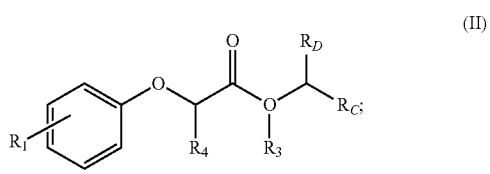

(II)

wherein $R_1$ is either ortho-$CH_3$, meta-$CH_3$, para-$CH_3$, $CF_2H$ $CF_3$, F, Cl, Br, OH, $NH_2$, CN, $NO_2$, $C_6H_{10}$, $C_6H_{13}$, $C_5H_{11}$, $C_4H_9$, $C_3H_7$, OX, or H;

wherein $R_1$ is $CH(CH_3)_2$, cyclopropyl, $CH_2CH(CH_3)_2$, $CH_2CH_3$, OH, or H;

wherein $R_C$ is a heterocyclic ring structure;

wherein $R_A$ is alkyl methyl, aryl methyl, OH, OMe, or $NH_2$;

Wherein $R_D$ is H, alkyl, OH, OX, where $R_D$ and $R_C$ are not concurrently $R_D=H$ and $R_C$=phenyl oxadiazole or a substituted phenyl oxadiazole;

where X is an alkyl or aryl; and

Where $R_1$ and $R_3$ are not concurrently $R_1=CH_3$, or $CH_2(CH_3)$, and $R_3=CH_2(CH_3)$.

8. The compound of claim 7, wherein $R_C$ is

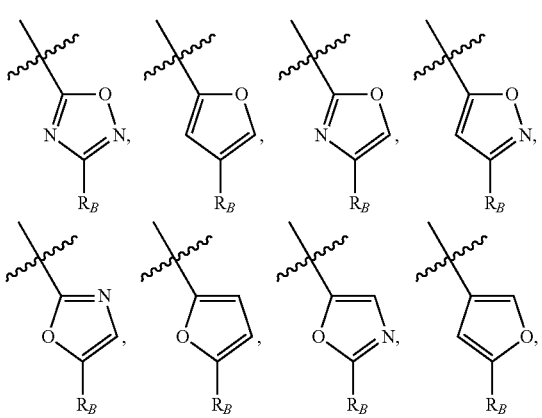

-continued

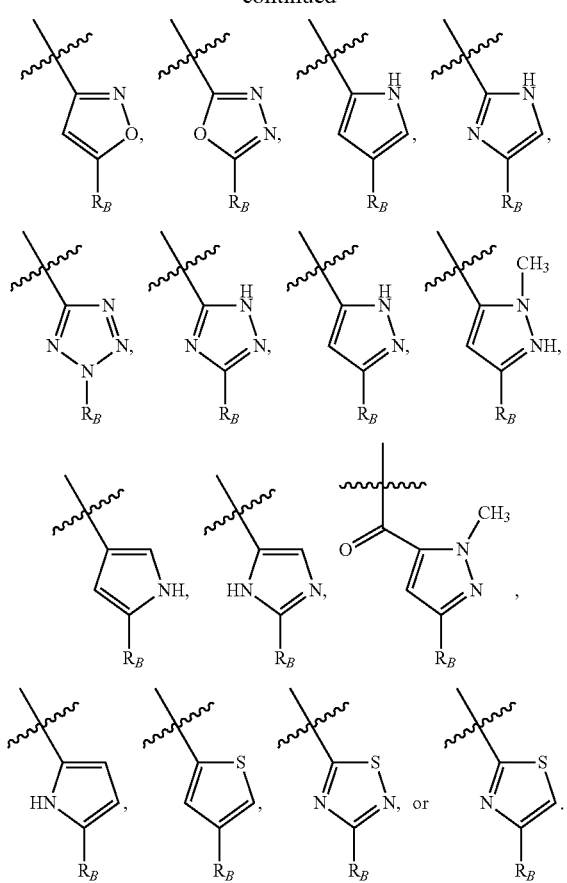

9. The compound of claim 8, wherein $R_B$ is

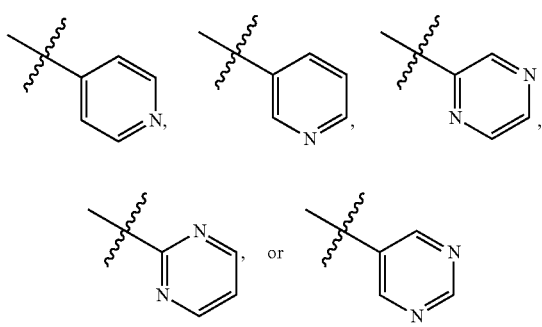

10. The compound of claim 8, wherein $R_C$ has the structure

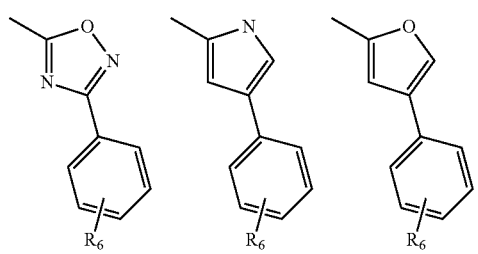

-continued

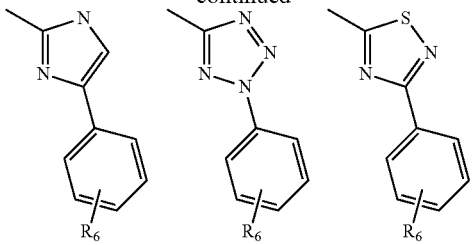

wherein $R_6$ is ortho $CH_3$, meta $CH_3$, para $CH_3$, $CF_3$, OH, $NH_2$, CN, $NO_2$, OX, Cl, or H;
where X is an alkyl or aryl$CH_3$.

11. The compound of claim 9, wherein $R_1$ and $R_2$ are not the same group.

12. The compound of claim 10, wherein $R_1$ and $R_6$ are not the same group.

13. The compound of claim 7, wherein the compound is an S-enantiomer.

14. A method of inhibiting the chymotrypsin-like activity of proteasome, comprising:
administering a therapeutically effective amount of a proteasome inhibitor,
Wherein the proteasome inhibitor is a compound of formula I:

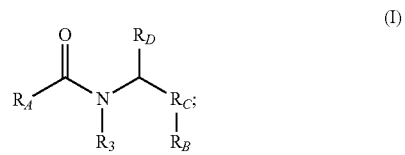

wherein $R_A$ is

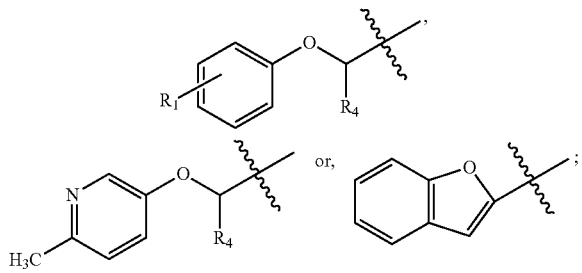

wherein $R_1$ is H, ethyl, isopropyl, propyl, isobutyl, Br, Ph, F, ortho-$CH_3$, meta-$CH_3$, para-$CH_3$, $CF_2H$, $CF_3$, F, Cl, Br, $NH_2$, CN, OX, OH, $C_6H_{10}$, $C_6H_{13}$, $C_5H_{13}$, $C_9H_9$, $C_3H_7$, or $NO_2$;
wherein $R_4$ is H, alkyl methyl, aryl methyl, OH, $OCH_3$, or $NH_2$;
where X is an aryl or alkyl;
wherein $R_3$ is H, isopropyl, or isobutyl;
wherein $R_B$ is

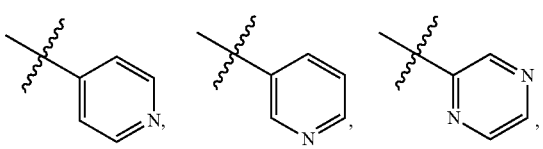

-continued

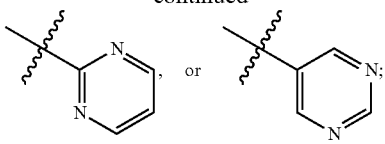 or wherein $R_C$ is a heterocyclic aromatic five-member ring structure, where the heterocyclic aromatic five-member ring structure further comprises at least one heteroatom consisting of O, N, or S;
Wherein $R_D$ is H, alkyl, OH, or OX;
where X is an aryl or alkyl; and
where $R_1$ and $R_3$ are not concurrently $R_3=CH_3$, ethyl, or $CH_2(CH_3)_2$, and $R_3=CH_3(CH_3)_2$.

15. The proteasome inhibitor of claim 1, wherein $R_A$ is

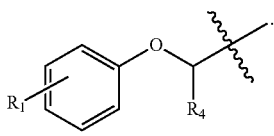

16. The proteasome inhibitor of claim 15, wherein $R_1$ is para-$CH_3$, $CF_3$, propyl, Cl, $C_3H_7$, $C_4H_9$, or isobutyl.

17. The proteasome inhibitor of claim 16, wherein $R_1$ and $R_3$ are not the same group.

18. The proteasome inhibitor of claim 14, wherein $R_C$ is

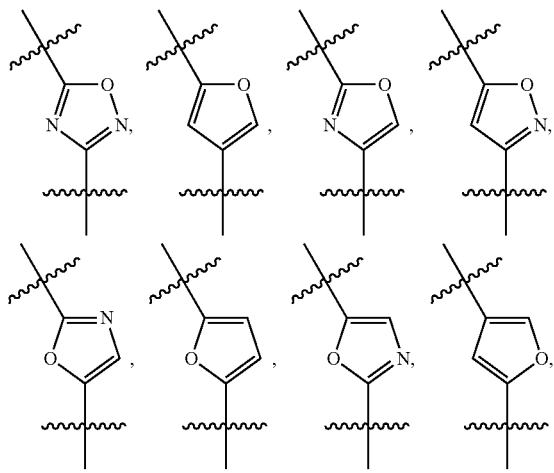

-continued

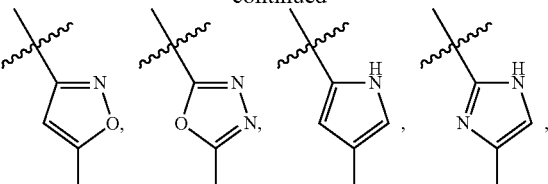

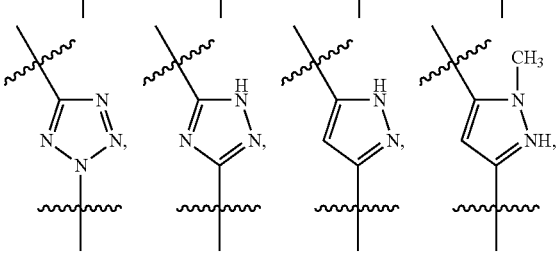

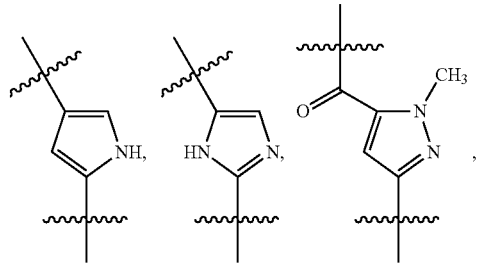

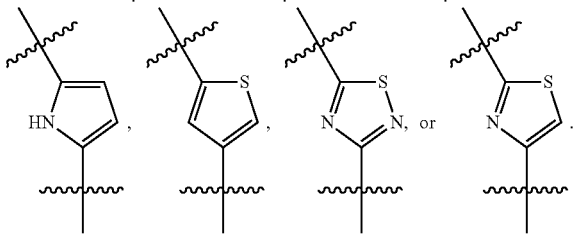

19. The proteasome inhibitor of claim 16, further comprising:
wherein $R_1$ is para-$CH_3$, $CF_3$, or Cl;
wherein $R_3$ is $CH_2(CH_3)_2$, or $CH_2CH(CH_3)_2$;
wherein $R_4$ is H;
wherein $R_5$ is H; and
wherein $R_2$ is H, Cl, $CF_3$, or $CH_3$.

20. The method of claim 14, wherein the compound is an S-enantiomer.

* * * * *